US012653911B2

(12) United States Patent
Xu et al.

(10) Patent No.: US 12,653,911 B2
(45) Date of Patent: Jun. 16, 2026

(54) STIMULI-RESPONSIVE NANOPARTICLES FOR BIOMEDICAL APPLICATIONS

(71) Applicant: The Brigham and Women's Hospital, Inc., Boston, MA (US)

(72) Inventors: Xiaoding Xu, Boston, MA (US); Jinjun Shi, Boston, MA (US); Omid C. Farokhzad, Boston, MA (US)

(73) Assignee: The Brigham And Women's Hospital, Inc., Boston, MA (US)

( * ) Notice: Subject to any disclaimer, the term of this patent is extended or adjusted under 35 U.S.C. 154(b) by 0 days.

(21) Appl. No.: 17/585,118

(22) Filed: Jan. 26, 2022

(65) Prior Publication Data

US 2022/0226510 A1 Jul. 21, 2022

Related U.S. Application Data

(63) Continuation of application No. 16/090,551, filed as application No. PCT/US2017/025772 on Apr. 3, 2017, now abandoned.

(60) Provisional application No. 62/317,033, filed on Apr. 1, 2016.

(51) Int. Cl.

| | |
|---|---|
| ***A61K 49/00*** | (2006.01) |
| ***A61K 9/1273*** | (2025.01) |
| ***A61K 9/51*** | (2006.01) |
| ***A61K 47/65*** | (2017.01) |
| ***C08F 293/00*** | (2006.01) |
| *A61K 31/711* | (2006.01) |
| *C08F 220/28* | (2006.01) |
| *C08F 220/34* | (2006.01) |

(52) U.S. Cl.
CPC ........ *A61K 49/0054* (2013.01); *A61K 9/1273* (2013.01); *A61K 9/5138* (2013.01); *A61K 9/5146* (2013.01); *A61K 9/5153* (2013.01); *A61K 47/65* (2017.08); *A61K 49/0021* (2013.01); *A61K 49/0032* (2013.01); *C08F 293/005* (2013.01); *A61K 31/711* (2013.01); *A61K 49/0093* (2013.01); *C08F 220/286* (2020.02); *C08F 220/34* (2013.01); *C08F 2438/01* (2013.01)

(58) Field of Classification Search
CPC .............. A61K 49/0054; A61K 9/1273; A61K 49/0093
See application file for complete search history.

(56) References Cited

U.S. PATENT DOCUMENTS

2010/0034748 A1* 2/2010 Li ..................... A61K 49/0032 424/9.4
2013/0136714 A1* 5/2013 Wang ................... A61K 9/0019 977/773

FOREIGN PATENT DOCUMENTS

| | | |
|---|---|---|
| CN | 104231193 | 12/2014 |
| WO | 2013152059 | 10/2013 |
| WO | 2016040814 | 3/2016 |

OTHER PUBLICATIONS https://www.thermofisher.com/antibody/product/CD31-Antibody-clone-2H8-Monoclonal/MA3105#:~:text=The%20MA3105%20immunogen%20is%20mouse%20PECAM1%20%28CD31%29.%20MA3105,a%20predicted%20molecular%20weight%20of%20approximately%2079%20kDa printed from web Apr. 5, 2023 (Year: 2023).*
Almeida, et al., "Temperature and pH stimuli-responsive polymers and their applications in controlled and self-regulated drug delivery," J. Applied Pharm. Sci., 02(06):1-10 (2012).
Chen, et al., "Current Multistage Drug Delivery Systems Based on the Tumor Microenvironment," Theranostics, 7(3):538-558 (2017).
Du, et al., "Synthesis and Characterization of Photo-Cross-Linked Hydrogels Based on Biodegradable Polyphosphoesters and Poly-(ethylene glycol) Copolymers," Biomacromolecules, 8(11):3375-3381 (2007).
Gandhi, et al., "Nanocarrier mediated Delivery of siRNA/miRNA in Combination with Chemotherapeutic Agents for Cancer Therapy: Current Progress and Advances", J. Control. Release, 0:238-256 (2014).
Haijun, et al., "Induction of apoptosis in non-small cell lung cancer by downregulation of MDM2 using pH-responsive PMPC-b-PDPA/siRNA complex nanoparticles," Biomaterials, 34(11):2738-2747 (2013).
International Search Report for PCT/US2017/025772 mailed Jun. 28, 2017.
James, et al., "Smart polymers for the controlled delivery of drugs—a concise overview,"Acta Pharma. Sinica B, 4(2):120-127 (2014).
Knop, et al., "Poly(ethylene glycol) in drug delivery: pros and cons as well as potential alternatives," Angew. Chem. International Edition, 49(36): 6288-6308 (2010).

(Continued)

*Primary Examiner* — James W Rogers
(74) *Attorney, Agent, or Firm* — Pabst Patent Group LLP

(57) ABSTRACT

Stimuli-responsive NPs with excellent stability, high loading efficiency, encapsulation of multiple agents, targeting to certain cells, tissues or organs of the body, can be used as delivery tools. These NPs contain a hydrophobic inner core and hydrophilic outer shell, which endows them with high stability and the ability to load therapeutic agents with high encapsulation efficiency. The NPs are preferably formed from amphiphilic stimulus-responsive polymers or a mixture of amphiphilic and hydrophobic polymers or compounds, at least one type of which is stimuli-responsive. These NPs can be made so that their cargo is released primarily within target certain cells, tissues or organs of the body, upon exposure to endogenous or exogenous stimuli. The rate of release can be controlled so that it may be a burst, sustained, delayed, or a combination thereof. The NPs have utility as research tools or for clinical applications including diagnostics, therapeutics, or combination of both.

9 Claims, 34 Drawing Sheets

Specification includes a Sequence Listing.

(56) References Cited

OTHER PUBLICATIONS

Lewis, et al., "Using Polymers as Endosomal Escape Agents for siRNA Delivery in vivo", TIDES Pre-Conference Workshop, 33 pages, May 12, 2014.
Li, et al., "Efficacious delivery of protein drugs to prostate cancer cells by PSMA-targeted pH-responsive chimaeric polymersomes," Journal of Controlled Release, 220(Pt B):704-714 (2015).
Mabrouk, et al., "Bursting of sensitive polymersomes including by curling," Proceedings National Academy of Sciences PNAS, 106(18):7294-7298 (2009).
Ryther, et al., "siRNA therapeutics: big potential from small RNAs", Gene Therapy, 12:5-11 (2005).
Sommer, et al., "Inflammation, tissue repair and fever, Essential of Pathophysiology—Concepts of Altered Health Sciences", 9: 495-514 (2006).
Wang, et al., "A Broad Nanoparticle-Based Strategy For Tumor Imaging by Nonlinear Amplification of Microenvironment Signals," Nature Materials, 13(2):204-212 (2013).
Wang, et al., "Hierarchical Targeting Strategy for Enhanced Tumor Tissue Accumulation/Retention and Cellular Internalization," Advanced materials, 28(34):7340-7364 (2016a).
Wang, et al., "Stimuli-Responsive Programmed Specific Targeting in Nanomedicine," ACS Nano 10(3):2991-2994 (2016b).
Xu, et al., "Enhancing tumor cell response to chemotherapy through nanoparticle-mediated codelivery of siRNA and cisplatin prodrug," Proc Natl Acad Sci USA, 110(46):18638-18643 (2013).
Xu, et al., "Multi-functional Envelope-Type siRNA Delivery Nanoparticle platform for Prostate Cancer Therapy," ACS Nano, 11(3):2618-2627 (2017).
Xu, et al., "Ultra-pH Responsive and Tumor-Penetrating Nanoplatform for Targeted siRNA Delivery with Robust Anti-Cancer Efficacy," Angew Chem International Edition, 55(25):7091-7094 (2016).
Yin, et al., "Crosslinked triblock copolymeric micelle for redox-responsive drug delivery," Colloids and Surfaces B Biointerfaces, 122:223-230 (2014).
Yu, et al. "Triple-Layered pH-Responsive Micelleplexes Loaded with si RNA and Cisplatin Prod rug for NF-Kappa B Targeted Treatment of Metastatic Breast Cancer", Theranostics, 6(1): 14- 27 (2016).

* cited by examiner

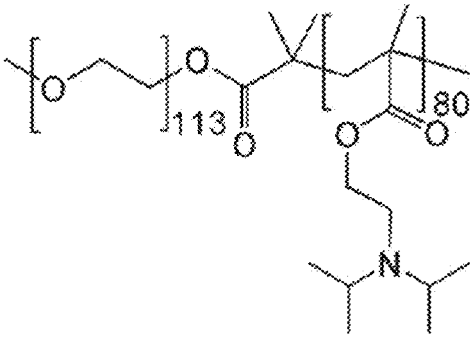
Meo-PEG-*b*-PDPA
FIG. 27A
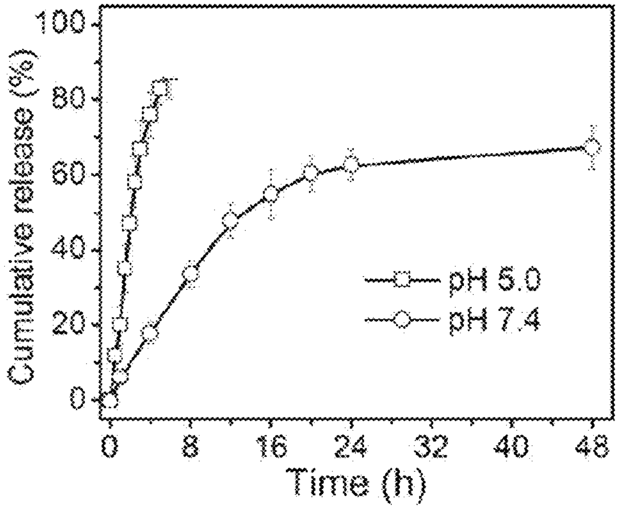
FIG. 27B
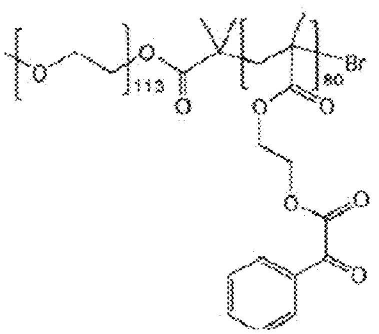
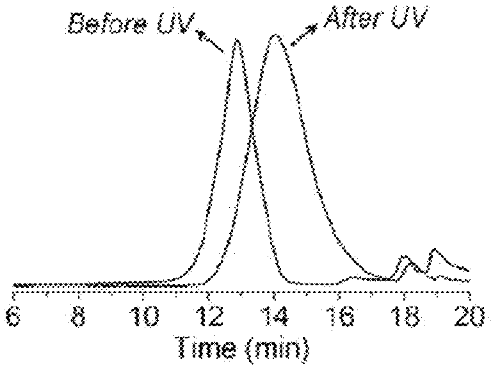
FIG. 28A
FIG. 28B

STIMULI-RESPONSIVE NANOPARTICLES FOR BIOMEDICAL APPLICATIONS

CROSS-REFERENCE TO RELATED APPLICATIONS

This application is a continuation of U.S. application Ser. No. 16/090,551, filed Oct. 1, 2018, which is a National Stage Entry under 35 U.S.C. § 371 of PCT/US2017/025772, filed Apr. 3, 2017, which claims benefit of and priority to U.S. Provisional Application No. 62/317,033, filed Apr. 1, 2016, which are hereby incorporated herein by reference in their entirety.

STATEMENT REGARDING FEDERALLY SPONSORED RESEARCH OR DEVELOPMENT

This invention was made with government support under W81XWH-15-1-0728 awarded by the Defense Health Agency, Medical Research and Development Branch, and CA160350, CA200900, EB015419, and CA151884 awarded by the National Institutes of Health. The government has certain rights in the invention.

REFERENCE TO SEQUENCE LISTING

The Sequence Listing submitted Apr. 3, 2017, as a text file named "BWH_23878_PCT_ST25.txt," created on Apr. 3, 2017, and having a size of 3,738 bytes is hereby incorporated by reference.

FIELD OF THE INVENTION

This invention is generally in the field of developing stimuli-responsive solid polymeric nanoparticles (NPs) which can be used to deliver therapeutic and diagnostic agents including nucleic acids, proteins, chemotherapeutic drugs, or other small molecules.

BACKGROUND OF THE INVENTION

Nanoparticles have become an important tool in many industries including healthcare. Biomedical application of NPs has introduced exciting opportunities for the improvement of disease diagnosis and treatment. In particular, stimuli-responsive NPs, which can undergo shape, structure and property change upon to endogenous or exogenous stimuli, play an increasingly important role in a diverse range of biomedical applications, such as controlled release of drugs, gene delivery and diagnostics. The stimuli-responsive characteristic may offer spatiotemporal control over the macroscopic properties of NPs, and thus the release of the encapsulated cargo can be performed directly at the desired site, minimizing toxic and side effects in surrounding, healthy tissue.

For example, the microenvironment in tumor tissue is different from the normal tissues. Compared to normal tissues, the pH in tumor tissue is more acidic, the tissue temperature is relatively higher, and some specific enzymes or chemicals are over-expressed. Therefore, developing stimuli-responsive NPs that can specifically respond to tumor microenvironment will accomplish the targeted delivery of cargos to tumor sites and thus and impair the toxic and side effects to healthy tissues.

The problem with the stimuli responsive NPs is that they often to not make it to area where release is desired, being phagocytozed, undergoing enzymatic attack, or becoming physically entrapped on their way to the desired target.

It is therefore an object of the present invention to provide stimuli-responsive nanoparticles (NPs) which can be used to deliver therapeutic and diagnostic agents including nucleic acids, proteins, chemotherapeutic drugs, or other small molecules, which have an increased efficacy in getting to the targeted tissue where release is to occur.

SUMMARY OF THE INVENTION

Stimuli-responsive NPs with excellent stability, high loading efficiency, encapsulation of multiple agents, targeting to specific cells, tissues or organs of the body, can be used as delivery tools. These NPs contain a hydrophobic inner core and hydrophilic outer shell, which endows them with high stability in water, aqueous buffers, serum and other biological fluids, or the circulatory system in vivo, and the ability to load therapeutic agents with high encapsulation efficiency. The diameters of the nanoparticles are between about 50 nm and about 500 nm, preferably between about 50 nm and about 350 nm. In some embodiments, the diameters of the nanoparticles are about 100 nm. The zeta potential of the nanoparticles are between about −50 mV and about +50 mV, preferably between about −25 mV and +25 mV, most preferably between about −10 mV and about +10 mv.

Nanoparticles formed from polymers in combination with stimuli responsive polymers, wherein the stimuli are selected from the group consisting of pH, temperature, light, redox change, over-expressed enzymes, hypoxia, sound, magnetic force, electrical energy, and combinations thereof, are described. Typically, the nanoparticles are formed by emulsion with a non-aqueous solvent, solvent extraction, nanoprecipitation, or a combination thereof.

Preferably, the nanoparticles are formed by self-assembly in an emulsion of a non-aqueous solution with an aqueous solution of a first amphiphilic polymer containing a polymer represented by Formula I:

$$(X)_m\text{—}(Y)_n \qquad \text{Formula I}$$

wherein m and n are independently integers between one and 1000, inclusive, X is a hydrophobic polymer and Y is a hydrophilic polymer, and at least one of X, Y, or both, is stimuli-responsive.

In some embodiments, the nanoparticles are formed by self-assembly of a mixture of polymers represented by Formula I and a second polymer containing a polymer represented by Formula II:

$$(Q)_c\text{-}(R)_d \qquad \text{Formula II}$$

wherein c and d are independently integers between zero and 1000, inclusive, with the proviso that the sum (c+d) is greater than one. Q and R are independently hydrophilic or hydrophobic polymers. Optionally, the nanoparticles are formed by self-assembly of a mixture of polymers represented by Formula I and Formula II, wherein the polymer represented by Formula I, Formula II, or both, contains a ligand, wherein the ligand is a targeting ligand, an adhesion ligand, a cell-penetrating ligand, and/or an endosomal-penetrating ligand. Preferably, the ligand is conjugated to the hydrophilic polymer.

In some embodiments, the nanoparticles are formed by self-assembly of a mixture of a stimuli-responsive hydrophobic polymer and, optionally a further polymer containing a polymer represented by Formula III:

$$(S)_e\text{-}(T)_f \qquad \text{Formula III}$$

wherein e and f are independently integers between one and 1000, inclusive, S is a hydrophilic polymer and T is a hydrophobic polymer. In some embodiments, the stimuli-responsive hydrophobic polymer, and/or the polymer represented by Formula III, contains a ligand, wherein the ligand is a targeting ligand, an adhesion ligand, a cell-penetrating ligand, or an endosomal-penetrating ligand.

The molecular weights of the polymers are between about 1 kDa and about 100 kDa, preferably between about 2 kDa and about 50 kDa. In some embodiments, the molecular weights of the polymers are about 2 kDa, 3 kDa, 10 kDa, 20 kDa, 30 kDa, or 00 kDa. In embodiments in which the polymer is amphiphilic, the amphiphilic polymer contains between about 5% and about 90% weight/weight of the hydrophobic polymer, preferably between about 10% and about 80% weight/weight of the hydrophobic polymer.

Optionally, the polymers that form the nanoparticles contain linkers between the blocks of hydrophilic and hydrophobic polymers, between the hydrophilic polymer and ligand, or both.

These stimuli-responsive NPs have two main components: 1) a hydrophobic core that is made with stimuli-responsive hydrophobic polymers or the hydrophobic end of amphiphilic polymers to encapsulate therapeutic and diagnostic agents including proteins or peptides, nucleic acids, lipids, sugars or polysaccharides, small molecules, or combinations thereof, and 2) a hydrophilic outer shell that allows the NPs to evade recognition by immune system components and increase blood circulation half-life. Hydrophobic polymers making up the hydrophobic core can be modified to accommodate the active agent to be encapsulated. In some embodiments, hydrophobic polymers, or hydrophobic segments of amphiphilic polymers, are modified with charged groups to allow loading of charged active agents in the hydrophobic core. For example, conjugating a hydrophobic component of a polymer with tetraethylenepentamine or 2-aminoethyl methacrylate will impart a positive charge to the hydrophobic core to help encapsulate negatively charged molecules such as nucleic acids.

The stimuli-responsive polymers are hydrophobic or amphiphilic, and can be, but are not limited to, pH-, hypoxia-, redox-, light-, temperature-, enzyme-, or ultrasound-responsive polymers. The NPs may also include a one or more additional components: 3) a targeting ligand that can specifically bind to its receptor on certain cells, tissues, or organs of the body; endosomal or cell penetrating molecule; or adhesion ligand.

The stimuli-responsive NPs are made by self-assembly in emulsions of an aqueous solution with a non-aqueous solution, resulting in a polymeric nanoparticle that may contain non-aqueous solvent residue. The amphiphilic copolymers are preferably polyethylene glycol (PEG) based copolymers. In a preferred embodiment, the NPs are prepared using a mixture of hydrophobic polymer and amphiphilic compound. The amphiphilic compound can include naturally derived lipids, lipid-like materials, surfactants, or synthesized amphiphilic compounds.

The NPs are useful for delivery of therapeutic, prophylactic, and/or diagnostic agents. In some embodiments, the NPs contain between about 1% and about 70% weight/weight of a therapeutic agent, a prophylactic agent, a diagnostic agent, or combinations thereof. Preferably, the NPs contain between about 5% and about 50% weight/weight, most preferably between about 10% and about 30% weight/weight of a therapeutic agent, a prophylactic agent, a diagnostic agent, or combinations thereof. These NPs can be made so that their cargo is released primarily within target certain cells, tissues or organs of the body, upon exposure to endogenous or exogenous stimuli (pH, temperature, redox, light, etc.). The rate of release can be controlled so that it may be a burst, sustained, delayed, or a combination thereof. The NPs have utility as research tools or for clinical applications including diagnostics, therapeutics, or combination of both.

One specific use of these stimuli-responsive NPs is in the field of small interference RNA (siRNA) delivery. RNA interference (RNAi) technology has gained broad interest among academic and industry investigators for its potential to treat a myriad of diseases. One major hurdle in clinical translation of RNAi therapeutics (e.g., siRNA) may be attributed to the lack of effective and non-toxic delivery vehicles to transport siRNA into diseased tissues and cells. Due to its polyanionic and macromolecular characteristics, naked siRNA cannot freely cross cellular membrane, and thus requires delivery vehicles to facilitate its intracellular uptake and endosomal escape, as well as to protect it from degradation during circulation. Specifically for cancer therapy, the barriers to effective in vivo siRNA delivery mainly include targeting to tumor, penetrating tumor tissue and cell membrane, escaping the endosome and releasing siRNAs in the cytoplasm. The stimuli-responsive NPs can respond to tumor or intracellular microenvironment, and thus improve the siRNA ability to target tumor tissue, escape from endosomes/lysosomes or efficiently release in cytoplasm for high-performance gene silencing.

Besides the delivery of siRNA, the stimuli-responsive NPs can be applied to the delivery of chemotherapeutic drugs or proteins for cancer therapy. The key principle of cancer therapy is to improve the therapeutic efficacy and impair the toxic and side effects. Owing to their scale and distinct physicochemical properties as well as the specific pathophysiological characteristics of tumors, NPs offer the potential to significantly improve cancer therapy. However, lack of active targeting to cancer cells and the undesired drug release in healthy tissue are the main barriers to clinical translation. The disclosed NPs that are selectively responsive to endogenous or exogenous stimuli offer spatiotemporal control of the delivery of anticancer therapeutics. Moreover, through surface-modification of these NPs by targeting ligand, it can accomplish the objective that targeted delivery of chemotherapeutic drugs or proteins to tumor tissues and then rapid drug release induced by the tumor microenvironment, which thus can minimize toxic and side effects to surrounding healthy tissue.

The delivery of imaging and/or therapeutic agents is an alternative use of the stimuli-responsive NPs for disease diagnostics or theranostic. The microenvironment of diseases is different from the normal tissues. For example, compared to normal tissues, the pH in tumor tissue is more acidic, the tissue temperature is relatively higher, and some specific enzymes or chemicals are over-expressed. Therefore, developing stimuli-responsive NPs that can specifically respond to tumor microenvironment will accomplish the site-specific and rapid release of imaging and/or therapeutic agents at tumor tissue for cancer diagnostics or theranostic.

(22B) biodistribution of the NPs in the tumors and main organs of the LNCaP xenograft tumor-bearing nude mice sacrificed 24 h post-injection of naked Cy5.5-siRNA, Cy5.5-siRNA-loaded NPsR10 and ACUPA-NPsR10, and PSMA antibody followed by Cy5.5-siRNA-loaded ACUPA-NPsR10.

Figure 23:
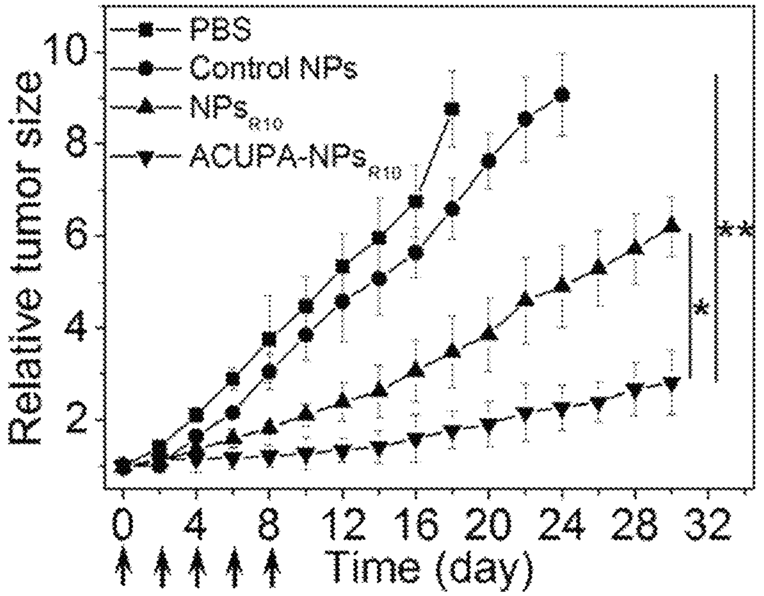
Figure 24:
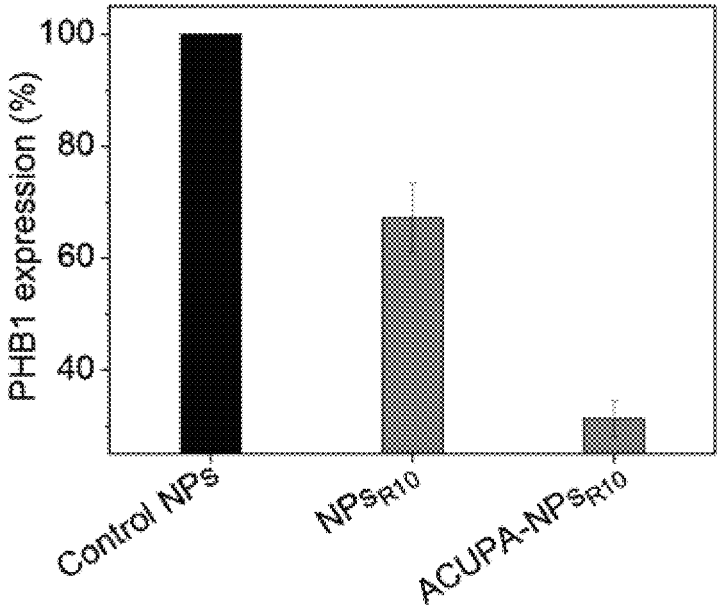

FIG. 23 is a graph showing relative tumor size over time (days) of the LNCaP xenograft tumor-bearing nude mice after treatment by PBS, control NPs, and PHB1 siRNA-loaded NPsR10 and ACUPA-NPsR10. The intravenous injections are indicated by the arrows. GL3 siRNA-loaded NPsR10 were used as a control. *$P<0.05$; **$P<0.01$ FIG. 24 is a bar graph showing PHB1 expression in LNCaP xenograft tumor of the mice treated with GL3 siRNA-loaded NPsR10 (Control NPs), and PHB1 siRNA-loaded NPsR10 and ACUPA-NPsR10.

Figure 25:
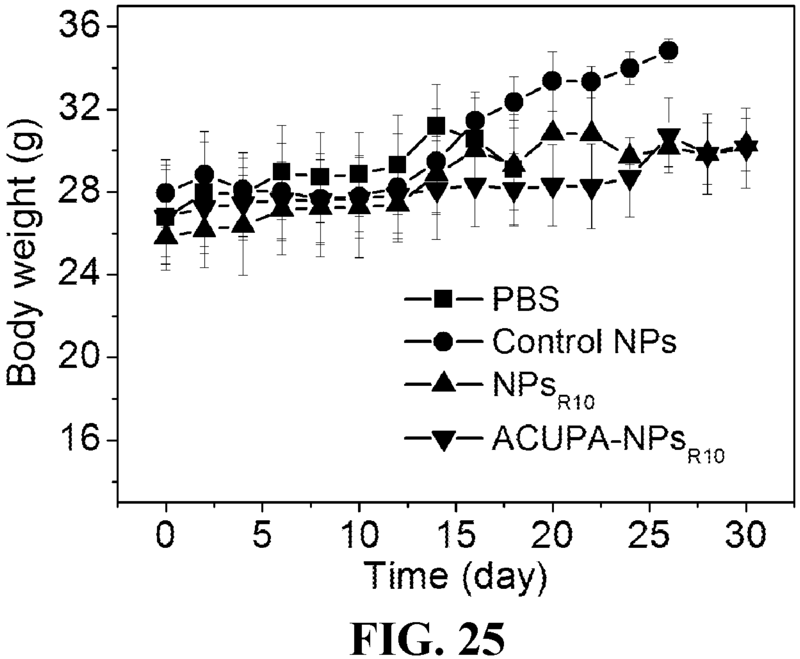

FIG. 25 is a graph showing body weight of the LNCaP xenograft tumor-bearing nude mice treated with PBS, GL3 siRNA loaded NPsR10 (Control NPs), and PHB1 siRNA-loaded NPsR10 and ACUPA-NPsR10.

Figures 26A, 26B:
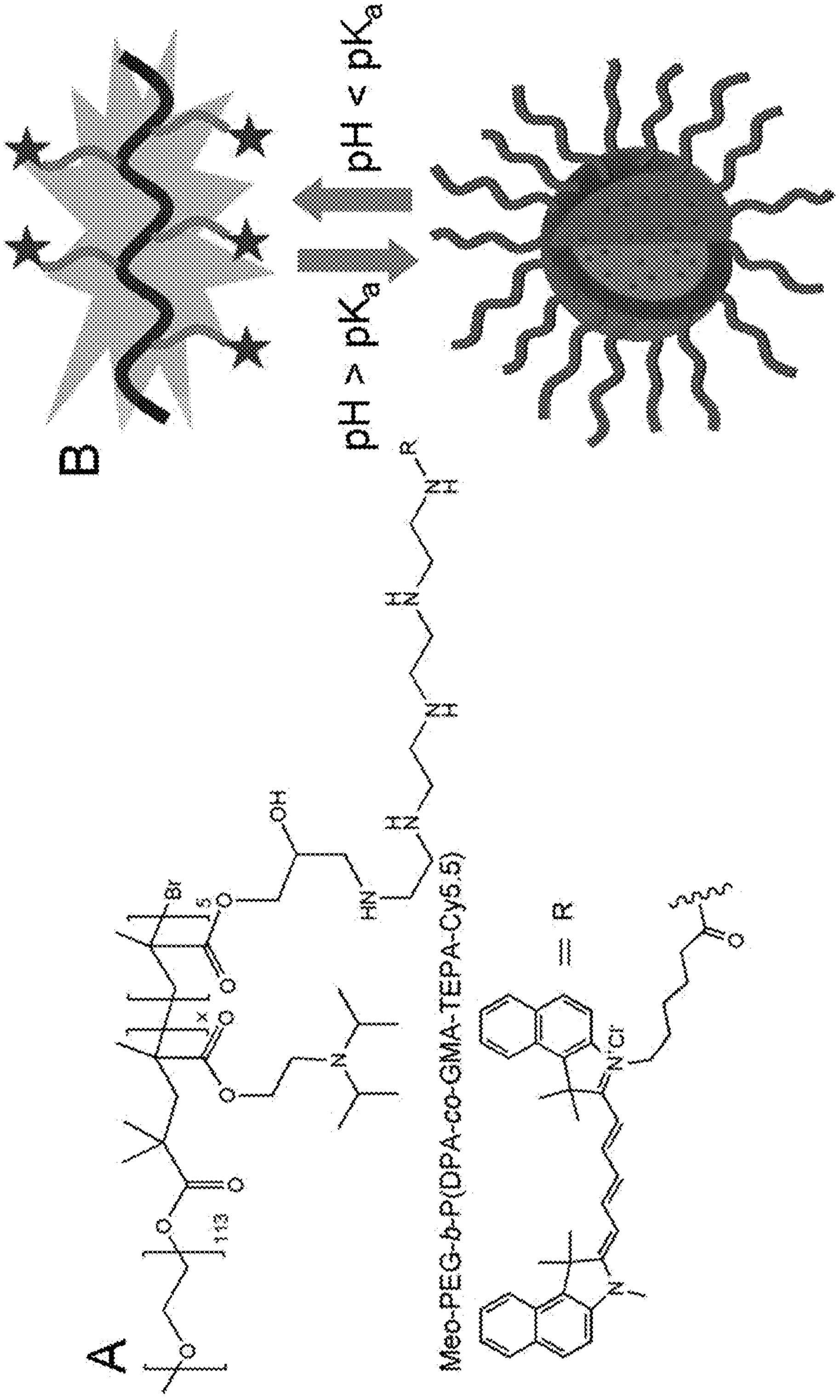

FIGS. 26A-26B are schematics of (26A) molecular structure of Cy5.5 conjugated ultra pH-responsive copolymer, Meo-PEG-b-P(DPA-co-GMA-TEPA-Cy5.5; (26B) the self-assembly of Meo-PEG-b-P(DPA-co-GMA-TEPA-Cy5.5) into nanoparticles with the aggregation of Cy5.5 inside the hydrophobic cores.

FIGS. 27A and 27B are (27A) a molecular structure of ultra pH-responsive polymer, Meo-PEG-b-PDPA and (27B) a graph showing cumulative release profile of PTX from the PTX loaded NPs of Meo-PEG-b-PDPA in PBS buffer at a pH of 7.4 and 5.0.

FIGS. 28A-28B are (28A) molecular structure of light-responsive polymer, Meo-PEG-b-POPEMA; and (28B) GPC profiles of the light-responsive Meo-PEG-b-POPEMA before and after 365 nm UV light irradiation.

Figures 29A, 29B:
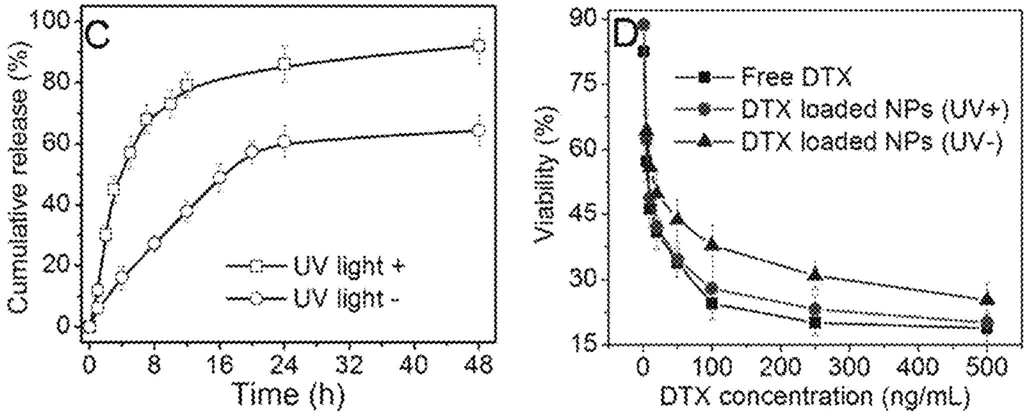

FIGS. 29A-29B are (29A) cumulative release profile over time (hours) of DTX from the DTX loaded NPs of Meo-PEG-b-POPEMA in PBS buffer (7.4); and (29B) cytotoxicity of free DTX and DTX loaded NPs of Meo-PEG-b-POPEMA against PC3 cells at increasing concentrations of DTX. After incubation with the free DTX or DTX loaded NPs for 8 h, the culture medium was replaced and UV irradiation was applied for 30 min and then the cells were further incubated for another 40 h.

Figure 30:
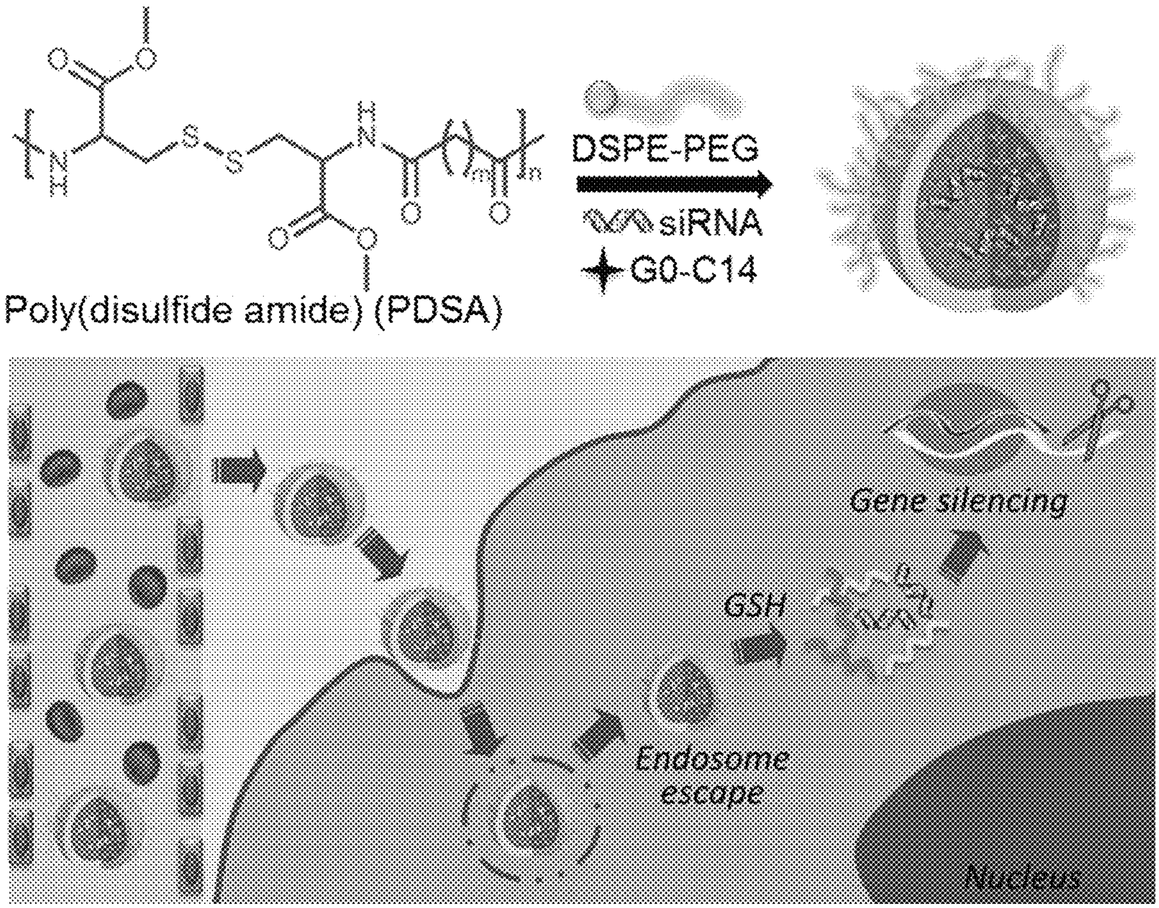

FIG. 30 is a schematic illustration of the self-assembly of redox-responsive polymer into spherical NPs for siRNA delivery and cancer therapy.

Figure 31A:
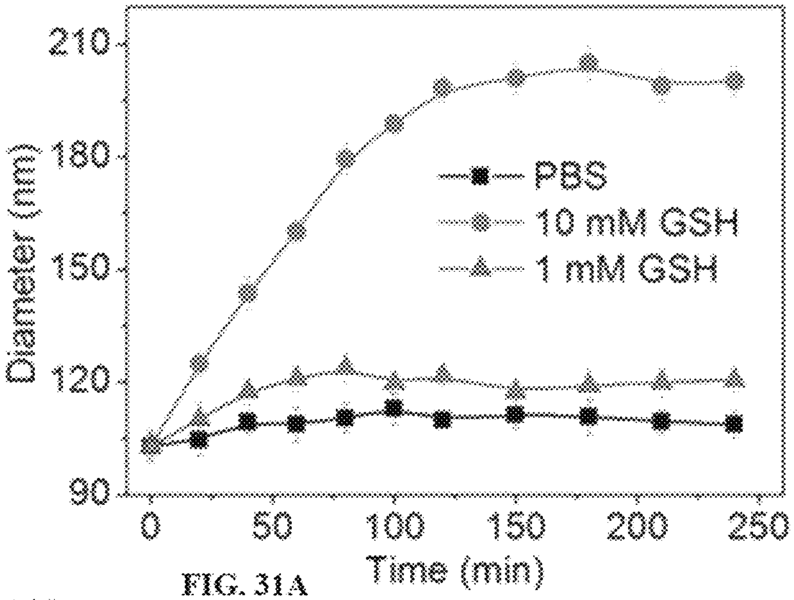
Figure 31B:
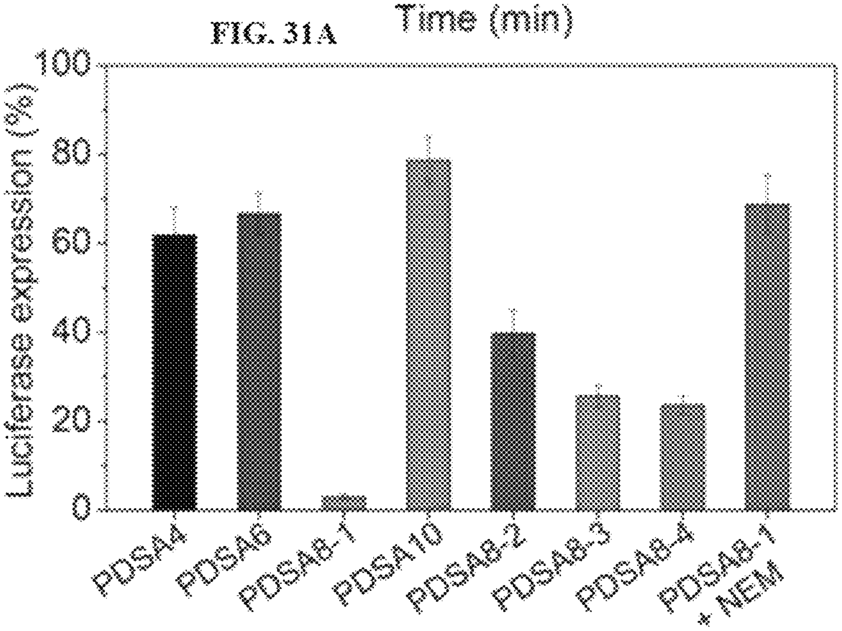

FIGS. 31A-31B are graphs showing (31A) size change over time (min) of the NPs of PDSA8-1 incubated in PBS buffer containing 10 mM GSH for 4 h; and (31B) firefly luciferase expression in Luc-HeLa cells transfected with GL3 siRNA loaded NPs of PDSA polymers at a 1 nM siRNA dose.

Figure 32:
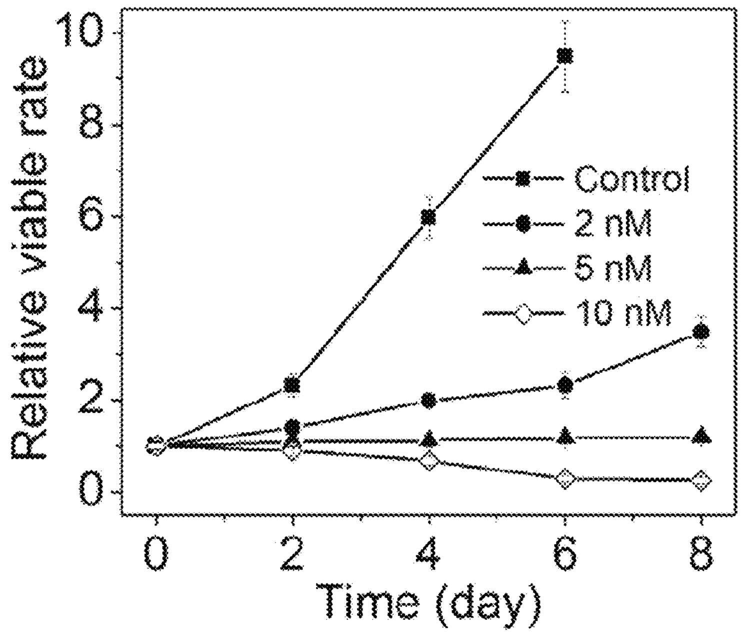

FIG. 32 is a graph showing proliferation over time (days) of PC3 cells treated with KIF11 siRNA loaded NPs of PDSA8-1. GL3 siRNA loaded NPs were used as a control.

Figure 33:
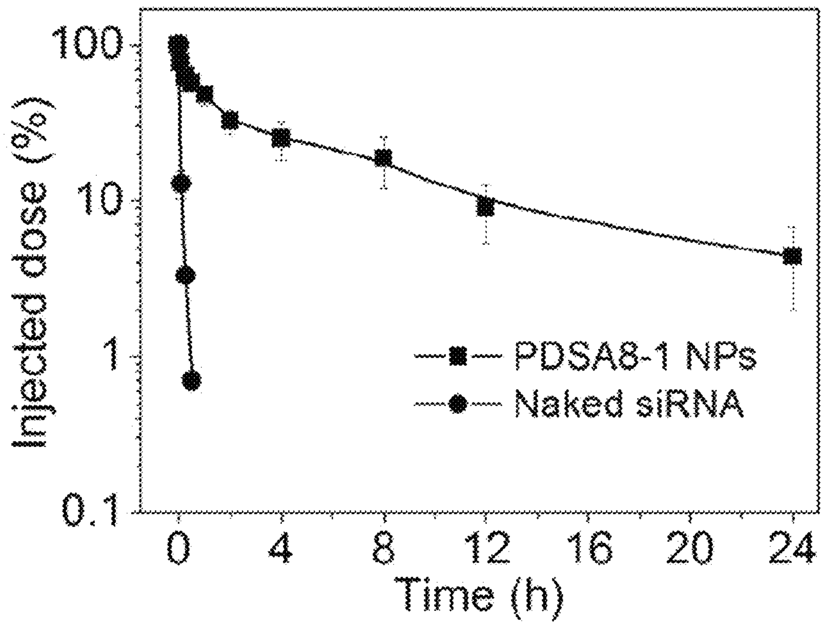

FIG. 33 is a graph showing pharmacokinetics over time (hours) of naked DY647-siRNA, and DY647-siRNA loaded NPs of PDSA8-1.

Figure 34:
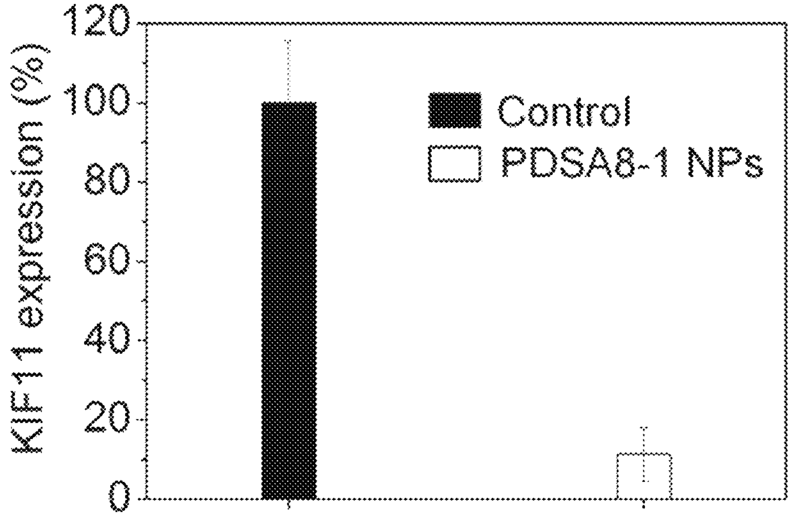

FIG. 34 is a bar graph showing relative levels of KIF11 expression by Western blot analysis in the PC3 tumor tissue after systemic treatment by KIF11 siRNA loaded NPs of PDSA8-1. GL3 siRNA loaded NPs were used as a control.

Figure 35:
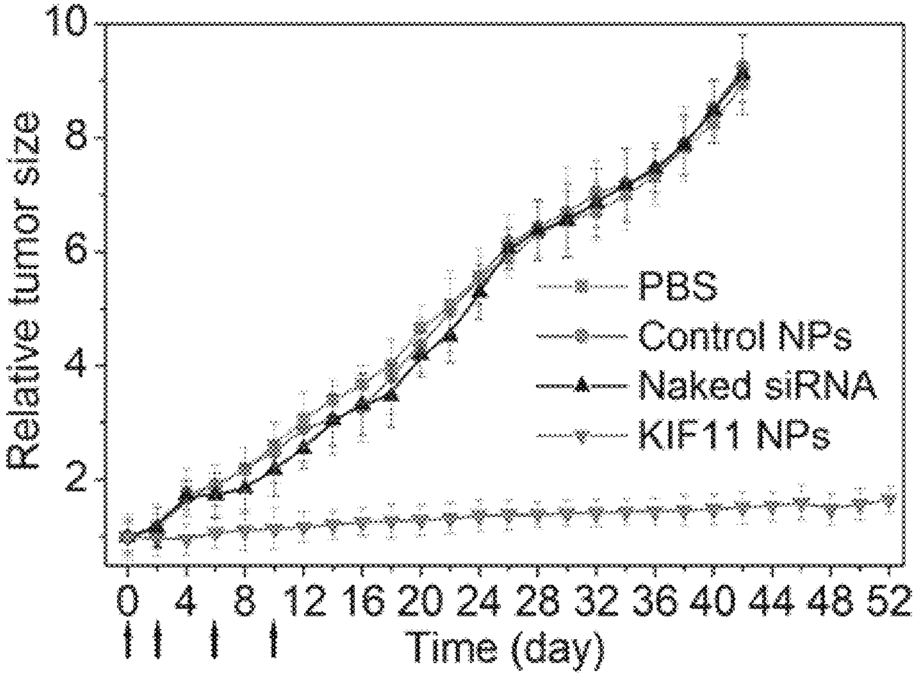

FIG. 35 is a graph showing relative tumor size over time (days) of the PC3 xenograft tumor-bearing nude mice after treatment by PBS, control NPs, naked KIF11 siRNA and KIF11 siRNA loaded NPs of PDSA8-1. The intravenous injections are indicated by the arrows. GL3 siRNA loaded NPs were used as a control.

Figure 36:
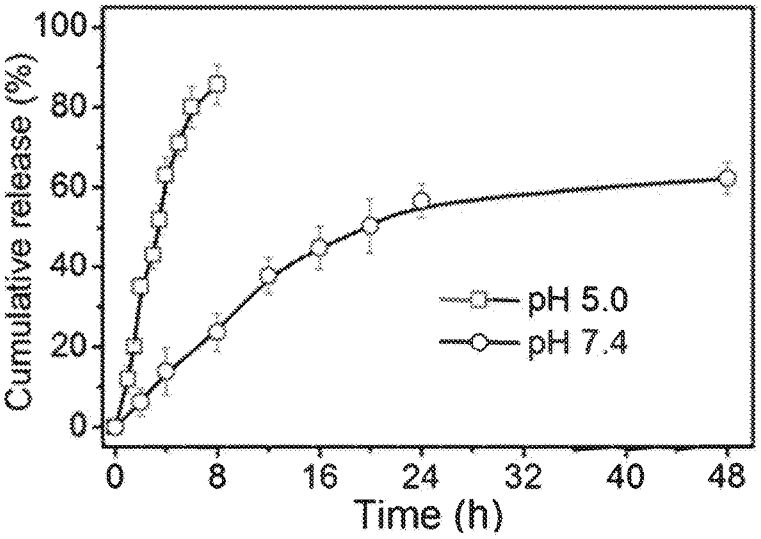

FIG. 36 is molecular structure of ultra pH-responsive polymer, PDPA; a graph showing cumulative release profile of PTX from the PTX loaded NPs of PDPA in PBS buffer at a pH of 7.4 and 5.0.

Figure 37:
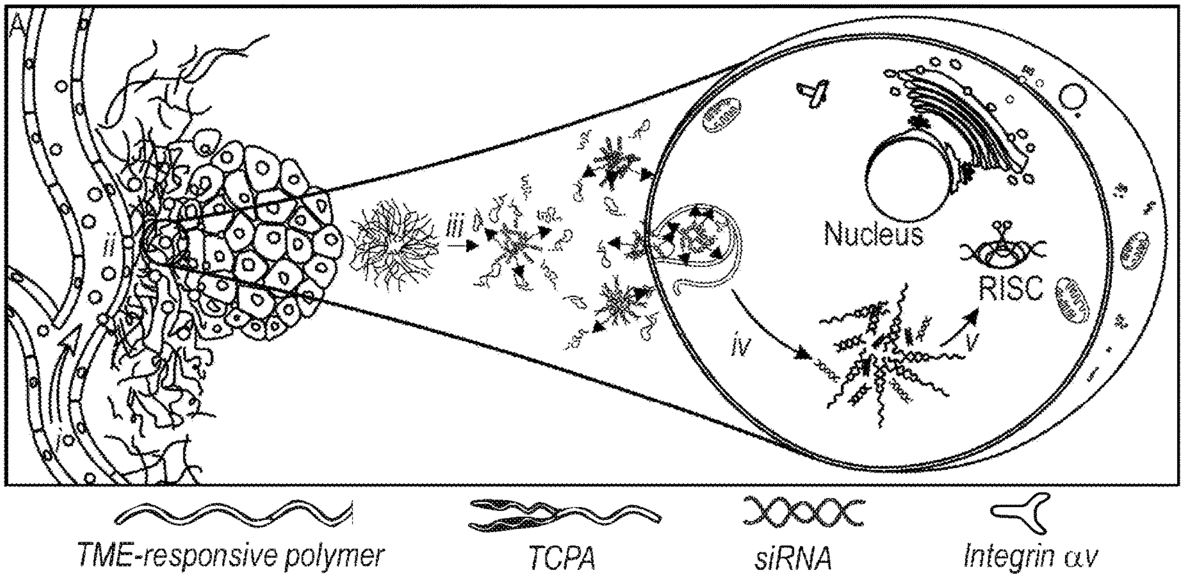
Figure 37:
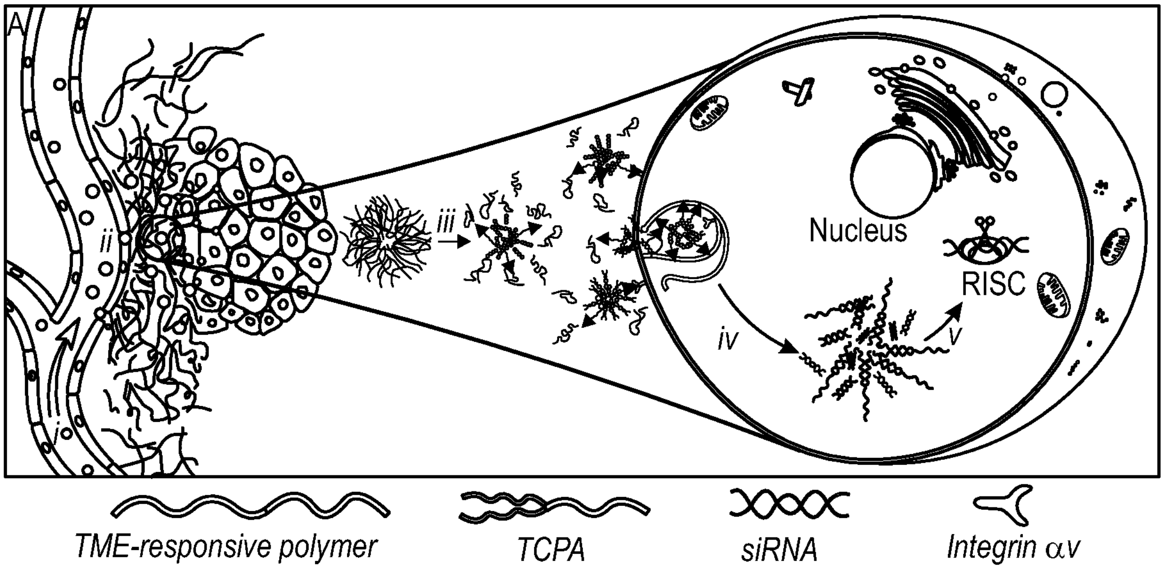

FIG. 37 a schematic illustration of illustration of the TME pH-responsive multistaged nanoplatform for systemic siRNA delivery and effective cancer therapy. After intravenous injection (i), the siRNA loaded NPs can first extravasate from leaky tumor vasculature and accumulate in the tumor tissue (ii). Subsequently, the NPs respond to TME pH to fast release siRNA/TCPA complexes (iii), which then target and penetrate tumor cells (iv) to eventually achieve efficient cytosolic siRNA delivery and gene silencing (v).

Figure 38A:
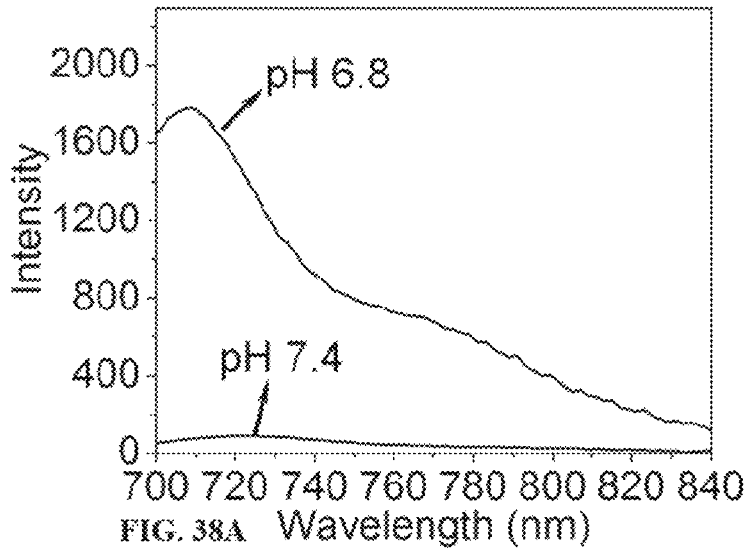
Figure 38B:
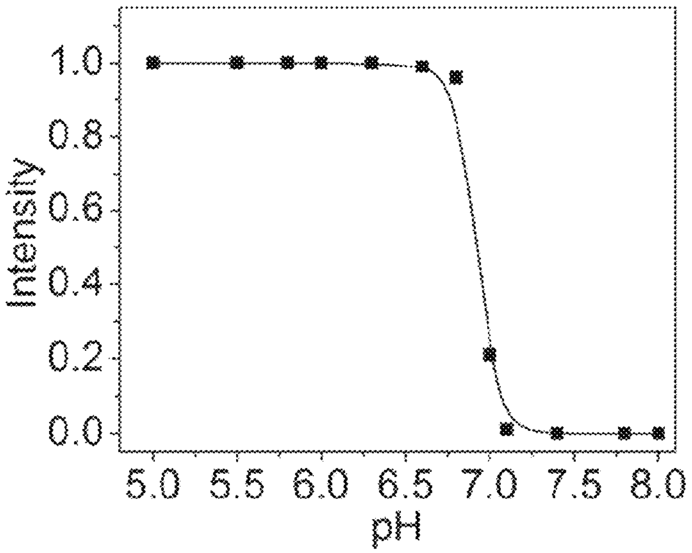

FIGS. 38A-38B are (38A) a graph showing emission fluorescence spectrum of Cy5.5-labelled TME pH-responsive NPs at different pHs. Ex=675 nm; (38B) a graph showing cumulative siRNA release from the DY-677 siRNA loaded TCPA2-NPs at pH 7.4 and pH 6.8.

Figure 39:
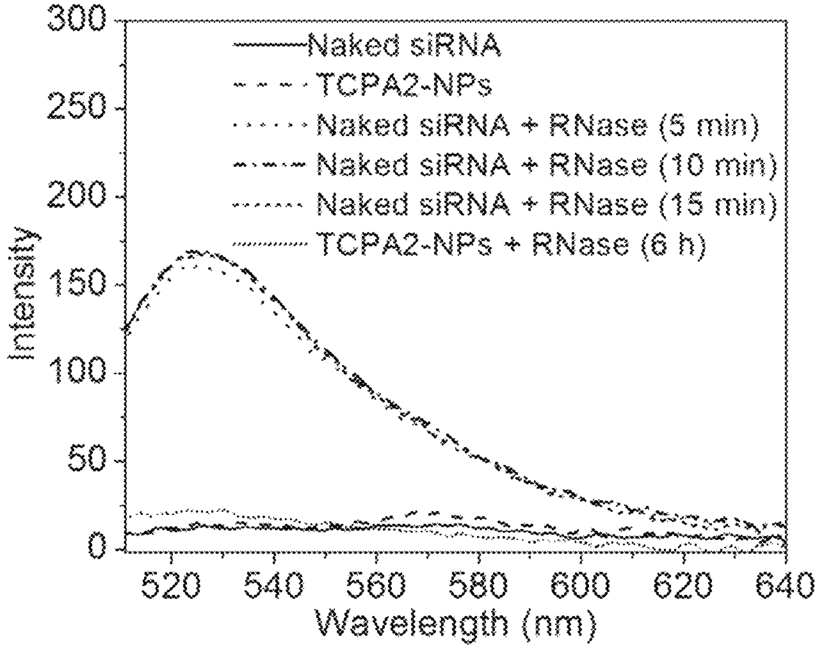

FIG. 39 is a graph showing fluorescent emission spectra of naked Luc siRNA, and Luc siRNA loaded TCPA2-NPs incubated with RNase for 5 min, 10 min, 15 min, and 6 hr. Fluorescein was labelled at 5'-end of the sense strand and its quencher Dabcyl was labeled at the 3'-end of the antisense strand.

Figure 40A:
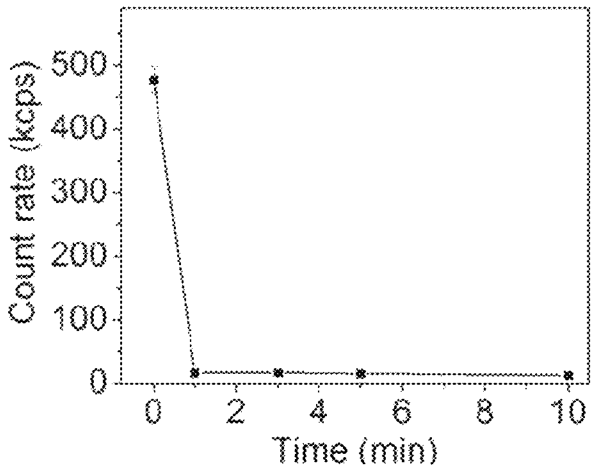
Figure 40B:
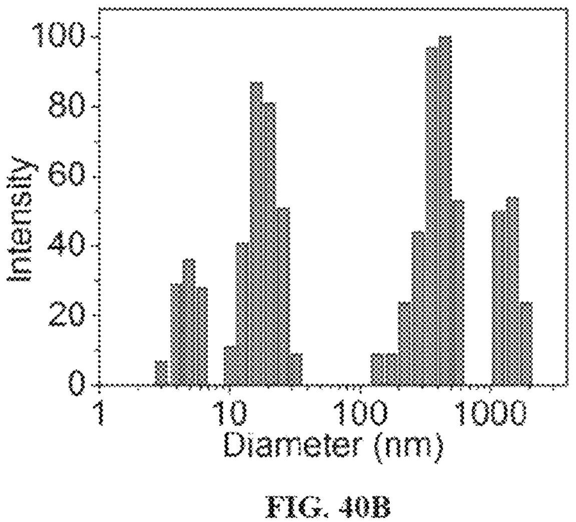
Figure 40C:
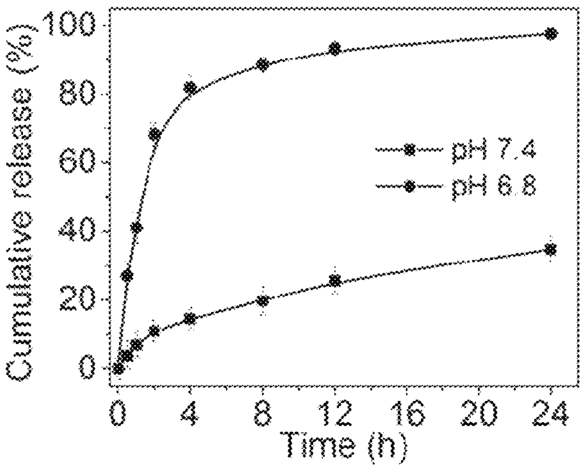

FIGS. 40A-40C are (40A) a plot showing count rate of the siRNA loaded TCPA2-NPs incubated in PBS buffer (pH 6.8) over a period of 10 min.; (40B) a bar graph showing size distribution of TCPA2-NPs incubated in PBS buffer at pH 6.8; (40C) a plot showing cumulative siRNA release from the DY-677 siRNA loaded TCPA2-NPs at pH 7.4, and pH 6.8.

FIGS. 41A-41D are (41A) a graph showing flow cytometry profile, and (41B) a bar graph showing MFI of Luc-HeLa cells incubated with DY677-siRNA loaded TCPA2-NPs at pH 7.4, and pH 6.8 for 2 hr. (41C) Luc expression in Luc-HeLa cells treated with Luc siRNA loaded TCPA2-NPs at pH 7.4, and pH 6.8; (41D) a bar graph showing viability of Luc-HeLa cells treated with Luc siRNA loaded TCPA2-NPs at different siRNA doses.

Figure 42A:
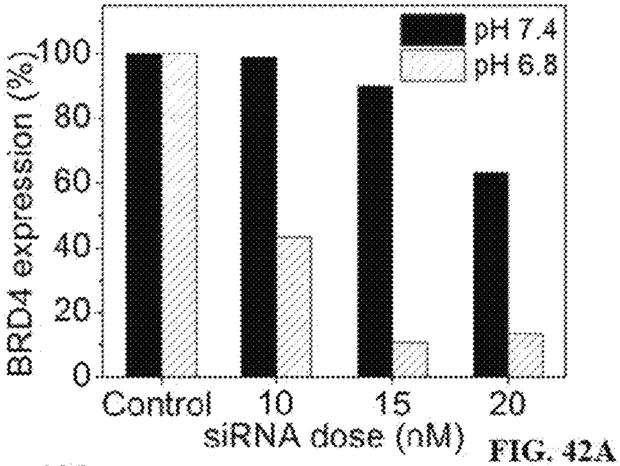
Figure 42B:
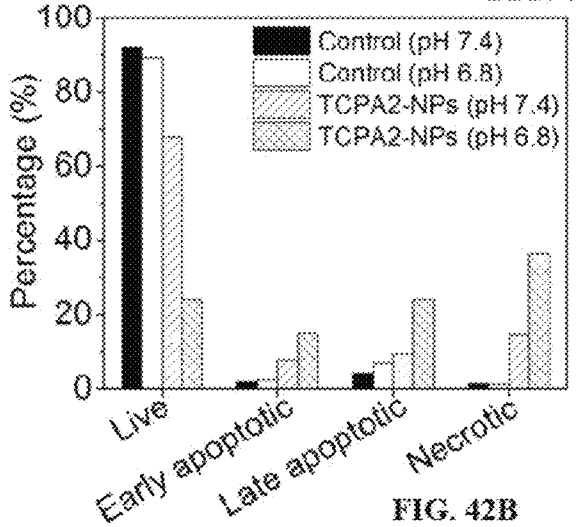
Figure 42C:
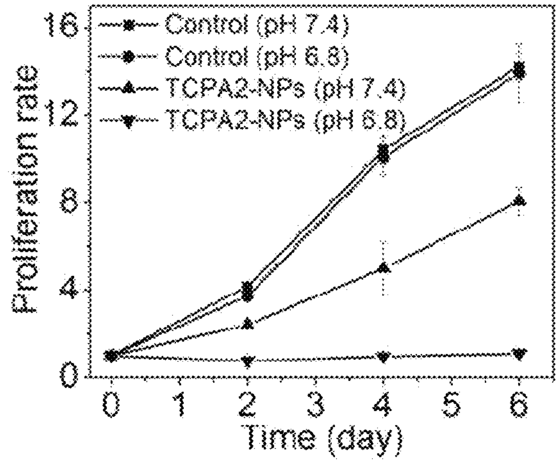

FIGS. 42A-42C are (FIG. 42A) a bar graph quantifying Western blot analysis of BRD4 expression in LNCaP cells treated with BRD4 siRNA loaded TCPA2-NPs at pH 7.4, and pH 6.8; (FIG. 42B) a bar graph summarizing flow cytometry analysis of apoptosis of LNCaP cells treated with BRD4 siRNA loaded TCPA2-NPs at a 20 nM siRNA dose at pH 7.4, and pH 6.8; (FIG. 42C) a plot showing proliferation profile of LNCaP cells treated with BRD4 siRNA loaded TCPA2-NPs at a 20 nM siRNA dose at pH 7.4, and pH 6.8. Luc siRNA loaded TCPA2-NPs were used as control.

Figure 43A:
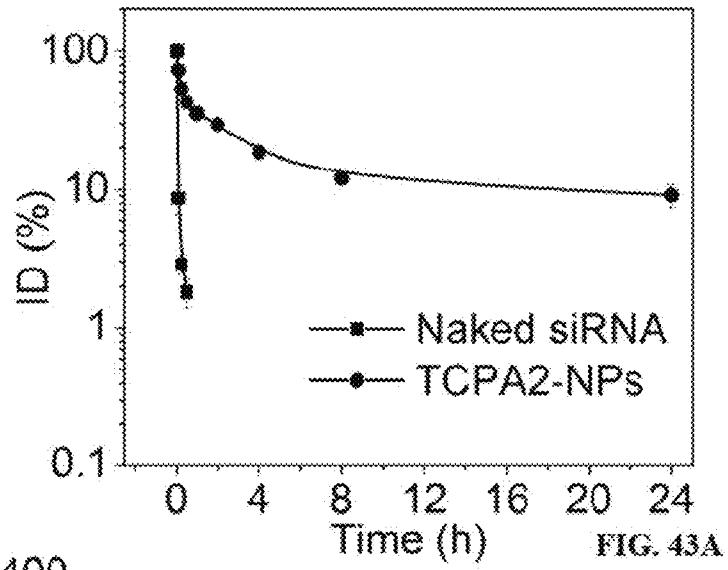
Figure 43B:
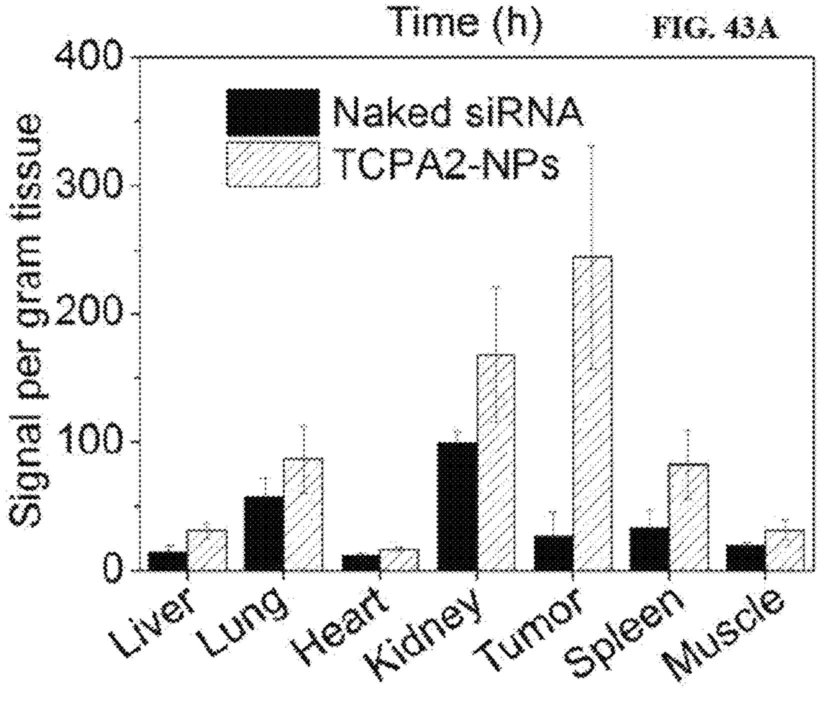

FIGS. 43A-43B are a plot (FIG. 43A) showing pharmacokinetics of naked DY677-siRNA and siRNA loaded TCPA2-NPs; and a bar graph (FIG. 43B) showing biodistribution of the NPs quantified from fluorescent images of the tumors and main organs of LNCaP xenograft tumor-bearing nude mice sacrificed 24 h post injection of naked DY677-siRNA and siRNA loaded TCPA2-NPs.

Figure 44A:
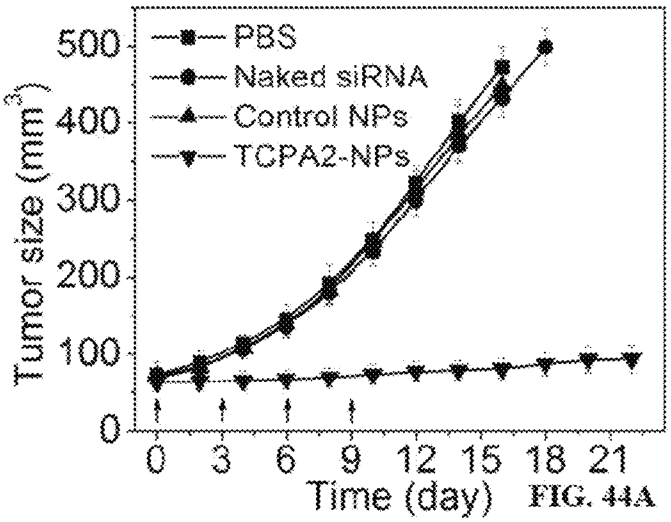
Figure 44B:
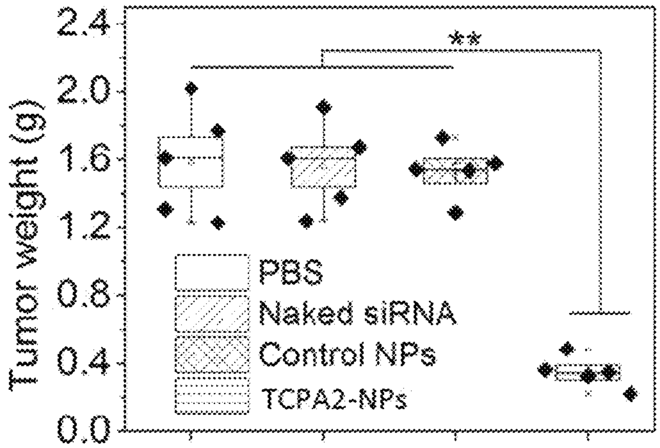

FIGS. 44A-44B are graphs showing relative tumor size (44A) and tumor weight (44B) of the LNCaP xenograft tumor-bearing nude mice (n=5) after systemic treatment by PBS, naked BRD4 siRNA, control NPs, and BRD4 siRNA loaded TCPA2-NPs, where intravenous injections are indicated by the arrows. Luc siRNA loaded TCPA2-NPs were used as control NPs.

DETAILED DESCRIPTION OF THE INVENTION

I. Definitions

"Binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions.

"Binding partner" as used herein refers to a molecule that can undergo binding with a particular molecule.

"Biological binding" defines a type of interaction that occurs between pairs of molecules including proteins, peptides, nucleic acids, glycoproteins, carbohydrates, or endogenous small molecules.

"Specific binding" as used herein refers to molecules, such as polynucleotides, that are able to bind to or recognize a binding partner (or a limited number of binding partners) to a substantially higher degree than to other, similar biological entities.

A "biocompatible polymer" is used here to refer to a polymer that does not typically induce an adverse response when inserted or injected into a living subject, for example, without significant inflammation and/or acute rejection of the polymer by the immune system, for instance, via a T-cell response.

A "copolymer" herein refers to more than one type of repeat unit present within the polymer defined below.

"Encapsulation efficiency" (EE) as used herein is the fraction of initial drug that is encapsulated by the nanoparticles (NPs).

"loading" as used herein refers to the mass fraction of encapsulated agent in the NPs.

A "polymer," as used herein, is given its ordinary meaning as used in the art, i.e., a molecular structure including one or more repeat units (monomers), connected by covalent bonds. The polymer may be a copolymer. The repeat units forming the copolymer may be arranged in any fashion. For example, the repeat units may be arranged in a random order, in an alternating order, or as a "block" copolymer, i.e., including one or more regions each including a first repeat unit (e.g., a first block), and one or more regions each including a second repeat unit (e.g., a second block), etc. Block copolymers may have two (a diblock copolymer), three (a triblock copolymer), or more numbers of distinct blocks.

A "polymeric conjugate" as used herein refers to two or more polymers (such as those described herein) that have been associated with each other, usually by covalent bonding of the two or more polymers together.

As used herein, a nanoparticle refers to a polymeric particle that can be formed using a solvent emulsion, spray drying, or precipitation in bulk or microfluids, wherein the solvent is removed to no more than an insignificant residue, leaving a solid (which may, or may not, be hollow or have a liquid filled interior) polymeric particle, unlike a micelle whose form is dependent upon being present in an aqueous solution.

As used herein, the term "carrier" or "excipient" refers to an organic or inorganic ingredient, natural or synthetic inactive ingredient in a formulation, with which one or more active ingredients are combined.

As used herein, the term "pharmaceutically acceptable" means a non-toxic material that does not interfere with the effectiveness of the biological activity of the active ingredients.

As used herein, the terms "effective amount" or "therapeutically effective amount" means a dosage sufficient to alleviate one or more symptoms of a disorder, disease, or condition being treated, or to otherwise provide a desired pharmacologic and/or physiologic effect. The precise dosage will vary according to a variety of factors such as subject-dependent variables (e.g., age, immune system health, etc.), the disease or disorder being treated, as well as the route of administration and the pharmacokinetics of the agent being administered.

As used herein, the term "prevention" or "preventing" means to administer a composition to a subject or a system at risk for or having a predisposition for one or more symptom caused by a disease or disorder to cause cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

The terms "bioactive agent" and "active agent", as used interchangeably herein, include, without limitation, physiologically or pharmacologically active substances that act locally or systemically in the body. A bioactive agent is a substance used for the treatment (e.g., therapeutic agent), prevention (e.g., prophylactic agent), diagnosis (e.g., diagnostic agent), cure or mitigation of disease or illness, a substance which affects the structure or function of the body, or pro-drugs, which become biologically active or more active after they have been placed in a predetermined physiological environment.

The terms "sufficient" and "effective", as used interchangeably herein, refer to an amount (e.g. mass, volume, dosage, concentration, and/or time period) needed to achieve one or more desired result(s).

The term "protein" "polypeptide" or "peptide" refers to a natural or synthetic molecule comprising two or more amino acids linked by the carboxyl group of one amino acid to the alpha amino group of another.

The term "polynucleotide" or "nucleic acid sequence" refers to a natural or synthetic molecule comprising two or more nucleotides linked by a phosphate group at the 3' position of one nucleotide to the 5' end of another nucleotide. The polynucleotide is not limited by length, and thus the polynucleotide can include deoxyribonucleic acid (DNA) or ribonucleic acid (RNA).

II. Stimuli-Responsive Nanoparticles

Figures 1A, 1B, 1C:
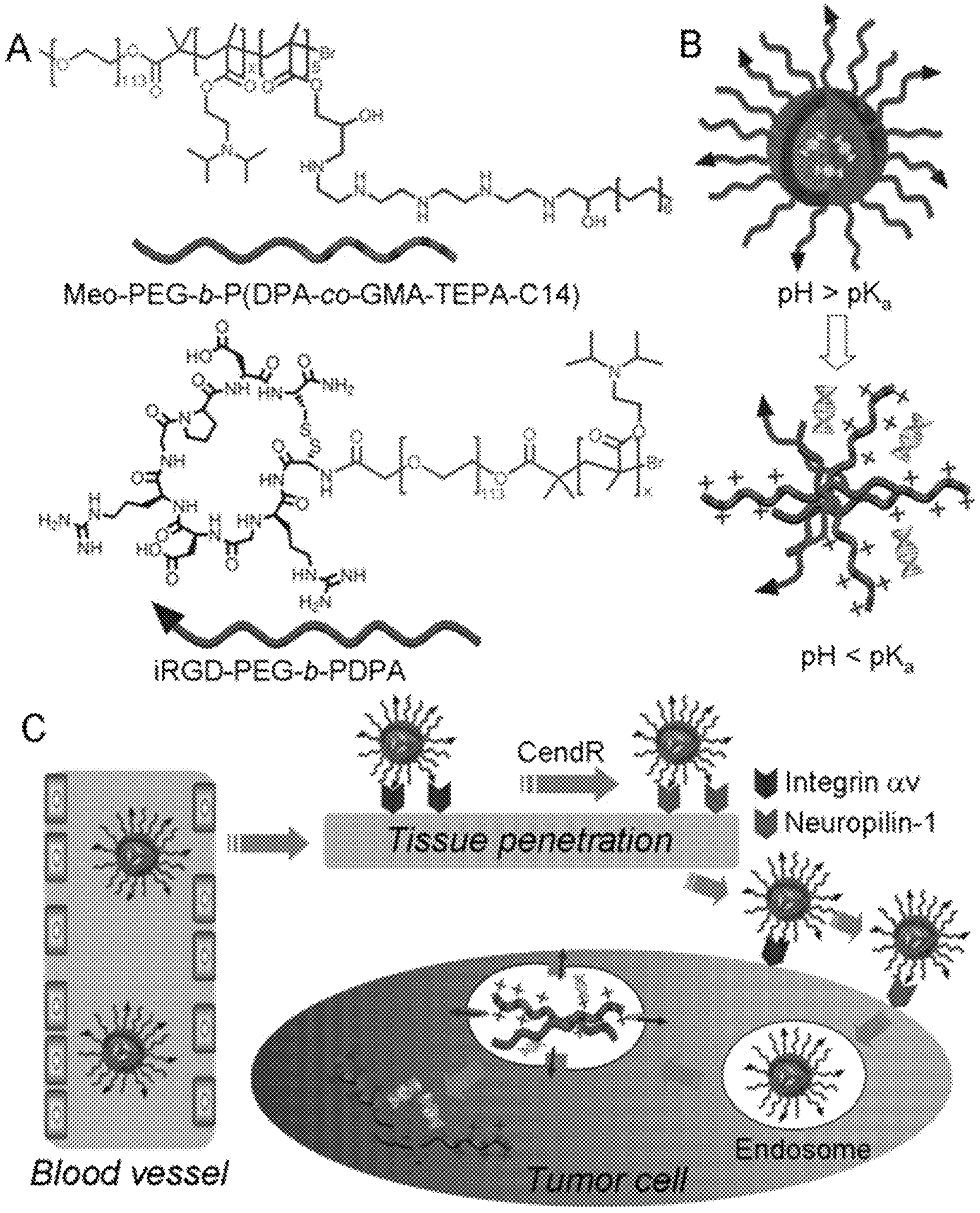
FIGS. 1A-1C are schematic illustrations of (1A) molecular structures of the ultra pH-responsive polymer, Meo-PEG-b-P(DPA-co-GMA-TEPA-C14), and the tumor-penetrating peptide-conjugated polymer, iRGD-PEG-b-PDPA; (1B) ultra pH-responsive and tumor-penetrating nanoplatform for siRNA loading and release; and (1C) the nanoplatform for targeted in vivo siRNA delivery and cancer therapy.

A long-circulating, optionally cell-penetrating, and stimuli-responsive NP platform for effective in vivo delivery of therapeutic, prophylactic and/or diagnostic agents is made of an amphiphilic polymer, most preferably a PEGylated polymer, which shows a response to a stimulus such as pH, temperature, or light, such as an ultra pH-responsive characteristic with a pKa close to the endosomal pH (6.0-6.5) (Wang Y et al, *Nat Mater,* 13, 204-212 (2014)). The polymer may include a targeting, cell penetrating, and/or adhesion molecule such as a tumor-targeting peptide iRGD (FIGS. 1A-1B). In some embodiments, the targeting, cell penetrating, and/or adhesion molecule are covalently conjugated to one or more of the polymer. In other embodiments, the targeting, cell penetrating, and/or adhesion molecule are associated with the nanoparticles formed by one or more polymers via non-covalent association.

Generally, the disclosed nanoparticles have prolonged circulation i.e., increased half-life in the blood compared to controls without stimuli-responsive element, PEGylation, targeting moiety, or combinations thereof. In some embodiments, the disclosed nanoparticles have a half-life of about, or more than, 3 hours, 4 hours, 5 hours, 6 hours, 7 hours, 8 hours, 9 hours, 10 hours, 11 hours, 12 hours, 24 hours, at least a day, or more than a day.

Typically, the disclosed nanoparticles have increased accumulation at target site such as tumor sites compared to controls without stimuli-responsive element, PEGylation, targeting moiety, or combinations thereof. Preferably, the disclosed nanoparticles have deeper penetration into the tumor tissues compared to controls without stimuli-responsive element, PEGylation, targeting moiety, or combinations thereof. In some embodiments, the disclosed nanoparticles have increased accumulation at target site by about, or more than, 50%, 100%, 200%, 300%, 400%, or 500%.

In preferred embodiments, the disclosed nanoparticles have enhanced uptake by tumor cells compared to controls without stimuli-responsive element, PEGylation, targeting moiety, or combinations thereof. In some embodiments, the disclosed nanoparticles have increased uptake by target cells by about, or more than, 50%, 100%, 200%, 300%, 400%, or 500%.

In further preferred embodiments, the disclosed nanoparticles have greater intracellular cargo release without stimuli-responsive element, PEGylation, targeting moiety, or combinations thereof. In some embodiments, the disclosed nanoparticles have increased intracellular cargo release in target cells by about, or more than, 50%, 100%, 200%, 300%, 400%, or 500%.

When tumor cells are targeted, the disclosed nanoparticles carrying active agents targeting tumor cells can suppress tumor growth. In some embodiments, the disclosed nanoparticles can reduce tumor growth by 10%, 20%, 30%, 40%, 50%, 60%, 70%, 80%, or 90%. When the active agent is siRNA or shRNA to knowndown a therapeutic target of the tumor cells, the disclosed nanoparticles can knockdown the particular target by 10%, 20%, 30%, 40%, 50%, 60%, 70%, 80%, or 90%.

Generally, stimuli-responsive nanoparticles are prepared using one or more amphiphilic copolymers through selection of a hydrophilic or hydrophobic polymer component of the copolymer, or by modification of the hydrophilic or hydrophobic polymers.

A. Polymers

Typically, the nanoparticles can be formed by self-assembly in an emulsion of a non-aqueous solvent with an aqueous solvent of a first amphiphilic polymer containing a polymer represented by Formula I.

$$(X)_m—(Y)_n \qquad \text{Formula I}$$

wherein, m and n are independently integers between one and 1000, inclusive. X is a hydrophobic polymer and Y is a hydrophilic polymer, and at least one of X, Y, or both, is stimuli-responsive.

In some embodiments, Y is methoxyl-polyethylene glycol (Meo-PEG). In one embodiment, X is selected from the group consisting of poly (2-(diisopropylamino) ethyl methacrylate (PDPA), poly(2-(hexamethyleneimino) ethyl methacrylate (PHMEMA), L-cystine-based poly(disulfide) (PDSA), and poly (2-(2-oxo-2-phenylacetoxy) ethyl methacrylate) (POPEMA). In some embodiments, X is a hydrophobic copolymer and/or Y is a hydrophilic copolymer. In one embodiment, X is poly (2-(diisopropylamino) ethylmethacrylate-co-glycidyl methacrylate (P(DPA-co-GMA)). Generally, the hydrophobic polymer X forms the hydrophobic core of the nanoparticle, suitable for encapsulating hydrophobic active agents within the nanoparticle.

In some embodiments, one or more parts of the hydrophobic polymer X is further modified with hydrophilic groups to impart charges such that the hydrophobic core of the nanoparticle contains an inner hydrophilic core for encapsulating hydrophilic active agents such as nucleic acids. Exemplary modifications include including 2-aminoethyl methacrylate (AMA), tetraethylenepentamine (TEPA), TEPA-C14. In one embodiment, X is P(DPA-co-GMA-TEPA), P(DPA-co-GMA-TEPA-C14), or poly (2-(hexamethyleneimino) ethyl methacrylate-co-2-aminoethyl methacrylate) (P(HMEMA-co-AMA)).

In preferred embodiments, the amphiphilic polymer represented by Formula I is selected from the group consisting of Meo-PEG-b-P(DPA-co-GMA), Meo-PEG-b-P(DPA-co-GMA-TEPA-C14), Meo-PEG-b-P(DPA-co-GMA-Rn), Meo-PEG-b-P(DPA-co-GMA-TEPA), Meo-PEG113-b-PDPA, Meo-PEG-b-PHMEMA, Meo-PEG-b-P(HMEMA-co-AMA), Meo-PEG-b-POPEMA, and combinations thereof.

In some embodiments, the first amphiphilic polymer represented by Formula I contains a ligand, wherein the ligand is a targeting ligand, an adhesion ligand, a cell-penetrating ligand, or an endosomal-penetrating ligand, conjugated to X, Y, or both. In some embodiments, the ligand is oligoarginine ($NH_2—R_n—CONH_2$, where n is any integer between about 6 to about 100, for example n=6, 8, 10, 20, or 30) attached to the hydrophobic polymer of Formula I, for example, Meo-PEG-b-P(DPA-co-GMA-R). In one embodiment, the ligand is $NH_2—R_8—CONH_2$ (SEQ ID NO:15).

Optionally, the nanoparticles are formed by self-assembly of a mixture of polymers represented by Formula I, and a second polymer containing a polymer represented by Formula II:

$$(Q)_c\text{-}(R)_d \qquad \text{Formula II}$$

wherein, c and d are independently integers between zero and 1000, inclusive, with the proviso that the sum (c+d) is greater than one. Q and R are independently hydrophilic or hydrophobic polymers.

In some embodiments, the nanoparticles are formed by self-assembly of a mixture of polymers represented by Formula I and Formula II, wherein the polymer represented by Formula I, Formula II, or both, contains a ligand, wherein the ligand is a targeting ligand, an adhesion ligand, a cell-penetrating ligand, or an endosomal-penetrating ligand, with the proviso that the ligand is conjugated to the hydrophilic polymer. Exemplary ligands include a disulfide-based cyclic arginine-glycine-aspartic acid (RGD) peptide (iRGD), a tumor targeting moiety S,S-2-[3-[5-amino-1-carboxypentyl]-ureido]-pentanedioic acid (ACUPA), and a fluorescent Cyanine 5.5 (CY5.5®) dye.

In one embodiment, the nanoparticles are formed by self-assembly of a mixture of methoxyl-polyethylene glycol-b-poly (2-(diisopropylamino) ethylmethacrylate-co-glycidyl methacrylate-tetraethylenepentamine-C14) (Meo-PEG-b-P(DPA-co-GMA-TEPA-C14)), and iRGD-PEG-b-PDPA. In another embodiment, the nanoparticles are formed by self-assembly of a mixture of methoxyl-polyethylene glycol-b-poly (2-(diisopropylamino) ethylmethacrylate-co-glycidyl methacrylate-oligoarginine) (Meo-PEG-b-P(DPA-co-GMA-Rn)), and ACUPA-PEG-b-PDPA.

Besides amphiphilic copolymers, hydrophobic polymers can be also used to develop stimuli-responsive NPs for various biomedical applications. In one embodiment, the hydrophobic polymer is poly (2-(diisopropylamino) ethyl methacrylate (PDPA), or derivatives thereof. In another embodiment, the hydrophobic polymer is poly (2-(2-oxo-2-phenylacetoxy) ethyl methacrylate) (POPEMA), or derivatives thereof. In a further embodiment, the hydrophobic polymer is poly (2-(2-oxo-2-phenylacetoxy) ethyl methacrylate) (POPEMA). Any hydrophobic polymers can be used to prepare amphiphilic polymers by conjugating to one or more hydrophobic polymers such as polyethylene glycol, or derivatives thereof.

In some embodiments, the nanoparticles are formed by self-assembly of a mixture of a stimuli-responsive hydrophobic polymer, and optionally, a further polymer containing a polymer represented by Formula III:

$$(S)_e\text{-}(T)_f \qquad \text{Formula III}$$

wherein, e and f are independently integers between zero and 1000, inclusive, with the proviso that the sum (e+f) is greater than one. S and T are independently a hydrophilic polymer or a hydrophobic polymer. In some embodiments, the stimuli-response hydrophobic polymer, the polymer represented by Formula III, or both contains a ligand, wherein the ligand is a targeting ligand, an adhesion ligand, a cell-penetrating ligand, and/or an endosomal-penetrating ligand, with the proviso that the ligand is conjugated to the hydrophilic polymer.

For hydrophobic polymers, their nanoparticles are generally prepared by using the mixture of the hydrophobic polymer and amphiphilic polymer or amphiphilic compound. The amphiphilic compound can include, but is not limited to, one or a plurality of naturally derived lipids, PEG-modified lipid, lipid-like materials, surfactants, or synthesized amphiphilic compounds. In one embodiment, the amphiphilic compound is a lipid-PEG such as 1, 2-distearoyl-sn-glycero-3-phosphoethanolamine-poly(ethylene glycol)-3000 (DSPE-PEG 3000).

In some embodiments, the nanoparticles are formed by self-assembly of a mixture of a stimuli-responsive hydrophilic polymer, and optionally, a further polymer containing a polymer represented by Formula III:

$$(S)_e\text{-}(T)_f \qquad \text{Formula III}$$

wherein, e and f are independently integers between zero and 1000, inclusive, with the proviso that the sum (e+f) is greater than one. S and T are independently a hydrophilic polymer or a hydrophobic polymer. Optionally, the first stimuli-response hydrophilic polymer, the polymer represented by Formula III, or both contains a ligand, wherein the ligand is a targeting ligand, an adhesion ligand, a cell-penetrating ligand, or an endosomal-penetrating ligand, with the proviso that the ligand is conjugated to the hydrophilic polymer.

Optionally, the polymers that form the nanoparticles contain linkers between the blocks of hydrophilic and hydrophobic polymers, between the hydrophilic polymer and ligand, or both.

Amphiphilic copolymers can spontaneously self-assemble in aqueous solution to form NPs with hydrophobic inner core and hydrophilic outer shells. The hydrophobic inner core can be used to deliver therapeutic, and/or diagnostic agents including nucleic acids, proteins, chemotherapeutic drugs, or small molecules. The incorporation of stimuli-responsive moieties to the hydrophobic core can easily accomplish the spatiotemporal control over the macroscopic properties of NPs, and thereby the release of the encapsulated cargo at the desired site.

The amphiphilic polymers are responsive to a stimulus. This may be a pH change, redox change, temperature change, exposure to light or other stimuli, including binding to a target, and sensing reduction in oxygen concentrations (hypoxia). The responsiveness may be imparted solely by the hydrophilic polymer, the hydrophobic polymer, or the conjugate per se. The nanoparticles are formed of a mixture or blend of polymers. Some may be the amphiphilic polymers, preferably copolymers of modified polyethylene glycol (PEG) and polyesters, such as various forms of PLGA-PEG or PLA-PEG copolymers, collectively referred to herein as "PEGylated polymers", some hydrophobic polymer such as PLGA, PLA or PGA, and/or some may be hydrophilic polymer such as a PEG, or PEG derivative. Some will be modified by conjugation to a targeting agent, a cell adhesion or a cell penetrating peptide.

The length of hydrophilic and/or hydrophobic polymers can be optimized to optimize encapsulation of agent to be delivered, i.e., encapsulation efficiency (EE %). As demonstrated in the examples, as the PDPA length increases, the EE % and size of the resulting NPs increase (Table 3), possibly because the increased PDPA length leads to an increase in the size of the hydrophobic core. Specifically, the EE % reaches almost 100% for the polymer with 80 (PDPA80) or 100 (PDPA100) DPA repeat units. Notably, using a mixture of Meo-PEG-b-P(DPA-co-GMA-TEPA-C14) (90 mol %) and tumor-penetrating polymer (iRGD-PEG-b-PDPA, 10 mol %, FIG. 1A) to prepare NPs does not cause obvious change in the EE % or particle size.

The amphiphilic polymers include a hydrophilic polymer. This is preferably at an end which can orient to the exterior of the nanoparticles when formed by emulsion techniques such as self-assembly.

Polymers and copolymers that can be used to make the nanoparticles disclosed herein include, but are not limited to, polymers including glycolic acid units, referred to herein as "PGA", and lactic acid units, such as poly-L-lactic acid, poly-D-lactic acid, poly-D,L-lactic acid, poly-L-lactide, poly-D-lactide, and poly-D,L-lactide, collectively referred to herein as "PLA", and caprolactone units, such as poly(8-caprolactone), collectively referred to herein as "PCL"; and copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA"; polyacrylates, polyanhydrides, poly (ester anhydrides), poly-4-hydroxybutyrate (P4HB) combinations and derivatives thereof.

The polymer is preferably a biocompatible polymer. One simple test to determine biocompatibility is to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise uptaken by such cells.

The biocompatible polymer is preferably biodegradable, i.e., the polymer is able to degrade, chemically and/or biologically, within a physiological environment, such as within the body.

Stimuli that the Polymers can be Responsive to

The polymers can be responsive to changes in pH-, redox-, light-, temperature-, enzyme-, ultrasound, or other stimuli such as a conformation change resulting from binding.

Almeida, et al. J. Applied Pharm.l Sci. 02 (06)01-10 (2012) is an excellent review of stimuli responsive polymers. The signs or stimuli that trigger the structural changes on smart polymers can be classified in three main groups: physical stimuli (temperature, ultrasound, light, mechanical stress), chemical stimuli (pH and ionic strength) and biological stimuli (enzymes and bio molecules).

Stimuli can be artificially controlled (with a magnetic or electric field, light, ultrasounds, etc.) or naturally promoted by internal physiological environment through a feedback mechanism, leading to changes in the polymer net that allow the drug delivery without any external intervention (for example: pH changes in certain vital organs or related to a disease; temperature change or presence of enzymes or other antigens) or by the physiological condition. In the presence of a sign or stimuli, changes can happen on the surface and solubility of the polymer as well as on sol-gel transition.

Smart polymers can be classified according to the stimuli they respond to or to their physical features. Regarding the physical shape, they can be classified as free linear polymer chain solutions, reversible gels covalently cross-linked and polymer chain grafted to the surface.

Stimuli responsive polymers are also reviewed by James, et al., Acta Pharma. Sinica B 4(2):120-127 (2014). The following is a list of exemplary polymers categorized by responsive to various stimuli:

- Temperature: POLOXAMERS, poly(N-alkylacrylamide)s, poly(N-vinylcaprolactam)s, cellulose, xyoglucan, and chitosan
- pH: poly(methacrylic acid)s, poly(vinylpyridine)s, and poly(vinylimmidazole)s
- light: modified poly(acrylamide)s
- electric field: sulfonated polystyrenes, poly(thiophene)s, and poly(ethyloxazoline)s
- ultrasound: ethylenevinylacetate These transitions are reversible and include changes in physical state, shape and solubility, solvent interactions, hydrophilic and lipophilic balances and conductivity. The driving forces behind these transitions include neutralisation of charged groups by the addition of oppositely charged polymers or by pH shift, and change in the hydrophilic/lipophilic balance or changes in hydrogen bonding due to increase or decrease in temperature. Responses of a stimulus-responsive polymer can be of various types. Responsiveness of a polymeric solution initiated by physical or chemical stimuli is limited to the destruction and formation of various secondary forces including hydrogen bonding, hydrophobic forces, van der Waals forces and electrostatic interaction. Chemical events include simple reactions such as oxidation, acid-base reaction, reduction and hydrolysis of moieties attached to the polymer chain. In some cases, dramatic conformational change in the polymeric structure occurs, e.g., degradation of the polymeric structure due to irreversible bond breakage in response to an external stimulus. Upon exposure to appropriate stimuli, some exemplary physicochemical properties include size, zeta potential and hydrophilic-hydrophobic balance of these nanoparticles.

pH Dependent Polymers

Exemplary pH dependent polymers include dendrimers formed of poly(lysine), poly(hydroxyproline), PEG-PLA, Poly(propyl acrylic acid), Poly(ethacrylic acid), CARBOPOLL®, Polysilamine, EUDRAGIT® 5-100 EUDRAGIT® L-100, Chitosan, PMAA-PEG copolymer, sodium alginate (Ca2+). The ionic pH sensitive polymers are able to accept or release protons in response to pH changes. These polymers contain acid groups (carboxylic or sulfonic) or basic groups (ammonium salts) so that the pH sensitive polymers are polyelectrolytes that have in their structure acid or basic groups that can accept or release protons in response to pH changes in the surrounding environment. pH values from several tissues and cell compartments can be used to trigger release in these tissues. For example, the pH of blood is 7.4-7.5; stomach is 1.0-3.0; duodenum is 4.8-8.2; colon is 7.0-7.5; lysosome is 4.5-5.0; Golgi complex is 6.4; tumor—extracellular médium is 6.2-7.2.

Examples of these polymers include polyacrylamide (PAAm), poly(acrylic acid) (PAA) (CARBOPOLl®) and derivatives, poly(methacrylic acid) (PMAA), poly(2-diethylaminoethyl methacrylate) (PDEAEMA), poly(ethylene imine), poly(L-lysine) and poly(N,N-dimethylaminoethylmethacrylate) (PDMAEMA). Polymers with functional acid groups pH sensitive polymers include poly(acrylic acid) (PAA) or poly(methacrylic) acid (PMAA) are polyanions that have in their structure a great number of ionizable acid groups, like carboxylic acid or sulfonic acid. The pH in which acids become ionized depends on the polymer's pKa (depends on the polymer's composition and molecular weight). Polymers with functional basic groups include polycations such as poly(4-vinylpyridine), poly(2-vinylpyridine) (PVP) and poly(vinylamine) (PVAm), are protonated at high pH values and positively ionized at neutral or low pH values, i.e., they go through a phase transition at pH 5 due to the deprotonation of the pyridine groups. Other polybases are poly(N,N-dimethylaminoethyl methacrylate) (PDMAEMA) and poly(2-diethylaminoethyl methacrylate) (PDEAEMA), with amino groups in their structure which in acid environments gain protons, and in basic environments release the protons. Examples of polycationic polyelectrolyte polymers are poly(N,N-dialkyl aminoethyl methacrylate), poly(lysine) (PL), poly(ethylenimine) (PEI) and chitosan. Commercially available polymers include EUDRAGIT L® and EUDRAGIT S® from Rohm Pharma GmbH (with methacrylic acid and methylmethacrylate in their composition), CMEC (a cellulose derivative) from Freund Sangyo Co., CAP by Wako Pure Chemicals Ltd., HP-50 and ASM by Shin-Etsu Chemical Co., Ltd.

There are several natural polymers (for example, albumin, gelatin and chitosan) that present pH sensibility. Chitosan is a cationic amino polysaccharide, derivative from chitin, that is biocompatible and resorbable. Additional examples include the anionic polymer PEAA (polyethacrylic acid) or by PPAA (polypropyl acrylic acid), Polypropylacrylic acid (PPAA) and polyethacrylic acid (PEAA), and poly(ethylene glycol)-poly(aspartame hydrazine doxorubicin) [(PEG-p (Asp-Hid-dox), and polycationic polymers, such as poly(2-diethylaminoethyl methacrylate) (PDEAEMA).

In one embodiment, the pH-sensitive polymer is poly (2-(diisopropylamino) ethylmethacrylate (PDPA), poly(2-(hexamethyleneimino) ethyl methacrylate (PHMEMA), or PEGylated derivatives, and/or copolymers thereof. Exemplary PEGylated derivatives and copolymers include Meo-PEG-b-PDPA, methoxyl-polyethylene glycol-b-poly (2-(diisopropylamino) ethylmethacrylate-co-glycidyl methacrylate) (Meo-PEG-b-P(DPA-co-GMA)), Meo-PEG-b-P(DPA-co-GMA-TEPA-C14), Meo-PEG-b-P(DPA-co-GMA-$R_n$), Meo-PEG-b-P(DPA-co-GMA-TEPA), methoxyl-polyethylene glycol-b-poly(2-(hexamethyleneimino) ethyl methacrylate) (Meo-PEG-b-PHMEMA), and Meo-PEG-b-P(HMEMA-co-AMA).

Temperature Dependent Polymers

Temperature dependent polymers are sensitive to the temperature and change their microstructural features in response to change in temperature. Thermo-responsive polymers present in their structure a very sensitive balance between the hydrophobic and the hydrophilic groups and a small change in the temperature can create new adjustments. If the polymeric solution has a phase below the critical solution temperature, it will become insoluble after heating. Above the critical solution temperature (LCST), the interaction strengths (hydrogen linkages) between the water molecules and the polymer become unfavorable, it dehydrates and a predominance of the hydrophobic interaction occurs, causing the polymer to swell. The LSCT is the critical temperature in which the polymeric solution shows a phase separation, going from one phase (isotropic state) to two phases (anisotropic state). The accumulation of temperature sensitive polymeric systems in solid tumors is due to the increased impermeability effect to the tumor vascular net retention and to the use of an external impulse (heat source) on the tumor area. This temperature increase promotes the changing of the microstructure of the polymeric system, turning it into gel and releasing the drug, thus increasing the drug in the intra-tumoral area and the therapeutic efficiency, and reducing the side effects (MacEwan et al., 2010).

Examples of thermosensitive polymers include the poly (N-substituted acrylamide) polymers such as poly(N-isopoprylacrilamide) (PNIPAAm), poly (N,N'-diethyl acrylamide), poly (dimethylamino ethyl methacrylate and poly (N-(L)-(1-hydroxymethyl) propyl methacrylamide). Other examples of thermo-responsive polymers are: copolymers blocks of poly(ethylene glycol)/poly(lactide-coglicolide) (PEG/PLGA, REGEL®), polyoxyethylenepolyoxypropylene (PEO/PPO), triple blocks of copolymers polyoxyethylene-polyoxypropylene-polyoxyethylene (PEO-PPOPEO) and poly(ethylene glycol)-poly(lactic acid)-poly(ethylene glycol) (PEG-PLA-PEG). Exemplary polymers and their LCST: PNIPAAm, LCST 32° C.; PDEAAm, LCST 26-35° C.; PDMAEMA, LCST 50° C.; poly(N-(L)-(hydroxymethyl)propylmethacrylamide), LCST 30° C.

An increase of the hydrophobic monomers (as, for example, the butyl methacrylate) or on the molecular weight, results in a LCST decrease (Jeong, Gutowska, 2002). The incorporation of hydrophilic monomers such as acrylic acid or hydroxyethyl methacrylate) fosters the creation of increases LCST. The co-polymers NIPAAm conjugated with hydrophilic unities such as acrylic acid promotes the increase of LCST to temperatures around 37° C., i.e., the body temperature. Polymers with 2-hydroxyethyl (methacrylate) (HEMA) promote the increase of LCST above the body temperature POLOXAMERs and derivatives are well known temperature sensitive polymers. The copolymer blocks based on PEO-PPO sequences constitutes one family of triple blocks of commercialized copolymers with the following names: PLURONICS®, POLOXAMERS® AND TETRONICS®. POLOXAMERS® are non-ionic polymers polyoxyethylenepolyoxypropylene-polyoxyethylene (PEOn-PPOn-PEOn), with many pharmaceutical uses (Ricci et al., 2005). The triple block of copolymers PEO-PPO-PEO (PLURONICS® or POLOXAMERS®) get into gel at body temperature in concentrations above 15% (m/m). The POLOXAMERs® normally used are: 188 (F-68), 237 (F-87), 338 (F-108) and 407 (F-127). "F" refers to the polymer in the form of flakes. PLURONICS® and TETRONICS® are polymers approved by FDA to be used as food additives, pharmaceutical ingredients, drug carriers in parenteral systems, tissue engineering and agricultural products. PLURONIC F-127 (Polaxamer 407, PF-127) can also be used as carrier in several routes of administration, including oral, cutaneous, intranasal, vaginal, rectal, ocular and parenteral. PLURONIC® F127 (PF-127) or POLOXAMER 407 (P407) (copolymer polyoxyethylene 106-polyoxypropylene 70-polyoxyethylene106) contains about 70% of ethylene oxide which contributes to its hydrophilicity.

Polymers with Dual Stimuli-Responsiveness

To obtain a temperature and pH sensitive polymer it is only necessary to combine temperature sensitive monomers (as, for example, poly(N-isopropylacrylamide-co-methacrylic acid and PNIPAm) with pH sensitive monomers (as, for example, AA and MAA).

Polymers with Binding or Biological Responsiveness

Biologically responsive polymer systems are increasingly important in various biomedical applications. The major advantage of bioresponsive polymers is that they can respond to the stimuli that are inherently present in the natural system. Bioresponsive polymeric systems mainly arise from common functional groups that are known to interact with biologically relevant species, and in other instances the synthetic polymer is conjugated to a biological component. Bioresponsive polymers are classified into antigen-responsive polymers, glucose-sensitive polymers, and enzyme-responsive polymers.

Glucose-responsive polymeric-based systems have been developed based on the following approaches: enzymatic oxidation of glucose by glucose oxidase, and binding of glucose with lectin or reversible covalent bond formation with phenylboronic acid moieties. Glucose sensitivity occurs by the response of the polymer toward the byproducts that result from the enzymatic oxidation of glucose. Glucose oxidase oxidises glucose resulting in the formation of gluconic acid and $H_2O_2$. For example, in the case of poly (acrylicacid) conjugated with the GOx system, as the blood glucose level is increased glucose is converted into gluconic acid which causes the reduction of pH and protonation of PAA carboxylate moieties, facilitating the release of insulin. Another system utilizes the unique carbohydrate binding properties of lectin for the fabrication of a glucose-sensitive system. Concanavalin A (Con A) is a lectin possessing four binding sites and has been used frequently in insulin-modulated drug delivery. In this type of system the insulin moiety is chemically modified by introducing a functional group (or glucose molecule) and then attached to a carrier or support through specific interactions which can only be interrupted by the glucose itself. The glycosylated insulin-Con A complex exploits the competitive binding behaviour of Con A with glucose and glycosylated insulin. The free glucose molecule causes the displacement of glycosylated Con A-insulin conjugates.

Another approach includes polymers with phenylboronic groups and polyol polymers that form a gel through complex formation between the pendant phenylborate and hydroxyl groups. Instead of polyol polymers, short molecules such as diglucosylhexadiamine have been used. As the glucose concentration increases, the crosslinking density of the gel decreases and as a result insulin is released from the eroded gel. The glucose exchange reaction is reversible and reformation of the gel occurs as a result of borate-polyol crosslinking.

Field-responsive polymers respond to the application of electric, magnetic, sonic or electromagnetic fields. The additional benefit over traditional stimuli-sensitive polymers is their fast response time, anisotropic deformation due to directional stimuli, and also a controlled drug release rate simply by modulating the point of signal control.

Light-Sensitive Polymers

A light-sensitive polymer undergoes a phase transition in response to exposure to light. These polymers can be classified into UV-sensitive and visible-sensitive systems on the basis of the wavelength of light that triggers the phase transition.

A variety of materials are known, such as a leuco-derivative molecule, bis(4-dimethylamino)phenylmethyl leucocyanide, which undergoes phase transition behaviour in response to UV light. Triphenylmethane-leuco derivatives dissociate into ion-pairs such as triphenylmethyl cations upon UV irradiation. At a fixed temperature these hydrogels swell discontinuously due to increased osmotic pressure in response to UV irradiation but shrink when the stimulus is removed. Another example is a thermosensitive diarylated pluronic F-127.

Visible light-sensitive polymeric materials can be prepared by incorporating photosensitive molecules such as chromophores (e.g., trisodium salt of copper chlorophyllin). When light of appropriate wavelength is applied, the chromophore absorbs light which is then dissipated locally as heat by radiationless transition, increasing the local temperature of the polymeric material, leading to alteration of the swelling behavior. The temperature increase directly depends on the chromophore concentration and light intensity.

Electric Field-Sensitive Polymers

Electric field-sensitive polymers change their physical properties in response to a small change in electric current. These polymers contain a relatively large concentration of ionisable groups along the back bone chain that are also pH-responsive. Electro-responsive polymers transform electric energy into mechanical energy. The electric current causes a change in pH which leads to disruption of hydrogen bonding between polymer chains, causing degradation or bending of the polymer chain. Major mechanisms involved in drug release from electro-responsive polymer are diffusion, electrophoresis of charged drug, forced convection of drug out of the polymer or degradation of the polymer.

Naturally occurring polymers such as chitosan, alginate and hyalouronic acid are commonly employed to prepare electro-responsive materials. Major synthetic polymers that have been used include allyl amine, vinyl alcohol, acrylonitrile, methacrylic acid and vinylacrylic acid. In some cases, combinations of natural and synthetic polymers have been used. Most polymers that exhibit electro-sensitive behavior are polyelectrolytes and undergo deformation under an electric field due to anisotropic swelling or deswelling as the charged ions move towards the cathode or anode. Neutral polymers that exhibit electro-sensitive behavior require the presence of a polarisable component with the ability to respond to the electric field. Another example of a material which can be used is poly(2-acrylamido-2-methylpropane sulphonic acid-co-n-butylmethacrylate).

B. Active Agents

In some embodiments, the NPs contain between about 1% and about 70% weight/weight of a therapeutic agent, a prophylactic agent, a diagnostic agent, or combinations thereof. Preferably, the NPs contain between about 5% and about 50% weight/weight, most preferably between about 10% and about 30% weight/weight of a therapeutic agent, a prophylactic agent, a diagnostic agent, or combinations thereof.

Active agent cargos to be delivered include therapeutic, nutritional, diagnostic, and prophylactic agents. The active agents can be small molecule active agents or biomacromolecules, such as proteins, polypeptides, sugars or carbohydrates, lipids, nucleic acids or small molecule compounds (typically 1 kD or less, but may be larger). Suitable small molecule active agents include organic and organometallic compounds. The small molecule active agents can be a hydrophilic, hydrophobic, or amphiphilic compound.

Active agents include synthetic and natural proteins (including enzymes, peptide-hormones, receptors, growth factors, antibodies, signaling molecules), and synthetic and natural nucleic acids (including RNA, DNA, anti-sense RNA, triplex DNA, inhibitory RNA (RNAi), and oligonucleotides), and biologically active portions thereof. Suitable active agents have a size greater than about 1,000 Da for small peptides and polypeptides, more typically at least about 5,000 Da and often 10,000 Da or more for proteins. Nucleic acids are more typically listed in terms of base pairs or bases (collectively "bp"). Nucleic acids with lengths above about 10 bp are typically used. More typically, useful lengths of nucleic acids for probing or therapeutic use will be in the range from about 20 bp (probes; inhibitory RNAs, etc.) to tens of thousands of bp for genes and vectors. The active agents may also be hydrophilic molecules, preferably having a low molecular weight.

Exemplary therapeutic agents that can be incorporated into particles include tumor antigens, CD4+ T-cell epitopes, cytokines, chemotherapeutic agents, radionuclides, small molecule signal transduction inhibitors, photothermal antennas, monoclonal antibodies, immunologic danger signaling molecules, other immunotherapeutics, enzymes, antibiotics, antivirals (especially protease inhibitors alone or in combination with nucleosides for treatment of HIV or Hepatitis B or C), anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, immunomodulators (including ligands that bind to Toll-Like Receptors (including, but not limited to, CpG oligonucleotides) to activate the innate immune system, molecules that mobilize and optimize the adaptive immune system, molecules that activate or up-regulate the action of cytotoxic T lymphocytes, natural killer cells and helper T-cells, and molecules that deactivate or down-regulate suppressor or regulatory T-cells), agents that promote uptake of particles into cells, nutraceuticals such as vitamins, and oligonucleotide drugs (including DNA, RNAs, antisense, aptamers, small interfering RNAs, ribozymes, external guide sequences for ribonuclease P, and triplex forming agents).

Exemplary diagnostic agents include paramagnetic molecules, fluorescent compounds, magnetic molecules, and radionuclides, x-ray imaging agents, and contrast agents.

As discussed in more detail below, in some embodiments, the particles include one or more anti-cancer agents.

In certain embodiments, the particle includes one or more immunomodulatory agents. Exemplary immunomodulatory agents include cytokines, xanthines, interleukins, interferons, oligodeoxynucleotides, glucans, growth factors (e.g., TNF, CSF, GM-CSF and G-CSF), hormones such as estrogens (diethylstilbestrol, estradiol), androgens (testosterone, HALOTESTIN® (fluoxymesterone)), progestins (MEGACE® (megestrol acetate), PROVERA® (medroxyprogesterone acetate)), and corticosteroids (prednisone, dexamethasone, hydrocortisone).

Examples of immunological adjuvants that can be associated with the particles include, but are not limited to, TLR ligands, C-Type Lectin Receptor ligands, NOD-Like Receptor ligands, RLR ligands, and RAGE ligands. TLR ligands can include lipopolysaccharide (LPS) and derivatives thereof, as well as lipid A and derivatives there of including, but not limited to, monophosphoryl lipid A (MPL), glycopyranosyl lipid A, PET-lipid A, and 3-O-desacyl-4'-monophosphoryl lipid A. In a specific embodiment, the immunological adjuvant is MPL. In another embodiment, the immunological adjuvant is LPS. TLR ligands can also include, but are not limited to, TLR3 ligands (e.g., polyinosinic-polycytidylic acid (poly(I:C)), TLR7 ligands (e.g., imiquimod and resiquimod), and TLR9 ligands.

The particles may also include antigens and/or adjuvants (i.e., molecules enhancing an immune response). Peptide, protein, and DNA based vaccines may be used to induce immunity to various diseases or conditions. Cell-mediated immunity is needed to detect and destroy virus-infected cells. Most traditional vaccines (e.g. protein-based vaccines) can only induce humoral immunity. DNA based vaccine can induce both humoral and cell-mediated immunity. DNA vaccines are relatively more stable and more cost-effective for manufacturing and storage. DNA vaccines consist of two major components, DNA carriers (or delivery vehicles) and DNAs encoding antigens. DNA carriers protect DNA from degradation, and can facilitate DNA entry to specific tissues or cells and expression at an efficient level.

Under the Biopharmaceutical Classification System (BCS), drugs can belong to four classes: class I (high permeability, high solubility), class II (high permeability, low solubility), class III (low permeability, high solubility) or class IV (low permeability, low solubility). Suitable active agents also include poorly soluble compounds; such as drugs that are classified as class II or class IV compounds using the BCS. Examples of class II compounds include: acyclovir, nifedipine, danazol, ketoconazole, mefenamic acid, nisoldipine, nicardipine, felodipine, atovaquone, griseofulvin, troglitazone glibenclamide and carbamazepine. Examples of class IV compounds include: chlorothiazide, furosemide, tobramycin, cefuroxmine, and paclitaxel.

An imaging, detectable or sensing moiety, i.e., a moiety that can be determined in some fashion, either directly or indirectly, may be bound to the NPs or to the polymers forming the NPs, or encapsulated therein. Representative imaging entities include, but are not limited to, fluorescent, radioactive, electron-dense, magnetic, or labeled members of a binding pair or a substrate for an enzymatic reaction, which can be detected. In some cases, the imaging entity itself is not directly determined, but instead interacts with a second entity in order to effect determination; for example, coupling of the second entity to the imaging entity may result in a determinable signal. Non-limiting examples of imaging moieties include, but are not limited to, fluorescent compounds such as FITC or a FITC derivative, fluorescein, green fluorescent protein ("GFP"), radioactive atoms such as $^{3}H$, $^{4}C$, $^{33}PP$, $^{32}P$, $^{125}I$, $^{131}I$, $^{35}S$, or a heavy metal species, for example, gold or osmium. As a specific example, an imaging moiety may be a gold nanoparticle. A diagnostic or imaging tag such as a fluorescent tag is chemically conjugated to a polymer to yield a fluorescently labeled polymer.

For imaging, radioactive materials such as Technetium99 ($^{99m}Tc$) or magnetic materials such as $Fe_2O_3$ could be used. Examples of other materials include gases or gas emitting compounds, which are radioopaque.

1. Nucleic Acid-Based Active Agents

The cargo can be a nucleic acid. An isolated nucleic acid can be, for example, a DNA, an RNA, or a nucleic acid analog. Nucleic acid analogs can be modified at the base moiety, sugar moiety, or phosphate backbone. Such modification can improve, for example, stability, hybridization, or solubility of the nucleic acid. Exemplary modifications include, 2'O-methyl, 2' methoxy-ethyl, phosphoramidate, methylphosphonate, and/or phosphorothioate backbone chemistry. Other non-limiting modifications are discussed in more detail below. The nucleic acid molecule can exist as a separate molecule independent of other sequences (e.g., a chemically synthesized nucleic acid, or a cDNA or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), etc. The nucleic acid can be an engineered nucleic acid such as a recombinant DNA molecule that is part of a hybrid or fusion nucleic acid.

The genetic material to be loaded into the particles is chosen on the basis of the desired effect of that genetic material on the cell into which it is intended to be delivered and the mechanism by which that effect is to be carried out. For example, the nucleic acid may be useful in gene therapy, for example in order to express a desired gene in a cell or group of cells. Nucleic acid can also be used in gene silencing. Such gene silencing may be useful in therapy to switch off aberrant gene expression. Nucleic acid can also be used for example to express one or more antigens against which it is desired to produce an immune response. Thus, the nucleic acid to be loaded into the particle can encode one or more antigens against which is desired to produce an immune response, including but not limited to tumour antigens, antigens from pathogens such as viral, bacterial or fungal pathogens, such as those discussed in more detail below. Therapeutic strategies for treating cancer, inflammation, injury, autoimmunity, and infections are discussed in more detail below.

a. Functional Nucleic Acids

In some embodiments, the active agent cargo is a functional nucleic acid. Functional nucleic acids are nucleic acid molecules that have a specific function, such as binding a target molecule or catalyzing a specific reaction. As discussed in more detail below, functional nucleic acid molecules can be divided into the following non-limiting categories: antisense molecules, RNAi including siRNA, miRNA, and piRNA, aptamers, ribozymes, triplex forming molecules, external guide sequences, and gene editing compositions. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA or the genomic DNA of a target polypeptide or they can interact with the polypeptide itself. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

i. Antisense

The functional nucleic acids can be antisense molecules. Antisense molecules are designed to interact with a target nucleic acid molecule through either canonical or non-canonical base pairing. The interaction of the antisense molecule and the target molecule is designed to promote the destruction of the target molecule through, for example, RNAse H mediated RNA-DNA hybrid degradation. Alternatively the antisense molecule is designed to interrupt a processing function that normally would take place on the target molecule, such as transcription or replication. Antisense molecules can be designed based on the sequence of the target molecule. There are numerous methods for optimization of antisense efficiency by finding the most accessible regions of the target molecule. Exemplary methods include in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$.

ii. Aptamers

The functional nucleic acids can be aptamers. Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with $K_d$'s from the target molecule of less than $10^{-2}$ M. It is preferred that the aptamers bind the target molecule with a $K_d$ less than $10^{-6}$, $10^{-8}$, $10^{-10}$, or $10^{-2}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a $K_d$ with the target molecule at least 10, 100, 1000, 10,000, or 100,000 fold lower than the $K_d$ with a background binding molecule. It is preferred when doing the comparison for a molecule such as a polypeptide, that the background molecule be a different polypeptide.

iii. Ribozymes

The functional nucleic acids can be ribozymes. Ribozymes are nucleic acid molecules that are capable of catalyzing a chemical reaction, either intramolecularly or intermolecularly. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence.

iv. Triplex Forming Oligonucleotides

The functional nucleic acids can be triplex forming molecules. Triplex forming functional nucleic acid molecules are molecules that can interact with either double-stranded or single-stranded nucleic acid. When triplex molecules interact with a target region, a structure called a triplex is formed in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$.

v. External Guide Sequences

The functional nucleic acids can be external guide sequences. External guide sequences (EGSs) are molecules that bind a target nucleic acid molecule forming a complex, which is recognized by RNase P, which then cleaves the target molecule. EGSs can be designed to specifically target an RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukaryotic cells. Representative examples of how to make and use EGS molecules to facilitate cleavage of a variety of different target molecules are known in the art.

vi. RNA Interference

In some embodiments, the functional nucleic acids induce gene silencing through RNA interference. Gene expression can also be effectively silenced in a highly specific manner through RNA interference (RNAi), which can generally be divided into three major classes based on their processing mechanisms and partner Argonaute proteins: micro RNAs (miRNAs), small interfering RNAs (siRNAs), and PIWI-interacting RNA (piRNAs) (Czech and Hannon, *Trends Biochem Sci.,* 2016 Jan. 19. pii: 50968-0004(15)00258-3. doi: 10.1016/j.tibs.2015.12.008. [Epub ahead of print].

RNAi silencing was originally observed with the addition of double stranded RNA (dsRNA) (Fire, et al. (1998) Nature, 391:806-11; Napoli, et al. (1990) Plant Cell 2:279-89; Hannon, (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, et al. (2001) Genes Dev., 15:188-200; Bernstein, et al. (2001) Nature, 409:363-6; Hammond, et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, a siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs.

Sequence specific gene silencing can be achieved in mammalian cells using synthetic, short double-stranded RNAs that mimic the siRNAs produced by the enzyme dicer (Elbashir, et al. (2001) Nature, 411:494 498) (Ui-Tei, et al.

(2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Texas), ChemGenes (Ashland, Massachusetts), Dharmacon (Lafayette, Colorado), Glen Research (Sterling, Virginia), MWB Biotech (Esbersberg, Germany), Proligo (Boulder, Colorado), and Qiagen (Vento, The Netherlands). siRNA can also be synthesized in vitro using kits such as Ambion's SILENCER® siRNA Construction Kit.

The production of siRNA from a vector is more commonly done through the transcription of a short hairpin RNAse (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors.

Micro RNAs (abbreviated miRNA) are small non-coding RNA molecules (containing about 22 nucleotides) that functions in RNA silencing and post-transcriptional regulation of gene expression. miRNAs resemble siRNAs of the RNA interference (RNAi) pathway, except miRNAs derive from regions of RNA transcripts that fold back on themselves to form short hairpins, whereas siRNAs derive from longer regions of double-stranded RNA (Bartel, et al., *Cell,* 116: 281-297 (2004)).

The biogenesis of miRNAs and siRNAs typically depends on RNase III type enzymes that convert their double-stranded RNA precursors into functional small RNAs. By contrast, piRNAs derive from single-stranded RNAs and, consequently, require alternative processing machinery.

Synthetic piRNAs can be used to block the synthesis of target proteins by binding to mRNAs, as has been attempted with miRNAs, might have the advantage of not requiring processing by enzymes such as Dicer, which is required by miRNAs. Additional speculative advantages of piRNAs over miRNAs include the possibility of targets with better specificity because each miRNA regulates several mRNAs and there is the potential to access undesirable long non-coding RNAs with possible implications in disease processes (Assumpgao, et al., *Epigenomics,* 7(6):975-984 (2015)). miRNA and piRNA can be the therapeutic agent or can be target sequences for post-transcriptional silencing. For example, synthetic piRNAs designed to couple to PIWI proteins and exert genomic silencing on PIWI genes at a transcriptional level is a possible strategy.

In some embodiment, the functional nucleic acid is siRNA, shRNA, miRNA, or piRNA. In some embodiments, the composition includes a vector expressing the functional nucleic acid. Methods of making and using vectors for in vivo expression of functional nucleic acids such as antisense oligonucleotides, siRNA, shRNA, miRNA, piRNA, EGSs, ribozymes, and aptamers are known in the art.

vii. Other Gene Editing Compositions

In some embodiments the functional nucleic acids are gene editing compositions. Gene editing compositions can include nucleic acids that encode an element or elements that induce a single or a double strand break in the target cell's genome, and optionally a polynucleotide. The compositions can be used, for example, to reduce or otherwise modify expression of a gene target.

1. Strand Break Inducing Elements

It will be appreciated that some of the embodiments discussed below include protein active agents. In some embodiments, the agents are packaged into particles as nucleic acids encoding the proteins (e.g., mRNA, expression vectors, etc.).

CRISPR/Cas

In some embodiments, the element that induces a single or a double strand break in the target cell's genome is a CRISPR/Cas system. CRISPR (Clustered Regularly Interspaced Short Palindromic Repeats) is an acronym for DNA loci that contain multiple, short, direct repetitions of base sequences. The prokaryotic CRISPR/Cas system has been adapted for use as gene editing (silencing, enhancing or changing specific genes) for use in eukaryotes (see, for example, Cong, *Science,* 15:339(6121):819-823 (2013) and Jinek, et al., *Science,* 337(6096):816-21 (2012)). By transfecting a cell with the required elements including a cas gene and specifically designed CRISPRs, the organism's genome can be cut and modified at any desired location. Methods of preparing compositions for use in genome editing using the CRISPR/Cas systems are described in detail in WO 2013/176772 and WO 2014/018423, which are specifically incorporated by reference herein in their entireties.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. One or more tracr mate sequences operably linked to a guide sequence (e.g., direct repeat-spacer-direct repeat) can also be referred to as pre-crRNA (pre-CRISPR RNA) before processing or crRNA after processing by a nuclease.

In some embodiments, a tracrRNA and crRNA are linked and form a chimeric crRNA-tracrRNA hybrid where a mature crRNA is fused to a partial tracrRNA via a synthetic stem loop to mimic the natural crRNA:tracrRNA duplex as described in Cong, *Science,* 15:339(6121):819-823 (2013) and Jinek, et al., *Science,* 337(6096):816-21 (2012)). A single fused crRNA-tracrRNA construct can also be referred to as a guide RNA or gRNA (or single-guide RNA (sgRNA)). Within an sgRNA, the crRNA portion can be identified as the 'target sequence' and the tracrRNA is often referred to as the 'scaffold'.

There are many resources available for helping practitioners determine suitable target sites once a desired DNA target sequence is identified. For example, numerous public resources, including a bioinformatically generated list of about 190,000 potential sgRNAs, targeting more than 40% of human exons, are available to aid practitioners in selecting target sites and designing the associate sgRNA to affect a nick or double strand break at the site. See also, crispr.u-psud.fr/, a tool designed to help scientists find CRISPR targeting sites in a wide range of species and generate the appropriate crRNA sequences.

In some embodiments, one or more vectors driving expression of one or more elements of a CRISPR system are introduced into a target cell such that expression of the elements of the CRISPR system direct formation of a CRISPR complex at one or more target sites. While the specifics can be varied in different engineered CRISPR systems, the overall methodology is similar. A practitioner interested in using CRISPR technology to target a DNA sequence can insert a short DNA fragment containing the target sequence into a guide RNA expression plasmid. The sgRNA expression plasmid contains the target sequence (about 20 nucleotides), a form of the tracrRNA sequence (the scaffold) as well as a suitable promoter and necessary elements for proper processing in eukaryotic cells. Such vectors are commercially available (see, for example, Addgene). Many of the systems rely on custom, complementary oligos that are annealed to form a double stranded DNA and then cloned into the sgRNA expression plasmid. Co-expression of the sgRNA and the appropriate Cas enzyme from the same or separate plasmids in transfected cells results in a single or double strand break (depending of the activity of the Cas enzyme) at the desired target site.

Zinc Finger Nucleases

In some embodiments, the element that induces a single or a double strand break in the target cell's genome is a nucleic acid construct or constructs encoding a zinc finger nucleases (ZFNs). ZFNs are typically fusion proteins that include a DNA-binding domain derived from a zinc-finger protein linked to a cleavage domain.

The most common cleavage domain is the Type IIS enzyme Fok1. Fok1 catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. *Proc., Natl. Acad. Sci. USA* 89 (1992):4275-4279; Li et al. *Proc. Natl. Acad. Sci. USA,* 90:2764-2768 (1993); Kim et al. *Proc. Natl. Acad. Sci. USA.* 91:883-887 (1994a); Kim et al. *J. Biol. Chem.* 269:31,978-31,982 (1994b). One or more of these enzymes (or enzymatically functional fragments thereof) can be used as a source of cleavage domains.

The DNA-binding domain, which can, in principle, be designed to target any genomic location of interest, can be a tandem array of $Cys_2His_2$ zinc fingers, each of which generally recognizes three to four nucleotides in the target DNA sequence. The $Cys_2His_2$ domain has a general structure: Phe (sometimes Tyr)-Cys-(2 to 4 amino acids)-Cys-(3 amino acids)-Phe (sometimes Tyr)-(5 amino acids)-Leu-(2 amino acids)-His-(3 amino acids)-His. By linking together multiple fingers (the number varies: three to six fingers have been used per monomer in published studies), ZFN pairs can be designed to bind to genomic sequences 18-36 nucleotides long.

Engineering methods include, but are not limited to, rational design and various types of empirical selection methods. Rational design includes, for example, using databases including triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,140,081; 6,453,242; 6,534,261; 6,610,512; 6,746,838; 6,866,997; 7,067,617; U.S. Published Application Nos. 2002/0165356; 2004/0197892; 2007/0154989; 2007/0213269; and International Patent Application Publication Nos. WO 98/53059 and WO 2003/016496.

Transcription Activator-Like Effector Nucleases

In some embodiments, the element that induces a single or a double strand break in the target cell's genome is a nucleic acid construct or constructs encoding a transcription activator-like effector nuclease (TALEN). TALENs have an overall architecture similar to that of ZFNs, with the main difference that the DNA-binding domain comes from TAL effector proteins, transcription factors from plant pathogenic bacteria. The DNA-binding domain of a TALEN is a tandem array of amino acid repeats, each about 34 residues long. The repeats are very similar to each other; typically they differ principally at two positions (amino acids 12 and 13, called the repeat variable diresidue, or RVD). Each RVD specifies preferential binding to one of the four possible nucleotides, meaning that each TALEN repeat binds to a single base pair, though the NN RVD is known to bind adenines in addition to guanine. TAL effector DNA binding is mechanistically less well understood than that of zinc-finger proteins, but their seemingly simpler code could prove very beneficial for engineered-nuclease design. TALENs also cleave as dimers, have relatively long target sequences (the shortest reported so far binds 13 nucleotides per monomer) and appear to have less stringent requirements than ZFNs for the length of the spacer between binding sites. Monomeric and dimeric TALENs can include more than 10, more than 14, more than 20, or more than 24 repeats.

Methods of engineering TAL to bind to specific nucleic acids are described in Cermak, et al, *Nucl. Acids Res.* 1-11 (2011). US Published Application No. 2011/0145940, which discloses TAL effectors and methods of using them to modify DNA. Miller et al. *Nature Biotechnol* 29: 143 (2011) reported making TALENs for site-specific nuclease architecture by linking TAL truncation variants to the catalytic domain of Fok1 nuclease. The resulting TALENs were shown to induce gene modification in immortalized human cells. General design principles for TALE binding domains can be found in, for example, WO 2011/072246.

2. Gene Altering Polynucleotides

The nuclease activity of the genome editing systems described herein cleave target DNA to produce single or double strand breaks in the target DNA. Double strand breaks can be repaired by the cell in one of two ways: non-homologous end joining, and homology-directed repair. In non-homologous end joining (NHEJ), the double-strand breaks are repaired by direct ligation of the break ends to one another. As such, no new nucleic acid material is inserted into the site, although some nucleic acid material may be lost, resulting in a deletion. In homology-directed repair, a donor polynucleotide with homology to the cleaved target DNA sequence is used as a template for repair of the cleaved target DNA sequence, resulting in the transfer of genetic information from a donor polynucleotide to the target DNA. As such, new nucleic acid material can be inserted/copied into the site.

Therefore, in some embodiments, the genome editing composition optionally includes a donor polynucleotide. The modifications of the target DNA due to NHEJ and/or homology-directed repair can be used to induce gene correction, gene replacement, gene tagging, transgene insertion, nucleotide deletion, gene disruption, gene mutation, etc.

Accordingly, cleavage of DNA by the genome editing composition can be used to delete nucleic acid material from a target DNA sequence by cleaving the target DNA sequence and allowing the cell to repair the sequence in the absence of an exogenously provided donor polynucleotide.

Alternatively, if the genome editing composition includes a donor polynucleotide sequence that includes at least a segment with homology to the target DNA sequence, the methods can be used to add, i.e., insert or replace, nucleic acid material to a target DNA sequence (e.g., to "knock in" a nucleic acid that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g., promoter, polyadenylation signal, internal ribosome entry sequence (IRES), 2A peptide, start codon, stop codon, splice signal, localization signal, etc.), to modify a nucleic acid sequence (e.g., introduce a mutation), and the like. As such, the compositions can be used to modify DNA in a site-specific, i.e., "targeted", way, for example gene knock-out, gene knock-in, gene editing, gene tagging, etc. as used in, for example, gene therapy.

In applications in which it is desirable to insert a polynucleotide sequence into a target DNA sequence, a polynucleotide including a donor sequence to be inserted is also provided to the cell. By a "donor sequence" or "donor polynucleotide" or "donor oligonucleotide" it is meant a nucleic acid sequence to be inserted at the cleavage site. The donor polynucleotide typically contains sufficient homology to a genomic sequence at the cleavage site, e.g., 70%, 80%, 85%, 90%, 95%, or 100% homology with the nucleotide sequences flanking the cleavage site, e.g., within about 50 bases or less of the cleavage site, e.g., within about 30 bases, within about 15 bases, within about 10 bases, within about 5 bases, or immediately flanking the cleavage site, to support homology-directed repair between it and the genomic sequence to which it bears homology. The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair. In some embodiments, the donor sequence includes a non-homologous sequence flanked by two regions of homology, such that homology-directed repair between the target DNA region and the two flanking sequences results in insertion of the non-homologous sequence at the target region.

b. Peptide and Protein Expression Constructs

In some embodiments, the active agent is a nucleic acid encoding a protein or a polypeptide. Although discussed here in the context of mRNA, it will be appreciated that the nucleic acid active agent can itself be an mRNA, or can be a DNA or other oligonucleotide encoding the mRNA (or a functional nucleic acid as discussed above). As discussed in more detail below, the nucleic acid active agents, including mRNA and functional nucleic acids, can be encoded by a nucleic acid that encodes the RNA. The nucleic acid can be operably linked to an expression control sequence. In some embodiments, the nucleic acid is a vector, integration construct, etc., that enables expression of the RNA in a cell.

The mRNA can be a mature mRNA or pre-mRNA. Thus in some embodiments, the mRNA includes introns. The mRNA can be a naturally occurring gene transcript, for example, a human gene transcript. The mRNA can be an artificial sequence that is not normally expressed in a naturally occurring organism. An exemplary artificial sequence is one that contains portions of gene sequences that are ligated together to form an open reading frame that encodes a fusion protein. The portions of that are ligated together can be from a single organism or from more than one organism.

The mRNA can encode a polypeptide that provides a therapeutic or prophylactic effect to an organism or that can be used to diagnose a disease or disorder in an organism. For example, for treatment of cancer, autoimmune disorders, parasitic, viral, bacterial, fungal or other infections, the polypeptide can be a ligand or receptor for cells of the immune system, or can function to stimulate or inhibit the immune system of an organism. Typically, it is not desirable to have prolonged ongoing stimulation of the immune system, nor necessary to produce changes which last after successful treatment, since this may then elicit a new problem. For treatment of an autoimmune disorder, it may be desirable to inhibit or suppress the immune system during a flare-up, but not long term, which could result in the patient becoming overly sensitive to an infection. Thus in some embodiments, delivery of mRNA for transient expression of the protein (or functional nucleic acid) is preferred to sustained expression by a vector or gene integration.

The mRNA can include a 5' cap. A 5' cap (also termed an RNA cap, an RNA 7-methylguanosine cap or an RNA m7G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation. The 5' cap may, for example, be m7G(5')ppp(5')G, m7G(5')ppp(5')A, G(5')ppp(5')G or G(5')ppp(5')A cap analogs, which are all commercially available. The 5' cap can also be an anti-reverse-cap-analog (ARCA) (see, e.g., Stepinski, et al., *RNA,* 7:1468-95 (2001)) or any other suitable analog. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The mRNA can contain an internal ribosome entry site (IRES) sequence. The IRES sequence may be any viral, chromosomal or artificially designed sequence which initiates cap-independent ribosome binding to mRNA and facilitates the initiation of translation.

The mRNA can include a 5' untranslated region. The 5' UTR is upstream from the coding sequence. Within the 5' UTR is a sequence that is recognized by the ribosome which allows the ribosome to bind and initiate translation. The mechanism of translation initiation differs in Prokaryotes and Eukaryotes.

The mRNA includes an "open reading frame" or "ORF," which is a series of nucleotides that contains a sequence of bases that could potentially encode a polypeptide or protein. An open reading frame is located between the start-code sequence (initiation codon or start codon) and the stop-codon sequence (termination codon). The ORF can be from a naturally occurring sequence from the genome of an organism.

The mRNA can include a 3' untranslated region. The 3' UTR is found immediately following the translation stop codon. The 3' UTR plays an important role in translation termination as well as post transcriptional gene expression.

In some embodiments, the mRNA is polyadenylated. "Polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA (SEQ ID NO:12) near the cleavage site. After the mRNA has been cleaved, adenosine residues are added to the free 3' end at the cleavage site.

RNA, including mRNA and RNA-based functional nucleic acids, can be prepared by in vitro transcription using, for example, a purified linear DNA template containing a promoter, ribonucleotide triphosphates, a buffer system that includes DTT and magnesium ions, and an appropriate phage RNA polymerase. The template can be a vector, PCR product, synthetic oligonucleotide, or cDNA.

3. Vectors

Nucleic acids, including constructs encoding mRNAs and functional nucleic acids such as those described above, can be inserted into vectors for expression in cells. As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence, or into a functional nucleic acids.

The vector can be a viral vector. Nucleic acid molecules encoding proteins or functional nucleic acids can be packaged into retrovirus vectors using packaging cell lines that produce replication-defective retroviruses, as is well-known in the art. Other virus vectors may also be used, including recombinant adenoviruses and vaccinia virus, which can be rendered non-replicating.

In some embodiments the nucleic acid is designed for integration into the host cell's genome. Nucleic acids that are delivered to cells which are to be integrated into the host cell genome, typically contain integration sequences. These sequences are often viral related sequences, particularly when viral based systems are used. Techniques for integration of genetic material into a host genome are also known and include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

4. Nucleic Acid Composition

The nucleic acid cargos can be DNA or RNA nucleotides which typically include a heterocyclic base (nucleic acid base), a sugar moiety attached to the heterocyclic base, and a phosphate moiety which esterifies a hydroxyl function of the sugar moiety. The principal naturally-occurring nucleotides comprise uracil, thymine, cytosine, adenine and guanine as the heterocyclic bases, and ribose or deoxyribose sugar linked by phosphodiester bonds.

In some embodiments, the oligonucleotides are composed of nucleotide analogs that have been chemically modified to improve stability, half-life, or specificity or affinity for a target receptor, relative to a DNA or RNA counterpart. The chemical modifications include chemical modification of nucleobases, sugar moieties, nucleotide linkages, or combinations thereof. As used herein 'modified nucleotide" or "chemically modified nucleotide" defines a nucleotide that has a chemical modification of one or more of the heterocyclic base, sugar moiety or phosphate moiety constituents. In some embodiments, the charge of the modified nucleotide is reduced compared to DNA or RNA oligonucleotides of the same nucleobase sequence. For example, the oligonucleotide can have low negative charge, no charge, or positive charge.

Typically, nucleoside analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). In some embodiments, the analogs have a substantially uncharged, phosphorus containing backbone.

a. Heterocyclic Bases

The principal naturally-occurring nucleotides include uracil, thymine, cytosine, adenine and guanine as the heterocyclic bases. The oligonucleotides can include chemical modifications to their nucleobase constituents. Chemical modifications of heterocyclic bases or heterocyclic base analogs may be effective to increase the binding affinity or stability in binding a target sequence. Chemically-modified heterocyclic bases include, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-.beta.-D-ribofuranosyl)pyridine (2-aminopyridine), and various pyrrolo- and pyrazolopyrimidine derivatives.

b. Sugar Modifications

Oligonucleotides can also contain nucleotides with modified sugar moieties or sugar moiety analogs. Sugar moiety modifications include, but are not limited to, 2-O-aminoethoxy, 2'-O-amonioethyl (2'-OAE), 2'-O-methoxy, 2'-O- methyl, 2-guanidoethyl (2'-OGE), 2'-0,4'-C-methylene (LNA), 2'-O-(methoxyethyl) (2'-OME) and 2'-O—(N-(methyl)acetamido) (2'-OMA). In some embodiments, the functional nucleic acid is a morpholino oligonucleotide. Morpholino oligonucleotides are typically composed of two more morpholino monomers containing purine or pyrimidine base-pairing moieties effective to bind, by base-specific hydrogen bonding, to a base in a polynucleotide, which are linked together by phosphorus-containing linkages, one to three atoms long, joining the morpholino nitrogen of one monomer to the 5' exocyclic carbon of an adjacent monomer. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337.

Important properties of the morpholino-based subunits typically include: the ability to be linked in a oligomeric form by stable, uncharged backbone linkages; the ability to support a nucleotide base (e.g. adenine, cytosine, guanine, thymidine, uracil or inosine) such that the polymer formed can hybridize with a complementary-base target nucleic acid, including target RNA, with high $T_m$, even with oligomers as short as 10-14 bases; the ability of the oligomer to be actively transported into mammalian cells; and the ability of an oligomer:RNA heteroduplex to resist RNAse degradation.

In some embodiments, oligonucleotides employ morpholino-based subunits bearing base-pairing moieties, joined by uncharged linkages, as described above.

c. Internucleotide Linkages

Oligonucleotides connected by an internucleotide bond that refers to a chemical linkage between two nucleoside moieties. Modifications to the phosphate backbone of DNA or RNA oligonucleotides may increase the binding affinity or stability oligonucleotides, or reduce the susceptibility of oligonucleotides nuclease digestion. Cationic modifications, including, but not limited to, diethyl-ethylenediamide (DEED) or dimethyl-aminopropylamine (DMAP) may be especially useful due to decrease electrostatic repulsion between the oligonucleotide and a target. Modifications of the phosphate backbone may also include the substitution of a sulfur atom for one of the non-bridging oxygens in the phosphodiester linkage. This substitution creates a phosphorothioate internucleoside linkage in place of the phosphodiester linkage. Oligonucleotides containing phosphorothioate internucleoside linkages have been shown to be more stable in vivo.

Examples of modified nucleotides with reduced charge include modified internucleotide linkages such as phosphate analogs having achiral and uncharged intersubunit linkages (e.g., Sterchak, E. P. et al., *Organic. Chem.*, 52:4202, (1987)), and uncharged morpholino-based polymers having achiral intersubunit linkages (see, e.g., U.S. Pat. No. 5,034,506), as discussed above. Some internucleotide linkage analogs include morpholidate, acetal, and polyamide-linked heterocycles.

The oligonucleotides can be locked nucleic acids. Locked nucleic acids (LNA) are modified RNA nucleotides (see, for example, Braasch, et al., *Chem. Biol.*, 8(1):1-7 (2001)). LNAs form hybrids with DNA which are more stable than DNA/DNA hybrids, a property similar to that of peptide nucleic acid (PNA)/DNA hybrids. Therefore, LNA can be used just as PNA molecules would be. LNA binding efficiency can be increased in some embodiments by adding positive charges to it. Commercial nucleic acid synthesizers and standard phosphoramidite chemistry are used to make LNAs.

In some embodiments, the oligonucleotides are composed of peptide nucleic acids. Peptide nucleic acids (PNAs) are synthetic DNA mimics in which the phosphate backbone of the oligonucleotide is replaced in its entirety by repeating N-(2-aminoethyl)-glycine units and phosphodiester bonds are typically replaced by peptide bonds. The various heterocyclic bases are linked to the backbone by methylene carbonyl bonds. PNAs maintain spacing of heterocyclic bases that is similar to conventional DNA oligonucleotides, but are achiral and neutrally charged molecules. Peptide nucleic acids are comprised of peptide nucleic acid monomers.

Other backbone modifications include peptide and amino acid variations and modifications. Thus, the backbone constituents of oligonucleotides such as PNA may be peptide linkages, or alternatively, they may be non-peptide peptide linkages. Examples include acetyl caps, amino spacers such as 8-amino-3,6-dioxaoctanoic acid (referred to herein as 0-linkers), amino acids such as lysine are particularly useful if positive charges are desired in the PNA, and the like. Methods for the chemical assembly of PNAs are well known. See, for example, U.S. Pat. Nos. 5,539,082, 5,527,675, 5,623,049, 5,714,331, 5,736,336, 5,773,571 and 5,786,571.

Oligonucleotides optionally include one or more terminal residues or modifications at either or both termini to increase stability, and/or affinity of the oligonucleotide for its target. Commonly used positively charged moieties include the amino acids lysine and arginine, although other positively charged moieties may also be useful. Oligonucleotides may further be modified to be end capped to prevent degradation using a propylamine group. Procedures for 3' or 5' capping oligonucleotides are well known in the art.

The functional nucleic acid can be single stranded or double stranded.

C. Tissue Targeting Ligands, Cell Adhesion Ligands, and Endosomal Uptake Ligands 1. Targeting Moieties The nanoparticles, cargo they contain, or a combination thereof can optionally include a targeting moiety, i.e., a moiety able to bind to or otherwise associate with a biological entity, for example, a membrane component, a cell surface receptor, or a molecule. In one embodiment, the targeting moiety has a specificity (as measured via a disassociation constant) of less than about 1 micromolar, at least about 10 micromolar, or at least about 100 micromolar. Numerous examples of targeting moieties are known, some of which are more selective than others. The ligand can be selected based on the disease to be treated, the target cells, tissue or organ, and the desired delivery strategy (e.g., into a cells or into the extracellular space). The particles or cargo can include two, three, or more targeting moieties. In some embodiments, some polymers of the particle have a targeting moiety attached thereto and others do not. In this way, the density of the targeting moiety on the surface of the particle can be manipulated.

The targeting signal can include a sequence of monomers that facilitates in vivo localization of the molecule. The monomers can be amino acids, nucleotide or nucleoside bases, or sugar groups such as glucose, galactose, and the like which form carbohydrate targeting signals. Exemplary targeting molecules include small molecules, peptides, aptamers, polynucleotides, and antibodies and antigen binding fragments thereof. In certain embodiments, the antibody is polyclonal, monoclonal, linear, humanized, chimeric or a fragment thereof. Representative antibody fragments are those fragments that bind the antibody binding portion such as Fab, Fab', F(ab'), Fv diabodies, linear antibodies, single chain antibodies and bispecific antibodies.

Targeting signals or sequences can be specific for a host, tissue, organ, cell, organelle, non-nuclear organelle, or cellular compartment. For example, in some embodiments the particle or a cargo thereof includes a cell-specific targeting domain, an organelle specific targeting domain to enhance delivery to a subcellular organelle, or a combination thereof. For example, the particle can include targeting moiety that directs the particle to a microenvironment where the cargo is released. A second targeting moiety on the cargo can then enhance delivery to cargo into a target cell or cell(s) in the microenvironment. In some embodiment, the particle includes a moiety that targets it to a tissue, cell or organ, and the cargo includes a moiety that enhances delivery of the cargo to a subcellular location such as an organelle.

General classes and methods of targeting are discussed here, and specific exemplary cell, tissue, organ, and microenvironment specific targets are discussed in more detail and the sections below devoted to therapeutic strategies and in the working Examples.

a. Cell Targeting

The particles, there cargo, or a combination thereof can be modified to target a specific cell type or population of cells.

For example, the particles and cargo can be modified with galactosyl-terminating macromolecules to target the polypeptide of interest to the liver or to liver cells. The modified particles and cargo selectively enters hepatocytes after interaction of the carrier galactose residues with the asialoglycoprotein receptor present in large amounts and high affinity only on these cells.

In some embodiments, the targeting signal binds to its ligand or receptor which is located on the surface of a target cell such as to bring the composition and cell membranes sufficiently close to each other to allow penetration of the composition into the cell.

The targeting molecule can be, for example, an antibody or antigen binding fragment thereof, an antibody domain, an antigen, a T-cell receptor, a cell surface receptor, a cell surface adhesion molecule, a major histocompatibility locus protein, a viral envelope protein and a peptide selected by phage display that binds specifically to a defined cell.

Targeting the particles or cargo to specific cells can be accomplished by modifying the particle or cargo to express specific cell and tissue targeting signals. These sequences target specific cells and tissues. In some embodiments the interaction of the targeting signal with the cell does not occur through a traditional receptor:ligand interaction. The eukaryotic cell comprises a number of distinct cell surface molecules. The structure and function of each molecule can be specific to the origin, expression, character and structure of the cell. Determining the unique cell surface complement of molecules of a specific cell type can be determined using techniques well known in the art.

One skilled in the art will appreciate that the tropism of the particles and cargo can be altered by changing the targeting signal. For example, the compositions can be modified to include cell surface antigen specific antibodies. Exemplary cell surface antigens are disclosed in Wagner et al., *Adv Gen,* 53:333-354 (2005). Tumor antigens discussed in more detail below.

It is known in the art that nearly every cell type in a tissue in a mammalian organism possesses some unique cell surface receptor or antigen. Thus, it is possible to incorporate nearly any ligand for the cell surface receptor or antigen as a targeting signal. For example, peptidyl hormones can be used a targeting moieties to target delivery to those cells which possess receptors for such hormones. Chemokines and cytokines can similarly be employed as targeting signals to target delivery of the complex to their target cells. A variety of technologies have been developed to identify genes that are preferentially expressed in certain cells or cell states and one of skill in the art can employ such technology to identify targeting signals which are preferentially or uniquely expressed on the target tissue of interest i. Brain Targeting The targeting signal can be directed to cells of the nervous system, including the brain and peripheral nervous system. Cells in the brain include several types and states and possess unique cell surface molecules specific for the type. Furthermore, cell types and states can be further characterized and grouped by the presentation of common cell surface molecules.

The targeting signal can be directed to specific neurotransmitter receptors expressed on the surface of cells of the nervous system. The distribution of neurotransmitter receptors is well known in the art and one so skilled can direct the compositions described by using neurotransmitter receptor specific antibodies as targeting signals. Furthermore, given the tropism of neurotransmitters for their receptors, in one embodiment the targeting signal consists of a neurotransmitter or ligand capable of specifically binding to a neurotransmitter receptor.

The targeting signal can be specific to cells of the nervous system which may include astrocytes, microglia, neurons, oligodendrites and Schwann cells. These cells can be further divided by their function, location, shape, neurotransmitter class and pathological state. Cells of the nervous system can also be identified by their state of differentiation, for example stem cells. Exemplary markers specific for these cell types and states are well known in the art and include, but are not limited to CD133 and Neurosphere.

ii. Muscle Targeting

The targeting signal can be directed to cells of the musculoskeletal system. Muscle cells include several types and possess unique cell surface molecules specific for the type and state. Furthermore, cell types and states can be further characterized and grouped by the presentation of common cell surface molecules.

For example, the targeting signal can be directed to specific neurotransmitter receptors expressed on the surface of muscle cells. The distribution of neurotransmitter receptors is well known in the art and one so skilled can direct the compositions described by using neurotransmitter receptor specific antibodies as targeting signals. Furthermore, given the tropism of neurotransmitters for their receptors, in some embodiments the targeting signal consists of a neurotransmitter. Exemplary neurotransmitters expressed on muscle cells that can be targeted include but are not limited to acetycholine and norepinephrine.

The targeting signal can be specific to muscle cells which consist of two major groupings, Type I and Type II. These cells can be further divided by their function, location, shape, myoglobin content and pathological state. Muscle cells can also be identified by their state of differentiation, for example muscle stem cells. Exemplary markers specific for these cell types and states are well known in the art include, but are not limited to MyoD, Pax7 and MR4.

iii. Antibodies

Another embodiment provides an antibody or antigen binding fragment thereof bound to the disclosed proteins of interest acting as the targeting signal. The antibodies or antigen binding fragment thereof are useful for directing the vector to a cell type or cell state. In one embodiment, the polypeptide of interest possesses an antibody binding domain, for example from proteins known to bind antibodies such as Protein A and Protein G from *Staphylococcus aureus*.

In some embodiments, the targeting domain includes all or part of an antibody that directs the vector to the desired target cell type or cell state. Antibodies can be monoclonal or polyclonal, but are preferably monoclonal. For human gene therapy purposes, antibodies are derived from human genes and are specific for cell surface markers, and are produced to reduce potential immunogenicity to a human host as is known in the art. For example, transgenic mice which contain the entire human immunoglobulin gene cluster are capable of producing "human" antibodies can be utilized. In one embodiment, fragments of such human antibodies are employed as targeting signals. In a preferred embodiment, single chain antibodies modeled on human antibodies are prepared in prokaryotic culture.

In preferred embodiments the polypeptide of interest is itself a fusion protein. The fusion protein can include, for example, a polynucleotide-binding polypeptide, a protein transduction domain, and optionally one or more targeting signals. Other exemplary fusion proteins containing a mitochondrial transcription factor polypeptide that are suitable for use as a polypeptide of interest are disclosed in U.S. Pat. Nos. 8,039,587, 8,062,891, 8,133,733.

b. Organelle Targeting

In some embodiments, the particle, cargo, or a combination thereof is modified to target a subcellular organelle. Targeting of the disclosed composition to organelles can be accomplished by modifying the composition to contain specific organelle targeting signals. These sequences can target organelles, either specifically or non-specifically. In some embodiments the interaction of the targeting signal with the organelle does not occur through a traditional receptor:ligand interaction.

The eukaryotic cell comprises a number of discrete membrane bound compartments, or organelles. The structure and function of each organelle is largely determined by its unique complement of constituent polypeptides. However, the vast majority of these polypeptides begin their synthesis in the cytoplasm. Thus organelle biogenesis and upkeep require that newly synthesized proteins can be accurately targeted to their appropriate compartment. This is often accomplished by amino-terminal signaling sequences, as well as post-translational modifications and secondary structure.

Organelles can have single or multiple membranes and exist in both plant and animal cells. Depending on the function of the organelle, the organelle can consist of specific components such as proteins and cofactors. The composition delivered to the organelle can enhance or inhibit to the functioning of the organelle. Exemplary organelles include the nucleus, mitochondrion, chloroplast, lysosome, peroxisome, Golgi, endoplasmic reticulum, and nucleolus. Some organelles, such as mitochondria and chloroplasts, contain their own genome. Nucleic acids are replicated, transcribed, and translated within these organelles. Proteins are imported and metabolites are exported.

There can be an exchange of material across the membranes of organelles. Synthetic organelles can be formed from lipids and can contain specific proteins within the lipid membranes. Additionally, the content of synthetic organelles can be manipulated to contain components for the translation of nucleic acids.

In certain embodiments the particle, the cargo, or a combination thereof specifically target mitochondria. Mitochondria contain the molecular machinery for the conversion of energy from the breakdown of glucose into adenosine triphosphate (ATP). The energy stored in the high energy phosphate bonds of ATP is then available to power cellular functions. Cells with high metabolic activity, such as heart muscle, have many well developed mitochondria.

Mitochondrial targeting agents can include a sequence of highly positively charged amino acids. This allows the protein to be targeted to the highly negatively charged mitochondria. Unlike receptor:ligand approaches that rely upon stochastic Brownian motion for the ligand to approach the receptor, such targeting signals are drawn to mitochondria because of charge. Therefore, in some embodiments, the mitochondrial targeting agent is a protein transduction domain including but not limited to the protein transduction domains discussed in more detail below.

Mitochondrial targeting agents also include short peptide sequences (Yousif, et al., *Chembiochem.,* 10(13):2131 (2009)), for example, mitochondrial transporters-synthetic cell-permeable peptides, also known as mitochondria-penetrating peptides (MPPs), that are able to enter mitochondria. MPPs are typically cationic, but also lipophilic; this combination of characteristics facilitates permeation of the hydrophobic mitochondrial membrane. For example, MPPs can include alternating cationic and hydrophobic residues (Horton, et al., *Chem Biol.,* 15(4):375-82 (2008)). Some MPPs include delocalized lipophilic cations (DLCs) in the peptide sequence instead of, or in addition to natural cationic amino acids (Kelley, et al., *Pharm. Res.,* 2011 Aug. 11 [Epub ahead of print]). Other variants can be based on an oligomeric carbohydrate scaffold, for example attaching guanidinium moieties due to their delocalized cationic form (Yousif, et al., *Chembiochem.,* 10(13):2131 (2009).

Mitochondrial targeting agents also include mitochondrial localization signals or mitochondrial targeting signals. Many mitochondrial proteins are synthesized as cytosolic precursor proteins containing a leader sequence, also known as a presequence, or peptide signal sequence. Many sequences are known in the art, see for example, U.S. Pat. No. 8,039,587. The identification of the specific sequences necessary for translocation of a linked compound into a mitochondrion can be determined using predictive software known to those skilled in the art.

In some embodiments the target moiety directs the composition to the nucleus. Nuclear localization signals (NLS) or domains are known in the art and include for example, SV 40 T antigen or a fragment thereof. The NLS can be simple cationic sequences of about 4 to about 8 amino acids, or can be bipartite having two interdependent positively charged clusters separated by a mutation resistant linker region of about 10-12 amino acids.

2. Endosomal Escape and Membrane Penetration

In some embodiments, the particles, cargo, or a combination thereof additionally or alternatively include a moiety that enhances escape from endosomes or macropinosomes. In some embodiments, particles enter cells through endocytosis and are entrapped in endosomes. These early endosomes subsequently fuse with sorting endosomes, which in turn transfer their contents to the late endosomes. Late endosomal vesicles are acidified (pH 5-6) by membrane-bound proton-pump ATPases. If the particles are not released from the endosome, for example, by pH-induced degradation and the associated "sponge" effect as discussed in more detail below, the endosomal content can be relocated to the lysosomes, which are further acidified (pH~4.5) and contain various nucleases that promote the degradation of nucleic acids. To avoid lysosomal degradation of cargo, particularly nucleic acid cargo, the particle including the cargo, or the cargo itself (following release from the particle) escapes from the endosome into the cytosol. This is particularly preferred for mRNA and functional nucleic acid cargos which may rely on cytosolic cellular machinery for their activity.

Strategies to promote endosomal release are known in the art, and include, for example, the use of fusogenic lipids, polymers with high buffering capacity and membrane-interacting peptides (exemplary strategies are reviewed in Dominska and Dykxhoom, *J Cell Sci,* 123: 1183-1189 (2010)). In particularly preferred embodiments, the endosomal escape sequence is a membrane interacting peptide. In some embodiments, the endosomal escape sequence is a protein transduction domain. Thus in some embodiments the endosomal escape sequence is part of, or consecutive with, the protein transduction domain. In some embodiments, the endosomal escape sequence is non-consecutive with the protein transduction domain or provided in the absence of a protein transduction domain. In some embodiments the endosomal escape sequence includes a portion of the hemagglutinin peptide from influenza (HA).

Examples of endosomal escape sequences are known in the art. See, for example, WO 2013/103972. Hatakeyama, et al., have described a fusogenic PEG-peptide-DOPE (PPD) construct and a pH-sensitive fusogenic GALA peptide (Hatakeyama, et al., *J Control. Release* 139, 127-132 (2009)) and that PPD constructs can be cleaved by matrix metalloproteinases that are specifically secreted by cancer cells, enhancing the delivery of siRNA complexed with this carrier to tumor cells (Hatakeyama, et al., *Gene Ther.,* 14, 68-77 (2007)).

Another membrane-destabilization mechanism takes advantage of the pore-forming ability of viroporins, highly hydrophobic proteins that create channels and facilitate ion flow across biological membranes (Gonzalez and Carrasco, *FEBS Lett.* 552, 28-34 (2003)). For example, peptides derived from the endodomain of the HIV gp41 envelope glycoprotein (sequence corresponding to residues 783-806 of gp160) form pores in the cell membrane by adopting an amphipathic α-helical structure (Costin et al., *Virol. J.,* 4:123 (2007)) and (Kwon et al., *Bioconjugate Chem.,* 19, 920-927 (2008)).

The influenza-derived fusogenic peptide diINF-7 has also been shown to enhance endosomal release (Oliveira et al., *Int. J Pharm.* 331, 211-214 (2007)).

3. Protein Transduction Domains

The particles, any of the active agents, but particularly protein and nucleic acid agents, or a combination thereof can include a protein transduction domain to improve delivery of the active agent across extracellular membranes, intracellular membranes, or the combination thereof. As used herein, a "protein transduction domain" or PTD refers to a polypeptide, polynucleotide, carbohydrate, organic or inorganic compound that facilitates traversing a lipid bilayer, micelle, cell membrane, organelle membrane, or vesicle membrane. A PTD attached to another molecule facilitates the molecule traversing membranes, for example going from extracellular space to intracellular space, or cytosol to within an organelle.

The protein transduction domain can be a polypeptide. A protein transduction domain can be a polypeptide including positively charged amino acids. Thus, some embodiments include PTDs that are cationic or amphipathic. Protein transduction domains (PTD), also known as a cell penetrating peptides (CPP), are typically polypeptides including positively charged amino acids. PTDs are known in the art, and include but are not limited to small regions of proteins that are able to cross a cell membrane in a receptor-independent mechanism (Kabouridis, P., Trends in Biotechnology (11):498-503 (2003)). Although several PTDs have been documented, the two most commonly employed PTDs are derived from TAT (Frankel and Pabo, *Cell,* 55(6):1189-93(1988)) protein of HIV and Antennapedia transcription factor from *Drosophila*, whose PTD is known as Penetratin (Derossi et al., *J Biol Chem.,* 269(14):10444-50 (1994)). Exemplary protein transduction domains include polypeptides with 11 Arginine residues, or positively charged polypeptides or polynucleotides having 8-15 residues, preferably 9-11 residues. The Antennapedia homeodomain is 68 amino acid residues long and contains four alpha helices. See Derossi, *JBC,* 1994, 269, 10444) which provides Antp peptide. Oligoarginine is another preferred PTA (8 arginines) (Goun et al *Bioconjugate Chem.* 2006, 17, 787)). Penetratin is an active domain of this protein which consists of a 16 amino acid sequence derived from the third helix of Antennapedia. TAT protein consists of 86 amino acids and is involved in the replication of HIV-1 (Vives, et al., *JBC,* 1997, 272, 16010)) of the parent protein that appears to be critical for uptake. TAT has been favored for fusion to proteins of interest for cellular import. Several modifications to TAT, including substitutions of Glutamine to Alanine, i.e., Q>A, have demonstrated an increase in cellular uptake anywhere from 90% (Wender et al., *Proc Natl Acad Sci USA.,* 97(24):13003-8 (2000)) to up to 33 fold in mammalian cells. (Ho et al., *Cancer Res.,* 61(2):474-7 (2001)).

4. Linkers

In different embodiments, the hydrophilic portion of the polymer can be connected to the hydrophobic portion by a cleavable linker, the diagnostic, therapeutic or prophylactic agent may be connected to the amphiphilic polymer by a cleavable linker, and/or the targeting moiety may be connected to the amphiphilic polymer by a cleavable linker. The linker may be hydrolyzed by a chemical or enzymatic process. Preferably, the linker is cleaved by hydrogen peroxide, which is produced at sites of inflammation or areas of high neutrophil concentration, thereby increasing the selectivity of the nanoparticles. For example, the linker may be hydrolyzed by a chemical or enzymatic process.

5. Exemplary Design Strategy

It will be appreciated that the stimuli-response particles and cargo each optionally including targeting moiety, protein transduction moieties, linkers, and other elements described herein are modular in nature and can be utilized in various combinations as selected by the user based on the intended use. Preferred uses and therapeutic strategies include, but are not limited to, those described in more detail below. Exemplary particles loaded with exemplary cargo and optionally including exemplary targeting and membrane escape elements are provided in, but not limited by the working Examples below. For example, in one non-limiting design strategy exemplified in Example 1, after encapsulating the agent(s) to be delivered, the resulting delivery system shows four unique features (FIG. 1C):

i) the surface-encoded iRGD peptide endows the NPs with tumor-targeting and tumor-penetrating abilities;
ii) the hydrophilic PEG shells prolong the blood circulation;

iii) a small population of cationic lipid-like grafts randomly dispersed in the hydrophobic poly(2-(diisopropylamino) ethylmethacrylate) (PDPA) segment can entrap siRNA in the hydrophobic cores of the NPs; and iv) the rapid protonation of the ultra pH-responsive PDPA segment induces the endosomal swelling via the "proton sponge" effect, which synergizes with the insertion of the cationic lipid-like grafts into endosomal membrane to induce membrane destabilization (Zhu X et al., *Proceedings of the National Academy of Sciences,* 112, 7779-7784 (2015)) and efficient endosomal escape.

III. Nanoparticle Formation

The nanoparticles are typically formed using an emulsion process, single or double, using an aqueous and a non-aqueous solvent. Typically, the nanoparticles contain a minimal amount of the non-aqueous solvent after solvent removal. Preferred methods of preparing these nanoparticles are described in the examples.

In one embodiment, nanoparticles are prepared using emulsion solvent evaporation method. A polymeric material is dissolved in a water immiscible organic solvent and mixed with a drug solution or a combination of drug solutions. The water immiscible organic solvent is preferably a GRAS ingredient such as chloroform, dichloromethane, and acyl acetate. The drug can be dissolved in, but is not limited to, one or a plurality of the following: acetone, ethanol, methanol, isopropyl alcohol, acetonitrile and Dimethyl sulfoxide (DMSO). An aqueous solution is then added into the resulting mixture solution to yield emulsion solution by emulsification. The emulsification technique can be, but not limited to, probe sonication or homogenization through a homogenizer.

In another embodiment, nanoparticles are prepared using nanoprecipitation methods or microfluidic devices. A polymeric material is mixed with a drug or drug combinations in a water miscible organic solvent. The water miscible organic solvent can be one or more of the following: acetone, ethanol, methanol, isopropyl alcohol, acetonitrile and Dimethyl sulfoxide (DMSO). The resulting mixture solution is then added to an aqueous solution to yield nanoparticle solution. The agents may be associated with the surface of, encapsulated within, surrounded by, and/or distributed throughout the polymeric matrix of the particles.

In another embodiment, nanoparticles are prepared by the self-assembly of the amphiphilic polymers, optionally including hydrophilic and/or hydrophobic polymers, using emulsion solvent evaporation, a single-step nanoprecipitation method, or microfluidic devices.

Two methods to incorporate targeting moieties into the nanoparticles include: i) conjugation of targeting ligands to the hydrophilic region (e.g. PEG) of polymers prior to nanoparticle preparation; and ii) incorporation of targeting molecules into nanoparticles where the PEG layer on the nanoparticle surface can be cleaved in the presence of a chemical or enzyme at tissues of interest to expose the targeting molecules.

The diameters of the nanoparticles range between about 50 nm and about 500 nm, preferably between about 50 nm and about 350 nm. In some embodiments, the diameters of the nanoparticles are about 100 nm. The zeta potential of the nanoparticles ranges between about −50 mV and about +50 mV, preferably between about −25 mV and +25 mV, most preferably between about −10 mV and about +10 mv.

IV. Formulations and Methods of Administration

A. Formulations

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes but is not limited to diluents, binders, lubricants, desintegrators, fillers, and coating compositions.

Pharmaceutical compositions can be for administration by parenteral (intramuscular, intraperitoneal, intravenous (IV) or subcutaneous injection), routes of administration and can be formulated in dosage forms appropriate for each route of administration. The compositions are most typically administered systemically.

Compounds and pharmaceutical compositions thereof can be administered in an aqueous solution, by parenteral injection. The formulation may also be in the form of a suspension or emulsion. In general, pharmaceutical compositions are provided including effective amounts of the active agent(s) and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives. Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

Preferably, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7.

Rapid escape and protection from the endosomal degradation can been achieved by the inclusion of fusogenic lipids such as 1,2-dioleoyl-sn-glycero-3-phosphoethanolamine (DOPE) in pH-sensitive and cationic liposome delivery systems. DOPE is a helper lipid capable of disrupting the endosomal membrane upon endosomal acidification by the formation of lipid hexagonal phases. Endosomal membrane disruption can release the DNA-based therapeutic and its delivery system into the cytoplasm. Lysosomatropic agents such as monensin and chloroquine, which raise the endosomal pH, block acidification, and thus inhibit lysozyme activity, have also been used to facilitate endosomal release of DNA. Endosomal degradation of DNA-based therapeutics can also be circumvented by the incorporation of viral peptides such as hemagglutinin HA2 and those derived from adenoviruses in their delivery systems. Hemagglutinin HA2 undergoes conformational transition and leads to the destruction of the endosome, thereby facilitating the release of the DNA-based therapeutic. Enhanced rapid endosomal escape and enhanced transfection have also been achieved using fusogenic peptides such as poly(L-lysine) (PLL) and cationic polymers such as polyethylenimine (PEI) and dendrimers.

Active agent(s) and compositions thereof can be formulated for pulmonary or mucosal administration. The administration can include delivery of the composition to the lungs, nasal, oral (sublingual, buccal), vaginal, or rectal mucosa. In a particular embodiment, the composition is formulated for and delivered to the subject sublingually.

In one embodiment, the compounds are formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The deep lung, or alveoli, is the primary target of inhaled therapeutic aerosols for systemic drug delivery.

Pulmonary administration of therapeutic compositions comprised of low molecular weight drugs has been observed, for example, beta-androgenic antagonists to treat asthma. Other therapeutic agents that are active in the lungs have been administered systemically and targeted via pulmonary absorption. Nasal delivery is useful for administration of therapeutics since the nose has a large surface area available for drug absorption due to the coverage of the epithelial surface by numerous microvilli, the subepithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per $cm^3$, porous endothelial basement membrane, and it is easily accessible.

The term aerosol as used herein refers to any preparation of a fine mist of particles, which can be in solution or a suspension, whether or not it is produced using a propellant. Aerosols can be produced using standard techniques, such as ultrasonication or high-pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

B. Methods of Administration

Suitable parenteral administration routes include intravascular administration (e.g., intravenous bolus injection, intravenous infusion, intra-arterial bolus injection, intra-arterial infusion and catheter instillation into the vasculature); peri- and intra-tissue injection (e.g., intraocular injection, intraretinal injection, or sub-retinal injection); subcutaneous injection or deposition including subcutaneous infusion (such as by osmotic pumps); direct application by a catheter or other placement device (e.g., an implant comprising a porous, non-porous, or gelatinous material).

The formulation can be administered in a single dose or in multiple doses. Certain factors may influence the dosage required to effectively treat a subject, including but not limited to the severity of the disease or disorder, previous treatments, the general health and/or age of the subject, and other diseases present. It will also be appreciated that the effective dosage of the oligonucleotide used for treatment may increase or decrease over the course of a particular treatment. Changes in dosage may result and become apparent from the results of diagnostic assays.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual polynucleotides, and can generally be estimated based on EC50s found to be effective in vitro and in vivo animal models.

Dosage levels on the order of about 1 mg/kg to 100 mg/kg of body weight per administration are useful in the treatment of a disease. One skilled in the art can also readily determine an appropriate dosage regimen for administering the disclosed polynucleotides to a given subject. For example, the formulation can be administered to the subject once, e.g., as a single injection, infusion or bolus. Alternatively, the formulation can be administered once or twice daily to a subject for a period of from about three to about twenty-eight days, or from about seven to about ten days.

V. Biomedical Applications and Therapeutic Strategies

Biomedical application of nanoparticles has introduced exciting opportunities for the improvement of disease diagnosis and treatment. Stimuli-responsive nanoparticles, which can undergo shape, structure and property change upon encountering endogenous or exogenous stimuli, can be used in diverse range of biomedical applications, such as drug controlled release, nucleic acid delivery, imaging, and diagnostics. The stimuli-responsive characteristic provides spatiotemporal control over the macroscopic properties of the nanoparticles, and thus the release of the encapsulated cargo can occur directly at the desired site, minimizing toxic and side effects in surrounding, healthy tissue. Dissociation of the particle and release of its cargo, can be driven by, for example, pH-, redox-, light-, temperature-, enzyme-, or ultrasound-responsive polymers composing the particles.

The stimuli that drive a response by the particle can be present within a cell (e.g., intracellularly) or outside cells in the extracellular microenvironment, or can be an external stimuli for example, light, heat, ultrasound, etc., which can be applied by the user to the target site. The particles can optionally include a targeting moiety or ligand. For embodiments in which intracellular release is desired, the targeting moiety or ligand is typically one that preferentially binds to the surface of a target cell and induces or allows the particle to be absorbed or internalized by, for example, endocytosis or micropinocytosis (Vranic et al., *Particle and Fibre Toxicology,* 10(2):(12 page) (2013)). For embodiments in which extracellular release is desired, the targeting moiety or ligand can be one that preferentially binds to an extracellular target in the desired microenvironment.

A. Exemplary Environments for Selective Delivery

1. Acidic Environment pH responsive nanoparticles can be used to target tissues with acidic extracellular pH. Although the nanoparticles can optionally include a cell, tissue, organ, or extracellular matrix-specific targeting moiety or ligand, a targeting moiety or ligand is not requirement. The pH responsive nanoparticles can be designed to have spherical morphology at a pH above pKa to protect cargo during systemic circulation and infiltration into tissues with extracellular pH at or around neutral or physiological pH. The particles can dissociate at a pH below pKa, releasing its cargo into the microenvironment. In this way, the particles selectively release their cargo at the target site.

pH responsive nanoparticles can also be used to deliver cargo into cells. Particles, preferable with a targeting moiety or ligand, can bind to a target cell and be absorbed or internalized. Upon encountering an acidic intracellular environment such as that of endosomes, the pH responsive particles can dissociate and release their cargo. The particles can also optionally include a moiety that enhances endosomal escape, such as oligoarginine. As illustrated in the working Examples below, particle dissociation within the endosome is believe to induce swelling of the endosome via “sponge” effect, thus achieving fast and high efficacy delivery of their cargo into the cytosol. Using an intracellular endosomal-release strategy, virtually any cell with endosomes (or another equivalently acidic intracellular environment, compartment, or organelle) can be the target cell. The addition of a targeting moiety can be used to accomplish selective delivery of the particle into target cells over non-target cells. pH responsive intracellular release can be most effective when the extracellular pH does not induce nanoparticle dissociation thus allowing the particles to absorbed or internalized by cells.

In some embodiments, cargo is released below physiological pH (e.g., 7.4, or 7.2), or below neutral pH (e.g., 7.0), or in a pH range of about 5.8 to about 7.3, or about 5.8 to about 6.9, or about 6.0 to about 6.5, or about 6.5 to about 6.9.

2. Temperature

In embodiments, cargo release is driven by a change in temperature. In the biomedical setting, a change in temperature will can be an increase or decrease from the physiological temperature of the subject being treated. Normal human body temperature, also referred to as normothermia or euthermia, depends upon the place in the body at which the measurement is made, the time of day, as well as the activity level of the person. Typically values for oral measurement (under the tongue) are 36.8±0.4° C. (98.2±0.72° F.) and internal (rectal, vaginal) measurement are 37.0° C. (98.6° F.) (*Harrison's Principles of Internal Medicine,* 18e, Longo, Editor, Fauci, et al., Editor, Kasper). Human temperature classifications can be, for example, Hypothermia<35.0° C. (95.0° F.); Normal 36.5-37.5° C. (97.7-99.5° F.), Fever>37.5 or 38.3° C. (99.5 or 100.9° F.), Hyperthermia>37.5 or 38.3° C. (99.5 or 100.9° F.), Hyperpyrexia>40.0 or 41.5° C. (104.0 or 106.7° F.). The particles can be designed for release within one or more of these temperature classifications, or a sub-range thereof. It will be appreciated that a subject's normal body temperature can fluctuate, for example, with the time of day, sleep vs. wake, eating vs. fasting, exercise, the amount of clothing being worn, the ambient temperature, the anxiety or excitement level of the subject, etc., as is known in the art. The particles can be tuned for release when body temperature drops below or exceeds a predetermined threshold, and therefore selectively release cargo during certain times of the day or night, caloric intake (or lack thereof), during exercise, anxiety, etc. The release can be local so systemic.

In addition of more global changes in overall body temperature, such as those introduced above, the particles can be tuned for release at sites of local temperature changes. For example, local, tissue-specific increase in tissue temperature can occur at sites of inflammation, injury, infection, and cancer (e.g., tumor) (Chapter Nine, *Inflammation, Tissue Repair, and Fever*, pages 150-167). The change in temperature can be relative to unaffected tissue and may occur in the presence or absence of a global change in body temperature.

3. Reduction-Oxidation (Redox)

The release of nanoparticle cargo can be induced by a reduction-oxidation (“redox”) reaction. In some embodiments, the polymers composing the particles include one or more disulfide bonds. The particles can release their cargo when disulfide bond is reduced upon exposure to a reducing agent. In some embodiments, the reducing agent is a glutathione. L-Glutathione (GSH) is a tripeptide molecule that can also act as an antioxidant. In cells, GSH reduces the disulfide bonds formed within cytoplasmic proteins to cysteines and reacts to other oxidized GSH to an oxidized form of glutathione disulfide (GSSG), also called L(−)-glutathione (Traverso, et al., *Oxidative Medicine and Cellular Longevity*, Volume 2013 (2013), Article ID 972913, 10 pages). As discussed in more detail below, intracellular levels of glutathione (GSH) are 100-1000 fold higher in cancer cells than in normal tissue, and thus redox-sensitive particles can be used to selective release cargo in cells with higher-than-normal GSH, such as cancer cells. For example, one study showed that intracellular GHS levels in normal lung cells were about 11.20±0.58 (SEM) nmol GSH/mg protein (24 patients) with a range from 6.1 to 17.5 nmol GSH/mg protein, while GHS level in adenocarcinomas was 8.83±0.96 nmol/mg protein (8 patients); large cell carcinomas was 8.25±2.51 nmol/mg protein (3 patients); and squamous cell carcinomas 23.25±5.99 nmol/mg protein (8 patients) (Cook, et al., *Cancer Research,* 51:4287-4294 (1991).

The Examples below show that cargo can be released redox-sensitive particles in matter of minutes in the presences of 10 nM GSH.

In some embodiments, the reducing agent is not endogenous to the cell, tissue, organ, or other microenvironment. For example, in some embodiments, the reducing agent is administered locally or systemically to trigger release of the cargo from the particles in a local or systemic fashion.

In addition to GSH, other reducing agents can also induce release of the cargo, however, it will be appreciated that in some embodiments, the use, or the amount that can be used, of certain reducing agents is limited in biological and therapeutic applications by their toxicity.

4. External Stimuli

As introduced above, release of nanoparticle cargo can be induced by external stimuli, such as light, temperature, or ultrasound. The stimuli can be applied globally, for example to the entire subject, or preferably to a more limited or local aspect thereof. For example, light, heat (or cold), or ultrasound can be administered to a specific tissue(s), location(s), or combination thereof to modulate selective release of cargo from particles accumulating or passing through the targeted tissue or location. For example, heat (or cold) can be applied to the target tissue or location to cause a local temperature shift that induces dissociation of the particle and release of its cargo. Radiation at different frequencies along the electromagnetic spectrum can also be used to release cargo. For example, particles can be formed that are sensitive to ionizing radiation, visible light, microwaves, or radiowaves. In particular embodiments, the particles are sensitive to visible light (e.g., near ultraviolet, near infrared, mid infrared, far infrared). Particles can also be formed that are sensitive to sound waves. For example, in particular embodiments, the particles release cargo in response to ultrasound.

In particular embodiments, the particles are sensitive to ultraviolet light. Ultraviolet (UV) light is an electromagnetic radiation with a wavelength shorter than that of visible light but longer than X-rays. The wavelength of UV light is typically from about 400 nm (750 THz) to about 10 nm (30 PHz). UV radiation can be divided into five categories: UV-A is about 320-400 nm, UV-B is 290-320 nm, UV-C is 220-209 nm, Far UV is 190-220 nm, and vacuum UV 40-190 nm. In some embodiments, the particles are sensitive to UV-A, UV-B, UV-C, or a combination thereof. The Examples below illustrate that particles can be formed that the release their cargo after exposure to UV light, for example 365 nm UV light (16 W), for different time periods. In some embodiments, the source provides a specific desired wavelength. In some embodiments, the source provides a range of wavelength.

The external stimuli can be provided by the practitioner using, for example, a piece of equipment that provides the stimuli. The stimuli can also be provided by the environment and may or may not be under the control of practitioner or user. For example, the sun generates visible light, heat, and UV radiation. Thus, in some embodiments, the particles are designed to release their cargo in response to the sun.

Exposure to external stimuli can be carried out over minutes, hours, days or weeks. In some embodiments, the exposure is between about 1 and about 120 minutes, for example, 10, 15, 30, 45, 60, 90, or 120 minutes. In some embodiments, the exposure is between about 1 and 48 hours, for example, 1, 2, 3, 4, 5, 10, 12.5, 15, 20, 24, 36, or 48 hours. In some embodiments, the exposure is over two or more days.

B. Preferred Tissues to Target and Therapeutic Strategies

As discussed above, the particles can be used to selectively target cells, tissues, organs, or microenvironments thereof. The selective release of cargo at a target site can be used in strategies to treat a variety of diseases and disorders. Suitable methods can include administering a subject an effective amount of nanoparticles containing a therapeutic cargo to reduce or alleviate one or more symptoms of the disease or disorder to be treated. The disclosed strategies can include targeting certain intracellular and/or extracellular environments for selective release based on response-inducing stimuli alone, or in combination with one or more targeting moieties that enhance delivery to a desired cell type, tissue, organ, microenvironment, subcellular organelle, or a combination thereof.

1. Tumor Targeting

Methods of treating cancer are provided. The nanoparticles can be designed, for example, for release in the tumor microenvironment or within a tumor cells, or in an immune response microenvironment or within an immune cell. Suitable methods can include administering a subject an effective amount of nanoparticles containing a therapeutic cargo to reduce or alleviate one or more symptoms of the cancer. The effect of the particles on the cancer can be direct or indirect. The compositions and methods described herein are useful for treating subjects having benign or malignant tumors by delaying or inhibiting the growth of a tumor in a subject, reducing the growth or size of the tumor, inhibiting or reducing metastasis of the tumor, and/or inhibiting or reducing symptoms associated with tumor development or growth.

The tumor microenvironment is the cellular environment in which the tumor exists, and can include surrounding blood vessels, immune cells, fibroblasts, bone marrow-derived inflammatory cells, lymphocytes, signaling molecules, and the extracellular matrix (ECM). The tumor and the surrounding microenvironment are closely related and interact constantly. Tumors can modulate the microenvironment by releasing extracellular signals, promoting tumor angiogenesis and inducing peripheral immune tolerance, while the immune cells in the microenvironment can affect the growth and evolution of cancerous cells. The microenvironment in tumor tissue is different from the normal tissues. Thus, in some embodiments, the stimuli-responsive polymers are design to trigger the structural changes in response to stimuli that is unique to the tumor microenvironment including but not limited to temperature, pH, ionic strength, composition/organization of the extracellular matrix (ECM), over-expressed molecules or enzymes, and hypoxia.

Compared to normal tissues, the pH in tumor tissue is more acidic, the tissue temperature is relatively higher, oxygen concentrations are reduced (hypoxia), and some specific enzymes or chemicals are over-expressed. Hypoxia is an important characteristic of the tumor microenvironment commonly found in cancers and a selection force for the glycolytic phenotype. Thus, in some embodiments, hypoxia-responsive stimula are used to selectively delivery cargo to an acidic tumor microenvironment. For example, a hydrophobically modified 2-nitroimidazole derivative conjugated to the backbone of the carboxymethyl dextran described to target hypoxia (Thambi T et al., *Biomaterials.* 2014 February; 35(5):1735-43) can be used with the nanoparticles.

The interstitial fluid of tumors and abscesses also has shown pH values of less than 6.0, averaging 0.2-0.6 units lower than mean extracellular pH of normal tissues (Kraus and Wolf, *Tumour Biol,* 17, 133-154 (1996)). Tumors commonly have an extracellular environment with a pH in the range of, for example, 6.5-6.9. See, for example, Balkwill, et al., *Journal of Cell Science,* 125(23):5591-6 (2012) and Kato, et al., *Cancer Cell International,* 13(89) (8 pages) (2013). Thus, in some embodiments, pH-sensitive nanoparticles are used to selectively deliver cargo to an acidic tumor microenvironment.

Tumors can also have elevated temperatures relative to the surround or otherwise normal or non-malignant tissue (see, e.g., Stefanadis, *JCO,* 19(3):676-681 (2001)). Therefore, temperature-responsive particles can also be utilized to selectively target tumors.

The intracellular levels of glutathione (GSH) are 100-1000 fold higher in cancer cells than in normal tissue. Redox-sensitive approach is particularly promising to enhance the exposure of cancer cells to therapeutic molecules. Thus, in some embodiments, redox-responsive particles can also be utilized for delivering cargo to tumor cells.

a. Tumor Targeting Moieties

In addition or alternative to selectively targeting cancer cells by targeting an acidic microenvironment, or one with an elevated temperature, cancer cells or their microenvironment can be specifically targeted relative to healthy or normal cells by including a targeting moiety. Tumor or tumor-associated neovasculature targeting domains can be ligands that bind to cell surface antigens or receptors that are specifically expressed on tumor cells or tumor-associated neovasculature or microenvironment, or are overexpressed on tumor cells or tumor-associated neovasculature or microenvironment as compared to normal tissue. Tumors also secrete a large number of ligands into the tumor microenvironment that affect tumor growth and development. Receptors that bind to ligands secreted by tumors, including, but not limited to growth factors, cytokines and chemokines, including the chemokines provided below, can also be used. Ligands secreted by tumors can be targeted using soluble fragments of receptors that bind to the secreted ligands. Soluble receptor fragments are fragments polypeptides that may be shed, secreted or otherwise extracted from the producing cells and include the entire extracellular domain, or fragments thereof. In some embodiments, the targeting moiety is an antibody, for example a single chain antibody, the binds to the target.

i. Cancer Antigens

Cancer antigens that can be targeted are well known in the art. The antigen expressed by the tumor may be specific to the tumor, or may be expressed at a higher level on the tumor cells as compared to non-tumor cells. Antigenic markers such as serologically defined markers known as tumor associated antigens, which are either uniquely expressed by cancer cells or are present at markedly higher levels (e.g., elevated in a statistically significant manner) in subjects having a malignant condition relative to appropriate controls, are contemplated for use in certain embodiments.

Tumor-associated antigens may include, for example, cellular oncogene-encoded products or aberrantly expressed proto-oncogene-encoded products (e.g., products encoded by the neu, ras, trk, and kit genes), or mutated forms of growth factor receptor or receptor-like cell surface molecules (e.g., surface receptor encoded by the c-erb B gene). Other tumor-associated antigens include molecules that may be directly involved in transformation events, or molecules that may not be directly involved in oncogenic transformation events but are expressed by tumor cells (e.g., carcinoembryonic antigen, CA-125, melonoma associated antigens, etc.) (see, e.g., U.S. Pat. No. 6,699,475; Jager, et al., Int. J. Cancer, 106:817-20 (2003); Kennedy, et al., Int. Rev. Immunol., 22:141-72 (2003); Scanlan, et al. Cancer Immun., 4:1 (2004)).

Genes that encode cellular tumor associated antigens include cellular oncogenes and proto-oncogenes that are aberrantly expressed. In general, cellular oncogenes encode products that are directly relevant to the transformation of the cell, and because of this, these antigens are particularly preferred targets for anticancer therapy. An example is the tumorigenic neu gene that encodes a cell surface molecule involved in oncogenic transformation. Other examples include the ras, kit, and trk genes. The products of proto-oncogenes (the normal genes which are mutated to form oncogenes) may be aberrantly expressed (e.g., overexpressed), and this aberrant expression can be related to cellular transformation. Thus, the product encoded by proto-oncogenes can be targeted. Some oncogenes encode growth factor receptor molecules or growth factor receptor-like molecules that are expressed on the tumor cell surface. An example is the cell surface receptor encoded by the c-erbB gene. Other tumor-associated antigens may or may not be directly involved in malignant transformation. These antigens, however, are expressed by certain tumor cells and may therefore provide effective targets. Some examples are carcinoembryonic antigen (CEA), CA 125 (associated with ovarian carcinoma), and melanoma specific antigens.

In ovarian and other carcinomas, for example, tumor associated antigens are detectable in samples of readily obtained biological fluids such as serum or mucosal secretions. One such marker is CA125, a carcinoma associated antigen that is also shed into the bloodstream, where it is detectable in serum (e.g., Bast, et al., *N. Eng. J. Med.,* 309:883 (1983); Lloyd, et al., *Int. J. Canc.,* 71:842 (1997). CA125 levels in serum and other biological fluids have been measured along with levels of other markers, for example, carcinoembryonic antigen (CEA), squamous cell carcinoma antigen (SCC), tissue polypeptide specific antigen (TPS), sialyl TN mucin (STN), and placental alkaline phosphatase (PLAP), in efforts to provide diagnostic and/or prognostic profiles of ovarian and other carcinomas (e.g., Sarandakou, et al., *Acta Oncol.,* 36:755 (1997); Sarandakou, et al., *Eur. J Gynaecol. Oncol.,* 19:73 (1998); Meier, et al., *Anticancer Res.,* 17(4B):2945 (1997); Kudoh, et al., *Gynecol. Obstet. Invest.,* 47:52 (1999)). Elevated serum CA125 may also accompany neuroblastoma (e.g., Hirokawa, et al., *Surg. Today,* 28:349 (1998), while elevated CEA and SCC, among others, may accompany colorectal cancer (Gebauer, et al., *Anticancer Res.,* 17(4B):2939 (1997)).

The tumor associated antigen, mesothelin, defined by reactivity with monoclonal antibody K-1, is present on a majority of squamous cell carcinomas including epithelial ovarian, cervical, and esophageal tumors, and on mesotheliomas (Chang, et al., *Cancer Res.,* 52:181 (1992); Chang, et al., *Int. J. Cancer,* 50:373 (1992); Chang, et al., *Int. J. Cancer,* 51:548 (1992); Chang, et al., *Proc. Natl. Acad. Sci.*

*USA,* 93:136 (1996); Chowdhury, et al., *Proc. Natl. Acad. Sci. USA,* 95:669 (1998)). Using MAb K-1, mesothelin is detectable only as a cell-associated tumor marker and has not been found in soluble form in serum from ovarian cancer patients, or in medium conditioned by OVCAR-3 cells (Chang, et al., *Int. J Cancer,* 50:373 (1992)). Structurally related human mesothelin polypeptides, however, also include tumor-associated antigen polypeptides such as the distinct mesothelin related antigen (MRA) polypeptide, which is detectable as a naturally occurring soluble antigen in biological fluids from patients having malignancies (see WO 00/50900).

A tumor antigen may include a cell surface molecule. Tumor antigens of known structure and having a known or described function, include the following cell surface receptors: HER1 (GenBank Accession No. U48722), HER2 (Yoshino, et al., *J. Immunol.,* 152:2393 (1994); Disis, et al., Canc. Res., 54:16 (1994); GenBank Acc. Nos. X03363 and M17730), HER3 (GenBank Acc. Nos. U29339 and M34309), HER4 (Plowman, et al., *Nature,* 366:473 (1993); GenBank Acc. Nos. L07868 and T64105), epidermal growth factor receptor (EGFR) (GenBank Acc. Nos. U48722, and K03193), vascular endothelial cell growth factor (GenBank No. M32977), vascular endothelial cell growth factor receptor (GenBank Acc. Nos. AF022375, 1680143, U48801 and X62568), insulin-like growth factor-I (GenBank Acc. Nos. X00173, X56774, X56773, X06043, European Patent No. GB 2241703), insulin-like growth factor-II (GenBank Acc. Nos. X03562, X00910, M17863 and M17862), transferrin receptor (Trowbridge and Omary, *Proc. Nat. Acad. USA,* 78:3039 (1981); GenBank Acc. Nos. X01060 and M11507), estrogen receptor (GenBank Acc. Nos. M38651, X03635, X99101, U47678 and M12674), progesterone receptor (GenBank Acc. Nos. X51730, X69068 and M15716), follicle stimulating hormone receptor (FSH-R) (GenBank Acc. Nos. Z34260 and M65085), retinoic acid receptor (GenBank Acc. Nos. L12060, M60909, X77664, X57280, X07282 and X06538), MUC-1 (Barnes, et al., *Proc. Nat. Acad. Sci. USA,* 86:7159 (1989); GenBank Acc. Nos. M65132 and M64928) NY-ESO-1 (GenBank Acc. Nos. AJ003149 and U87459), NA 17-A (PCT Publication No. WO 96/40039), Melan-A/MART-1 (Kawakami, et al., *Proc. Nat. Acad. Sci. USA,* 91:3515 (1994); GenBank Acc. Nos. U06654 and U06452), tyrosinase (Topalian, et al., *Proc. Nat. Acad. Sci. USA,* 91:9461 (1994); GenBank Acc. No. M26729; Weber, et al., *J Clin. Invest,* 102:1258 (1998)), Gp-100 (Kawakami, et al., *Proc. Nat. Acad. Sci. USA,* 91:3515 (1994); GenBank Acc. No. S73003, Adema, et al., *J Biol. Chem.,* 269:20126 (1994)), MAGE (van den Bruggen, et al., *Science,* 254:1643 (1991)); GenBank Acc. Nos. U93163, AF064589, U66083, D32077, D32076, D32075, U10694, U10693, U10691, U10690, U10689, U10688, U10687, U10686, U10685, L18877, U10340, U10339, L18920, U03735 and M77481), BAGE (GenBank Acc. No. U19180; U.S. Pat. Nos. 5,683,886 and 5,571,711), GAGE (GenBank Acc. Nos. AF055475, AF055474, AF055473, U19147, U19146, U19145, U19144, U19143 and U19142), any of the CTA class of receptors including in particular HOM-MEL-40 antigen encoded by the SSX2 gene (GenBank Acc. Nos. X86175, U90842, U90841 and X86174), carcinoembryonic antigen (CEA, Gold and Freedman, *J. Exp. Med.,* 121:439 (1985); GenBank Acc. Nos. M59710, M59255 and M29540), and PyLT (GenBank Acc. Nos. J02289 and J02038); p97 (melanotransferrin) (Brown, et al., *J. Immunol.,* 127:539-46 (1981); Rose, et al., *Proc. Natl. Acad. Sci. USA,* 83:1261-61 (1986)).

Additional tumor associated antigens include prostate surface antigen (PSA) (U.S. Pat. Nos. 6,677,157; 6,673,545); β-human chorionic gonadotropin β-HCG) (McManus, et al., *Cancer Res.,* 36:3476-81 (1976); Yoshimura, et al., *Cancer,* 73:2745-52 (1994); Yamaguchi, et al., *Br. J. Cancer,* 60:382-84 (1989): Alfthan, et al., *Cancer Res.,* 52:4628-33 (1992)); glycosyltransferase s-1,4-N-acetylgalactosaminyltransferases (GalNAc) (Hoon, et al., *Int. J Cancer,* 43:857-62 (1989); Ando, et al., *Int. J Cancer,* 40:12-17 (1987); Tsuchida, et al., *J. Natl. Cancer,* 78:45-54 (1987); Tsuchida, et al., *J. Natl. Cancer,* 78:55-60 (1987)); NUC18 (Lehmann, et al., *Proc. Natl. Acad. Sci. USA,* 86:9891-95 (1989); Lehmann, et al., *Cancer Res.,* 47:841-45 (1987)); melanoma antigen gp75 (Vijayasardahi, et al., *J Exp. Med.,* 171:1375-80 (1990); GenBank Accession No. X51455); human cytokeratin 8; high molecular weight melanoma antigen (Natali, et al., *Cancer,* 59:55-63 (1987); keratin 19 (Datta, et al., *J. Clin. Oncol.,* 12:475-82 (1994)).

Tumor antigens of interest include antigens regarded in the art as "cancer/testis" (CT) antigens that are immunogenic in subjects having a malignant condition (Scanlan, et al., *Cancer Immun.,* 4:1 (2004)). CT antigens include at least 19 different families of antigens that contain one or more members and that are capable of inducing an immune response, including but not limited to MAGEA (CT1); BAGE (CT2); MAGEB (CT3); GAGE (CT4); SSX (CT5); NY-ESO-1 (CT6); MAGEC (CT7); SYCP1 (C8); SPANXB1 (CT11.2); NA88 (CT18); CTAGE (CT21); SPA17 (CT22); OY-TES-1 (CT23); CAGE (CT26); HOM-TES-85 (CT28); HCA661 (CT30); NY-SAR-35 (CT38); FATE (CT43); and TPTE (CT44).

Additional tumor antigens that can be targeted, including a tumor-associated or tumor-specific antigen, include, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triosephosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68KP1, CO-029, FGF-5, G250, Ga733 (EpCAM), HTgp-175, M344, MA-50, MG7-Ag, MOV18, NB\70K, NY—CO-1, RCAS1, SDCCAG16, TA-90 (Mac-2 binding protein\cyclophilin C-associated protein), TAAL6, TAG72, TLP, and TPS. Other tumor-associated and tumor-specific antigens are known to those of skill in the art and are suitable for targeting the disclosed nanoparticles.

In some embodiments, the tumor antigen to be targeted is prostate-specific membrane antigen (PSMA). Thus, tumor targeting moieties include any agonist, or antagonists of PSMA, or any derivatives thereof. In some embodiments, the tumor targeting moiety is S,S-2-[3-[5-amino-1-carboxypentyl]-ureido]-pentanedioic acid (ACUPA), or derivatives thereof.

ii. Antigens Associated with Tumor Neovasculature

The antigen may be specific to tumor neovasculature or may be expressed at a higher level in tumor neovasculature when compared to normal vasculature. Exemplary antigens that are over-expressed by tumor-associated neovasculature as compared to normal vasculature include, but are not limited to, integrins including αvβ3, αvβ5, αvβ6, α2β1, α5β1, α6β1, and α6β4, VEGF/KDR, Tie2, vascular cell adhesion molecule (VCAM), endoglin, and $\alpha_5\beta_3$ integrin/vitronectin. Other antigens that are over-expressed by tumor-associated neovasculature as compared to normal vasculature are known to those of skill in the art and are suitable for targeting by the nanoparticles.

In some embodiment, the antigen associated with tumor neovasculature to be targeted is integrin αvβ3. Thus, tumor targeting moieties include any agonist, or antagonists of integrin αvβ3, or any derivatives thereof. In some embodiments, the tumor targeting moiety is a disulfide-based cyclic arginine-glycine-aspartic acid (RGD) peptide called iRGD, that is, CRGDRGPDC (SEQ ID NO:11), or derivatives thereof. In some embodiments, iRGD is conjugated to one or more of the amphiphilic ploymers, for example, in the form of iRGD-PEG-b-PDPA, as shown below in the Examples. In further embodiments, one or more of the amphiphilic ploymers conjugated with RGD include a membrane-penetrating motif such as oligoarginine. Examples include $C_{17}H_{35}$CONH-GR8GRGDS-OH (TCPA1); $C_{17}H_{35}$CONH—($C_{17}H_{35}$CONH)KR8GRGDS-OH (TCPA2) shown in Example 8.

iii. Chemokines/Chemokine Receptors

In another embodiment, the particles contain a domain that specifically binds to a chemokine or a chemokine receptor. Chemokines are soluble, small molecular weight (8-14 kDa) proteins that bind to their cognate G-protein coupled receptors (GPCRs) to elicit a cellular response, usually directional migration or chemotaxis. Tumor cells secrete and respond to chemokines, which facilitate growth that is achieved by increased endothelial cell recruitment and angiogenesis, subversion of immunological surveillance and maneuvering of the tumoral leukocyte profile to skew it such that the chemokine release enables the tumor growth and metastasis to distant sites. Thus, chemokines are vital for tumor progression.

Based on the positioning of the conserved two N-terminal cysteine residues of the chemokines, they are classified into four groups namely CXC, CC, CX3C and C chemokines. The CXC chemokines can be further classified into ELR+ and ELR− chemokines based on the presence or absence of the motif 'glu-leu-arg (ELR motif)' preceding the CXC sequence. The CXC chemokines bind to and activate their cognate chemokine receptors on neutrophils, lymphocytes, endothelial and epithelial cells. The CC chemokines act on several subsets of dendritic cells, lymphocytes, macrophages, eosinophils, natural killer cells but do not stimulate neutrophils as they lack CC chemokine receptors except murine neutrophils. There are approximately 50 chemokines and only 20 chemokine receptors, thus there is considerable redundancy in this system of ligand/receptor interaction.

Chemokines elaborated from the tumor and the stromal cells bind to the chemokine receptors present on the tumor and the stromal cells. The autocrine loop of the tumor cells and the paracrine stimulatory loop between the tumor and the stromal cells facilitate the progression of the tumor. Notably, CXCR2, CXCR4, CCR2 and CCR7 play major roles in tumorigenesis and metastasis. CXCR2 plays a vital role in angiogenesis and CCR2 plays a role in the recruitment of macrophages into the tumor microenvironment. CCR7 is involved in metastasis of the tumor cells into the sentinel lymph nodes as the lymph nodes have the ligand for CCR7, CCL21. CXCR4 is mainly involved in the metastatic spread of a wide variety of tumors.

Any one or more of the above listed tumor antigens suitable for targeting the nanoparticles to the site of tumor cells are also considered suitable to be used for therapeutic, and/or diagnostic purposes such as knockdown targets by shRNA, and/or siRNA.

Other suitable oncogenic molecules as therapeutic, and/or diagnostic targets include molecules involved in tumor-associated pathways such as those involved in cancer metabolism including glycolysis, glutaminolysis, autophagy (Galluzzi L et al., *Nat Rev Drug Discov.* 12, 829-846 (2013); Rubinsztein D C et al., *Nat Rev Drug Discov.* 2012 September; 11(9): 709-730.). Other exemplary pathways associated with tumor cells include PI3/AKT pathway, Kelch-like ECH-associated protein 1 (KEAP1)/NRF2 (nuclear factor, erythroid 2-like 2, NFE2L2) pathway, hypoxia-associated pathways, DNA repair pathways, and other pathways involved in cell division, apoptosis, cell cycle control.

Some exemplary metabolic targets for therapeutic, and/or diagnostic purposes include glucose transporter (GLUTs), hexokinase, phosphofructokinase inhibitor, glyceraldehyde-3-phosphate dehydrogenase (GAPDH), phosphoglycerate mutase (PGM), enolase (ENO), lactate dehydrogenase, pyruvate dehydrogenase kinase (PDK), glucose-6-phosphate dehydrogenase (G6PD), tricarboxylic acid (TCA) cycle, monocarboxylate transporter (MCTs), HSP90 inhibitor, CPT1, oxidative phosphorylation, glutamate dehydrogenase, mitochondrial citrate transporter SLC25A1 (CIC), dihydroorotate dehydrogenase, neutral amino acid transporter SLC1A5, glutamate dehydrogenase 1 (GDH1); glutaminase (GLS); glutamate oxaloacetate transaminase 2 (GOT2); γ-l-glutamyl-p-nitroanilide (GPNA); glutamate pyruvate transaminase 2 (GPT2); L-type amino acid transporter 1 (LAT1).

Additional targets for therapeutic, and/or diagnostic purposes are BET (bromodomain and extra-terminal) proteins including BRD2, BRD3, BRD4 and BRDT; kinesins including KIF11 (also known as EG5) and centromere-associated protein E (CENPE); surviving (an inhibitor of apoptosis protein), and prohibitin including PHB1 and PHB2.

b. Cancers to be Treated

The types of cancer that can be treated with the provided compositions and methods include, but are not limited to, the following: bladder, brain, breast, cervical, colo-rectal, esophageal, kidney, liver, lung, nasopharangeal, pancreatic, prostate, skin, stomach, uterine, ovarian, testicular and the like. Administration is not limited to the treatment of an existing tumors but can also be used to prevent or lower the risk of developing such diseases in an individual, i.e., for prophylactic use. Potential candidates for prophylactic vaccination include individuals with a high risk of developing cancer, i.e., with a personal or familial history of certain types of cancer.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The cargo can be an anticancer agent for example anti-proliferative agent, a pro-apoptotic agent, or other cytotoxic agent, including, but not limited to, chemotherapeutic drugs and functional nucleic acids.

c. Preferred Cargos

The preferred cargos for treating cancers are known in the art and include, for example, anti-cancer agents and immunotherapeutic agents.

Representative anti-cancer agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), antibodies to vascular endothelial growth factor (VEGF) such as bevacizumab (AVASTIN®), other anti-VEGF compounds; thalidomide (THALOMID®) and derivatives thereof such as lenalidomide (REVLIMID®); endostatin; angiostatin; receptor tyrosine kinase (RTK) inhibitors such as sunitinib (SUTENT®); tyrosine kinase inhibitors such as sorafenib (Nexavar®), erlotinib (Tarceva®), pazopanib, axitinib, and lapatinib; transforming growth factor-α or transforming growth factor-β inhibitors, and antibodies to the epidermal growth factor receptor such as panitumumab (VECTIBIX®) and cetuximab (ERBITUX®).

In some embodiments, the particles include nucleic acid cargo, including, but not limited to functional nucleic acids, expression constructs or mRNA, or a combination thereof. For example, in some embodiments, a functional nucleic acid is designed to reduce expression of an oncogene, for example a growth factor (e.g., c-Sis), mitogen, receptor tyrosine kinase (e.g., EGFR, PDGFR, VEGFR, HER2/neu), cytoplasmic tyrosine kinase (e.g., Src, Syk-ZAP-70, BTK families) cytoplasmic serine/threonine kinases (or a regulator subunit thereof) (e.g., Raf, cyclin-dependent kinases), regulatory GTPases (e.g., Ras), transcription factors (e.g., myc), angiogenesis (e.g., VEGF).

In some embodiments, the cargo is a functional nucleic acid that targets a factor that contributes to chemotherapy resistance, for example, drug efflux pumps, anti-apoptotic defense mechanisms, etc. Specific targets include, but are not limited to, glycoprotein (P-gp), Multidrug resistant protein 1 (MRP-1), and B-cell lymphoma (BCL-2). RNAi-chemotherapeutic drug combinations have also been found to be effective against different molecular targets as well and can increase the sensitization of cancer cells to therapy several folds (Gandhi, et al., *J Control Release.* 2014 Nov. 28; 0: 238-256).

Additionally or alternatively, mRNA can be introduced to enhance the fight against the tumor. For example, in some embodiments, the mRNA is delivered into the cancer cells. Such mRNA can enhance apoptosis or sensitivity to drugs or other treatments such as radiation.

Functional nucleic acids, mRNA, or a combination thereof can be introduced into cells that induce, program, or activate non-cancer cells to attack the cancer cells. For example, in some embodiments, the cargo is a nucleic acid that primes T cells or other immune cells for immunotherapy against the cancer. Immunotherapeutic methods, including CAR T cell therapy and other strategies for activation of immune cells against target antigens, and inhibition of immune check points leading to T cell exhaustion, anergy, or deactivation were well known in the art. The disclosed particles can be used in vitro or in vivo to introduce nucleic acids into targets including immune cells, to, for example, increase antigen-specific proliferation of T cells, enhance cytokine production by T cells, stimulate differentiation, stimulate effector functions of T cells, promote T cell survival, overcome T cell exhaustion, overcome T cell anergy or a combination thereof. Immune cells, including but not limited to, neutrophils, lymphocytes, dendritic cells, macrophages, eosinophils, natural killer cells, can be the target of therapy.

2. Inflammation and Infection

Methods of treating inflammation and infection are provided. The nanoparticles can be designed, for example, for release in the microenvironment of inflammation, injury, and infection, or immune or pro-inflammatory cells, or within immune or inflammatory cells themselves. Suitable methods can include administering a subject an effective amount of nanoparticles containing a therapeutic cargo to reduce or alleviate one or more symptoms of the inflammation, injury, or infection. The effect on the inflammation, injury, or infection can be direct or indirect. Administration is not limited to the treatment of an existing inflammation, injury, and infection, but can also be used to prevent or lower the risk of developing such diseases in an individual, i.e., for prophylactic use. A characteristic feature of the inflammation is local acidosis, which is attributed to the local increase of lactic-acid production by the anaerobic, glycolytic activity of infiltrated neutrophils and to the presence of short-chain, fatty acid by-products of bacterial metabolism (Grinstein, et al., *Clin. Biochem.* 24, 241-247 (1991) and Ehrich, W. E. (1961) *Inflammation* Allgower, M. eds. *Progress in Surgery* vol. 1, 1-70 S. Karger Basel, Switzerland). An acidic extracellular pH is also found in the epidermis and plays an important protective role against bacterial infection (Lardner, et al., *Journal of Leukocyte Biology,* 69(4):522-530 (2001)). As discussed above, local, tissue-specific increase in tissue temperature can occur at site of inflammation, injury, and infection. Similar to selectively targeting the tumor microenvironment, the pH and temperature sensitive particles can be utilized to delivery and selectively release cargo at sites of inflammation, injury, and infection.

As with cancer, in addition or alternative to selectively targeting cancer cells by targeting an acidic microenvironment, or one with an elevated temperature, cancer cells or their microenvironment can be specifically targeted relative to healthy or normal cells by including a targeting moiety. Preferred targeting domains target the molecule to areas of inflammation, injury, or infection. Exemplary targeting domains are antibodies, or antigen binding fragments thereof that are specific for inflamed tissue or to a proinflammatory cytokine including but not limited to IL17, IL-4, IL-6, IL-12, IL-21, IL-22, and IL-23. In the case of neurological disorders such as Multiple Sclerosis, the targeting domain may target the molecule to the CNS or may bind to VCAM-1 on the vascular epithelium. Additional targeting domains can be peptide aptamers specific for a proinflammatory molecule. In other embodiments, the particles can include a binding partner specific for a polypeptide displayed on the surface of an immune cell, for example a T cell. In still other embodiments, the targeting domain specifically targets activated immune cells. Preferred immune cells that are targeted include Th0, Th1, Th17 and Th22 T cells, other cells that secrete, or cause other cells to secrete inflammatory molecules including, but not limited to, IL-1β, TNF-α, TGF-beta, IFN-γ, IL-17, IL-6, IL-23, IL-22, IL-21, and MMPs, and Tregs. For example, a targeting domain for Tregs may bind specifically to CD25.

In some embodiments, the target site is neutrophils, which may phagocytize the particles to release a therapeutic and/or diagnostic agent at the site of inflammation. Proteins constitutively expressed on the surface of neutrophils that are important for recognition of the endothelial inflammatory signals include the glycoprotein P-selectin glycoprotein ligand-1 (PSGL-1) and L-selectin.

Other agents to be targeted include those associated with the disease. For example, a plaque targeted peptide can be one or more of the following: Collagen IV, CREKA (SEQ ID NO:13), LyP-I, CRKRLDRNC (SEQ ID NO:14), or their combinations at various molar ratios.

In another embodiment, particles can contain a targeting domain to target the molecule to an organ or tissue that is being transplanted. For example, the targeting domain can be an antibody, antigen binding fragment thereof, or another binding partner specific for a polypeptide displayed on the surface of cells specific to the type of organ or tissue being transplanted.

a. Inflammation

Inflammation is typically a localized physical condition in which part of the body becomes reddened, swollen, hot, and often painful, especially as a reaction to injury or infection. Inflammation is a protective response that involves immune cells, blood vessels, and molecular mediators, the purpose of which is to eliminate the cause of cell injury, remove necrotic cells and tissues damaged from the injury and the inflammatory process, and to initiate tissue repair. The compositions can be used to treat acute and chronic inflammation.

The inflammation can be caused by an infection such as those described below or can be caused by a non-infectious mechanism. For example, inflammation is associated with atherosclerosis, type III hypersensitivity, trauma, and ischaemia. Inflammation can be associated with autoimmune diseases, transplantation, graft verse host disease, and conditions driven by immune responses. In some embodiments, the particles are used to deliver a cargo for treatment of an inflammatory or autoimmune disease or disorder such as rheumatoid arthritis, systemic lupus erythematosus, alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia—fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

Preferred cargos for treating inflammation and autoimmune diseases include, but are not limited to, anti-inflammatory agents and immunosuppressive agents.

In some embodiments, the cargo is an immunosuppressive agents (e.g., antibodies against other lymphocyte surface markers (e.g., CD40, alpha-4 integrin) or against cytokines), other fusion proteins (e.g., CTLA-4-Ig (ORENCIA®), TNFR-Ig (Enbrel®)), TNF-α blockers such as Enbrel, Remicade, Cimzia and Humira, cyclophosphamide (CTX) (i.e. ENDOXAN®, CYTOXAN®, NEOSAR®, PROCYTOX®, REVIMMUNE™), methotrexate (MTX) (i.e. RHEUMATREX®, TREXALL®), belimumab (i.e. BENLYSTA®), or other immunosuppressive drugs (e.g., cyclosporin A, FK506-like compounds, rapamycin compounds, or steroids), anti-proliferatives, cytotoxic agents, or other compounds that may assist in immunosuppression.

The cargo can function to inhibit or reduce T cell activation and cytokine production. In one such embodiment, the additional therapeutic agent is a CTLA-4 fusion protein, such as CTLA-4 Ig (ABATACEPT®). CTLA-4 Ig fusion proteins compete with the co-stimulatory receptor, CD28, on T cells for binding to CD80/CD86 (B7-1/B7-2) on antigen presenting cells, and thus function to inhibit T cell activation. In a preferred embodiment, the additional therapeutic agent is a CTLA-4-Ig fusion protein known as BELATACEPT®. BELATACEPT® contains two amino acid substitutions (L104E and A29Y) that markedly increase its avidity to CD86 in vivo. In another embodiment, the additional therapeutic agent is Maxy-4.

The cargo can treat chronic transplant rejection or GvHD, whereby the treatment regimen effectively targets both acute and chronic transplant rejection or GvHD. In a preferred embodiment the second therapeutic is a TNF-α blocker.

The cargo can increase the amount of adenosine in the serum, see, for example, WO 08/147482. In a preferred embodiment, the second therapeutic is CD73-Ig, recombinant CD73, or another agent (e.g. a cytokine or monoclonal antibody or small molecule) that increases the expression of CD73, see for example WO 04/084933. In another embodiment the second therapeutic agent is Interferon-beta.

The cargo can increase Treg activity or production. Exemplary Treg enhancing agents include but are not limited to glucocorticoid fluticasone, salmeteroal, antibodies to IL-12, IFN-γ, and IL-4; vitamin D3, and dexamethasone, and combinations thereof. Antibodies to other proinflammatory molecules can also be used. Preferred antibodies bind to IL-6, IL-23, IL-22 or IL-21.

The cargo can be a rapamycin compound. As used herein the term "rapamycin compound" includes the neutral tricyclic compound rapamycin, rapamycin derivatives, rapamycin analogs, and other macrolide compounds which are thought to have the same mechanism of action as rapamycin (e.g., inhibition of cytokine function). The language "rapamycin compounds" includes compounds with structural similarity to rapamycin, e.g., compounds with a similar macrocyclic structure, which have been modified to enhance their therapeutic effectiveness. Exemplary Rapamycin compounds are known in the art (See, e.g. WO95122972, WO 95116691, WO 95104738, U.S. Pat. Nos. 6,015,809; 5,989, 591; 5,567,709; 5,559,112; 5,530,006; 5,484,790; 5,385, 908; 5,202,332; 5,162,333; 5,780,462; 5,120,727).

The language "FK506-like compounds" includes FK506, and FK506 derivatives and analogs, e.g., compounds with structural similarity to FK506, e.g., compounds with a similar macrocyclic structure which have been modified to enhance their therapeutic effectiveness. Examples of FK506-like compounds include, for example, those described in WO 00101385. In some embodiments, the language "rapamycin compound" does not include "FK506-like compounds."

Other suitable therapeutics include, but are not limited to, anti-inflammatory agents. The anti-inflammatory agent can be non-steroidal, steroidal, or a combination thereof. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

In some embodiments, the cargo is a functional nucleic acid that targets a factor that contributes to inflammation, the activation or persistence of pro-inflammatory cells, a pro-inflammatory response, active immune response, an autoimmune response, etc. Specific targets include, for example, pro-inflammatory molecules such as IL-1β, TNF-α, TGF-beta, IFN-γ, IL-17, IL-6, IL-23, IL-22, IL-21, and MMPs.

Additionally or alternatively, mRNA can be introduced to reduce the inflammation or autoimmune response.

Functional nucleic acids, mRNA, or a combination thereof can be introduced into cells that inhibit the development of naïve T cells into Th1, Th17, Th22 or other cells that secrete, or cause other cells to secrete, inflammatory molecules. The cargo can increase the number or activity of Tregs. The cargo can promote or enhance production of IL-10 or another anti-inflammatory cytokine. In some embodiments, the cargo enhances the differentiation, recruitment and/or expansion of Treg cells in the region of inflammation, autoimmune activity, or tissue engraftment. Exemplary functional nucleic acid targets for treating autoimmune disease are reviewed in Pauley and Cha, *Pharmaceuticals* 2013, 6(3), 287-294; and discussed in, for example, Kim, et al., *Molecular Therapy*, (2010) 18 5, 993-1001, Laroui, et al., *Molecular Therapy* (2014); 22 1, 69-80, Ponnappa, et al., *Curr Opin Investig Drugs.* 2009 May; 10(5):418-24; Abrams, et al., *Molecular Therapy*, (2010) 18 1, 171-180, Leuschner, et al., *Nature biotechnology* 29.11 (2011): 1005-1010. PMC. Web. 29 Mar. 2016.

In some embodiments, the cargo is a nucleic acid that encodes an anti-inflammatory cytokine, for example, (IL)-1 receptor antagonist, IL-4, IL-6, IL-10, IL-11, or IL-13 (Opal and DePalo, et al., *Chest.* (2000)117(4):1162-72).

b. Infections

Similarly, in some embodiments, the disclosed particles are used to deliver a cargo for treatment of an infectious disease. Infectious diseases that can be treated, prevented, and/or managed using the disclosed nanoparticles can be caused by infectious agents including but not limited to bacteria, fungi, protozae, and viruses. Viral diseases include, for example, those caused by hepatitis type A, hepatitis type B, hepatitis type C, influenza (e.g., influenza A or influenza B), varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral meningitis, encephalitis, dengue or small pox.

Bacterial diseases can be caused by bacteria (e.g., *Escherichia coli, Klebsiella pneumoniae, Staphylococcus aureus, Enterococcus faecalis, Proteus vulgaris, Staphylococcus viridans*, and *Pseudomonas aeruginosa*) include, for example, mycobacteria *rickettsia, mycoplasma, neisseria, S. pneumonia, Borrelia burgdorferi* (Lyme disease), *Bacillus antracis* (anthrax), tetanus, *streptococcus, staphylococcus, mycobacterium*, pertissus, cholera, plague, diptheria, *chlamydia, S. aureus* and *legionella.*

Protozoal diseases caused by protozoa include, for example, *leishmania*, kokzidioa, trypanosome *schistosoma* or malaria. Parasitic diseases caused by parasites include *chlamydia* and *rickettsia.*

Fungal infections include, but are not limited to, *Candida* infections, zygomycosis, *Candida* mastitis, progressive disseminated trichosporonosis with latent trichosporonemia, disseminated candidiasis, pulmonary paracoccidioidomycosis, pulmonary aspergillosis, *Pneumocystis carinii* pneumonia, cryptococcal meningitis, coccidioidal meningoencephalitis and cerebrospinal vasculitis, *Aspergillus niger* infection, *Fusarium* keratitis, paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, *Cryptococcus neoformans* infection, fungal peritonitis, *Curvularia geniculata* infection, staphylococcal endophthalmitis, sporotrichosis, and dermatophytosis.

Prepared cargo for treating infections can including anti-infectives such as Difloxacin Hydrochloride; Lauryl Isoquinolinium Bromide; Moxalactam Disodium; Omidazole; Pentisomicin; Sarafloxacin Hydrochloride; Protease inhibitors of HIV and other retroviruses; Integrase Inhibitors of HIV and other retroviruses; Cefaclor (Ceclor); Acyclovir (Zovirax); Norfloxacin (Noroxin); Cefoxitin (Mefoxin); Cefuroxime axetil (Ceftin); or Ciprofloxacin (Cipro).

In some embodiments, the cargo is antibiotic such as a beta-lactam (e.g., penicillins, cephalosporins, monobactams, and carbapenems), a cephalosporins, a monobactam, a carbapenem, a macrolide, a lincosamide, streptogramin, an aminoglycoside, a quinolone, a sulfonamide, a tetracycline, a glyopeptide, lipoglycopeptide, rifamycin, a polypeptide, or a tuberactinomycin.

In some embodiments, the cargo is a functional nucleic acid that targets a factor that contributes to anti-infective drug resistance, for example, drug efflux pumps, anti-apoptotic defense mechanisms, etc., or infected cells or the pathogens themselves. In some embodiments, the functional nucleic acid specifically targets a gene expressed by the pathogen. See, for example, Fischer, et al., *Cell Research*, (2004) 14, 460-466, which describes RNAi strategies for targeting viral infection. Additionally or alternatively, mRNA can be introduced to enhance the fight against the infection.

As in described above in the context of cancer, functional nucleic acids, mRNA, or a combination thereof can be introduced into cells that induce, program, or activate cells to resolve an infection. For example, in some embodiments, the cargo is a nucleic acid that primes T cells or other immune cells for immunotherapy against the infection. Immunotherapeutic methods, including CAR T cell therapy and other strategies for activation of immune cells against target antigens, and inhibition of immune check points leading to T cell exhaustion, anergy, or deactivation were well known in the art. The disclosed particles can be used in vitro or in vivo to introduce nucleic acids into targets including immune cells, to, for example, increase antigen-specific proliferation of T cells, enhance cytokine production by T cells, stimulate differentiation, stimulate effector functions of T cells, promote T cell survival, overcome T cell exhaustion, overcome T cell anergy or a combination thereof. Immune cells, including but not limited to, neutrophils, lymphocytes, dendritic cells, macrophages, eosinophils, natural killer cells, can be the target of therapy.

The present invention will be further understood by reference to the following non-limiting examples.

Example 1: Ultra pH-Responsive and Tumor-Penetrating Nanoplatform for Targeted siRNA Delivery with Robust Anti-Cancer Efficacy

Methods and Materials

Materials

Methoxyl-polyethylene glycol (Meo-$PEG_{113}$-OH) and hydroxyl polyethylene glycol carboxylic acid (HO-$PEG_{113}$-COOH) were purchased from JenKem Technology and used as received. Internalizing RGD (iRGD) with the sequence CRGDRGPDC (SEQ ID NO:11) was obtained from GL Biochem Ltd. 2-(Diisopropyl amino) ethyl methacrylate (DPA-MA), glycidyl methacrylate (GMA), and methyl methacrylate (MMA) were provided by Sigma-Aldrich and passed over an alumina column before use in order to remove the hydroquinone inhibitors. α-Bromoisobutyryl bromide, triethylamine (TEA), N,N,N',N',N'-pentamethyldiethylenetriamine (PMDETA), copper (I) bromide (CuBr), N,N'-dimethylformamide (DMF), tetraethylenepentamine (TEPA), 1,2-epoxyhexadecane, isopropyl alcohol, and dichloromethane (DCM) were acquired from Sigma-Aldrich and used directly. Lipofectamine 2000 (Lipo2K) was purchased from Invitrogen. Steady-Glo luciferase assay system was provided by Promega. GL3, fluorescent dye (DY547, DY647 and DY677) labeled GL3 and survivin siRNAs were acquired from Dharmacon. The siRNA sequences are as follows: GL3 siRNA, 5'-CUU ACG CUG AGU ACU UCG AdTdT-3' (sense) (SEQ ID NO:1) and 5'-UCG AAG UAC UCA GCG UAA GdTdT-3' (antisense)) (SEQ ID NO:2); survivin siRNA, 5'-GGA CCA CCG CAU CUC UAC AdTdT-3' (sense) (SEQ ID NO:3) and 5'-UGU AGA GAU GCG GUG GCU CdTdT-3' (antisense) (SEQ ID NO:4). PHB1 siRNA, 5'-GCG ACG ACC UUA CAG AGC GUU-3' (sense) (SEQ ID NO:5) and 5'-CGC UCU GUA AGG UCG UCG CUU-3' (antisense) (SEQ ID NO:6); KIF11 siRNA, 5'-GAA UAG GGU UAC AGA GUU GUU-3' (sense) (SEQ ID NO:7) and 5'-CAA CUC UGU AAC CCU AUU CUU-3' (antisense) (SEQ ID NO:8). The fluorescent dyes DY547 and DY647 were labeled at the 5'-end of the sense strand of GL3 siRNA. DY677 was labeled at the 5'-end of both the sense and antisense strands of GL3 siRNA. HeLa cells stably expressing firefly and *Renilla* luciferase (Luc-HeLa) were obtained from Alnylam Pharmaceuticals, Inc. The cells were incubated in RPMI-1640 medium (Invitrogen) with 10% fetal bovine serum (FBS, Sigma-Aldrich) and 1% penicillin/streptomycin (Sigma-Aldrich). All other reagents and solvents are of analytical grade and used without further purification.

Synthesis of Meo-PEG-Br and Br-PEG-COOH

Meo-$PEG_{113}$-OH (8 g, 1.6 mmol) and TEA (1.3 mL, 9.6 mmol) were dissolved in 250 mL of DCM. In an ice-salt bath, α-bromoisobutyryl bromide (1 mL, 8 mmol) dissolved in 10 mL of DCM was added dropwise. After stirring for 24 h, the mixture was washed with 1 M NaOH (3×50 mL), 1 M HCl (3×50 mL), and deionized water (3×50 mL), respectively. After drying over anhydrous $MgSO_4$, the solution was concentrated, and cold ether was added to precipitate the product. After re-precipitation thrice, the product was collected as white powder after drying under vacuum. The synthesis of Br-PEG-COOH was carried out according to a method similar to that described above, by changing Meo-$PEG_{113}$-OH with HO-$PEG_{113}$-COOH. The synthesis scheme of Br-PEG-COOH is shown below.

Synthesis of methoxyl-polyethylene glycol-b-poly (2-(diisopropylamino) ethylmethacrylate-co-glycidyl methacrylate) (Meo-PEG-b-P(DPA-co-GMA))

Meo-PEG-b-P(DPA-co-GMA) copolymers with different compositions were synthesized by atom transfer radical polymerization (ATRP). Meo-$PEG_{113}$-b-P($DPA_{80}$-co-$GMA_5$) is used as an example to illustrate the procedure. DPA-MA (2.6 g, 12 mmol), GMA (0.11 g, 0.75 mmol), Meo-PEG-Br (0.75 g, 0.15 mmol), and PMDETA (31.5 μL, 0.15 mmol) were added to a polymerization tube. DMF (3 mL) and 2-propanol (3 mL) were then added to dissolve the monomer and initiator. After three cycles of freeze-pump-thaw to remove oxygen, CuBr (21.6 mg, 0.15 mmol) was added under nitrogen atmosphere and the polymerization tube was sealed under vacuum. After polymerization at 40° C. for 24 h, tetrahydrofuran (THF) was added to dilute the product, which was then passed through a neutral $Al_2O_3$ column to remove the catalyst. The resulting THF solution was concentrated and the residue was dialyzed against THF, followed by deionized water. The expected copolymer was collected as a white powder after freeze-drying under vacuum. The synthesis scheme is shown below. The feed compositions of the copolymers are summarized in Table 1.

TABLE 1

Feed compositions and characterizations of Meo-PEG-b-P(DPA-co-GMA)

| No. | Repeat unit (DPA) a | Repeat unit (GMA) a | $M_{n, GPC}$ (x$10^{-4}$ Da) b | PDI b | $M_{n, NMR}$ (x$10^{-4}$ Da) a | pKa c |
|---|---|---|---|---|---|---|
| PDPA40-GMA5 | 39 | 5 | 1.44 | 1.19 | 1.42 | 6.34 |
| PDPA50-GMA5 | 50 | 5 | 1.68 | 1.12 | 1.66 | 6.31 |
| PDPA60-GMA5 | 58 | 5 | 1.69 | 1.18 | 1.83 | 6.29 |
| PDPA70-GMA5 | 69 | 5 | 1.94 | 1.24 | 2.06 | 6.26 |
| PDPA80-GMA5 | 80 | 5 | 2.19 | 1.29 | 2.29 | 6.24 |
| PDPA100-GMA5 | 99 | 5 | 2.87 | 1.14 | 2.71 | 6.21 |

a Determined by $^1$HNMR using $CDCl_3$ as solvent.
b Number-averaged ($M_n$) and polydispersity index (PDI) were determined by GPC using THF as the eluent.

Synthesis of Meo-PEG-b-P(DPA-co-GMA-TEPA)

Meo-PEG-b-P(DPA-co-GMA-TEPA) was synthesized via the ring opening reaction between TEPA and the epoxy group of GMA repeating unit. In brief, Meo-PEG-b-P(DPA-co-GMA) (1.5 g) dissolved in DMF (20 mL) was added dropwise to the DMF solution (5 mL) of TEPA (30-fold molar excess relative to the GMA repeating unit). After reaction at 60° C. for 7 h, the mixture was transferred to a dialysis tube and then dialyzed against deionized water. The Meo-PEG-b-P(DPA-co-GMA-TEPA) was finally collected as a white powder after freeze-drying under vacuum. The synthesis route of Meo-PEG-b-P(DPA-co-GMA-TEPA) is shown below.

Synthesis of Meo-PEG-b-P(DPA-co-GMA-TEPA-C14)

Meo-PEG-b-P(DPA-co-GMA-TEPA) (1 g) and 1,2-epoxyhexadecane (equal molar amount relative to TEPA repeating unit) were dissolved in DMF (20 mL) and the solution was stirred at 70° C. for 5 h. Subsequently, the solution was transferred to a dialysis tube and then dialyzed against DMF, followed by deionized water. The Meo-PEG-b-P(DPA-co-GMA-TEPA-C14) was obtained as a white powder after freeze-drying under vacuum. The detailed synthesis of Meo-PEG-b-P(DPA-co-GMA-TEPA-C14) is shown below. Synthesis of Meo-PEG-b-P(DPA-co-GMA-TEPA-Cy5.5)

Meo-PEG-b-P(DPA-co-GMA-TEPA) (0.2 g) and Cy5.5 NHS ester (1.5-fold molar excess relative to the TEPA repeating unit) were well dissolved in 5 mL of THF. After constantly stirring in dark for 48 h, the solution was dialyzed against deionized water and the product was collected after freeze-drying. The synthesis of Meo-PEG-b-P(DPA-co-GMA-TEPA-Cy5.5) is shown below.

Synthesis Scheme of Meo-PEG-b-P(DPA-co-GMA-TEPA-Cy5.5)

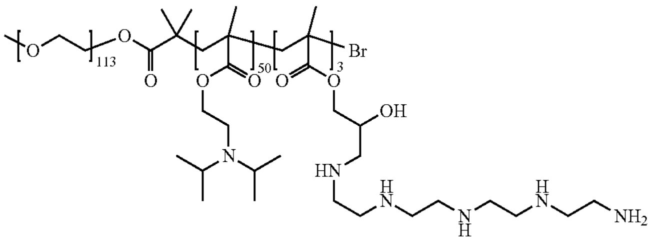

Meo-PEG-b-P(DPA-co-GMA-TEPA)

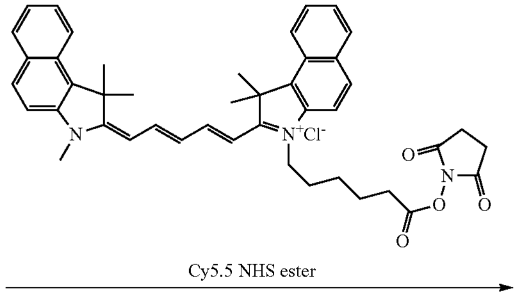

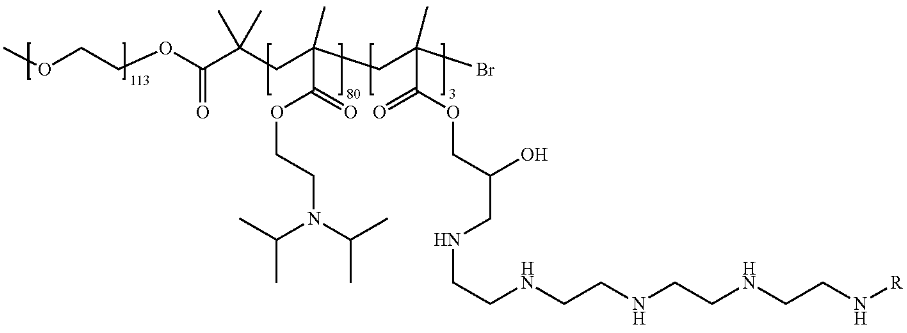

Meo-PEG-b-P(DPA-co-GMA-TEPA-Cys5.5)

-continued

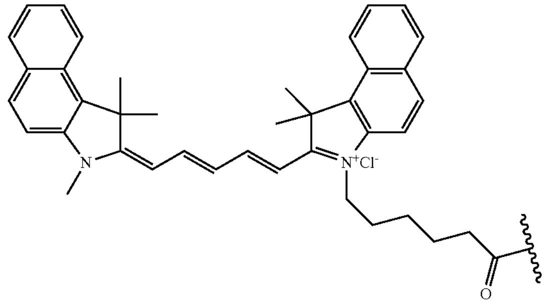

= R

Synthesis of HOOC-PEG-b-PDPA

HOOC-PEG-b-PDPA copolymers were also synthesized by the ATRP method. DPA-MA (1.73 g, 8 mmol), Br-PEG-COOH (0.5 g, 0.1 mmol), and PMDETA (21 μL, 0.1 mmol) were added to a polymerization tube. Subsequently, DMF (2 mL) and 2-propanol (2 mL) were added to dissolve the monomer and initiator. After three cycles of freeze-pump-thaw to remove oxygen, CuBr (14.4 mg, 0.1 mmol) was added under nitrogen atmosphere and the polymerization tube was sealed under vacuum. After polymerization at 40° C. for 24 h, tetrahydrofuran (THF) was added to dilute the product, which was then passed through a neutral $Al_2O_3$ column to remove the catalyst. The obtained THF solution was concentrated and the residue was dialyzed against deionized water. The HOOC-PEG-b-PDPA was obtained as a white powder after freeze-drying under vacuum. The synthesis scheme is shown below. The feed compositions are summarized in Table 2.

TABLE 2

Feed compositions and characterizations of HOOC-PEG-b-PDPA

| No. | Repeat unit (DPA) [a] | $M_{n,GPC}$ ($\times10^{-4}$ Da) [b] | PDI [b] | $M_{n,NMR}$ ($\times10^{-4}$ Da) [a] |
|---|---|---|---|---|
| HOOC-PEG-b-$PDPA_{40}$ | 36 | 1.31 | 1.34 | 1.27 |

TABLE 2-continued

Feed compositions and characterizations of HOOC-PEG-b-PDPA

| No. | Repeat unit (DPA) [a] | $M_{n,GPC}$ ($\times10^{-4}$ Da) [b] | PDI [b] | $M_{n,NMR}$ ($\times10^{-4}$ Da) [a] |
|---|---|---|---|---|
| HOOC-PEG-b-$PDPA_{50}$ | 45 | 1.49 | 1.28 | 1.48 |
| HOOC-PEG-b-$PDPA_{60}$ | 55 | 1.76 | 1.29 | 1.69 |
| HOOC-PEG-b-$PDPA_{70}$ | 64 | 1.92 | 1.27 | 1.89 |
| HOOC-PEG-b-$PDPA_{80}$ | 76 | 2.04 | 1.24 | 2.14 |
| HOOC-PEG-b-$PDPA_{100}$ | 92 | 2.57 | 1.19 | 2.48 |

[a] Determined by $^1$HNMR using $CDCl_3$ as solvent.
[b] Number-averaged (Mn) and polydispersity index (PDI) were determined by GPC using THF as the eluent.

Synthesis of iRGD-PEG-b-PDPA

HOOC-PEG-b-PDPA copolymer (0.2 g), iRGD peptide (1.5-fold molar excess relative to the terminal carboxylic acid group), EDC·HCl (3-fold molar excess relative to the terminal carboxylic acid group), and NHS (3-fold molar excess relative to the terminal carboxylic acid group) were well dissolved in pH 5.0 water. The mixture was stirred at room temperature for 48 h. The solution was subsequently dialyzed against deionized water and the expected iRGD-PEG-PDPA was collected after freeze-drying.

Synthesis Scheme of iRGD-PEG-b-PDPA

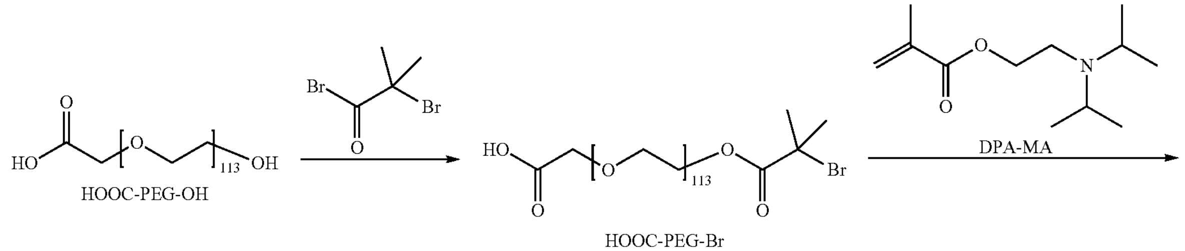

HOOC-PEG-OH

HOOC-PEG-Br

-continued

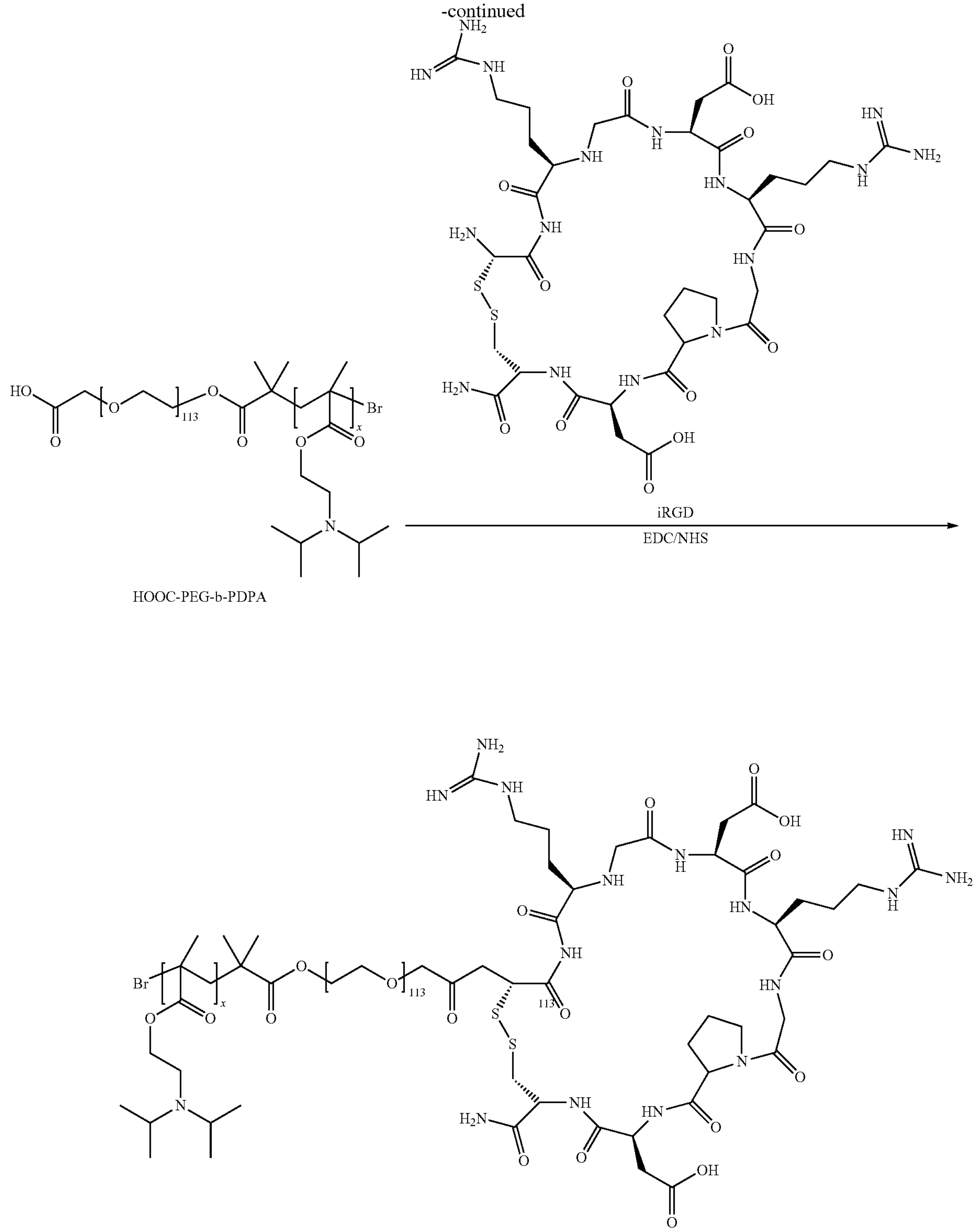

HOOC-PEG-b-PDPA iRGD-PEG-b-PDPA

Synthesis of Control Copolymers

The control copolymers, methoxyl-poly ethylene glycol-b-poly (methyl methacrylate-co-glycidyl methacrylate) (Meo-PEG$_{113}$-b-P(MMA$_{80}$-co-GMA$_5$)) Meo-PEG$_{113}$-b-P(MMA$_{80}$-co-GMA$_5$-TEPA$_5$), HOOC-PEG$_{113}$-b-PMMA$_{80}$, iRGD-PEG$_{113}$-b-PMMA$_{80}$, and Meo-PEG$_{113}$-b-P(MMA$_{80}$-co-GMA$_5$-TEPA$_5$-C14) were synthesized according to the method described above, by changing the monomer DPA-MA with MMA. The chemical structure of iRGD-PEG$_{113}$-b-PMMA$_{80}$ and Meo-PEG$_{113}$-b-P(MMA$_{80}$-co-GMA$_5$-TEPA$_5$-C14) is shown below.

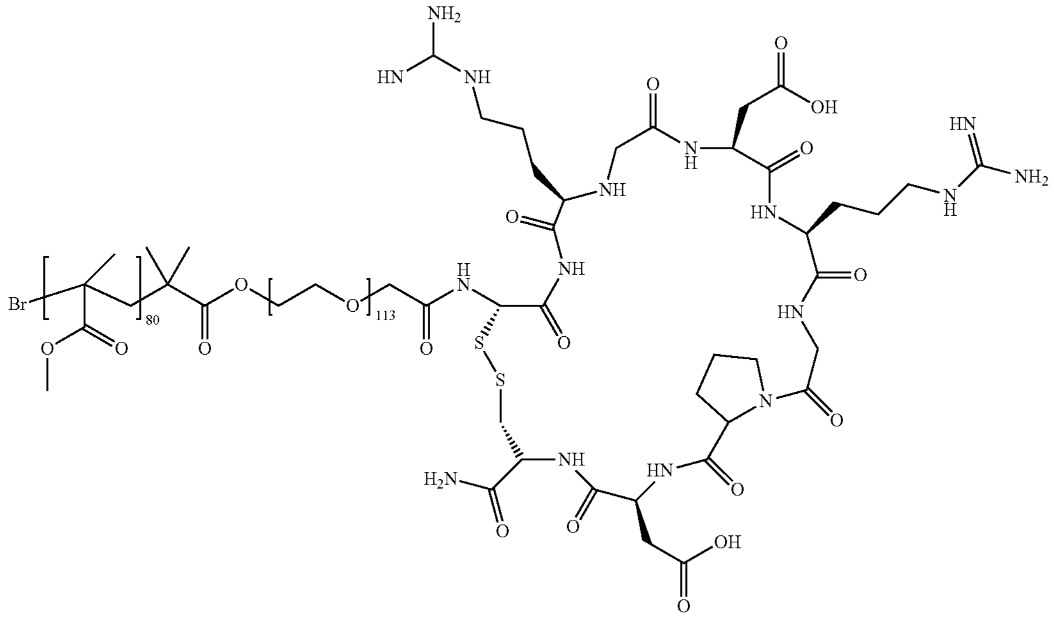

iRGD-PEG$_{113}$-b-PMMA$_{80}$

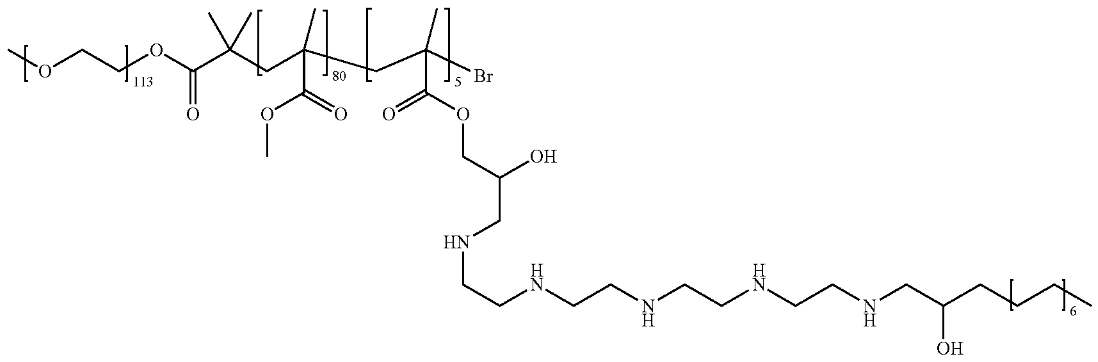

Meo-PEG$_{113}$-b-P(MMA$_{80}$-co-GMA$_5$-TEPA-C14)

Gel Permeation Chromatography (GPC)

Number- and weight-average molecular weights ($M_n$ and $M_w$, respectively) of the polymers were determined by a gel permeation chromatographic system equipped with a Waters 2690D separations module and a Waters 2410 refractive index detector. THF was used as the eluent at a flow rate of 0.3 mL/min. Waters millennium module software was used to calculate molecular weight on the basis of a universal calibration curve generated by polystyrene standard of narrow molecular weight distribution.

$^1$H Nuclear Magnetic Resonance ($^1$HNMR)

The $^1$HNMR spectra of the polymers were recorded on a Mercury VX-300 spectrometer at 400 MHz (Varian, USA), using $CDCl_3$ as a solvent and TMS as an internal standard.

Acid-Base Titration

Meo-PEG-b-P(DPA-co-GMA-TEPA-C14) was dispersed in deionized water, and a concentrated HCl aqueous solution was added until complete dissolution of the copolymer (1 mg/mL). Subsequently, 1 M NaOH aqueous solution was added in 1-5 μL increments. After each addition, the solution was constantly stirred for 3 min, and the solution pH was measured using a pH meter. The $pK_a$ of the copolymer was determined as the pH at which 50% copolymer turns ionized.

Preparation and Characterization of Nanoparticles (NPs)

Meo-PEG-b-P(DPA-co-GMA-TEPA-C14) was dissolved in THF to form a homogenous solution with a concentration of 4 mg/mL. Subsequently, a certain volume of this THF solution was taken and mixed with 1 nmol siRNA (0.1 nmol/μL aqueous solution) in a N/P molar ratio of 40:1. Under vigorous stirring (1000 rpm), the mixture was added dropwise to 2.5 mL of deionized water. The NP dispersion formed was transferred to an ultrafiltration device (EMD Millipore, MWCO 100 K) and centrifuged to remove the organic solvent and free compounds. After washing with PBS (pH 7.4) solution (3×5 mL), the siRNA loaded NPs were dispersed in 1 mL of phosphate buffered saline (PBS, pH 7.4) solution. Size and zeta potential were determined by dynamic light scattering (DLS, Brookhaven Instruments Corporation). The morphology of NPs was visualized on a Tecnai G2 Spirit BioTWIN transmission electron microscope (TEM). Before observation, the sample was stained with 1% uranyl acetate and dried under air. To determine siRNA encapsulation efficiency, DY547-labelled GL3 siRNA loaded NPs were prepared according to the method described above. A small volume (50 μL) of the NP solution was withdrawn and mixed with 20-fold DMSO. The fluorescence intensity of DY547-labelled GL3 siRNA was measured using a Synergy HT multi-mode microplate reader (BioTek Instruments) and compared to the free DY547-labelled GL3 siRNA solution (1 nmol/mL PBS solution).

To prepare the iRGD-NPs, Meo-PEG-b-P(DPA-co-GMA-TEPA-C14) (4 mg/mL in THF) was mixed with 1 nmol siRNA (0.1 nmol/μL aqueous solution) in a N/P molar ratio of 40:1. Then iRGD-PEG-b-PDPA (4 mg/mL in THF, 10 mol % compared to Meo-PEG-b-P(DPA-co-GMA-TEPA-C14)) was added, and the mixture was added dropwise to 2.5 mL of deionized water. The iRGD-NPs were purified by an ultrafiltration device (EMD Millipore, MWCO 100 K) and finally dispersed in 1 mL of PBS. The siRNA encapsulation efficiency was examined by replacing the siRNA with DY547-labelled GL3 siRNA.

Evaluation of pH Responsiveness

The THF solution of Meo-PEG-b-P(DPA-co-GMA-TEPA-C14) (4 mg/mL) and Meo-PEG-b-P(DPA-co-GMA-TEPA-Cy5.5) (4 mg/mL) was mixed in a volume ratio of 8:2. Under vigorously stirring (1000 rpm), 0.5 mL of the mixture was added dropwise to 5 mL of deionized water. After collection and purification by an ultrafiltration device (EMD Millipore, MWCO 100 kDa), the NPs formed were dispersed in 1 mL of deionized water. Subsequently, 1 M NaOH or HCl was added in 1-5 μL increments, and the fluorescence intensity of the NPs was measured on a Synergy HT multi-mode microplate reader. The normalized fluorescence intensity (NFI) vs. pH profile was used to quantitatively assess the pH responsiveness. NFI is calculated as follows:

$$NFI=(F-F_{min})/(F_{max}-F_{min})$$

where F is the fluorescence intensity of the NPs at any given pH value and $F_{max}$ and $F_{min}$ are the maximal and minimal fluorescence intensity of the NPs, respectively.

In Vitro siRNA Release

DY547-labelled GL3 siRNA-loaded NPs were prepared as described above. Subsequently, the NPs were dispersed in 1 mL of PBS (pH 7.4) and then transferred to a Float-a-lyzer G2 dialysis device (MWCO 100 kDa, Spectrum) that was immersed in PBS (pH 7.4) at 37° C. At a predetermined interval, 5 μL of the NP solution was withdrawn and mixed with 20-fold DMSO. The fluorescence intensity of DY547-labelled siRNA was determined by Synergy HT multi-mode microplate reader.

Cell Culture

Human cervical cancer cell line with the expression of luciferase (Luc-HeLa) and prostate cancer cell line (PC3) were incubated in RPMI1640 medium with 10% FBS at 37° C. in a humidified atmosphere containing 5% $CO_2$.

Luciferase Silencing.

Luc-HeLa cells were seeded in 96-well plates (5,000 cells per well) and incubated in 0.1 mL of RPMI1640 medium with 10% FBS for 24 h. Thereafter, the GL3 siRNA-loaded NPs were added. After 24 h incubation, the cells were washed with fresh medium and allowed to incubate for another 48 h. The expression of firefly luciferase in HeLa cells was determined using Steady-Glo luciferase assay kits. Cytotoxicity was measured using alamarBlue assay according to the manufacturer's protocol. The luminescence or fluorescence intensity was measured using a microplate reader, and the average value of three independent experiments was collected. As a control, the silencing effect of Lipo2K/GL3 siRNA complexes was also evaluated according to the procedure described above and compared to that of GL3 siRNA-loaded NPs.

Determination of the Expression of Integrins $\alpha_v\beta_3$ and $\alpha_v\beta_5$ Luc-HeLa and PC3 cells were seeded in 6-well plates (50,000 cells per well) and incubated in 1 mL of RPMI1640 medium containing 10% FBS for 24 h. Thereafter, 10 μL of FITC-conjugated anti-human CD51/61 antibody (BioLegend) or FITC-conjugated anti-human integrin $\alpha_v\beta_5$ antibody (EMD Millipore) were added, and the cells were allowed to incubate for another 4 h. After removing the medium and washing with PBS (pH 7.4) solution thrice, the cells were collected for flow cytometry quantitative analysis (BD FACSAria™ III, USA).

Confocal Laser Scanning Microscope (CLSM)

Luc-HeLa and PC3 cells (20,000 cells) were seeded in discs and incubated in 1 mL of RPMI1640 medium containing 10% FBS for 24 h. Subsequently, the DY547-labelled GL3 siRNA-loaded NPs or iRGD-NPs were added, and the cells were allowed to incubate for 1 or 4 h. After removing the medium and subsequently washing with PBS (pH 7.4) solution thrice, the endosomes and nuclei were stained by lysotracker green and Hoechst 33342, respectively. The cells were then viewed under a FV1000 CLSM (Olympus).

Flow Cytometry

Luc-HeLa and PC3 cells were seeded in 6-well plates (50,000 cells per well) and incubated in 1 mL of RPMI1640 medium containing 10% FBS for 24 h. Subsequently, the DY547-labelled GL3 siRNA-loaded NPs or iRGD-NPs were added, and the cells were allowed to incubate for another 4 h. After removing the medium and subsequently washing with PBS (pH 7.4) solution thrice, the cells were collected for flow cytometry quantitative analysis.

In Vitro Survivin Silencing

PC3 cells were seeded in 6-well plates (50,000 cells per well) and incubated in 1 mL of RPMI1640 medium containing 10% FBS for 24 h. Subsequently, the cells were transfected with the survivin siRNA-loaded NPs or iRGD-NPs for 24 h. After washing the cells with PBS thrice, the cells were further incubated in fresh medium for another 48 h. Thereafter, the cells were digested by trypsin and the proteins were extracted using modified radioimmunoprecipitation assay lysis buffer (50 mM Tris-HCl pH 7.4, 150 mM NaCl, 1% NP-40 substitute, 0.25% sodium deoxycholate, 1 mM sodium fluoride, 1 mM $Na_3VO_4$, 1 mM EDTA), supplemented with protease inhibitor cocktail and 1 mM phenylmethanesulfonyl fluoride (PMSF). The expression of survivin was examined using the western blot analysis described below.

Western Blot Analysis

Equal amounts of protein, as determined with a bicinchoninic acid (BCA) protein assay kit (Pierce/Thermo Scientific) according to the manufacturer's instructions, were added to SDS-PAGE gels and separated by gel electrophoresis. After transferring the proteins from gel to polyvinylidene difluoride membrane, the blots were blocked with 3% BSA in TBST (50 mM Tris-HCl pH 7.4, 150 mM NaCl, and 0.1% Tween 20) and then incubated with a mixture of survivin rabbit antibody (Cell Signaling) and beta-actin rabbit antibody (Cell Signaling). The expression of survivin was detected with horseradish peroxidase (HRP)-conjugated secondary antibody (anti-rabbit IgG HRP-linked antibody, Cell Signaling) and an enhanced chemiluminescence (ECL) detection system (Pierce).

In Vitro Cell Proliferation

PC3 cells were seeded in 6-well plates (20,000 cells per well) and incubated in 1 mL of RPMI1640 medium containing 10% FBS for 24 h. Thereafter, the cells were transfected with the survivin siRNA-loaded NPs or iRGD-NPs for 24 h and then washed with fresh medium for further incubation. At predetermined intervals, the cytotoxicity was measured by alamarBlue assay according to the manufacturer's protocol. After each measurement, the alamarBlue agent was removed and the cells were incubated in fresh medium for further proliferation.

Animals

Healthy male BALB/c mice (4-5 weeks old) were purchased from Charles River Laboratories. All in vivo studies were performed in accordance with National Institutes of Health animal care guidelines and in strict pathogen-free conditions in the animal facility of Brigham and Women's Hospital. Animal protocol was approved by the Institutional Animal Care and Use Committees on animal care (Harvard Medical School).

PC3 Xenograft Tumor Model

The tumor model was constructed by subcutaneous injection with 200 μL of PC3 cell suspension (a mixture of RPMI 1640 medium and Matrigel in 1:1 volume ratio) with a density $1\times10^7$ cells/mL into the back region of healthy male BALB/c nude mice. When the volume of the PC3 tumor xenograft reached ~100 $mm^3$, the mice were used for the following in vivo experiments.

Pharmacokinetics Study

Healthy male BALB/c mice were randomly divided into three groups (n=3) and given an intravenous injection of either (i) free DY647-labelled GL3 siRNA, (ii) DY647-labelled GL3 siRNA-loaded NPs, or (iii) DY647-labelled GL3 siRNA-loaded iRGD-NP at 650 μg siRNA dose per kg mouse weight. At predetermined time intervals, orbital vein blood (20 μL) was withdrawn using a tube containing heparin, and the wound was pressed for several seconds to stop the bleeding. The fluorescence intensity of DY647-labelled siRNA in the blood was determined by microplate reader. The blood circulation half-life (t1/2) was calculated by first-order decay fit.

Biodistribution

PC3 tumor-bearing male BALB/c nude mice were randomly divided into three groups (n=3) and given an intravenous injection of either (i) free DY677-labelled GL3 siRNA, (ii) DY677-labelled GL3 siRNA-loaded NPs or (iii) DY677-labelled GL3 siRNA-loaded iRGD-NPs at 650 μg siRNA dose per kg mouse weight. Twenty-four hours after the injection, the mice were imaged using the Maestro 2 In-Vivo Imaging System (Cri Inc). Organs and tumors were then harvested and imaged. To quantify the accumulation of NPs in tumors and organs, the fluorescence intensity of each tissue was quantified by Image-J.

Immunofluorescence Staining

PC3 tumor-bearing male BALB/c nude mice were randomly divided into three groups (n=3) and intravenously injected with either (i) free DY677-labelled GL3 siRNA, (ii) DY677-labelled GL3 siRNA-loaded NPs or (iii) DY677-labelled GL3 siRNA-loaded iRGD-NPs at 650 μg siRNA dose per kg mouse weight. Four hours after injection, the mice were sacrificed and the tumors were harvested, followed by fixing with 4% paraformaldehyde, embedding in paraffin, and cutting into sections. To image the tumor vasculature, the slices were heated at 60° C. for 1 h and washed with xylene, ethanol, and PBS thrice. After blocking with 10% FBS for 1.5 h, the slices were incubated with rat anti-mouse CD31 antibody (Abcam) at 4° C. for 1 h. After washing with PBS/0.2% triton X-100 thrice, Alexa Flour 488-conjugated secondary antibody (Goat anti-rat IgG, Abcam) was added for 1 h to stain the slices. Thereafter, the slices were washed with PBS thrice and then stained with Hoechst 33342. The images of the tumor vasculature were viewed on a FLV1000 CLSM.

In Vivo Survivin Silencing

PC3 tumor-bearing male BALB/c nude mice were randomly divided into two groups (n=3) and intravenously injected with (i) survivin siRNA-loaded NPs or (ii) survivin siRNA-loaded iRGD-NPs for three consecutive days. Twenty-four hours after the final injection, mice were sacrificed and tumors were harvested. The proteins in the tumor were extracted using modified radioimmunoprecipitation assay lysis buffer (50 mM Tris-HCl pH 7.4, 150 mM NaCl, 1% NP-40 substitute, 0.25% sodium deoxycholate, 1 mM sodium fluoride, 1 mM $Na_3VO_4$, 1 mM EDTA), supplemented with protease inhibitor cocktail and 1 mM phenylmethanesulfonyl fluoride (PMSF). The expression of survivin was examined using the aforementioned western blot analysis.

Inhibition of Tumor Growth

PC3 tumor-bearing male BALB/c nude mice were randomly divided into four groups (n=5) and intravenously injected with (i) PBS, (ii) GL3 siRNA-loaded NPs, (iii) survivin siRNA-loaded NPs or (iv) survivin siRNA-loaded iRGD-NPs at 650 μg siRNA dose per kg mouse weight once every two days. All the mice were administrated by administered five consecutive injections and the tumor growth was monitored every two days by measuring perpendicular diameters using a caliper and tumor volume was calculated as follows:

$$V=W^2\times L/2$$

where W and L are the shortest and longest diameters, respectively.

Histology

Healthy male BALB/c mice were randomly divided into three groups (n=3) and administered daily intravenous injections of either (i) PBS, (ii) survivin siRNA-loaded NPs or (iii) survivin siRNA-loaded iRGD-NPs at 650 μg siRNA dose per kg mouse weight. After three consecutive injections, the main organs were collected 2 days post the final injection, fixed with 4% paraformaldehyde, and embedded in paraffin. Tissue sections were stained with H&E and viewed under optical microscope.

Results

A long-circulating, optionally cell-penetrating, and stimuli-responsive NP platform for effective in vivo delivery of therapeutic, prophylactic and/or diagnostic agents is made of an amphiphilic polymer, most preferably a PEGylated polymer, which shows a response to a stimulus such as pH, temperature, or light, such as an ultra pH-responsive characteristic with a pKa close to the endosomal pH (6.0-6.5) (Wang Y et al, *Nat Mater,* 13, 204-212 (2014)). The polymer may include a targeting or cell penetrating or adhesion molecule such as a tumor-penetrating peptide iRGD (FIGS. 1A-1B).

As demonstrated by example 1, after encapsulating the agent(s) to be delivered, the resulting delivery system shows four unique features (FIG. 1C):

i) the surface-encoded iRGD peptide endows the NPs with tumor-targeting and tumor-penetrating abilities;
ii) the hydrophilic PEG shells prolong the blood circulation;
iii) a small population of cationic lipid-like grafts randomly dispersed in the hydrophobic poly(2-(diisopropylamino) ethylmethacrylate) (PDPA) segment can entrap siRNA in the hydrophobic cores of the NPs; and
iv) the rapid protonation of the ultra pH-responsive PDPA segment induces the endosomal swelling via the "proton sponge" effect, which synergizes with the insertion of the cationic lipid-like grafts into endosomal membrane to induce membrane destabilization (Zhu X et al., *Proceedings of the National Academy of Sciences,* 112, 7779-7784 (2015)) and efficient endosomal escape.

The amphiphilic polymer, methoxyl-polyethylene glycol-b-poly (2-(diisopropylamino) ethylmethacrylate-co-glycidyl methacrylate) (Meo-PEG-b-P(DPA-co-GMA)) was first synthesized (Table 1), which was further grafted by tetraethylenepentamine (TEPA) and 1,2-epoxyhexadecane to obtain Meo-PEG-b-P(DPA-co-GMA-TEPA-C14).

Synthesis Scheme of
Meo-PEG-b-P(DPA-co-GMA-TEPA-C14)

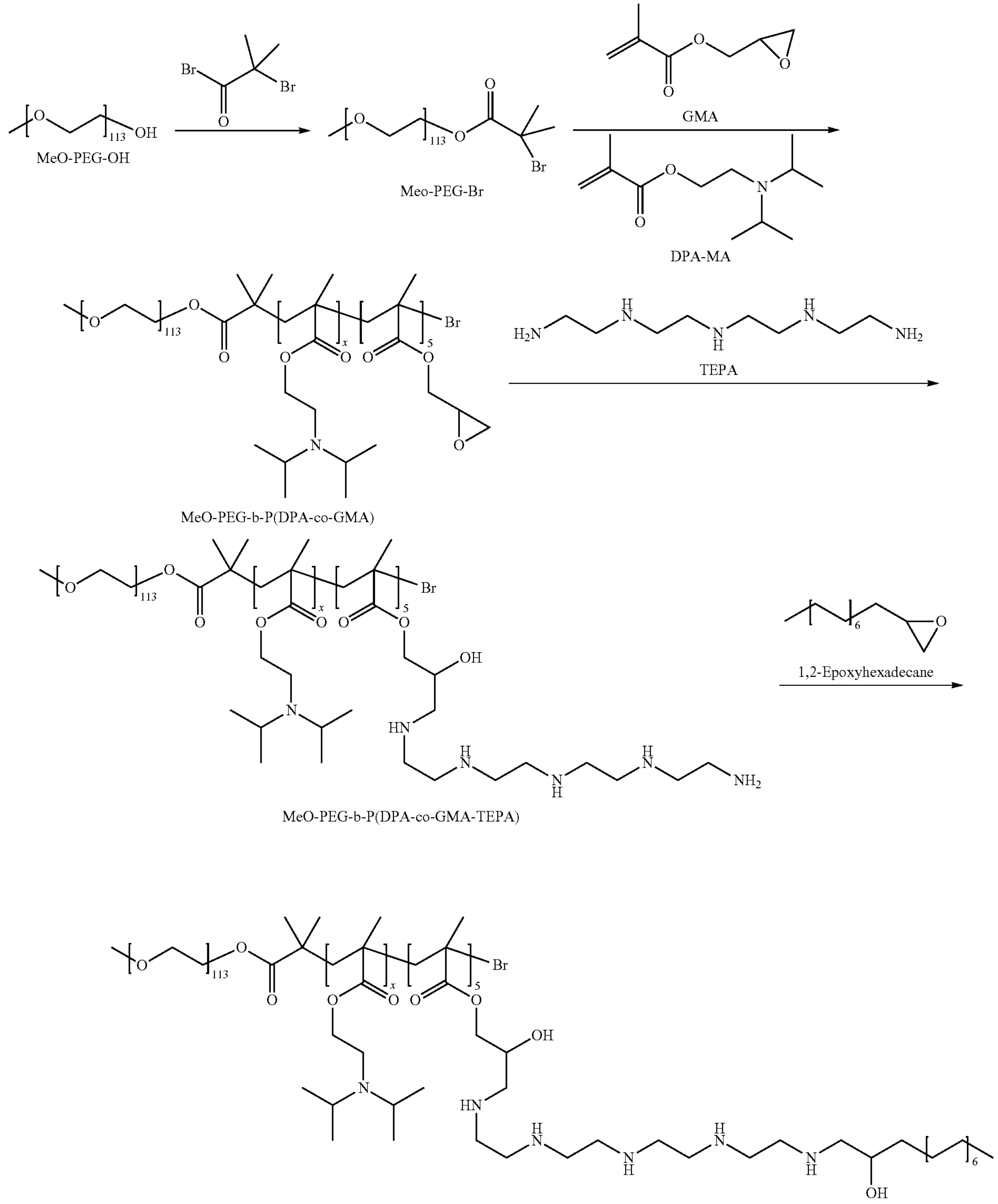

MeO-PEG-b-P(DPA-co-GMA-TEPA-C14)

The length of PDPA segment was varied to adjust siRNA encapsulation efficiency (EE %). As the PDPA length increases, the EE % and size of the resulting NPs increase (Table 3), possibly because the increased PDPA length leads to an increase in the size of the hydrophobic core. Specifically, the EE % reaches almost 100% for the polymer with 80 (PDPA80) or 100 (PDPA100) DPA repeat units. Notably, using a mixture of Meo-PEG-b-P(DPA-co-GMA-TEPA-C14) (90 mol %) and tumor-penetrating polymer (iRGD-PEG-b-PDPA, 10 mol %, FIG. 1A) to prepare NPs does not cause obvious change in the EE % or particle size (Table 4).

TABLE 3

Size, zeta potential, siRNA encapsulation efficiency (EE %), and pH responsiveness of the NPs prepared from Meo-PEG-b-P(DPA-co-GMA-TEPA-C14)

| No. | Polymer abbreviation | DPA repeating units a | pKa of polymer b | Size (nm) c | Zeta potential (mv) | EE % d | ΔpH10%-90% |
|---|---|---|---|---|---|---|---|
| NPs40 | PDPA40 | 39 | 6.34 | 62.5 | 4.79 | 54.6 | 0.45 |
| NPs50 | PDPA50 | 50 | 6.31 | 69.6 | 5.26 | 59.6 | 0.40 |
| NPs60 | PDPA60 | 58 | 6.29 | 75.9 | 3.13 | 65.6 | 0.37 |
| NPs70 | PDPA70 | 69 | 6.26 | 66.0 | 6.44 | 69.7 | 0.35 |
| NPs80 | PDPA80 | 80 | 6.24 | 69.7 | 3.81 | 99.7 | 0.34 |
| NPs100 | PDPA100 | 99 | 6.21 | 82.3 | 9.26 | 100 | 0.33 |

a Determined by $^1$HNMR shown in Table 1.
b Determined by acid-base titration
c Determined by dynamic light scattering (DLS).
d DY547-labelled GL3 siRNA was used to examine the EE %.

Figure 2A:
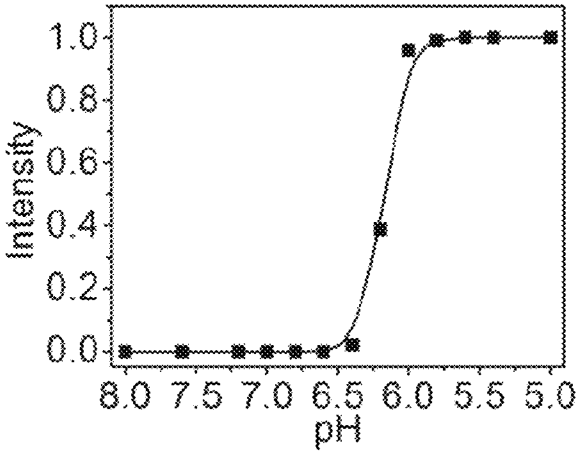
FIGS. 2A-2B are graphs showing pH-dependent release from NPs of PDPA80. (2A) Normalized fluorescence intensity as a function of pH for the Cy.5.5-labelled NPs of PDPA80. (2B) In vitro siRNA release from the NPs of PDPA80 at 37° C. from pH 7.4 and pH 6.0.
Figure 2B:
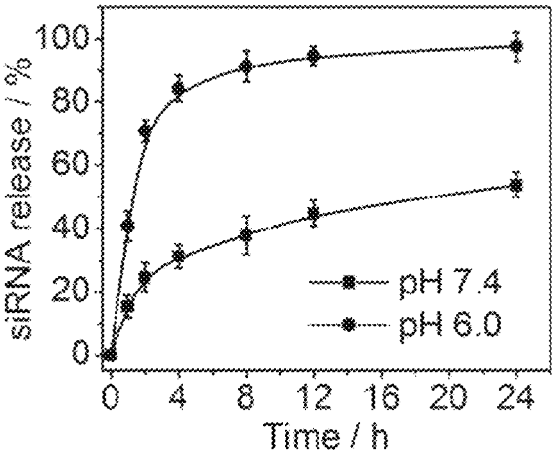

The polymer, PDPA80 (pKa 6.24, Table 3), was chosen for pH response evaluation by incorporating a near-infrared dye, Cy5.5, into its PDPA segment. Due to the quenching of the aggregated fluorophores inside the hydrophobic cores of the NPs (Wang Y et al, *Nat Mater,* 13, 204-212 (2014)), there is no fluorescence signal at a pH above pKa of PDPA80. In contrast, at a pH below pKa, the protonated PDPA segment induces the disassembly of the NPs and a dramatic increase in the fluorescence signal. Measurement of the fluorescence intensity as a function of pH for the Cy.5.5-labelled NPs of PDPA80 reveals that the pH difference from 10 to 90% fluorescence activation (ΔpH10-90%) is 0.34 (FIG. 2A and Table 3) (Wang Y et al, *Nat Mater,* 13, 204-212 (2014)), which is much smaller than that of small molecule dyes (about 2 pH units) (Urano Y et al., *Nat Med,* 15, 104-109 (2009)), indicating the ultra-fast pH response of PDPA80. This characteristic is confirmed by transmission electron microscope (TEM). The spherical siRNA-loaded NPs could be visualized at a pH of 6.5, with an average size of 69.7 nm determined by dynamic light scattering (DLS, Table 3). If altering pH to 6.0, there are no observable NPs after 20 min incubation. With this morphological change, the NPs offer super-fast release of DY547-labelled GL3 siRNA (DY547-siRNA) (FIG. 2B). Around 90% loaded siRNA has been released within 4 h at a pH of 6.0. Within the same time frame, less than 30% of the loaded siRNA is released at a pH of 7.4.

TABLE 4

Size, zeta potential and siRNA encapsulation efficiency (EE %) of the iRGD-NPs of prepared from the mixture of Meo-PEG-b-P(DPA-co-GMA-TEPA-C14) and iRGD-PEG-b-PDPA [a]

| No. | Size (nm) [b] | Zeta potential (mv) | EE % [c] |
|---|---|---|---|
| iRGD-NPs$_{40}$ | 64.2 | 3.26 | 55.1 |
| iRGD-NPs$_{50}$ | 68.3 | 3.98 | 59.7 |
| iRGD-NPs$_{60}$ | 82.1 | 5.69 | 66.4 |
| iRGD-NPs$_{70}$ | 76.5 | 7.18 | 69.6 |
| iRGD-NPs$_{80}$ | 70.7 | 5.26 | 99.8 |
| iRGD-NPs$_{100}$ | 86.3 | 8.93 | 100 |

[a] The molar ratio of Meo-PEG-b-P(DPA-co-GMA-TEPA-C14) and iRGD-PEG-b-PDPA is 9:1.
[b] Determined by dynamic light scattering (DLS).
[c] DY547-labelled GL3 siRNA was used to examine the EE %.

Figure 3A:
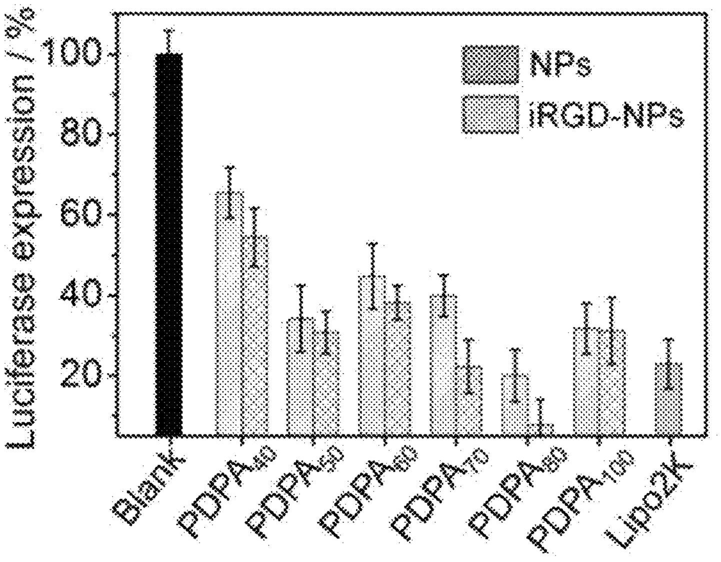
FIGS. 3A-3D are (3A) Luciferase expression in Luc-HeLa cells transfected with siRNA-loaded NPs at a 10 nM siRNA dose. (3B) Flow cytometry profile of Luc-HeLa cells incubated with the siRNA-loaded NPs80 and iRGD-NPs80 for 4 h. (3C) A histogram showing relative survivin expression determined by Western blot analysis in PC3 cells treated by survivin siRNA-loaded NPs80 or survivin siRNA-loaded iRGD-NPs80. (3D) A graph showing proliferation of PC3 cells incubated with survivin siRNA-loaded NPs80 and iRGD-NPs80 at a 10 nM siRNA dose. GL3 siRNA-loaded NPs80 were used as a control.
Figure 3B:
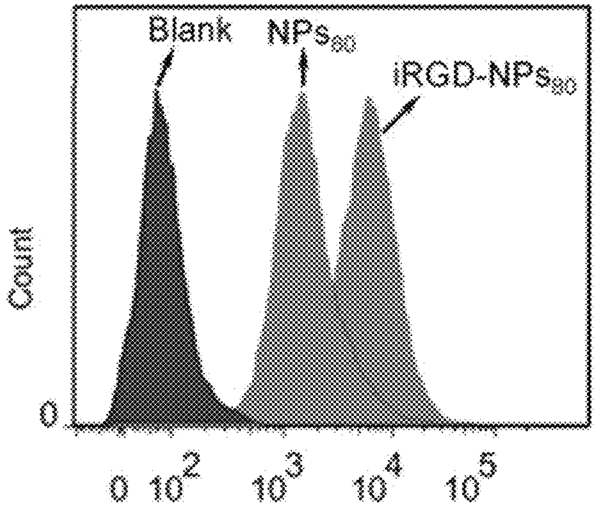
Figure 3C:
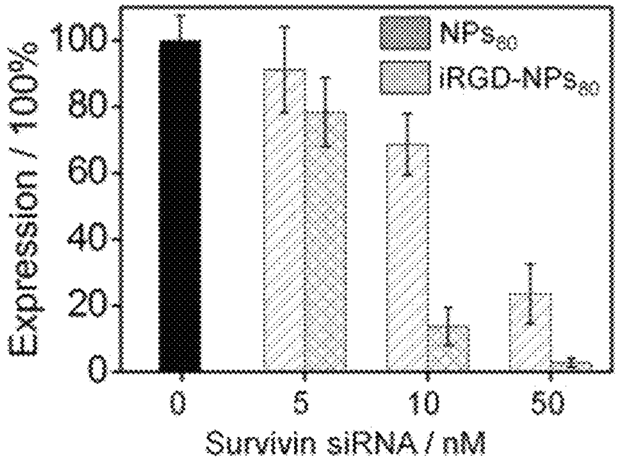
Figure 4:
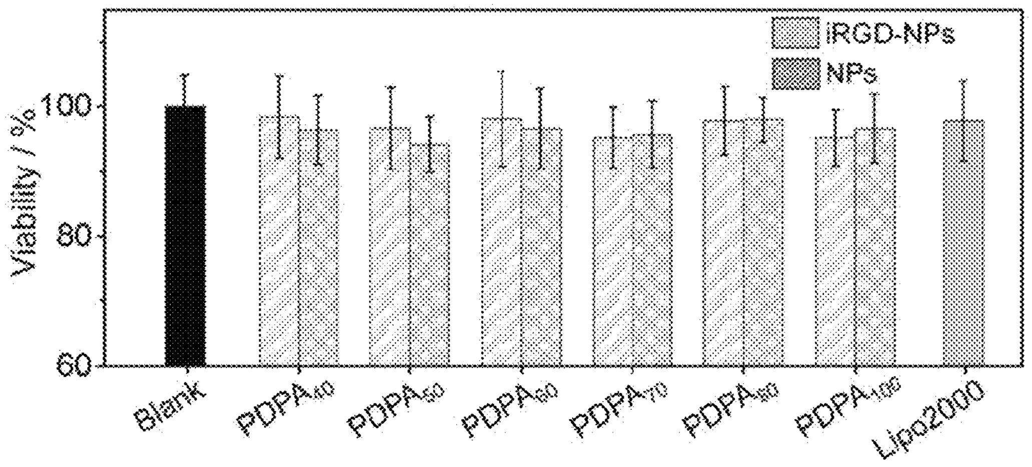
FIG. 4 is a bar graph showing cell viability of Luc-HeLa cells in the presence of 10 nM siRNA dose of the GL3 siRNA-loaded NPs and Lipo2K-GL3 siRNA complex. Blank: cells incubated with free medium.
Figure 5A:
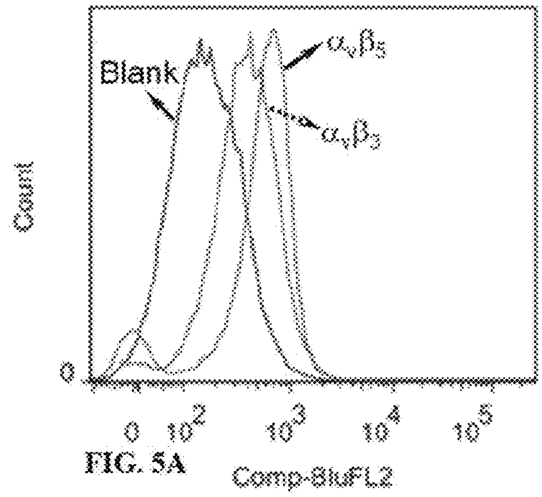
FIGS. 5A-5D are graphs showing relative fluorescence intensity of integrins $\alpha v\beta 3$ and $\alpha v\beta 5$ on Luc-HeLa (5A, 5C) and PC3 (5B, 5D) cells determined by flow cytometry analysis. Blank: cells incubated with free medium; MFI-mean fluorescence intensity.
Figure 5B:
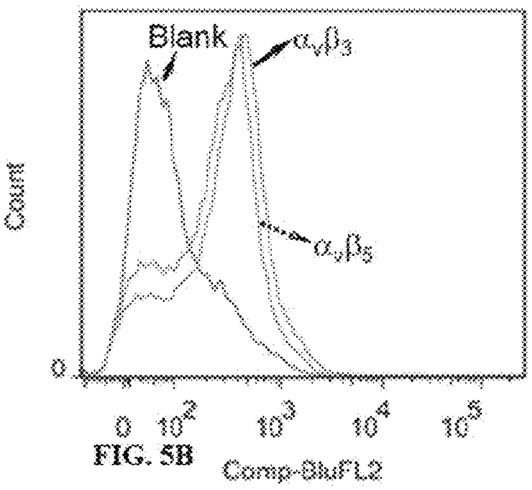
Figure 5C:
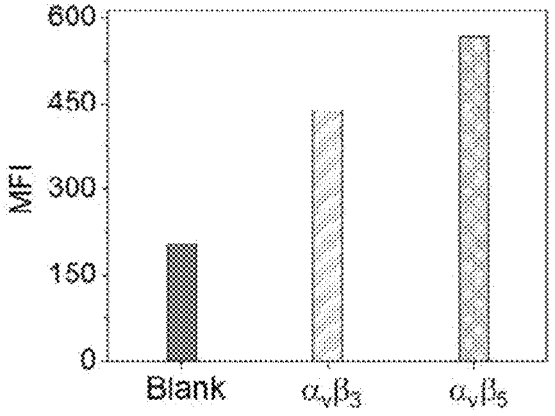
Figure 5D:
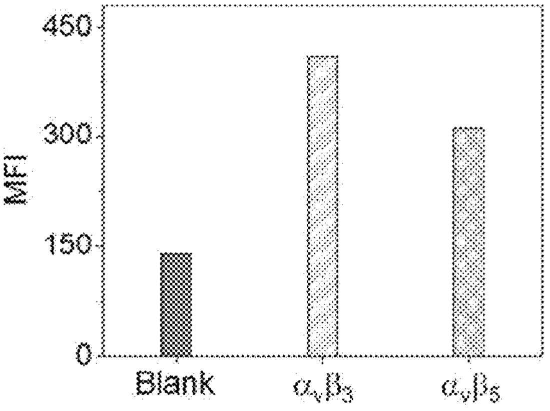
Figure 6A:
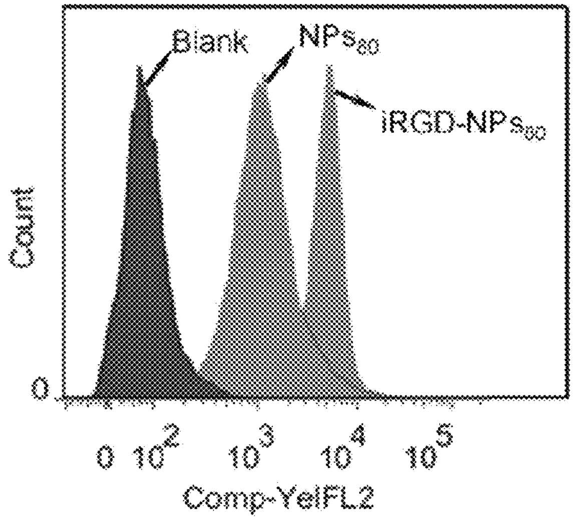
FIGS. 6A-6C are graphs showing relative fluorescence intensity of DY745-siRNA-loaded NPs80 and iRGD-NPs80. (6A) Flow cytometry profile of PC3 cells incubated with DY745-siRNA-loaded NPs80 and iRGD-NPs80 for 4 h at a 10 nM siRNA dose. Mean fluorescence intensity (MFI) of Luc-HeLa 6(B) and PC3 (6C) cells incubated with DY547-siRNA-loaded NPs80 and iRGD-NPs80 for 4 h at a 10 nM siRNA dose. *p<0.05.
Figure 6B:
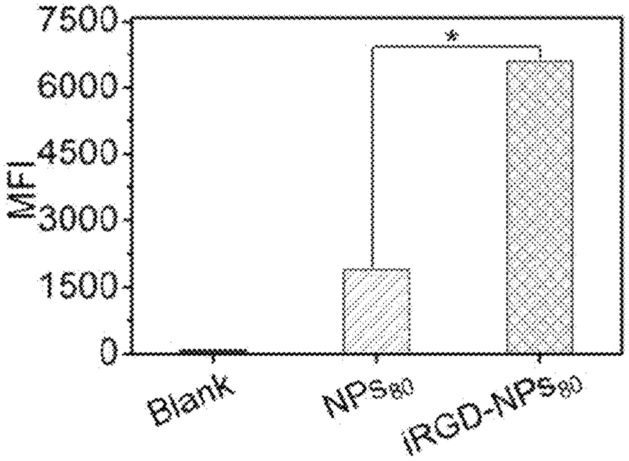
Figure 6C:
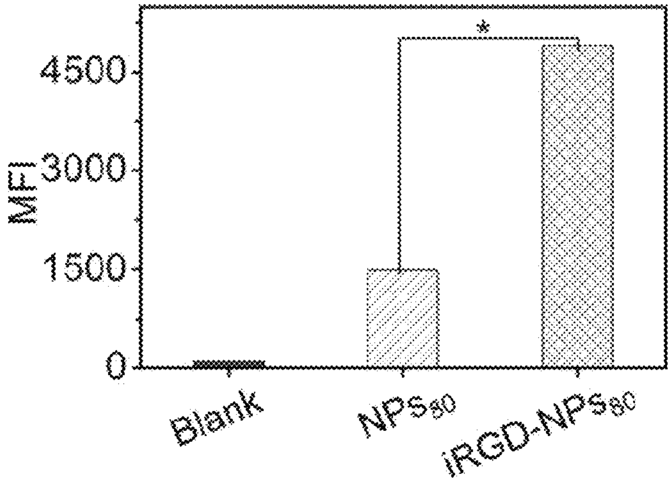

Luciferase-expressing HeLa (Luc-HeLa) cells were used to evaluate the gene silencing efficacy. GL3 siRNA was employed to suppress luciferase expression. All the siRNA-loaded NPs show a reduction in luciferase expression at a 10 nM siRNA dose (FIG. 3A), with the differential silencing efficacy depending upon the polymer structure. In comparison, the NPs with iRGD peptide (denoted iRGD-NPs) offer much better gene silencing efficacy. In particular, the iRGD-NPs$_{80}$ prepared from PDPA80 show the best gene silencing efficacy, i.e., >90% knockdown in luciferase expression without obvious cytotoxicity (FIG. 4). Cell viability of Luc-HeLa cells in the presence of 10 nM siRNA dose of the GL3 siRNA-loaded NPs formed with PDPA40, PDPA50, PDPA60, PDPA70, PDPA80, or PDPA100; and Lipo2K-GL3 siRNA complex was compared to cells incubated with free medium. No obvious cytotoxicity was observed with these NPs (FIG. 4).

Figure 7A:
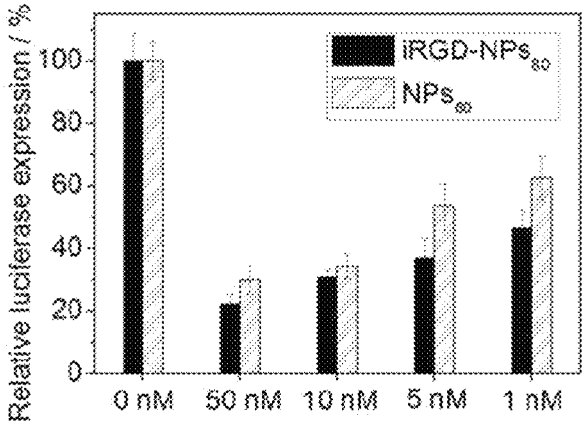
FIGS. 7A-7D are histograms showing firefly luciferase expression in Luc-HeLa cells transfected with GL3 siRNA-loaded NPs of (7A) Meo-PEG113-b-P(DPA80-co-GMA5-TEPA), and (7B) Meo-PEG113-b-P(MMA80-co-GMA5-TEPA-C14) at a siRNA dose from 0-50 nM; and cytotoxicity of GL3 siRNA-loaded NPs of (7C) Meo-PEG113-b-P (DPA80-co-GMA5-TEPA) and (7D) Meo-PEG113-b-P (MMA80-co-GMA5-TEPA-C14) against Luc-HeLa cells at a siRNA dose 0-50 nM.
Figure 7B:
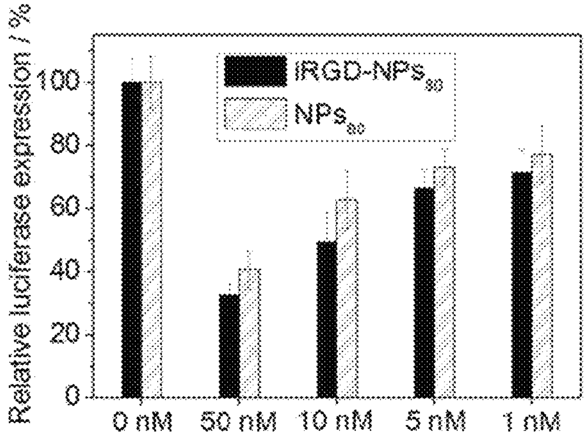
Figure 7C:
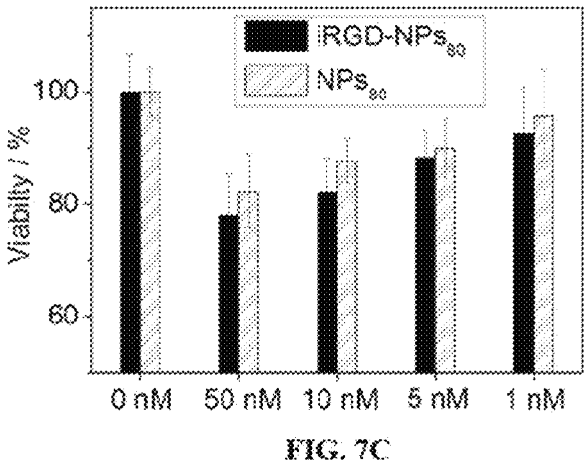
Figure 7D:
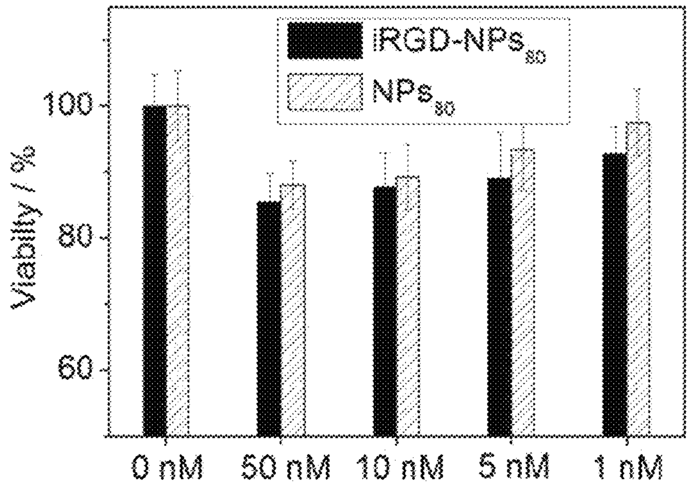

After acquiring the nanoplatform with optimal silencing efficacy (iRGD-NPs$_{80}$), flow cytometry was employed to evaluate its in vitro tumor-targeting ability. With the specific recognition between integrins ($\alpha_v\beta_3$ and $\alpha_v\beta_5$, FIGS. 5A-5D) on Luc-HeLa cells and iRGD, the uptake of DY547-siRNA-loaded iRGD-NPs$_{80}$ is more than 3-fold higher than that of iRGD-absent NPs$_{80}$ (FIGS. 3B and 6A-6C), demonstrating the excellent tumor-targeting ability of iRGD- $NPs_{80}$. Endosomal escape ability was assessed by staining the endosomes with lysotracker green. Fluorescent image of Luc-HeLa cells incubated with the siRNA-loaded iRGD-$NPs_{80}$ showed that a majority of the internalized siRNA-loaded NPs entered the cytoplasm after 4 h incubation, indicating the effective endosomal escape of the iRGD-$NPs_{80}$. In comparison, for the iRGD-NPs prepared from polymer without lipid-like grafts or pH response (FIGS. 7A-7D), the endosome escape ability is relatively weaker, thus leading to a much lower silencing efficacy (FIGS. 7A-7B).

Figure 3D:
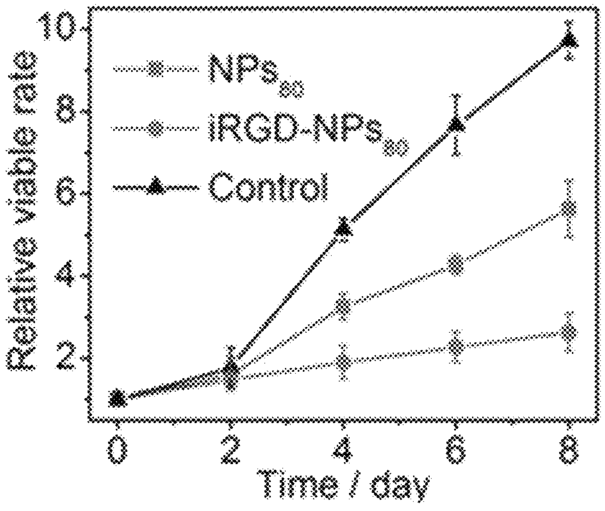

The iRGD-NPs80 was further tested on whether it can downregulate survivin expression, an inhibitor of apoptosis protein that is over-expressed in most cancers (Altieri D C et al., *Nat Rev Cancer,* 3, 46-54 (2003)). PC3 cells, a prostate cancer cell line showing targeted uptake of iRGD-NPs (FIGS. 5A-5D and 6A-6C) where the uptake of DY547-siRNA-loaded iRGD-$NPs_{80}$ is also about 3-fold higher than that of iRGD-absent $NPs_{80}$, were used as a model cell line. Western blot analysis was carried out for determining survivin expression in PC3 cells treated by survivin siRNA-loaded $NPs_{80}$ or survivin siRNA-loaded iRGD-$NPs_{80}$. The western blot analysis indicates that the survivin siRNA-loaded iRGD-$NPs_{80}$ significantly suppress survivin expression (>80% knockdown) at a 10 nM siRNA dose. At a 50 nM siRNA dose, survivin expression is nearly absent (<3%, FIG. 7C). The similar result can be also found in the immunofluorescence staining analysis of PC3 cells treated by survivin siRNA-loaded $NPs_{80}$ or survivin siRNA-loaded iRGD-$NPs_{80}$ at a 10 nM siRNA dose. Very weak red fluorescence corresponding to the residual survivin can be observed in the cells treated with iRGD-$NPs_{80}$ at a 10 nM siRNA dose. With such suppressed survivin expression, the proliferation rate of PC3 cells is very slow. There is only 2.5-fold increase in cell number after 8 days incubation (FIG. 3D).

Figure 8A:
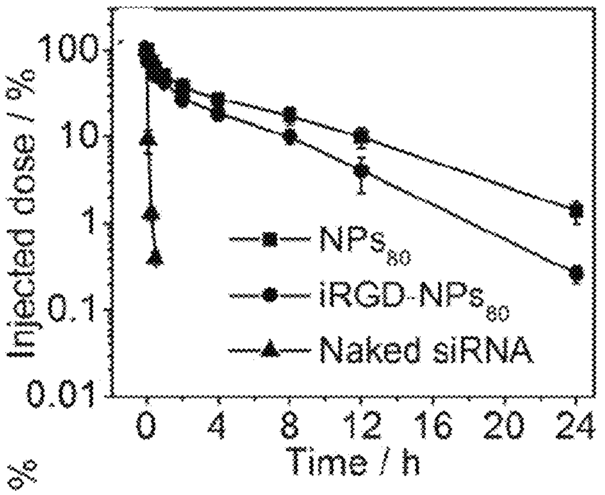
FIGS. 8A-8B are graphs showing (8A) pharmacokinetics of naked siRNA, and siRNA-loaded NPs; (8B) biodistribution of the NPs in the PC3 xenograft tumor-bearing mice sacrificed at 24 h post-injection of naked siRNA, and siRNA-loaded NPs.
Figure 8B:
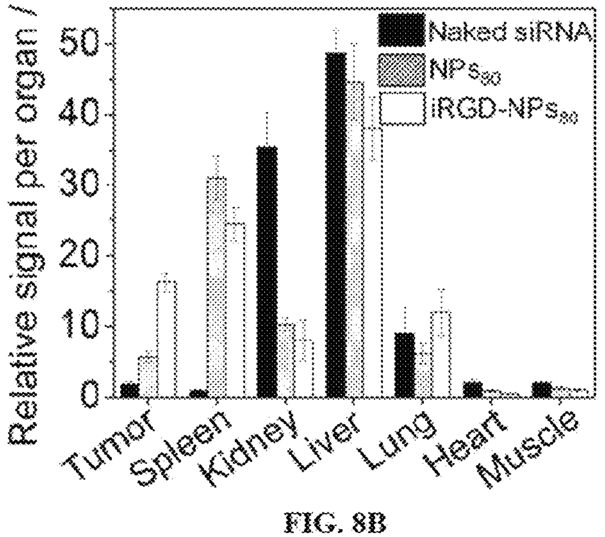
Figure 15A:
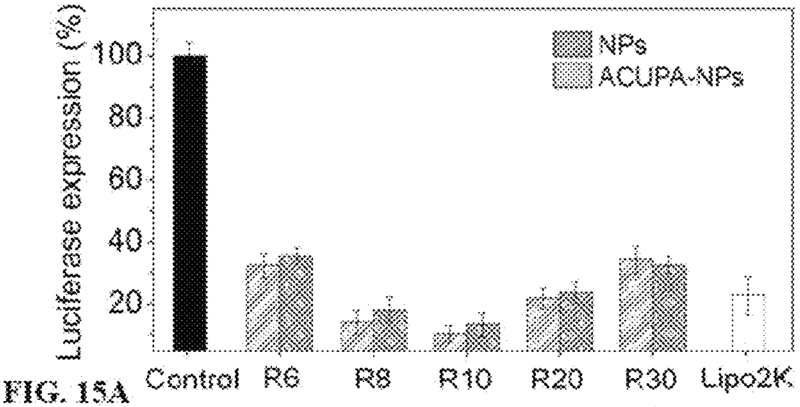
FIGS. 15A-15C are graphs showing (15A) firefly luciferase expression in Luc-HeLa cells transfected with GL3 siRNA-loaded NPs of Meo-PEG-b-P(DPA-co-GMA-Rn) and Lipo2K-siRNA complex at a 10 nM siRNA dose; (15B) flow cytometry profile of Luc-HeLa cells incubated with the DY547-siRNA-loaded NPsR10 and ACUPA-NPsR10 for 4 h; and (15C) a graph showing proliferation over time (days) of LNCaP cells treated with PHB1 siRNA-loaded NPsR10 and ACUPA-NPsR10 at a 10 nM siRNA dose. GL3 siRNA-loaded NPsR10 were used as a control.

After validating the efficient gene silencing of iRGD-$NPs_{80}$, their in vivo tumor-targeting ability was assessed. Pharmacokinetics was first examined by intravenous injection of DY647-siRNA-loaded NPs. As shown in FIG. 15A, the blood half-life ($t_{1/2}$) of iRGD-$NPs_{80}$ is around 3.56 h, which is far longer than that of naked siRNA ($t_{1/2}$<10 min). This prolonged blood circulation is mainly due to the protection of PEG outer layer and small particle size (Knop K et al., *Angewandte Chemie International Edition,* 49, 6288-6308(2010)). The in vivo tumor-targeting ability was evaluated by intravenously injecting DY677-siRNA-loaded NPs into PC3 xenograft tumor-bearing mice. Overlaid fluorescent image of PC3 xenograft tumor-bearing mice at 24 h post-injection of naked siRNA and siRNA-loaded NPs showed that, with the iRGD-mediated tumor-targeting, the iRGD-$NPs_{80}$ show a much higher tumor accumulation than that of $NPs_{80}$ at 24 h post-injection. The tumors and main organs were harvested and the biodistribution is shown in FIG. 8B. Naked siRNA has a characteristic biodistribution, i.e., high accumulation in kidney but extremely low accumulation in tumor. With the specific recognition between iRGD and integrins $\alpha_v\beta_3$ and $\alpha_v\beta_5$ over-expressed on tumor cells and angiogenic tumor vasculature (Wang Y et al., *Nat Mater,* 13, 204-212 (2014); Sugahara K N et al., *Cancer Cell,* 16, 510-520(2009)), the tumor accumulation of the iRGD-$NPs_{80}$ is around 3-fold higher that of $NPs_{80}$.

To evaluate the tumor-penetrating ability of the iRGD-$NPs_{80}$, the tumors were collected at 4 h post-injection of the DY677-siRNA-loaded NPs and then sectioned for immunofluorescence staining. There is nearly no naked siRNA in the tumor section. For the $NPs_{80}$, the number of NPs in tumor section is very low. Additionally, most of these NPs are positioned in the tumor vessels, and only a small number reach the extravascular tumor parenchyma. In contrast, highly concentrated iRGD-$NPs_{80}$ with bright red fluorescence could be visualized in the tumor section. Remarkably, a majority of these NPs can cross tumor vessels and reach the extravascular tumor parenchyma, strongly demonstrating the deep tumor-penetrating characteristic of iRGD-$NPs_{80}$.

Figure 9:
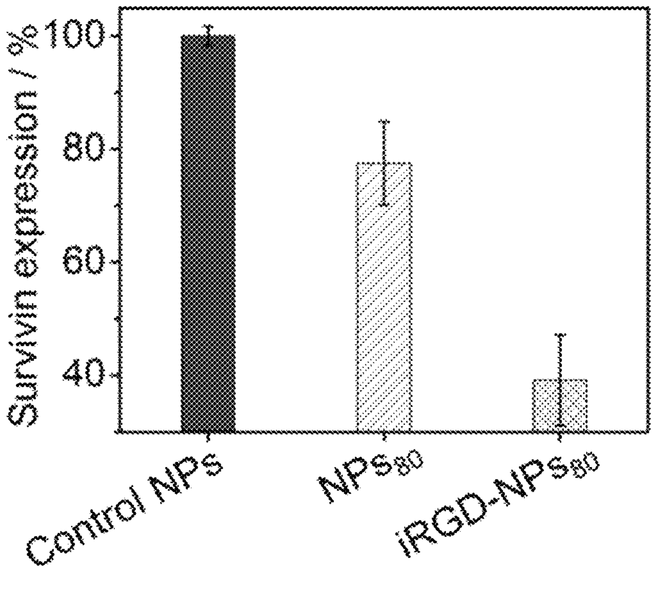
FIG. 9 is a bar graph showing survivin expression in PC3 xenograft tumor of the mice treated by GL3 siRNA-loaded NPs80 (Control NPs), and survivin siRNA-loaded NPs80 and iRGD-NPs80.
Figure 10:
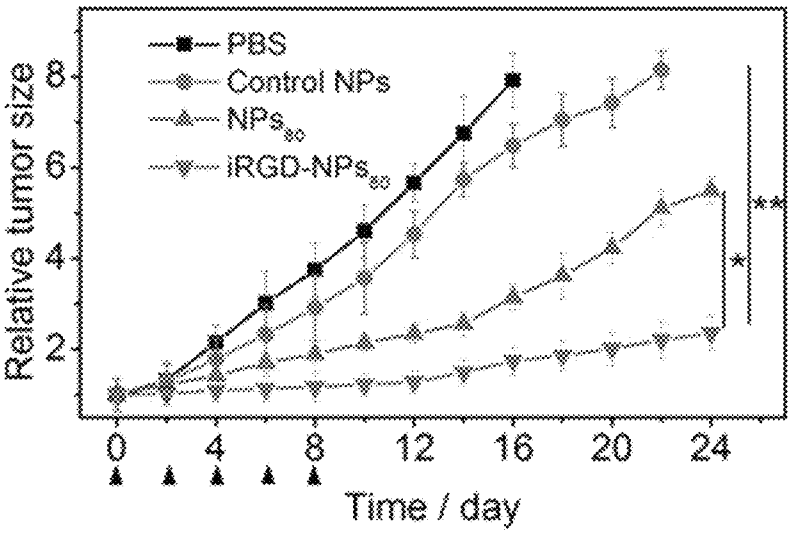
FIG. 10 is a graph showing relative tumor size over time (days) of the PC3 xenograft tumor-bearing mice after treatment by PBS, control NPs, and survivin siRNA-loaded NPs. The intravenous injections are indicated by the arrows. *P<0.05; **P<0.01.
Figure 11:
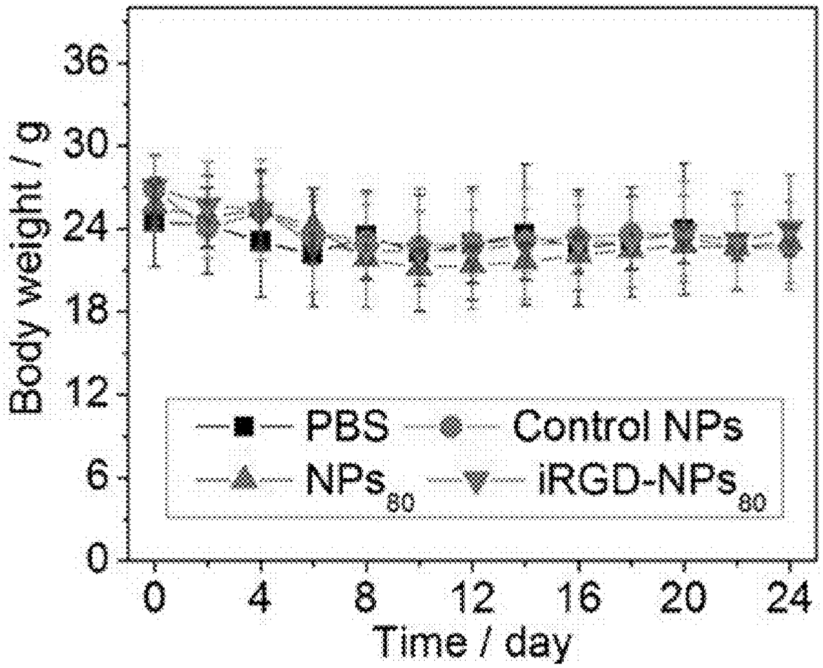
FIG. 11 is graph showing body weight over time (days) of the PC3 xenograft tumor-bearing nude mice treated with PBS, GL3 siRNA-loaded NPs80 (Control NPs), and survivin siRNA-loaded NPs80 and iRGD-NPs80.

Finally, the in vivo inhibition of survivin expression and anti-cancer efficacy was evaluated. The survivin siRNA-loaded NPs were intravenously injected into the PC3 xenograft tumor-bearing mice (650 μg/kg siRNA dose, n=3) for three consecutive days. Western blot analysis of survivin expression in the PC3 tumor tissue after systemic treatment by control NPs (GL3 siRNA-loaded $NPs_{80}$), survivin siRNA-loaded NPs and survivin siRNA-loaded iRGD-$NPs_{80}$ showed that the siRNA-loaded NPs indeed suppressed survivin expression in tumor. In particular, the administration of survivin siRNA-loaded iRGD-$NP_{80}$ induces more than 60% knockdown in survivin expression, whereas survivin siRNA-loaded NPs induced about 25% knockdown in survivin expression (FIG. 9). Thus, survivin siRNA-loaded iRGD-$NPs_{80}$ showed around 3-fold greater knockdown in survivin expression than that of $NPs_{80}$. Notably, the administration of NPs shows negligible in vivo side effects. To confirm whether the NP-mediated survivin silencing has an anti-cancer effect, the survivin siRNA-loaded NPs were intravenously injected to the mice once every two days at a 650 μg/kg siRNA dose (n=5). After five consecutive injections (FIG. 10), the tumor growth is inhibited compared to the mice treated with PBS or GL3 siRNA-loaded NPs (Control NPs). Harvested PC3 tumor from each group at day 16 was compared with GL3 siRNA-loaded $NPs_{80}$ as a control. Particularly, with the excellent tumor-targeting and penetrating abilities, the iRGD-$NPs_{80}$ can significantly suppress tumor growth, and there is only around 2-fold increase in tumor size at day 24. The PC3 xenograft tumor-bearing nude mice treated with PBS, GL3 siRNA-loaded $NPs_{80}$ (Control NPs), or survivin siRNA-loaded $NPs_{80}$ and iRGD-$NPs_{80}$ were monitored for body weight but no significant difference was noticed (FIG. 11).

In summary, an ultra pH-responsive and tumor-penetrating nanoplatform for targeted systemic siRNA delivery has been developed. The in vitro and in vivo results demonstrate that this polymeric NP has a long blood circulation, and can efficiently target tumor and penetrate tumor parenchyma, leading to efficient gene silencing and tumor growth inhibition. The polymeric nanoplatform reported herein may represent a robust siRNA delivery vehicle for the treatment of a myriad of important diseases including cancer.

Example 2: Ultra pH-Responsive and Tumor-Penetrating Nanoplatform for Targeted siRNA Delivery with Robust Anti-Cancer Efficacy

Methods and Materials

Materials

Methoxyl-polyethylene glycol (Meo-$PEG_{113}$-OH) and hydroxyl polyethylene glycol carboxylic acid (HO-$PEG_{113}$-COOH) were purchased from JenKem Technology and used as received. Oligoarginine (NH2-Rn—CONH2, n=6, 8, 10, 20, 30) was provided by MIT Biopolymer facility. Allyl protected S,S-2-[3-[5-amino-1-carboxypentyl]-ureido]-pentanedioic acid (ACUPA) was kindly provided by BIND Therapeutics as a gift. 2-(Diisopropyl amino) ethyl methacrylate (DPA-MA) and glycidyl methacrylate (GMA) were provided by Sigma-Aldrich and passed over an alumina column before use in order to remove the hydroquinone inhibitors. α-Bromoisobutyryl bromide, N,N'-dimethylformamide (DMF), triethylamine (TEA), N,N,N',N',N'-pentamethyldiethylenetriamine (PMDETA), copper (I) bromide (CuBr), tetraethylenepentamine (TEPA), isopropyl alcohol, p-toluenesulfinate tetrahydrate (PTSF), tetrakis(triphenylphosphine) palladium ($Pd(PPh_3)_4$) and dichloromethane (DCM) were acquired from Sigma-Aldrich and used directly. Lipofectamine 2000 (Lipo2K) was purchased from Invitrogen. Steady-Glo luciferase assay system was provided by Promega. GL3, fluorescent dye (DY547, DY647 and Cy5.5) labeled GL3 and PHB1 siRNAs were acquired from Dharmacon. The siRNA sequences are as follows: GL3 siRNA, 5'-CUU ACG CUG AGU ACU UCG AdTdT-3' (sense) (SEQ ID NO:1) and 5'-UCG AAG UAC UCA GCG UAA GdTdT-3' (antisense) (SEQ ID NO:2); PHB1 siRNA, 5'-GCG ACG ACC UUA CAG AGC GUU-3' (sense) (SEQ ID NO:5) and 5'-CGC UCU GUA AGG UCG 0UCG CUU-3' (antisense) (SEQ ID NO:6). The fluorescent dyes DY-547 and DY-647 were labeled at the 5'-end of the sense strand of GL3 siRNA. Cy5.5 was labeled at the 5'-end of both the sense and antisense strands of GL3 siRNA. HeLa cells stably expressing firefly and *Renilla* luciferase (Luc-HeLa) were obtained from Alnylam Pharmaceuticals, Inc. The cells were incubated in RPMI 1640 medium (Invitrogen) with 10% fetal bovine serum (FBS, Sigma-Aldrich). All other reagents and solvents are of analytical grade and used without further purification.

Synthesis of Meo-PEG-Br and Br-PEG-COOH

Meo-$PEG_{113}$-OH (8 g, 1.6 mmol) and TEA (1.3 mL, 9.6 mmol) were dissolved in 250 mL of DCM. In an ice-salt bath, α-bromoisobutyryl bromide (1 mL, 8 mmol) dissolved in 10 mL of DCM was added dropwise. After stirring for 24 h, the mixture was washed with 1 M NaOH (3×50 mL), 1 M HCl (3×50 mL), and deionized water (3×50 mL). After drying over anhydrous $MgSO_4$, the solution was concentrated, and cold ether was added to precipitate the product. After re-precipitating thrice, the product was collected as white powder after drying under vacuum. The synthesis of Br-PEG-COOH was carried out according to a method similar to that described above, by changing Meo-$PEG_{113}$-OH with HO-$PEG_{113}$-COOH. The synthesis scheme of Meo-PEG-Br is shown below.

Synthesis of methoxyl-polyethylene glycol-b-poly (2-(diisopropylamino) ethylmethacrylate-co-glycidyl methacrylate) (Meo-PEG-b-P(DPA-co-GMA))

Meo-PEG-b-P(DPA-co-GMA) copolymer was synthesized by atom transfer radical polymerization (ATRP). DPA-MA (2.6 g, 12 mmol), GMA (0.07 g, 0.45 mmol), Meo-PEG-Br (0.75 g, 0.15 mmol), and PMDETA (31.5 μL, 0.15 mmol) were added to a polymerization tube. DMF (3 mL) and 2-propanol (3 mL) were then added to dissolve the monomer and initiator. After three cycles of freeze-pump-thaw to remove oxygen, CuBr (21.6 mg, 0.15 mmol) was added under nitrogen atmosphere and the polymerization tube was sealed under vacuum. After polymerization at 40° C. for 24 h, tetrahydrofuran (THF) was added to dilute the product, which was then passed through a neutral $Al_2O_3$ column to remove the catalyst. The resulting THF solution was concentrated and the residue was dialyzed against THF, followed by deionized water. The expected copolymer was collected as a white powder after freeze-drying under vacuum. The synthesis scheme is shown below.

Synthesis of Meo-PEG-b-P(DPA-co-GMA-Rn)

Meo-PEG-b-P(DPA-co-GMA-Rn) was synthesized via the ring opening reaction between the amino group of $NH_2$—Rn—$CONH_2$ and the epoxy group of the GMA repeating unit. In brief, Meo-PEG-b-P(DPA-co-GMA) (1 g) dissolved in DMF (15 mL) was added dropwise to the DMF solution (10 mL) of $NH_2$—Rn—$CONH_2$ (10-fold molar excess relative to the GMA repeating unit). After reaction at 60° C. for 7 h, the mixture was transferred to a dialysis tube and then dialyzed against deionized water. The Meo-PEG-b-P(DPA-co-GMA-Rn) was finally collected as a white powder after freeze-drying under vacuum.

The synthesis route of Meo-PEG-b-P(DPA-co-GMA-Rn) is shown below.

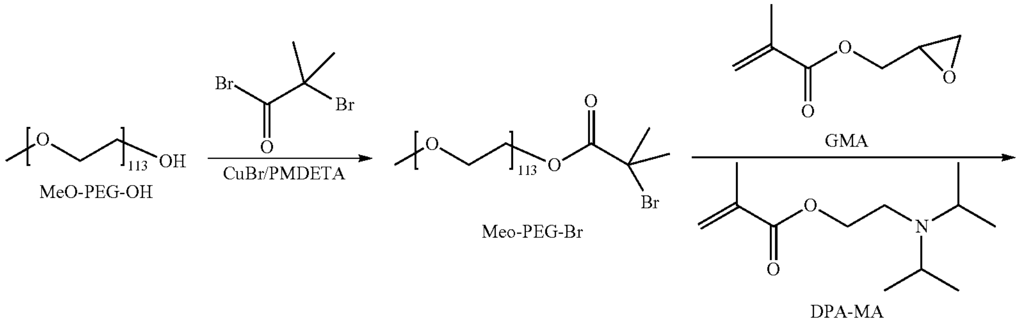

-continued

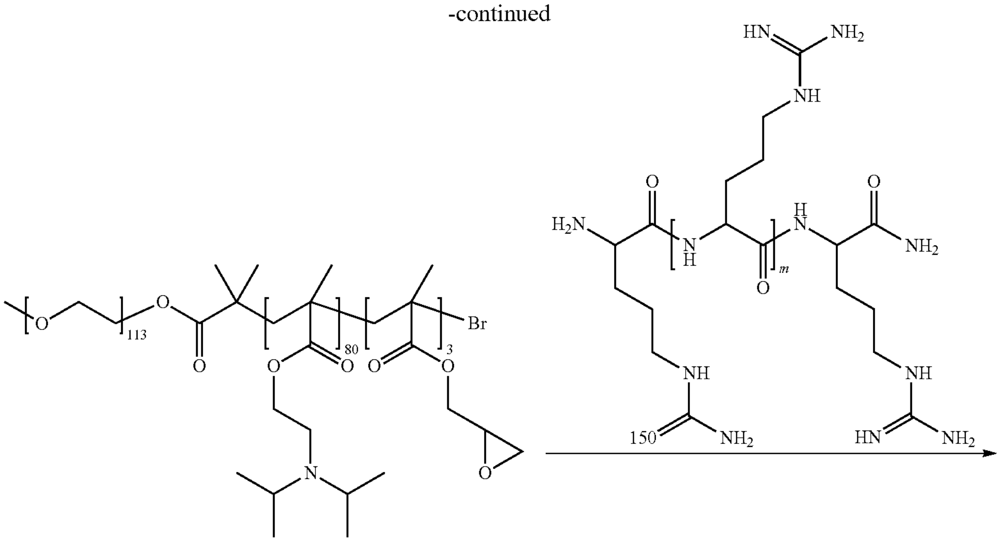

MeO-PEG-b-P(DPA-co-GMA)

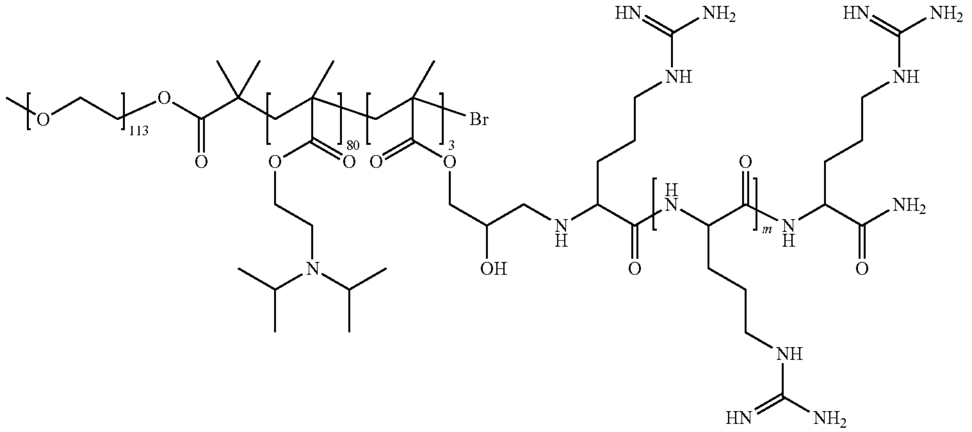

MeO-PEG-b-P(DPA-co-GMA-Rn) (n = 6, 8, 10, 20, 30)

Synthesis of Meo-PEG-b-P(DPA-co-GMA-TEPA)

Meo-PEG-b-P(DPA-co-GMA-TEPA) was synthesized via the ring opening reaction between TEPA and the epoxy group of the GMA repeating unit. In brief, Meo-PEG-b-P(DPA-co-GMA) (1 g) dissolved in DMF (15 mL) was added dropwise to the DMF solution (5 mL) of TEPA (30-fold molar excess relative to the GMA repeating unit). After reacting at 60° C. for 7 h, the mixture was transferred to a dialysis tube and then dialyzed against deionized water. The Meo-PEG-b-P(DPA-co-GMA-TEPA) was finally collected as a white powder after freeze-drying under vacuum. The synthesis route of Meo-PEG-b-P(DPA-co-GMA-TEPA) is shown below.

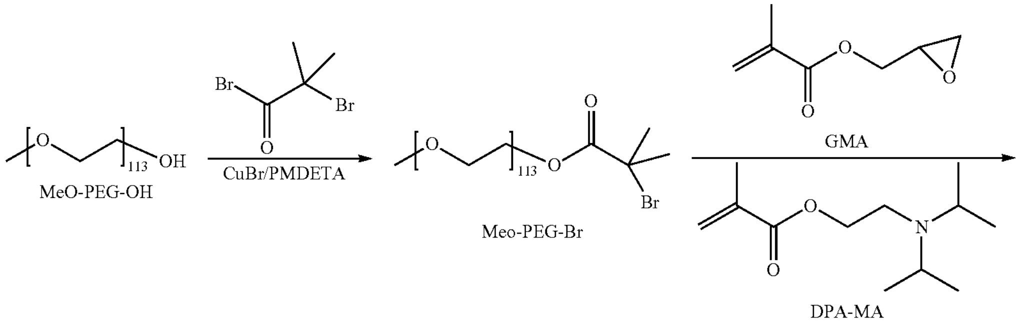

MeO-PEG-OH

Meo-PEG-Br

DPA-MA

-continued

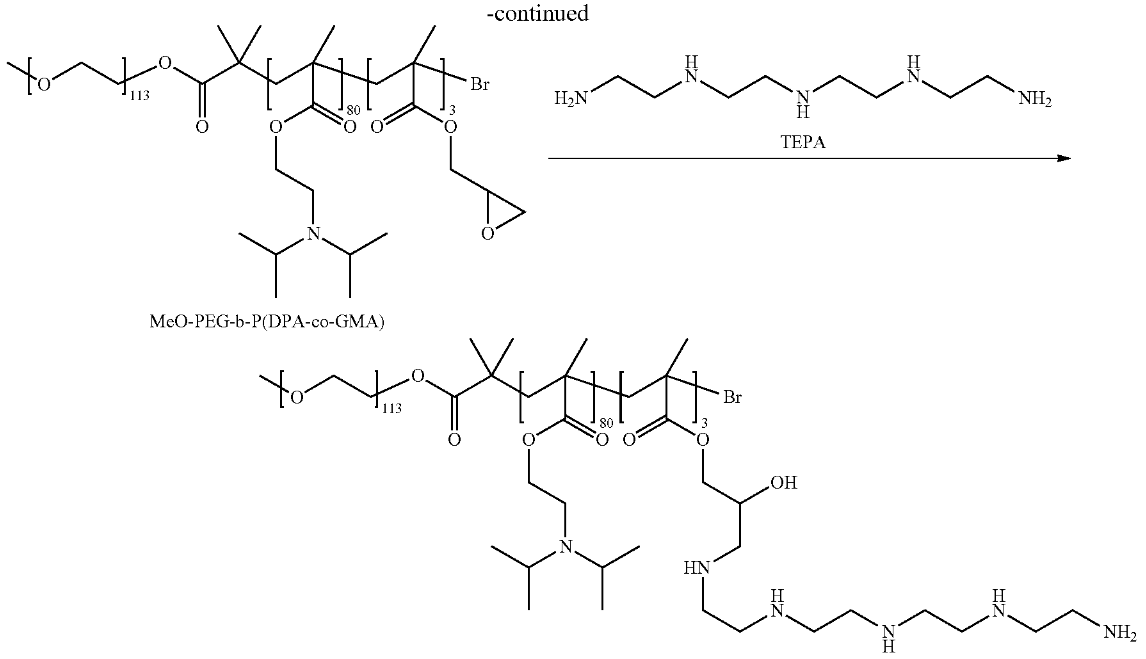

MeO-PEG-b-P(DPA-co-GMA)

MeO-PEG-b-P(DPA-co-GMA-TEPA)

Synthesis of Meo-PEG-b-P(DPA-co-GMA-TEPA-Cy5.5)

Meo-PEG-b-P(DPA-co-GMA-TEPA) (0.2 g) and Cy5.5 NHS ester (1.5-fold molar excess relative to the TEPA repeating unit) were well dissolved in 5 mL of THF. After constantly stirring in dark for 48 h, the solution was dialyzed against deionized water and the product was collected after freeze-drying.

The synthesis of Meo-PEG-b-P(DPA-co-GMA-TEPA-Cy5.5) is shown below.

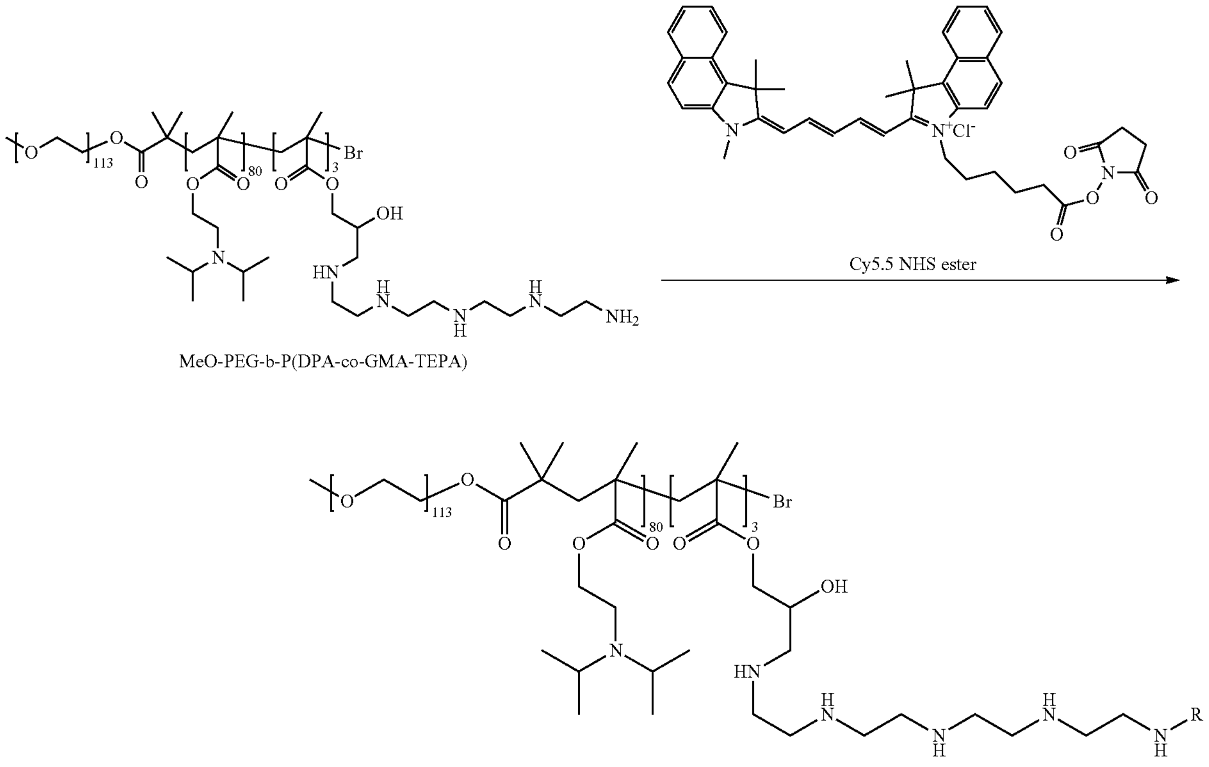

MeO-PEG-b-P(DPA-co-GMA-TEPA)

MeO-PEG-b-P(DPA-co-GMA-TEPA-Cy5.5)

-continued

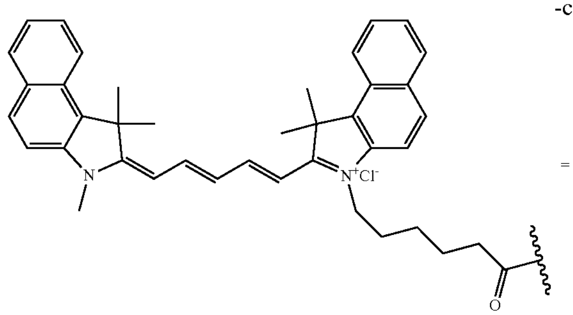

= R

Synthesis of HOOC-PEG-b-PDPA

HOOC-PEG-b-PDPA copolymers were also synthesized by the ATRP method. For example, DPA-MA (1.73 g, 8 mmol), Br-PEG-COOH (0.5 g, 0.1 mmol), and PMDETA (21 μL, 0.1 mmol) were added to a polymerization tube. Subsequently, DMF (2 mL) and 2-propanol (2 mL) were added to dissolve the monomer and initiator. After three cycles of freeze-pump-thaw to remove oxygen, CuBr (14.4 mg, 0.1 mmol) was added under nitrogen atmosphere and the polymerization tube was sealed under vacuum. After polymerization at 40° C. for 24 h, tetrahydrofuran (THF) was added to dilute the product, which was then passed through a neutral $Al_2O_3$ column to remove the catalyst. The obtained THF solution was concentrated and the residue was dialyzed against deionized water. The HOOC-PEG-b-PDPA was obtained as a white powder after freeze-drying under vacuum. The synthesis route of HOOC-PEG-b-PDPA is shown below.

Synthesis of Allyl-protected ACUPA-PEG-b-PDPA

HOOC-PEG-b-PDPA copolymer (1 g), allyl protected ACUPA (5-fold molar excess relative to the terminal carboxylic acid group), EDC·HCl (3-fold molar excess relative to the terminal carboxylic acid group), and NHS (3-fold molar excess relative to the terminal carboxylic acid group) were well dissolved in 15 mL of THF. The mixture was stirred at room temperature for 48 h. The solution was subsequently dialyzed against DMF for 48 h followed by deionized water. The expected allyl-protected ACUPA-PEG-PDPA was collected after freeze-drying. The synthesis route of Allyl-protected ACUPA-PEG-b-PDPA is shown below.

Synthesis of ACUPA-PEG-b-PDPA

Allyl-protected ACUPA-PEG-PDPA (1 g) was well dissolved in 15 mL of THF and $Pd(PPh_3)_4$ (42 mg) was added. Under stirring, PTSF (155 mg) dissolved in 2.5 mL of methanol was added to the suspension of Allyl protected ACUPA-PEG-PDPA and $Pd(PPh_3)_4$. After reacting in dark for 2 h, the suspension was transferred to a dialysis tube (MWCO 3500) and dialyzed against toluene for 48 h. Thereafter, the solution was removed by rotary evaporation and the residue was dissolved in 15 mL of THF. After dialyzing against deionized water for 48 h, the ACUPA-PEG-PDPA was collected through freeze-drying.
The synthesis route of ACUPA-PEG-b-PDPA is shown below.

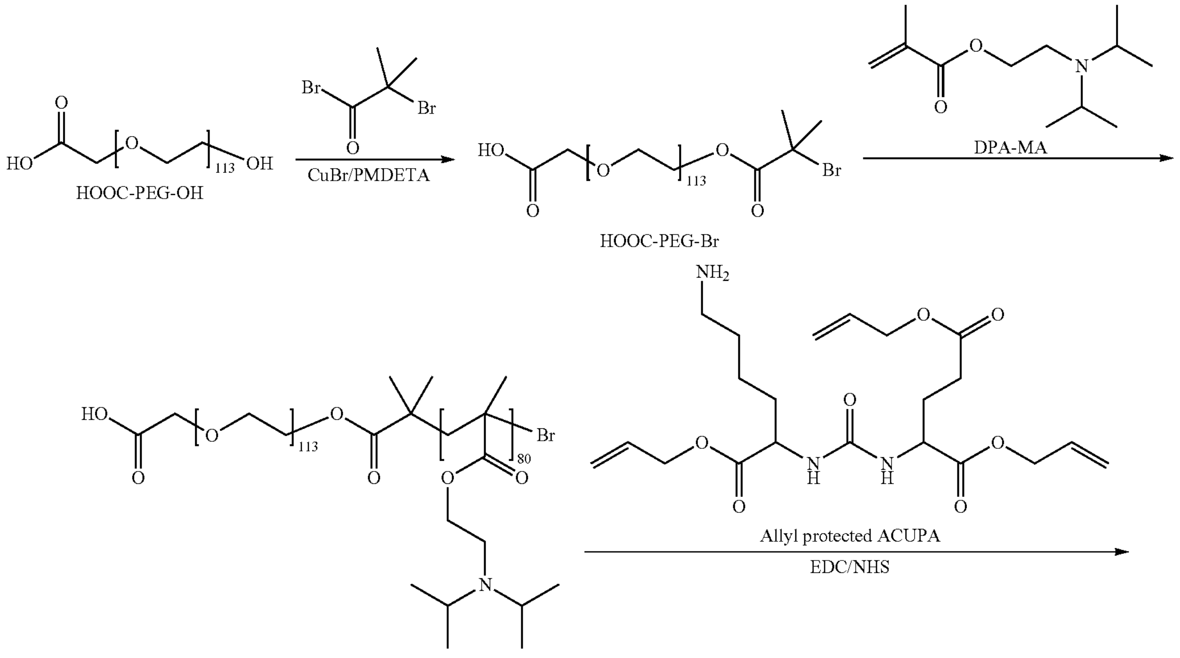

-continued

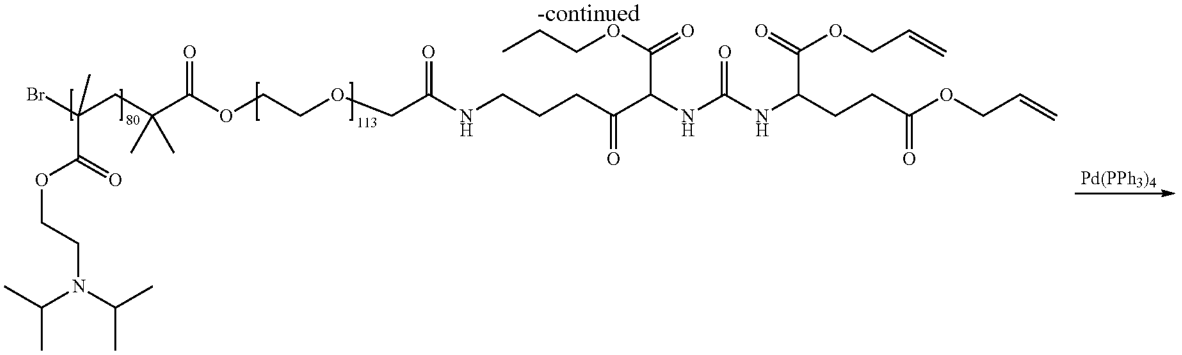

Allyl protected ACUPA-PEG-b-PDPA

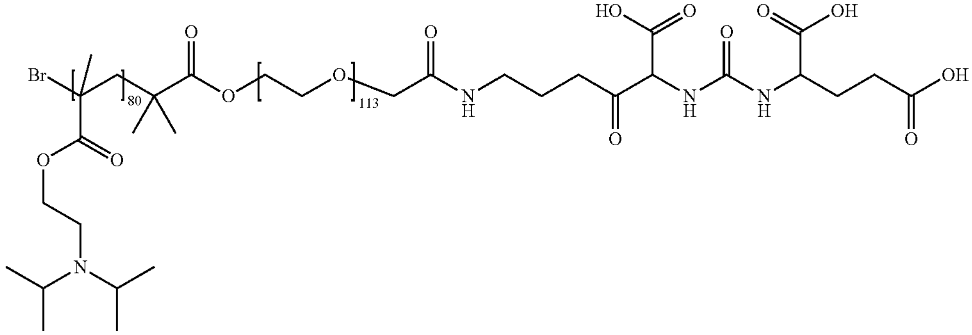

ACUPA-PEG-b-PDPA

Gel Permeation Chromatography (GPC)

Number- and weight-average molecular weights (Mn and Mw, respectively) of the polymers were determined by a gel permeation chromatographic system equipped with a Waters 2690D separations module and a Waters 2410 refractive index detector. THF was used as the eluent at a flow rate of 0.3 mL/min. Waters millennium module software was used to calculate molecular weight on the basis of a universal calibration curve generated by polystyrene standard of narrow molecular weight distribution.

$^1$H Nuclear Magnetic Resonance ($^1$HNMR)

The $^1$HNMR spectra of the polymers were recorded on a Mercury VX-300 spectrometer at 400 MHz (Varian, USA), using $CDCl_3$ as a solvent and TMS as an internal standard.

Acid-Base Titration

Meo-PEG-b-P(DPA-co-GMA-Rn) was dispersed in deionized water, and a concentrated HCl aqueous solution was added until the copolymer was completely dissolved (1 mg/mL). Subsequently, 1 M NaOH aqueous solution was added in 1-5 μL increments. After each addition, the solution was constantly stirred for 3 min, and the solution pH was measured using a pH meter. The pKa of the copolymer was determined as the pH at which 50% of the copolymer turns ionizes.

Preparation and Characterization of Nanoparticles (NPs)

Meo-PEG-b-P(DPA-co-GMA-Rn) was dissolved in THF to form a homogenous solution with a concentration of 4 mg/mL. Subsequently, a certain volume of this THF solution was taken and mixed with 1 nmol siRNA (0.1 nmol/μL aqueous solution) in an N/P molar ratio of 80:1. Under vigorously stirring (1000 rpm), the mixture was added dropwise to 4 mL of deionized water. The NP dispersion formed was transferred to an ultrafiltration device (EMD Millipore, MWCO 100 K) and centrifuged to remove the organic solvent and free compounds. After washing with PBS (pH 7.4) solution (3×5 mL), the siRNA loaded NPs were dispersed in 1 mL of phosphate buffered saline (PBS, pH 7.4) solution. Size and zeta potential were determined by dynamic light scattering (DLS, Brookhaven Instruments Corporation). The morphology of NPs was visualized on a Tecnai G2 Spirit BioTWIN transmission electron microscope (TEM). Before observation, the sample was stained with 1% uranyl acetate and dried under air. To determine the siRNA encapsulation efficiency, DY547-labelled GL3 siRNA (DY547-siRNA) loaded NPs were prepared according to the method described above. A small volume (50 μL) of the NP solution was withdrawn and mixed with 20-fold DMSO. The fluorescence intensity of DY547-siRNA was measured using a Synergy HT multi-mode microplate reader (BioTek Instruments) and compared to the free DY-547 labelled GL3 siRNA solution (1 nmol/mL PBS solution).

To prepare the ACUPA-NPs, Meo-PEG-b-P(DPA-co-GMA-Rn) (4 mg/mL in THF) was mixed with 1 nmol siRNA (0.1 nmol/μL aqueous solution) in a N/P molar ratio of 80:1. Then ACUPA-PEG-b-PDPA (4 mg/mL in THF, 10 mol % compared to Meo-PEG-b-P(DPA-co-GMA-Rn)) was added, and the mixture was added dropwise to 4 mL of deionized water. The ACUPA-NPs were purified by an ultrafiltration device (EMD Millipore, MWCO 100 K) and finally dispersed in 1 mL of PBS. The siRNA encapsulation efficiency was examined by replacing the siRNA with DY-547 labelled GL3 siRNA.

Evaluation of pH Sensitivity

The THF solution of Meo-PEG-b-P(DPA-co-GMA-Rn) (4 mg/mL) and Meo-PEG-b-P(DPA-co-GMA-TEPA-Cy5.5) (4 mg/mL) was mixed in a volume ratio of 8:2. Under vigorously stirring (1000 rpm), 0.2 mL of the mixture was added dropwise to 2 mL of deionized water. After collection and purification by an ultrafiltration device (EMD Millipore, MWCO 100 kDa), the NPs formed were dispersed in 1 mL of deionized water. Subsequently, 1 M NaOH or HCl was added in 1-5 μL increments, and the fluorescence intensity of the NPs was measured on a Synergy HT multi-mode microplate reader. The normalized fluorescence intensity (NFI) vs. pH profile was used to quantitatively assess the pH responsiveness. NFI is calculated as follows:

$$NFI=(F-F\min)/(F\max-F\min)$$

where F is the fluorescence intensity of the NPs at any given pH value and Fmax and Fmin are the maximal and minimal fluorescence intensity of the NPs, respectively.

In Vitro siRNA Release

DY547-siRNA-loaded NPs were prepared as described above. Subsequently, the NPs were dispersed in 1 mL of PBS (pH 7.4) and then transferred to a Float-a-lyzer G2 dialysis device (MWCO 100 kDa, Spectrum) that was immersed in PBS (pH 7.4) at 37° C. At a predetermined interval, 5 μL of the NP solution was withdrawn and mixed with 20-fold DMSO. The fluorescence intensity of DY547-siRNA was determined by Synergy HT multi-mode microplate reader.

Cell Culture

Human cervical cancer cell line with the expression of luciferase (Luc-HeLa) and prostate cancer (PCa) cell lines (LNCaP, PC3, DU145, 22RV1) were incubated in RPMI 1640 medium with 10% FBS at 37° C. in a humidified atmosphere containing 5% $CO_2$.

Luciferase Silencing

Luc-HeLa cells were seeded in 96-well plates (5,000 cells per well) and incubated in 0.1 mL of RPMI 1640 medium with 10% FBS for 24 h. Thereafter, the GL3 siRNA-loaded NPs were added. After incubating for 24 h, the cells were washed with fresh medium and allowed to incubate for another 48 h. The expression of firefly luciferase in HeLa cells was determined using Steady-Glo luciferase assay kits. Cytotoxicity was measured using the alamarBlue assay according to the manufacturer's protocol. The luminescence or fluorescence intensity was measured using a microplate reader, and the average value of five independent experiments was collected. As a control, the silencing effect of Lipo2K/GL3 siRNA complexes was also evaluated according to the procedure described above and compared to that of GL3 siRNA-loaded NPs.

Determination of the Expression of Prostate Specific Membrane Antigen (PSMA)

The PCa cell lines were seeded in 6-well plates (50,000 cells per well) and incubated in 1 mL of RPMI 1640 medium containing 10% FBS for 24 h. Thereafter, 10 μL of PE-conjugated anti-human PSMA antibody (BioLegend) was added, and the cells were allowed to incubate for another 4 h. After removing the medium and washing with PBS (pH 7.4) solution thrice, the cells were collected for flow cytometry quantitative analysis (DXP11 Analyzer).

Evaluation of Endosomal Escape

Luc-HeLa cells (20,000 cells) were seeded in discs and incubated in 1 mL of RPMI 1640 medium containing 10% FBS for 24 h. Subsequently, the DY547-siRNA-loaded NPs were added, and the cells were allowed to incubate for 1 or 2 h. After removing the medium and subsequently washing with PBS (pH 7.4) solution thrice, the endosomes and nuclei were stained with lysotracker green and Hoechst 33342, respectively. The cells were then viewed under a FV1000 confocal laser scanning microscope (CLSM, Olympus).

Flow Cytometry

Luc-HeLa and PCa cell lines (LNCaP, PC3, DU145) were seeded in 6-well plates (50,000 cells per well) and incubated in 1 mL of RPMI 1640 medium containing 10% FBS for 24 h. Subsequently, the DY547-siRNA-loaded NPs or ACUPA-NPs were added, and the cells were allowed to incubate for another 4 h. After removing the medium and subsequently washing with PBS (pH 7.4) solution thrice, the cells were collected for flow cytometry quantitative analysis.

In Vitro PHB1 Silencing

LNCaP cells were seeded in 6-well plates (50,000 cells per well) and incubated in 1 mL of RPMI 1640 medium containing 10% FBS for 24 h. Subsequently, the cells were transfected with the PHB1 siRNA-loaded NPs or ACUPA-NPs for 24 h. After washing the cells with PBS thrice, the cells were further incubated in fresh medium for another 48 h. Thereafter, the cells were digested by trypsin and the proteins were extracted using modified radioimmunoprecipitation assay lysis buffer (50 mM Tris-HCl pH 7.4, 150 mM NaCl, 1% NP-40 substitute, 0.25% sodium deoxycholate, 1 mM sodium fluoride, 1 mM Na3VO4, 1 mM EDTA), supplemented with protease inhibitor cocktail and 1 mM phenylmethanesulfonyl fluoride (PMSF). The expression of PHB1 was examined using the following western blot analysis.

Western Blot Analysis

Equal amounts of protein, as determined with a bicinchoninic acid (BCA) protein assay kit (Pierce/Thermo Scientific) according to the manufacturer's instructions, were added to SDS-PAGE gels and separated by gel electrophoresis. After transferring the proteins from gel to polyvinylidene difluoride membrane, the blots were blocked with 3% BSA in TBST (50 mM Tris-HCl pH 7.4, 150 mM NaCl, and 0.1% Tween 20) and then incubated with a mixture of PHB1 rabbit antibody (Cell Signaling) and R-actin rabbit antibody (Cell Signaling). The expression of PHB1 was detected with horseradish peroxidase (HRP)-conjugated secondary antibody (anti-rabbit IgG HRP-linked antibody, Cell Signaling) and an enhanced chemiluminescence (ECL) detection system (Pierce).

In Vitro Cell Proliferation

LNCaP cells were seeded in 6-well plates (20,000 cells per well) and incubated in 1 mL of RPMI 1640 medium containing 10% FBS for 24 h. Thereafter, the cells were transfected with the PHB1 siRNA-loaded NPs or ACUPA-NPs for 24 h and then washed with fresh medium for further incubation. At predetermined intervals, the cytotoxicity was measured using the alamarBlue assay according to the manufacturer's protocol. After each measurement, the alamarBlue agent was removed and the cells were incubated in fresh medium for further proliferation.

LNCaP Xenograft Tumor Model

The tumor model was constructed by subcutaneous injection with 200 μL of LNCaP cell suspension (a mixture of RPMI 1640 medium and Matrigel in 1:1 volume ratio) with a density of $3\times10^7$ cells/mL into the back region of healthy male BALB/c nude mice. When the volume of the PC3 tumor xenograft reached ~50 $mm^3$, the mice were used for the following in vivo experiments.

Pharmacokinetics Study

Healthy male BALB/c mice were randomly divided into three groups (n=3) and given an intravenous injection of either (i) free DY647-labelled GL3 siRNA (DY647-siRNA), (ii) DY647-siRNA-loaded NPs, or (iii) DY647-siRNA-loaded ACUPA-NPs at a 650 μg/kg siRNA dose. At predetermined time intervals, orbital vein blood (20 μL) was withdrawn using a tube containing heparin, and the wound was pressed for several seconds to stop the bleeding. The fluorescence intensity of DY-647 labelled siRNA in the blood was determined using a microplate reader. The blood circulation half-life (t½) was calculated by first-order decay fit.

Biodistribution

LNCaP tumor-bearing male BALB/c nude mice were randomly divided into four groups (n=3) and given an intravenous injection of either (i) free Cy5.5-labelled GL3 siRNA (Cy5.5-siRNA), (ii) Cy5.5-siRNA-loaded NPs, (iii) Cy5.5-siRNA-loaded ACUPA-NPs or (iv) PSMA antibody (5 mg/kg dose) 15 min followed by Cy5.5-siRNA loaded ACUPA-NPs at a 650 μg/kg siRNA dose. Twenty-four hours after the injection, the mice were imaged using the Maestro 2 In-Vivo Imaging System (Cri Inc). Main organs and tumors were then harvested and imaged. To quantify the accumulation of NPs in tumors and organs, the fluorescence intensity of each tissue was quantified by Image-J.

In Vivo PHB1 Silencing

LNCaP tumor-bearing male BALB/c nude mice were randomly divided into two groups (n=3) and intravenously injected with (i) PHB1 siRNA-loaded NPs or (ii) PHB1 siRNA-loaded ACUPA-NPs for three consecutive days. Twenty-four hours post the final injection, mice were sacrificed and tumors were harvested. The proteins in the tumor were extracted using modified radioimmunoprecipitation assay lysis buffer (50 mM Tris-HCl pH 7.4, 150 mM NaCl, 1% NP-40 substitute, 0.25% sodium deoxycholate, 1 mM sodium fluoride, 1 mM Na3VO4, 1 mM EDTA), supplemented with protease inhibitor cocktail and 1 mM phenylmethanesulfonyl fluoride (PMSF). The expression of PHB1 was examined using the aforementioned western blot analysis.

Inhibition of Tumor Growth

LNCaP tumor-bearing male BALB/c nude mice were randomly divided into four groups (n=5) and intravenously injected with (i) PBS, (ii) GL3 siRNA-loaded NPs, (iii) PHB1 siRNA-loaded NPs or (iv) PHB1 siRNA-loaded ACUPA-NPs at a 650 μg/kg siRNA dose once every two days. All the mice were administrated five consecutive injections and the tumor growth was monitored every two days by measuring perpendicular diameters using a caliper and tumor volume was calculated as follows:

$$V=W^2 \times L/2$$

where W and L are the shortest and longest diameters, respectively.

Histology

Healthy male BALB/c mice were randomly divided into three groups (n=3) and administered daily intravenous injections of either (i) PBS, (ii) PHB1 siRNA-loaded NPs or (iii) PHB1 siRNA-loaded ACUPA-NPs at a 650 μg/kg siRNA dose. After five consecutive injections (once every two days), the main organs were collected 2 days post the final injection, fixed with 4% paraformaldehyde, and embedded in paraffin. Tissue sections were stained with hematoxylin-eosin (H&E) and viewed under an optical microscope.

Results

Figures 12A, 12B, 12C:
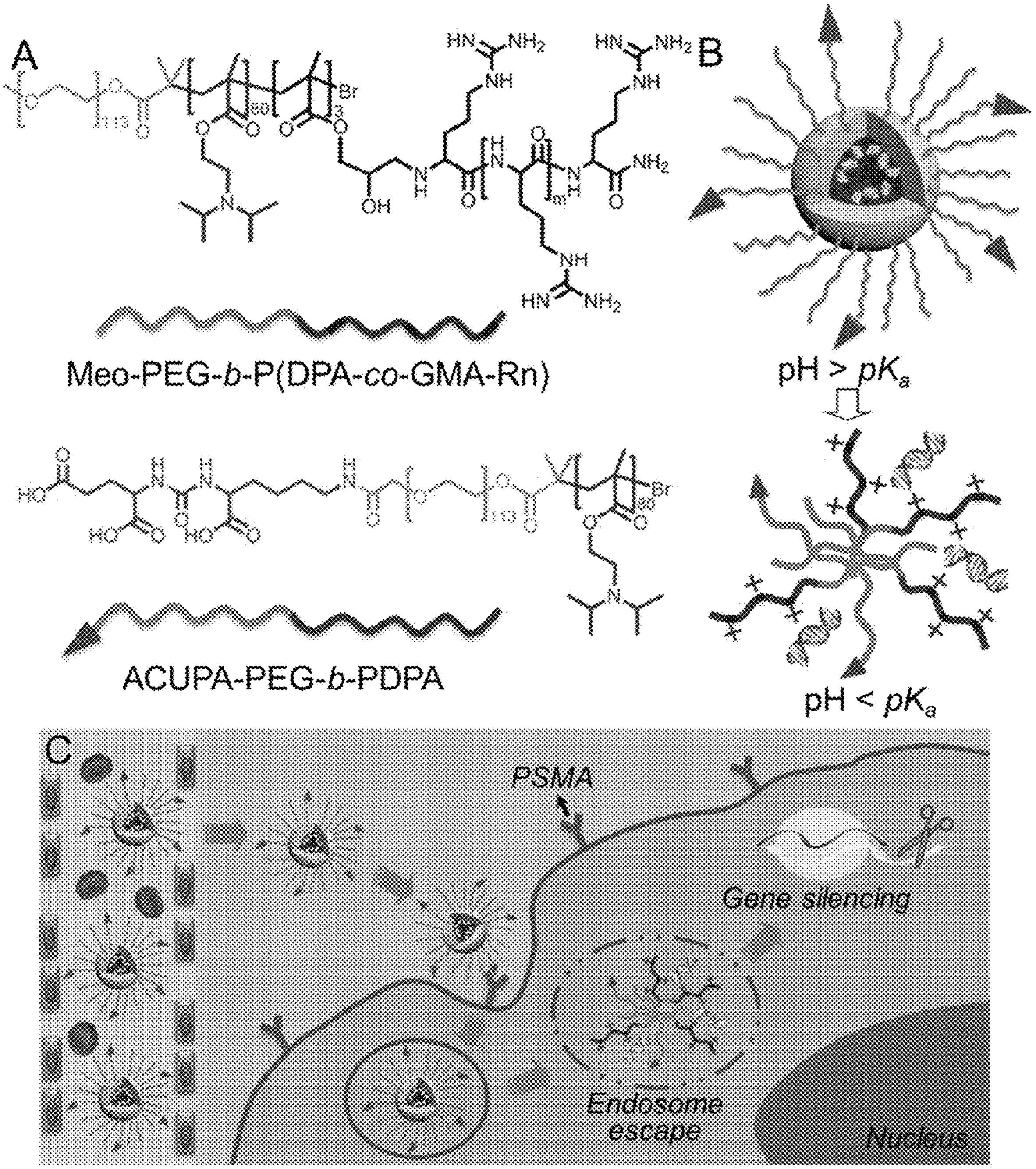
FIGS. 12A-12C are schematic illustrations of (12A) molecular structures of the oligoarginine-functionalized ultra pH-responsive polymer, Meo-PEG-b-P(DPA-co-GMA-Rn), and PCa-specific polymer, ACUPA-PEG-b-PDPA; (12B) endosomal membrane-penetrating and ultra pH-responsive nanoplatform for siRNA loading and release; and (12C) the nanoplatform for in vivo PCa-specific siRNA delivery and cancer therapy.

A high loading, biosafe and long-circulating siRNA delivery nanoplatform that shows high prostate specificity and excellent endosomal escape capability for PCa therapy is developed. To construct this robust nanoplatform, a library of ultra pH-responsive PEGylated polymers were developed, containing membrane-penetrating oligoarginine grafts and an S,S-2-[3-[5-amino-1-carboxypentyl]-ureido]-pentanedioic acid (ACUPA) terminus. ACUPA is a small molecule target ligand that can specifically bind to prostate specific membrane antigen (PSMA), which is abundantly expressed in PCa, in both its metastatic form and the hormone-refractory form (Israeli, R et al., *Cancer Research,* 53, (2), 227-230 (1993); Murphy, G P et al., *Cancer,* 83, (11), 2259-2269 (1998); Dhar, S et al., *Proceedings of the National Academy of Sciences,* 105, (45), 17356-17361 (2008)). The resulting polymer/siRNA nanoassembly is expected to have the following unique features (FIG. 12): i) the surface-encoded ACUPA moieties endow the NPs with high PCa specificity and selectivity; ii) the hydrophilic PEG shells allow the NPs to escape immunological recognition, thus improving blood circulation (Knop, K et al., *Angewandte Chemie International Edition,* 49, (36), 6288-6308 (2010); Guo, X et al., *Accounts of Chemical Research,* 45, 971-979 (2012); Bertrand, N et al., *Advanced Drug Delivery Reviews,* 66, 2-25(2014); iii) a small population of cationic membrane-penetrating oligoarginine grafts randomly dispersed in the hydrophobic poly(2-(diisopropylamino) ethylmethacrylate) (PDPA) segment can strongly entrap a high amount of siRNA into the hydrophobic cores of the NPs; iv) the rapid protonation of the ultra pH-responsive PDPA segment with a pKa close to endosomal pH (6.0-6.5) causes the swelling of endosomes via the "proton sponge" effect (Yu, H et al., *ACS Nano,* 5, 9246-9255 (2011); Zhou, K et al., *Angewandte Chemie International Edition,* 50, 6109-6114 (2011)), which works alongside the membrane-penetrating oligoarginine grafts to induce efficient and fast release of siRNA in cytoplasm to inhibit tumor growth (Chen, J X et al., *ACS Applied Materials & Interfaces,* 6, (1), 593-598 (2014); Chen, J X et al., *Biomaterials,* 32, (6), 1678-1684 (2011); Lim, Y B et al., *M Angewandte Chemie International Edition,* 46, 9011-9014(2007).

Atom-transfer radical polymerization (ATRP) was employed to synthesize the PEGlyated polymer, methoxyl-polyethylene glycol-b-poly (2-(diisopropylamino) ethylmethacrylate-co-glycidyl methacrylate) (Meo-PEG-b-P(DPA-co-GMA)). The epoxy group was subsequently subjected to attack by oligoarginine ($R_n$, n=6, 8, 10, 20, 30) to endow the resulting polymer (Meo-PEG-b-P(DPA-co-GMA-$R_n$) with siRNA loading and endosomal membrane-penetrating abilities. The PCa-specific PEGylated polymer, ACUPA-PEG-b-PDPA was also prepared by ATRP, followed by conjugation with ACUPA.

Figure 13A:
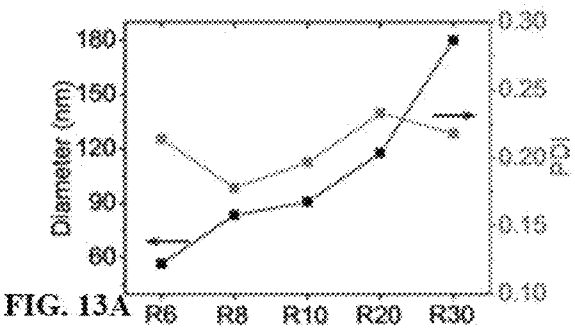
FIGS. 13A-13D are graphs showing (13A) size and polydispersity (PDI) of the GL3 siRNA-loaded NPs of Meo-PEG-b-P(DPA-co-GMA-Rn) as a function of number of arginine residues; (13B) Zeta potential (ζ) and encapsulation efficiency (EE %) of the GL3 siRNA-loaded NPs of Meo-PEG-b-P(DPA-co-GMA-Rn) as a function of number of arginine residues; (13C) acid-base titration profile of Meo-PEG-b-P(DPA-co-GMA-R10) at increasing NaOH concentrations. (13D) In vitro release of DY745-siRNA over time (hours) from the NPs of Meo-PEG-b-P(DPA-co-GMA-R10) at a pH of 6.0 and 7.4.
Figure 13B:
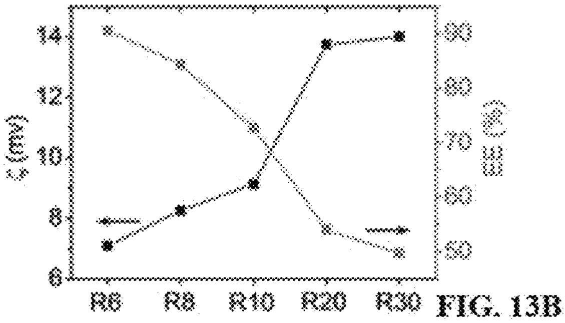

The length of the oligoarginine grafts was varied to adjust the siRNA loading ability and physiochemical properties of the NPs. The siRNA-loaded NPs were prepared by mixing siRNA aqueous solution with the tetrahydrofuran (THF) solution of Meo-PEG-b-P(DPA-co-GMA-Rn) at a N/P molar ratio of 80:1. The amphiphilic nature of the polymers induces self-assembly into NPs with siRNA entrapped in the hydrophobic cores. As the number of arginine residues increases from 6 to 30, the size of the resulting NPs increases from 56.6 to 189.9 nm (FIG. 13A, Table 5), but siRNA encapsulation efficiency (EE %) decreases from 90.6% to 49.7% (FIG. 13B). One possible reason is that enhancing overall hydrophilicity of the amphiphilic polymers by increasing the length of the oligoarginine grafts leads to the formation of looser NPs with weaker siRNA loading ability. This also results in an increased zeta potential (FIG. 13B). Notably, there is no obvious change in the EE % or size of the NPs made with the mixture of Meo-PEG-b-P(DPA-co-GMA-Rn) (90 mol %) and ACUPA-PEG-b-PDPA (10 mol %) (Table 6).

TABLE 5

Size, zeta potential, siRNA encapsulation efficiency (EE %), and pH responsiveness of the NPs from Meo-PEG-b-P(DPA-co-GMA-Rn)

| No. | Size (nm) [a] | Zeta potential (mv) | EE % [b] | pKa [b] | ΔpH 10-90% |
|---|---|---|---|---|---|
| NPsR6 | 56.6 | 7.09 | 90.6 | 6.24 | 0.32 |
| NPsR8 | 83.4 | 8.26 | 84.4 | 6.27 | 0.36 |
| NPsR10 | 90.8 | 9.13 | 72.7 | 6.31 | 0.39 |
| NPsR20 | 117.8 | 13.74 | 54 | 6.42 | 0.46 |
| NPsR30 | 179.9 | 14.01 | 49.7 | 6.49 | 0.51 |

[a] Determined by dynamic light scattering (DLS).
[b] DY-547-labelled GL3 siRNA was used to examine the EE %.
[c] Corresponding to the pKa of the polymer determined by acid-base titration.

TABLE 6

Size, zeta potential and siRNA encapsulation efficiency (EE %) of the iRGD-NPs of prepared from the mixture of Meo-PEG-b-P(DPA-co-GMA-Rn) and ACUPA-PEG-b-PDPA [a]

| No. | Size (nm) [b] | Zeta potential (mv) | EE % [c] |
|---|---|---|---|
| ACUPA-NPsR6 | 58.7 | 6.97 | 92.1 |
| ACUPA-NPsR8 | 85.9 | 7.92 | 86.9 |
| ACUPA-NPsR10 | 93.6 | 8.87 | 76.1 |
| ACUPA-NPsR20 | 119.4 | 13.46 | 58.2 |
| ACUPA-NPsR30 | 184.1 | 13.78 | 51.8 |

[a] The molar ratio of Meo-PEG-b-P(DPA-co-GMA-Rn) and ACUPA-PEG-b-PDPA is 9:1.
[b] Determined by dynamic light scattering (DLS).
[c] DY-547-labelled GL3 siRNA was used to examine the EE %.

Figure 13C:
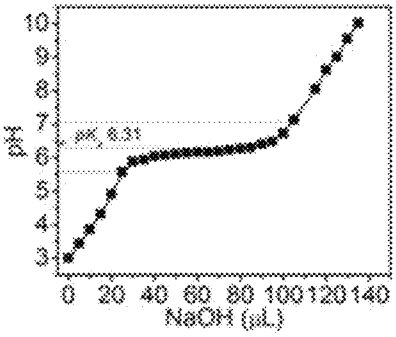
Figure 13D:
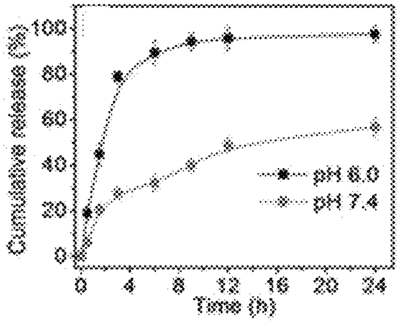
Figure 14:
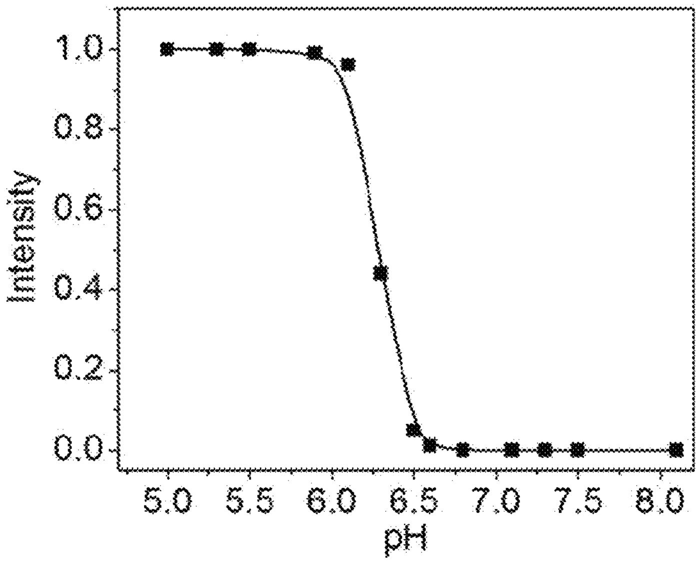
FIG. 14 is a graph showing normalized fluorescence intensity as a function of pH for the Cy.5.5 labelled NPs of Meo-PEG-b-P(DPA-co-GMA-R10).

The amphiphilic polymer, Meo-PEG-b-P(DPA-co-GMA-R10) (pKa 6.31, FIG. 13C) was used to investigate its pH sensitivity. The transmission electron microscope (TEM) image of the GL3 siRNA-loaded NPs of Meo-PEG-b-P(DPA-co-GMA-R10) incubated in PBS buffer at a pH of 6.5 indicated that this amphiphilic copolymer was able to assemble with siRNA to form spherical NPs at a pH of 6.5, with an average size of 90.8 nm determined by dynamic light scattering (DLS, FIG. 13A). When the solution pH decreases to 6.0, there are no observable NPs after 20 min incubation using TEM imaging, indicating a very fast pH sensitivity. To further evaluate the pH sensitivity, a near-infrared dye, Cy5.5-conjugated PEGylated polymer, was mixed with Meo-PEG-b-P(DPA-co-GMA-R10) to prepare the NPs with the aggregation of fluorophores inside the hydrophobic cores. Fluorescent images of the Cy.5.5 labelled NPs of Meo-PEG-b-P(DPA-co-GMA-R10) at different pH indicated that, with the quenching of the fluorophores, fluorescence signal is absent at a pH above pKa. However, protonation of the PDPA segment at pH below pKa causes the NPs to disassemble, leading to a dramatic increase in the fluorescence signal. Measuring the fluorescence intensity upon the pH change reveals that the pH difference from 10 to 90% fluorescence activation (ΔpH10-90%) is 0.39 (FIG. 14) (Wang, Y et al., *Nat Mater,* 13, (2), 204-212 (2014)). This value is much smaller than that of small molecule dyes (about 2 pH units) with the same degree of fluorescence intensity change (Urano, Y et al., *Nat Med,* 15, (1), 104-109 (2009)), demonstrating the ultra-fast pH response rate of Meo-PEG-b-P(DPA-co-GMA-R10). This characteristic allows the NPs of this polymer to show a super-fast release of DY547-labelled GL3 siRNA (DY547-siRNA) at a pH below pKa. As shown in FIG. 13D, around 80% of the loaded siRNA has been released within 3 h at a pH of 6.0. Within the same time frame, less than 30% of the loaded siRNA is released at a pH of 7.4.

Figure 18:
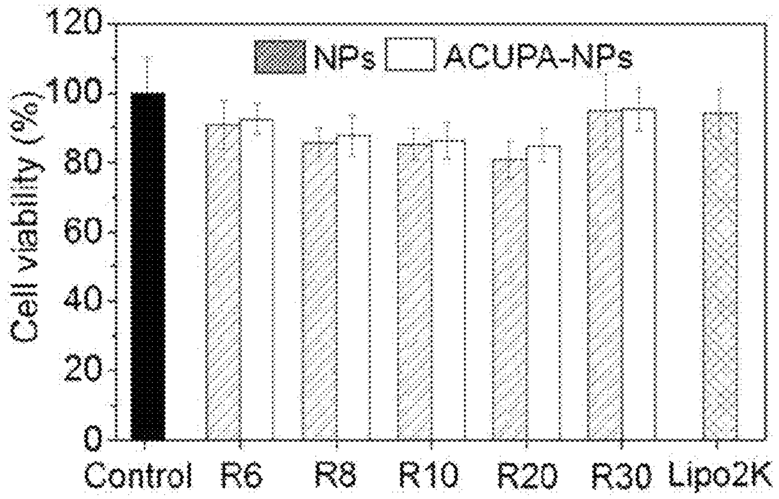
FIG. 18 is a bar graph showing cytotoxicity of the GL3 siRNA loaded NPs and Lipo2K-GL3 siRNA complex against Luc-HeLa cells at a 10 nM siRNA dose. Control: cells incubated with free medium.

Luciferase-expressing HeLa (Luc-HeLa) cells, which are genetically modified to stably express both firefly and *Renilla* luciferase, were employed to evaluate the gene silencing efficacy of the siRNA-loaded NPs. The GL3 siRNA was used to selectively suppress firefly luciferase expression. *Renilla* luciferase expression was used as an internal cell viability control. As shown in FIG. 15A, all the siRNA-loaded NPs can suppress the firefly luciferase expression at a 10 nM siRNA dose, with the differential silencing efficacy depending on the length of the oligoarginine grafts. However, there is no obvious difference between the NPs with and without the ACUPA ligand. The main reason is the extremely low PSMA expression in HeLa cells (FIGS. 16A-16F), which leads to a lack of any significant difference in cellular uptake between these two types of NPs (FIGS. 17A-17F). Among these nanoplatforms, the NPs self-assembled from Meo-PEG-b-P(DPA-co-GMA-R8) or Meo-PEG-b-P(DPA-co-GMA-R10) show a better gene silencing efficacy. In Particular, the NPs made with Meo-PEG-b-P(DPA-co-GMA-R10) can reduce the firefly luciferase expression by about 90%, which is significantly more than the commercial lipofectamine 2000 (Lipo2K) treatment, which is capable of around 70% knockdown in luciferase expression. Notably, there is no obvious cytotoxicity of NPs used for these in vitro transfection experiments (FIG. 18). Cytotoxicity of the GL3 siRNA loaded NPs with varying length of the oligoarginine grafts, R6, R8, R10, R20, and R30; and Lipo2K-GL3 siRNA complex, against Luc-HeLa cells at a 10 nM siRNA dose was compared with free medium. No obvious cytotoxicity of these NPs was observed.

Figure 19A:
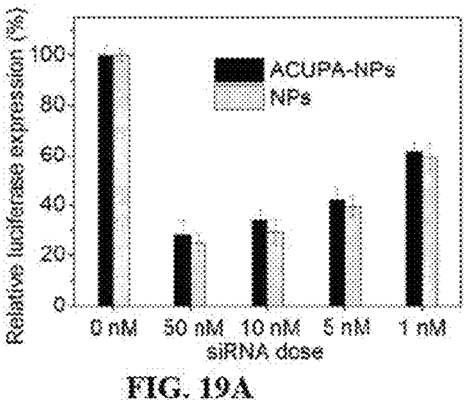
FIGS. 19A-19B are bar graphs showing (19A) firefly luciferase expression in Luc-HeLa cells transfected with GL3 siRNA-loaded NPs and ACUPA-NPs of Meo-PEG-b-P(DPA-co-GMA-TEPA) at a siRNA dose from 0-50 nM; (19B) cytotoxicity of GL3 siRNA-loaded NPs and ACUPA-NPs of Meo-PEG-b-P(DPA-co-GMA-TEPA) against Luc-HeLa cells at a siRNA dose of 0-50 nM.
Figure 19B:
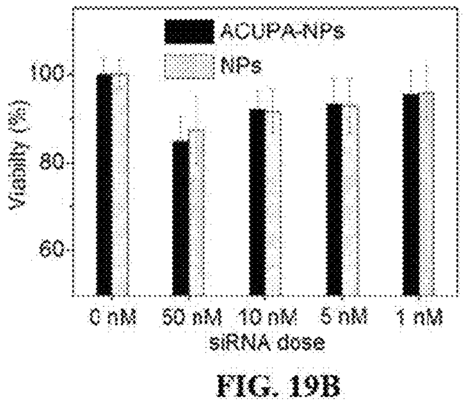

To validate the contention that the optimal silencing efficacy of the NPs prepared from Meo-PEG-b-P(DPA-co-GMA-R10) (NPsR10 and ACUPA-NPsR10) is attributable to their excellent endosomal escape capability, lysotracker green was used to label the endosomes and examined the intracellular distribution of the DY547-siRNA-loaded NPsR10. The confocal laser scanning microscope (CLSM) images of Luc-HeLa cells incubated with the DY547-siRN-loaded NPsR10 for 2 h showed that a majority of the internalized siRNA-loaded NPs enter the cytoplasm after 2 h incubation, dramatically demonstrating the excellent endosomal escape ability of the NPs. If the R10 grafts are replaced by tetraethylenepentamine (Meo-PEG-b-P(DPA-co-GMA-TEPA), the endosomal escape ability of the resulting NPs is comparatively weaker, leading to a much lower silencing efficacy (FIGS. 19A-19B). This suggests that the “proton sponge” effect alone is insufficient for endosomal escape (Yu, H et al., *ACS Nano,* 5, 9246-9255 (2011); Won, Y Y et al., *Journal of Controlled Release,* 139, (2), 88-93 (2009)). Additionally, the better silencing efficacy of NPsR8 and NPsR10 also agrees with the contention that the length of oligoarginine for the most efficient membrane penetration is between 8 and 10 arginine residues (Mitchell, D J et al., *The Journal of Peptide Research,* 56, (5), 318-325 (2000); Suzuki, T et al., *Journal of Biological Chemistry,* 277, 2437-2443 (2002); Fuchs, S M et al., *Cell. Mol. Life Sci.,* 63, 1819-1822 (2006))

Figure 15B:
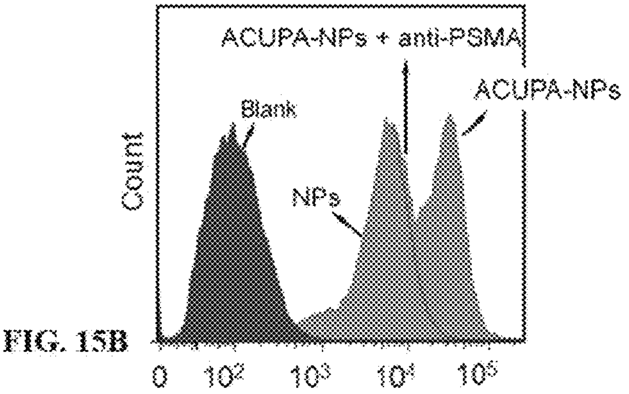
Figure 16A:
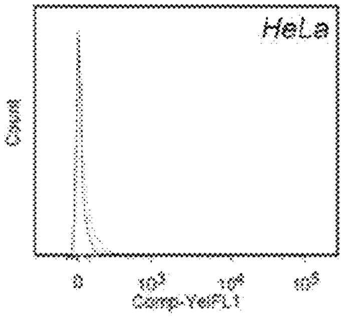
FIGS. 16A-16F are graphs showing flow cytometry profiles of PSMA on Luc-HeLa (16A) and PCa cells including PC3 (16B), DU145 (16C), 22RV1 (16D), and LNCaP (16E) determined by flow cytometry analysis. (16F) is a summary bar graph showing the fluorescence intensity of PSMA in Luc-HeLa, PC3, DU145, 22RV1, and LNCaP cells. Blank: cells incubated with free medium; MFI-mean fluorescence intensity.
Figure 16B:
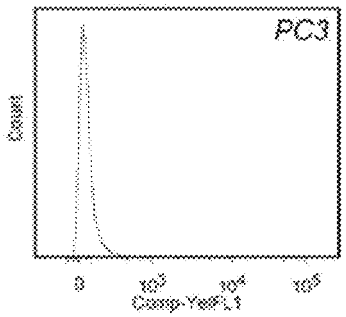
Figure 16C:
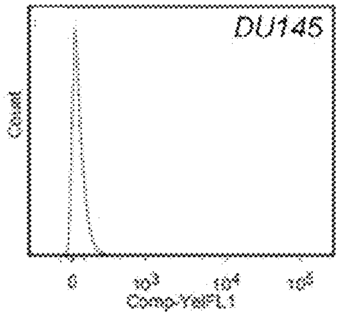
Figure 16D:
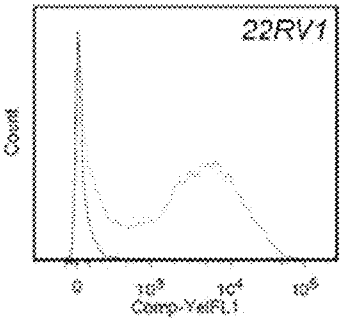
Figure 16E:
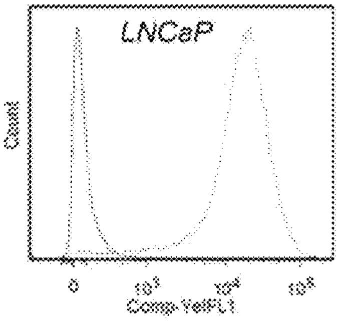
Figure 16F:
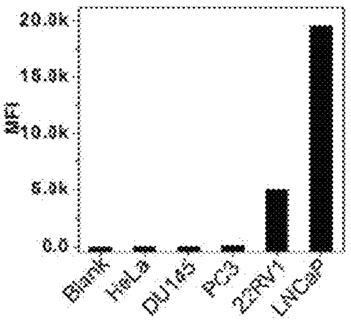
Figure 17A:
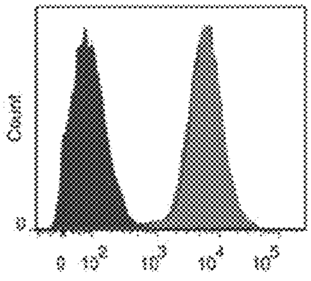
FIGS. 17A-17F are flow cytometry profiles and mean fluorescence intensity (MFI) of Luc-HeLa (17A, 17D), PC3 (17B, 17E) and DU145 (17C, 17F) cells incubated with DY547-siRNA loaded NPsR10 and ACUPA-NPsR10 for 4 h at a 10 nM siRNA dose. Blank: cells incubated with free medium.
Figure 17B:
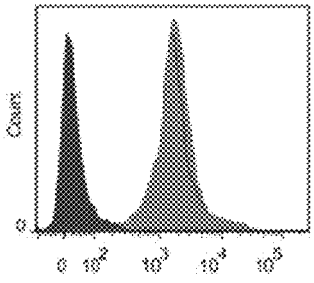
Figure 17C:
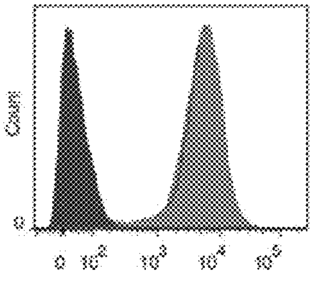
Figure 17D:
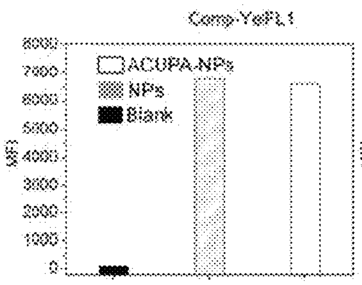
Figure 17E:
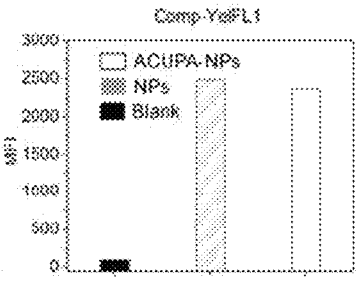
Figure 17F:
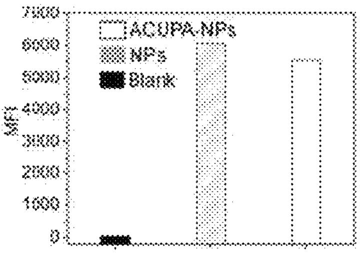
Figure 20:
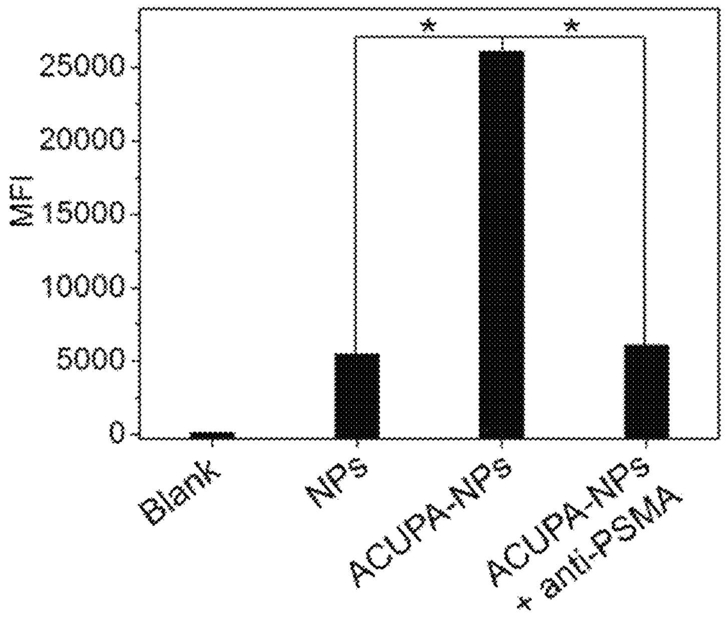
FIG. 20 is a bar graph showing Mean fluorescence intensity (MFI) determined by the flow cytometry profiles of LNCaP cells incubated with DY547-siRNA-loaded NPsR10 and ACUPA-NPsR10 for 4 h, and anti-PSMA for 30 min followed by ACUPA-NPsR10 for another 4 h at a 10 nM siRNA dose. Blank: cells incubated with free medium. *P<0.5

After screening the nanoplatform with optimal silencing efficacy, its PCa specificity was evaluated. LNCaP cells, a PCa cell line with over-expressed PSMA (FIG. 16E) (Farokhzad, O C et al., *Proceedings of the National Academy of Sciences,* 103, (16), 6315-6320 (2006)), were chosen for incubation with the NPs. From the flow cytometry profile in FIG. 15B, unlike the Luc-HeLa cells, LNCaP cells showed around 5-fold stronger uptake of the DY547-siRNA-loaded ACUPA-NPsR10 than that of NPsR10 (FIG. 20). If the cells are pre-treated with the anti-PSMA antibody for 30 min followed by ACUPA-NPsR10 for another 4 h at a 10 nM siRNA dose, there is no obvious difference in cellular uptake between ACUPA-NPsR10 and NPsR10, indicating that the high cellular uptake of ACUPA-NPsR10 is built on the specific recognition between the ACUPA ligand and the over-expressed PSMA on LNCaP cells. To further validate this ACUPA-mediated PCa specificity, two other PCa cell lines with extremely low PSMA expression, PC3 and DU145 cells, similar to that of HeLa cells (FIGS. 16A-16C), were also incubated with the DY547-siRNA-loaded NPs. With the absence of specific interaction between the ACUPA ligand and PSMA, HeLa, PC3, and DU145 cell lines show similar ability to internalize the ACUPA-NPsR10 and NPsR10 (FIGS. 17A-17F). A summary bar graph showing the fluorescence intensity of PSMA in Luc-HeLa, PC3, DU145, 22RV1, and LNCaP cells (FIG. 16F). DU145 cells express moderate amount of PSMA but at less 30% of that of LNCaP cells.

Figure 15C:
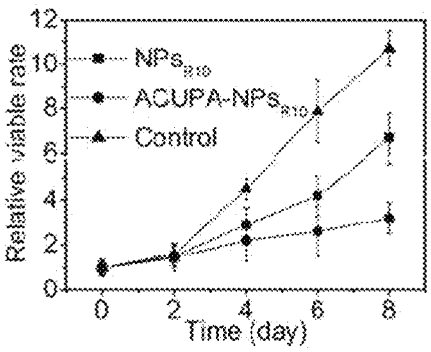
Figure 21:
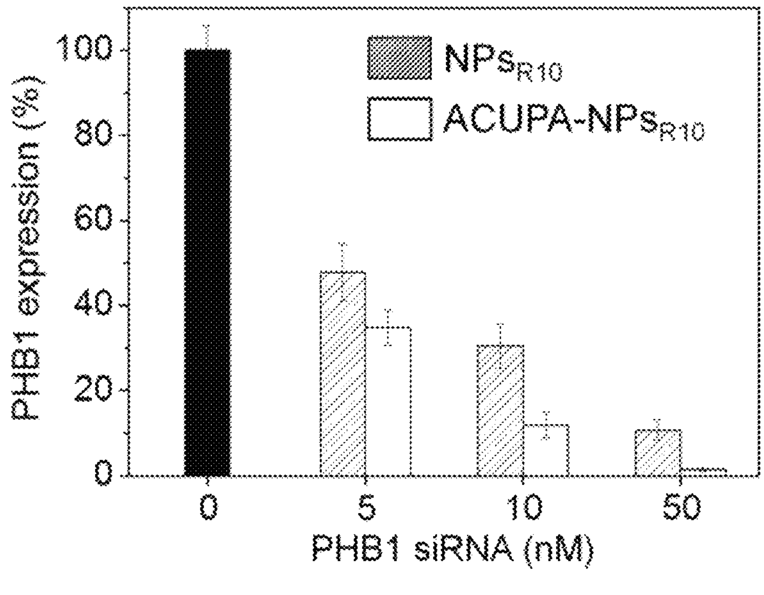
FIG. 21 is a bar graph showing relative expression of PHB1 determined by Western blot analysis in LNCaP cells treated with PHB1 siRNA-loaded NPsR10 and ACUPA-NPsR10. GL3 siRNA-loaded NPsR10 were used as a control.

Based on the high PCa specificity of ACUPA-NPsR10, it was further examined whether this siRNA delivery nanoplatform can be used to silence a potential therapeutic target in LNCaP cells. Prohibitin1 (PHB1) is a highly conserved and multifunctional 32 kDa protein that regulates various cell behaviors such as proliferation, apoptosis, and transcription (Thuaud, F et al., *Chemistry & Biology* 20, (3), 316-331; Theiss, A L et al., *Biochimica et Biophysica Acta* (*BBA*)—*Molecular Cell Research,* 1813, (6), 1137-1143 (2011)). Upregulation of PHB1 has been found in most cancers including PCa and is associated with drug resistance (Kapoor, S. *Human Pathology* 44, (4), 678-679; Gregory-Bass, R C et al., *International Journal of Cancer,* 122, (9), 1923-1930 (2008)). Western blot was employed to investigate the knockdown efficacy of PHB1 siRNA-loaded ACUPA-NPsR10. Western blot analysis of PHB1 expression in LNCaP cells treated with PHB1 siRNA-loaded NPsR10 and ACUPA-NPsR10 indicated that this siRNA delivery nanoplatform can knock down PHB1 by around 90% at a 10 nM siRNA dose. Additionally, the PHB1 expression is nearly absent (<2%) at a 50 nM siRNA dose. However, more than 30% of PHB is still expressed in the cells incubated with the siRNA-loaded NPsR10 at a 10 nM siRNA dose (FIG. 21). A similar tendency can be also found in the immunofluorescence staining analysis. Immunofluorescence analysis of the LNCaP cells treated by PHB1 siRNA-loaded NPsR10 at a 10 nM siRNA dose showed that red fluorescence corresponding to residual PHB1 expression can be observed in the LNCaP cells treated by siRNA-loaded NPsR10 at a 10 nM siRNA dose. In contrast, there is nearly no red fluorescence in the cells treated by siRNA-loaded ACUPA-NPsR10. With this suppressed PHB1 expression, LNCaP cells show a very slow proliferation rate (FIG. 15C). After 8 days incubation, there is only roughly a 3-fold increase in the cell number at a 10 nM siRNA dose. In contrast, there is around a 7-fold or 11-fold increase in the number of cells treated with PHB1 or GL3 siRNA-loaded NPsR10.

Figure 22A:
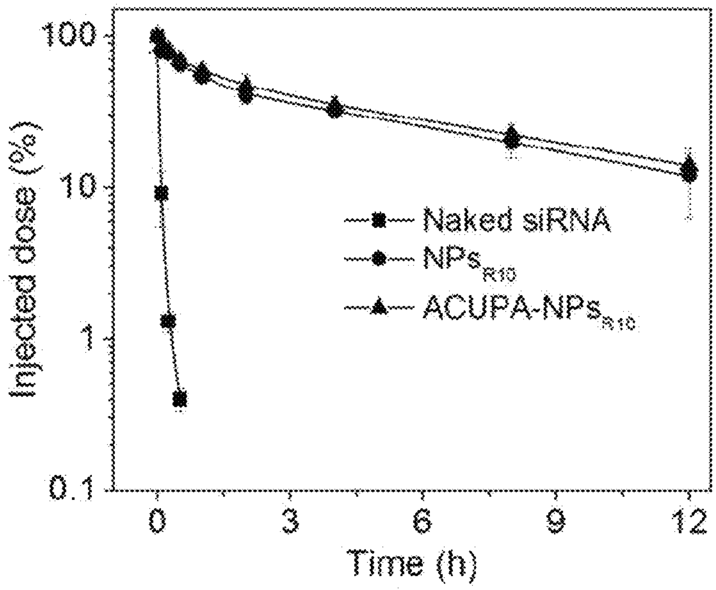
FIGS. 22A-22B are graphs showing (22A) pharmacokinetics over time (hours) of naked DY647-siRNA, and DY647-siRNA-loaded NPsR10 and ACUPA-NPsR10.
Figure 22B:
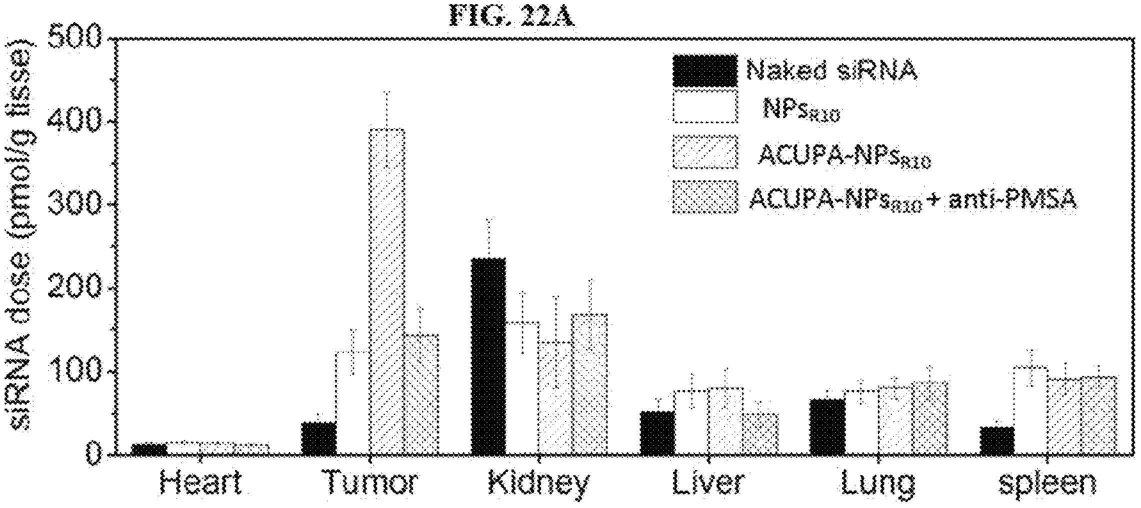

After proving the in vitro PCa-specificity of the ACUPA-NPsR10, their pharmacokinetics and in vivo PCa-specificity was evaluated. The pharmacokinetics of the ACUPA-NPsR10 was examined by intravenous injection of DY647 labelled GL3 siRNA (DY647-siRNA) loaded NPs to healthy mice (650 μg/kg siRNA dose, n=3). As shown in FIG. 22, the blood half-life (t1/2) of ACUPA-NPsR10 is around 4.56 h, far longer than naked siRNA (t1/2<30 min). This better stability is mainly attributed to protection by the PEG outer layer and small particle size (Knop, K et al., *Angewandte Chemie International Edition,* 49, 6288-6308 (2010); Guo, X et al., *Accounts of Chemical Research,* 45, 971-979 (2012); Bertrand, N et al., *Advanced Drug Delivery Reviews,* 66, 2-25(2014). Moreover, due to the negative nature of the surface-encoded ACUPA ligand with three carboxylic acid groups, the ACUPA-NPsR10 show a much longer blood circulation than NPsR10 (t½=4.18 h). The in vivo PCa-specificity of ACUPA-NPsR10 was assessed by intravenously injecting Cy5.5 labelled GL3 siRNA (Cy5.5-siRNA) loaded NPs to LNCaP xenograft tumor-bearing mice (650 μg/kg siRNA dose, n=3). Overlaid fluorescent image of the LNCaP xenograft tumor-bearing nude mice 24 h post-injection of naked Cy5.5-siRNA, Cy5.5-siRNA-loaded NPsR10 and ACUPA-NPsR10, and PSMA antibody followed by Cy5.5-siRNA-loaded ACUPA-NPsR10 showed the fluorescent image of the mice at 24 h post-injection. There is almost no accumulation of naked siRNA in the tumor. However, the ACUPA-NPsR10 shows high accumulation in the tumor corresponding to the bright fluorescence. In the absence of the PSMA-specific ACUPA ligand, the accumulation of NPsR10 in the tumor is much lower compared to ACUPA-NPsR10. If first injecting the PSMA antibody (5 mg/kg dose) followed by ACUPA-NPsR10, the blocked PSMA leads to a decrease in the accumulation of ACUPA-NPsR10 in tumor, highlighting the important effect of specific interaction between PSMA and the ACUPA ligand on the PCa-specificity of ACUPA-NPsR10. To analyze the accumulation of NPs in tumor and other organs, the tumor and main organs of mice 24 h post-injection were harvested and the biodistribution of the NPs determined. The naked siRNA presents a characteristic biodistribution, i.e., high accumulation in kidney but extremely low accumulation in tumor (Zhu X et al., *Proceedings of the National Academy of Sciences,* 112, (25), 7779-7784 (2015)). With the specific recognition between the ACUPA ligand and PSMA over-expressed on LNCaP xenograft tumor, the accumulation of ACUPA-NPsR10 in tumor is around 3-fold higher than that of NPsR10 or that found in mice pre-treated with PSMA antibody.

Finally, the in vivo inhibition of PHB1 expression and anti-tumor efficacy was evaluated. To examine the inhibition of PHB1 expression in tumor tissue, PHB1 siRNA-loaded NPs were intravenously injected to LNCaP xenograft tumor-bearing mice (650 μg/kg siRNA dose, n=3) on three consecutive days and in vivo PHB1 expression was examined by western blot. Western blot analysis of PHB1 expression in the LNCaP tumor tissue after systemic treatment by control NPs, PHB1 siRNA-loaded NPsR10 and PHB1 siRNA-loaded ACUPA-NPsR10 indicated that the siRNA loaded NPs inhibited PHB1 expression. With the ACUPA ligand targeting tumor tissues, injection of siRNA-loaded ACUPA-NPsR10 leads to more than 70% knockdown of PHB1 expression. In contrast, there is only around 33% knockdown for mice treated with siRNA-loaded NPsR10 (FIG. 24). In addition, the administration of NPs shows neglectable in vivo side effects. After five consecutive injections of the NPs to healthy mice (once every two days at a 650 μg/kg siRNA dose, n=3), there are no noticeable histological changes in the tissues from heart, liver, spleen, lung or kidney. To determine whether this NP-mediated PHB1 silencing has an anti-tumor effect, the PHB1 siRNA-loaded NPs were intravenously injected to the LNCaP xenograft tumor-bearing mice (once every two days at a 650 μg/kg siRNA dose, n=5). As shown in FIG. 23, the siRNA loaded NPs do indeed inhibit tumor growth. In particular, due to their excellent PCa specificity, the siRNA-loaded ACUPA-NPsR10 significantly suppress tumor growth after five consecutive injections and there is less than a 3-fold increase in the tumor size at 30 days after the first injection However, for the mice treated with GL3 siRNA-loaded NPsR10 (Control NPs) or PBS, more than 6-fold or 8-fold increase in the tumor size can be found at 18 days after the first injection. Moreover, the administration of the siRNA-loaded ACUPA-NPsR10 shows no obvious influence on body weight (FIG. 25), demonstrating the good biocompatibility of this nanoplatform.

In conclusion, an oligoarginine-functionalized and ultra pH-responsive nanoplatform for PCa-specific siRNA delivery has been developed. This nanoplatform can specifically deliver siRNA to PCa through the recognition between the ACUPA ligand and over-expressed PSMA on PCa cells. With the endosome swelling induced by ultra pH-responsive characteristic along with the oligoarginine-mediated endosomal membrane penetration, this nanoplatform can efficiently escape from endosomes and rapidly release therapeutic siRNA in the cytoplasm, leading to a significant inhibition of cancer-associated PHB1 expression and tumor growth. The targeted membrane-penetrating and ultra pH-responsive nanoplatform is effective as a robust siRNA delivery vehicle for PCa-specific therapy.

Example 3: Ultra pH-Responsive Nanoparticles (NPs) as Nanoprobe for Cancer Diagnosis

Methods and Materials

Synthesis of Meo-PEG-Br and Br-PEG-COOH

The detailed synthesis is same as the description in Examples 1 and 2.

Synthesis of methoxyl-polyethylene glycol-b-poly (2-(diisopropylamino) ethylmethacrylate-co-glycidyl methacrylate) (Meo-PEG-b-P(DPA-co-GMA))

Meo-PEG113-b-P(DPA80-co-GMA5) copolymer was synthesized according to the same method described in Example 1.

Synthesis of Meo-PEG-b-P(DPA-co-GMA-TEPA)

Meo-PEG-b-P(DPA-co-GMA-TEPA) was synthesized according to the same method described in Example 1.

Synthesis of Meo-PEG-b-P(DPA-co-GMA-TEPA-Cy5.5)

Meo-PEG-b-P(DPA-co-GMA-TEPA) (0.2 g) and Cy5.5 NHS ester (1.5-fold molar excess relative to the TEPA repeating unit) were well dissolved in 5 mL of THF. After constantly stirring in dark for 48 h, the solution was dialyzed against deionized water and the product was collected after freeze-drying. The synthesis scheme is shown above.

Synthesis of Meo-PEG-b-P(DPA-co-GMA-TEPA-C14)

Meo-PEG-b-P(DPA-co-GMA-TEPA-C14) was synthesized according to the same method described in Example 1.

Preparation of Cy5.5-Labelled NPs

The THF solution of Meo-PEG-b-P(DPA-co-GMA-TEPA-C14) (4 mg/mL) and Meo-PEG-b-P(DPA-co-GMA-TEPA-Cy5.5) (4 mg/mL) was mixed in a volume ratio of 8:2. Under vigorously stirring (1000 rpm), 0.5 mL of the mixture was added dropwise to 5 mL of deionized water. After collection and purification by an ultrafiltration device (EMD Millipore, MWCO 100 kDa), the NPs formed were dispersed in 1 mL of PBS buffers (pH 7.4). The size and zeta potential of the Cy5.5-labelled NPs were determined by DLS. The morphology of NPs was visualized on TEM. Before observation, the sample was stained with 1% uranyl acetate and dried under air.

Evaluation of pH Responsiveness

The Cy5.5-labelled NPs were prepared as described above and then dispersed in 1 mL of deionized water. Subsequently, 1 M NaOH or HCl was added in 1-5 μL increments, and the fluorescence intensity of the NPs was measured on a Synergy HT multi-mode microplate reader. The normalized fluorescence intensity (NFI) vs. pH profile was used to quantitatively assess the pH responsiveness. NFI is calculated as follows:

$$NFI=(F-F_{min})/(F_{max}-F_{min})$$

where F is the fluorescence intensity of the NPs at any given pH value and $F_{max}$ and $F_{min}$ are the maximal and minimal fluorescence intensity of the NPs, respectively.

Results

Imaging agents such as fluorescent dye can also be conjugated to the ultra pH-responsive copolymer to prepare dye-labelled NPs for disease diagnostics. The fluorescent dye can be, but is not limited to, Cy5.5. Cy5.5 was conjugated to the structure of the ultra pH-responsive copolymer (FIG. 26A). This dye-labelled copolymer can self-assemble into NPs with the aggregation of fluorophores inside the hydrophobic cores (FIG. 26B). Due to the quenching of the fluorophores, fluorescence signal is absent at a pH above pKa. However, protonation of the PDPA segment at pH below pKa causes the NPs to disassemble, leading to a dramatic increase in the fluorescence signal. Measuring the fluorescence intensity upon the pH change reveals that the pH difference from 10 to 90% fluorescence activation (ΔpH10-90%) is 0.39 (FIG. 2A). This value is much smaller than that of small molecule dyes (about 2 pH units) with the same degree of fluorescence intensity change, demonstrating the ultra-fast pH response characteristic of the NPs. Compared to normal tissue, the microenvironment of tumor tissue is weakly acidic. Therefore, the dye-labelled ultra pH-responsive NPs can be applied for targeted cancer diagnostics.

Example 4: Ultra pH-Responsive Nanoplatform for Anticancer Drug Delivery and Cancer Therapy

Methods and Materials

Synthesis of Meo-PEG-Br and Br-PEG-COOH

The detailed synthesis is same as the description in Examples 1 and 2.

Synthesis of methoxyl-polyethylene glycol-b-poly (2-(diisopropylamino) ethylmethacrylate) (Meo-PEG-b-PDPA)

Meo-PEG113-b-PDPA80 copolymer was synthesized by using ATRP method. In brief, DPA-MA (2.6 g, 12 mmol), Meo-PEG-Br (0.75 g, 0.15 mmol), and PMDETA (31.5 μL, 0.15 mmol) were added to a polymerization tube. DMF (3 mL) and 2-propanol (3 mL) were then added to dissolve the monomer and initiator. After three cycles of freeze-pump-thaw to remove oxygen, CuBr (21.6 mg, 0.15 mmol) was added under nitrogen atmosphere and the polymerization tube was sealed under vacuum. After polymerization at 40° C. for 24 h, tetrahydrofuran (THF) was added to dilute the product, which was then passed through a neutral $Al_2O_3$ column to remove the catalyst. The resulting THF solution was concentrated and the residue was dialyzed against THF, followed by deionized water. The expected copolymer was collected as a white powder after freeze-drying under vacuum.

Acid-Base Titration

Meo-PEG-b-PDPA was dispersed in deionized water, and a concentrated HCl aqueous solution was added until the copolymer was completely dissolved (1 mg/mL). Subsequently, 1 M NaOH aqueous solution was added in 1-5 μL increments. After each addition, the solution was constantly stirred for 3 min, and the solution pH was measured using a pH meter. The pKa of the copolymer was determined as the pH at which 50% of the copolymer turns ionizes.

Preparation and Characterization of Nanoparticles (NPs)

Meo-PEG-b-PDPA was dissolved in THF to form a homogenous solution with a concentration of 5 mg/mL. Subsequently, a certain volume of this THF solution was taken and added dropwise to 4 mL of deionized water under vigorously stirring (1000 rpm). The NP dispersion formed was transferred to an ultrafiltration device (EMD Millipore, MWCO 100 K) and centifuged to remove the organic solvent and free compounds. After washing with PBS (pH 7.4) solution (3×5 mL), the NPs were dispersed in 1 mL of phosphate buffered saline (PBS, pH 7.4) solution. Size and zeta potential were determined by DLS. The morphology of NPs was visualized on TEM. Before observation, the sample was stained with 1% uranyl acetate and dried under air.

To prepare the PTX loaded NPs, a certain volume of polymer solution (5 mg/mL in THF) was taken and mixed with PTX (20 μL, 20 mg/mL THF solution). Under vigorously stirring (1000 rpm), the mixture was added dropwise to 4 mL of deionized water. The NPs were collected and purified according to the same method describe above. To determine the PTX encapsulation efficiency, a small volume (50 μL) of the NP solution was withdrawn and mixed with 20-fold DMSO. The UV absorption was examined on a UV-Vis spectrometer and compared to the free PTX solution (5 μL stock solution mixed with 20-fold DMSO).

In Vitro Drug Release

The PTX loaded NPs were prepared as described above. Subsequently, the NPs were dispersed in 1 mL of PBS (pH 7.4) and then transferred to a Float-a-lyzer G2 dialysis device (MWCO 100 kDa, Spectrum) that was immersed in PBS (pH 7.4) at 37° C. At a predetermined interval, 5 μL of the NP solution was withdrawn and mixed with 20-fold DMSO. The UV absorption was examined on a UV-Vis spectrometer and compared to the standard PTX work curve. The average value of three independent experiments was collected and the cumulative PTX release was calculated as follows:

$$\text{Cumulative PTX release } (\%)=(M_t/M_\infty)\times 100$$

where $M_t$ is the amount of PTX released from the micelles and $M_\infty$ is the amount of PTX loaded in the micelles.

In Vitro Cytotoxicity

Prostate cancer cells (PC3, DU145 and LNCaP) were seeded in a 96-well plate with a density of 5000 cells/well. After the incubation in 100 μL of RPMI-1640 containing 10% FBS for 24 h, a fixed amount of PTX loaded NPs dispersed in 100 μL of RPMI-1640 was added and the cells were allowed to incubate for another 48 h. After replacing the medium with 100 μL of fresh RPMI-1640, 10 μL of alamarBlue agent was added to each well and the cells were further incubated for 1 h. The cytotoxicity was measured using the alamarBlue assay according to the manufacturer's protocol. The average value of six independent experiments was collected and the cell viability was calculated as follows:

$$\text{Viability } (\%)=(OD_{treated}/OD_{control})\times 100$$

where $OD_{control}$ is obtained in the absence of the PTX loaded NPs and $OD_{treated}$ is obtained in the presence of the PTX loaded NPs.

Results

Chemotherapeutic drugs can be also encapsulated into the ultra pH-responsive NPs for disease treatment. The chemotherapeutic drugs can be, but are not limited to, docetaxel (DTX), paclitaxel (PTX), doxorubicin (DOX), mitoxantrone (MTX), etc. Ultra pH-responsive PEGylated copolymer was synthesized (FIG. 27A), which can co-assemble with anticancer drug PTX to form spherical NPs with PTX loaded in their hydrophobic core as observed in TEM images taken of the NPs of Meo-PEG-b-PDPA in PBS buffer at a pH of 7.4. The PTX loading efficacy is more than 10% and the size of the PTX loaded NPs is around 100 nm. TEM images of the NPs of Meo-PEG-b-PDPA in PBS buffer at a pH of 5.0 showed that with the rapid protonation of the ultra pH-responsive copolymer, there are no observable NPs at a pH below pKa, thus leading to a super-fast PTX release (FIG. 27B).

Example 5: Light-Responsive Nanoplatform for Anticancer Drug Delivery and Cancer Therapy

Methods and Materials

Synthesis of 2-(2-oxo-2-phenylacetoxy) ethyl methacrylate (OPEMA)

Phenylglyoxylic acid (PGA, 13.5 g, 90 mmol), 2-hydroxyethyl methacrylate (HEMA, 21.06 g, 162 mmol), and 4-dimethylaminopyridine (DMAP) were well dissolved 200 mL of DCM. In an ice-salt bath, N,N'-dicyclohexylcarbodiimide (DCC, 22.2 g, 108 mmol) dissolved in 110 mL of DCM was added. After reaction at room temperature overnight, the mixture was filtered and filtration was washed with water (3×50 mL), 10% HCl (3×50 mL), and saturated Na2CO3 solution (3×50 mL). After drying over anhydrous Na2SO4, the solvent was removed and the final product was collected as powder. The synthesis scheme is shown below.

Synthesis of Meo-PEG-Br and Br-PEG-COOH

The detailed synthesis is same as the description in Examples 1 and 2.

Synthesis of methoxyl-polyethylene glycol-b-poly (2-(2-oxo-2-phenylacetoxy) ethyl methacrylate) (Meo-PEG-b-POPEMA)

Meo-PEG113-b-POPEMA80 copolymer was synthesized using ATRP method. In brief, OPEMA (3.15 g, 12 mmol), Meo-PEG-Br (0.75 g, 0.15 mmol), and PMDETA (31.5 μL, 0.15 mmol) were added to a polymerization tube. DMF (3 mL) and 2-propanol (3 mL) were then added to dissolve the monomer and initiator. After three cycles of freeze-pump-thaw to remove oxygen, CuBr (21.6 mg, 0.15 mmol) was added under nitrogen atmosphere and the polymerization tube was sealed under vacuum. After polymerization at 40° C. for 24 h, tetrahydrofuran (THF) was added to dilute the product, which was then passed through a neutral $Al_2O_3$ column to remove the catalyst. The resulting THF solution was concentrated and the residue was dialyzed against THF, followed by deionized water. The expected copolymer was collected as a white powder after freeze-drying under vacuum.

The synthesis scheme is shown below.

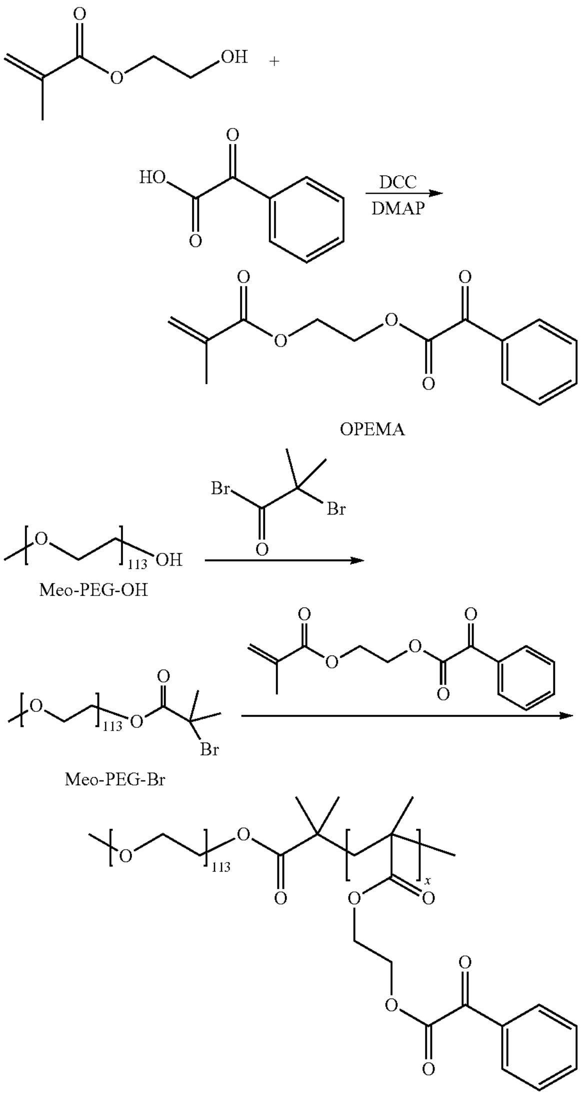

OPEMA

Meo-PEG-OH

Meo-PEG-Br

Meo-PEG-b-P(DPA-co-OPEMA)

Preparation and Characterization of Nanoparticles (NPs)

Meo-PEG-b-POPEMA was dissolved in THF to form a homogenous solution with a concentration of 10 mg/mL. Subsequently, a certain volume of this THF solution was taken and added dropwise to 5 mL of deionized water under vigorously stirring (1000 rpm). The NP dispersion formed was transferred to an ultrafiltration device (EMD Millipore, MWCO 100 K) and centrifuged to remove the organic solvent and free compounds. After washing with PBS (pH 7.4) solution (3×5 mL), the NPs were dispersed in 1 mL of phosphate buffered saline (PBS, pH 7.4) solution. Size and zeta potential were determined by DLS. The morphology of NPs was visualized on TEM. Before observation, the sample was stained with 1% uranyl acetate and dried under air.

Determination of Light-Sensitivity

The NPs of Meo-PEG-b-POPEMA were prepared as described above and then dispersed in 1 mL of deionized water. The solution of the NPs was placed under 365 nm UV light (16 W) for different time periods. The size of the NPs was examined at pre-determined time points. After 24 h UV irradiation, the solution was freeze-dried and the sample was dissolved in DMF for GPC analysis.

Preparation of Drug Loaded NPs

To prepare the drug loaded NPs, a certain volume of the polymer solution (10 mg/mL in THF) was taken and mixed with PTX (20 μL, 20 mg/mL THF solution). Under vigorously stirring (1000 rpm), the mixture was added dropwise to 4 mL of deionized water. The NPs were collected and purified according to the same method describe above. To determine the PTX encapsulation efficiency, a small volume (50 μL) of the NP solution was withdrawn and mixed with 20-fold DMSO. The UV absorption was examined on a UV-Vis spectrometer and compared to the free PTX solution (5 μL stock solution mixed with 20-fold DMSO).

In Vitro Drug Release

The PTX loaded NPs were prepared as described above. Subsequently, the NPs were dispersed in 1 mL of PBS (pH 7.4) and then transferred to a Float-a-lyzer G2 dialysis device (MWCO 100 kDa, Spectrum) that was immersed in PBS (pH 7.4) at 37° C. At a predetermined interval, 5 μL of the NP solution was withdrawn and mixed with 20-fold DMSO. The UV absorption was examined on a UV-Vis spectrometer and compared to the standard PTX work curve. The average value of three independent experiments was collected and the cumulative PTX release was calculated as follows:

$$\text{Cumulative PTX release }(\%)=(M_t/M_\infty)\times 100$$

where $M_t$ is the amount of PTX released from the micelles and $M_\infty$ is the amount of PTX loaded in the micelles.

In Vitro Cytotoxicity

Prostate cancer cells (PC3, DU145 and LNCaP) were seeded in a 96-well plate with a density of 5000 cells/well. After the incubation in 100 μL of RPMI-1640 containing 10% FBS for 24 h, a fixed amount of PTX loaded NPs dispersed in 100 μL of RPMI-1640 was added and the cells were allowed to incubate for another 48 h. After replacing the medium with 100 μL of fresh RPMI-1640, 10 μL of alamarBlue agent was added to each well and the cells were further incubated for 1 h. The cytotoxicity was measured using the alamarBlue assay according to the manufacturer's protocol. The average value of six independent experiments was collected and the cell viability was calculated as follows:

$$\text{Viability }(\%)=(OD_{treated}/OD_{control})\times 100$$

where $OD_{control}$ is obtained in the absence of the PTX loaded NPs and $OD_{treated}$ is obtained in the presence of the PTX loaded NPs.

Results

Stimuli-responsive amphiphilic copolymers can be used to prepare the NPs for delivery of therapeutic and diagnostic agents including but not limited to genes, chemotherapeutic drugs, or other small molecules. These amphiphilic polymers can be, but not limited to, light-, redox-, and temperature-responsive polymers. The light-sensitive monomer, 2-(2-oxo-2-phenylacetoxy) ethyl methacrylate (OPEMA) was synthesized, and atom-transfer radical polymerization (ATRP) was used to synthesize the PEGylated light-sensitive copolymer: (FIG. 28A). Under 365 nm UV light irradiation, this copolymer can be degraded and there is significant decrease in its molecular weight (FIG. 28B). Due to the amphiphilic nature, this copolymer can self-assemble into spherical NPs with an average size of 80 nm as seen in TEM images of the NPs of Meo-PEG-b-POPEMA in PBS buffer (pH 7.4) before 365 nm UV light irradiation. Under 365 nm UV light irradiation for 30 min, there are no observed NPs under transmission electron microscope observed in the TEM images of the NPs of Meo-PEG-b-POPEMA in PBS buffer (pH 7.4). This morphological change leads to a rapid release of loaded anticancer drug DTX (FIG. 29A) and efficient anticancer activity (FIG. 29B).

Example 6: Fast Redox-Responsive Nanoplatform for siRNA Delivery with Robust Anti-Cancer Efficacy

Methods and Materials

Synthesis of the L-cystine-based poly(disulfide) (PDSA) Polymers

PDSA polymers were prepared by one-step polycondensation of L-cystine dimethyl ester dihydrochloride ((H-Cys-OMe)2.2HCl) and dichlorides or Bis-nitrophenol esters of different fatty diacids. A standard synthesis procedure was carried out as follows: (H-Cys-OMe)2.2HCl (10.0 mmol) and triethylamine (15 mmol) were dissolved in 20.0 mL DMSO, then the dichloride of fatty acid (10.0 mmol) DMSO solution (10.0 mL) was added into the cystine mixture solution dropwise. The solution was stirred for 15 mins to obtain a uniform mixture, precipitated twice in 250 mL of cold ethyl ether, and dried under reduced atmosphere. The final product was a yellow or brown yellow powder. The synthesis scheme is shown below.

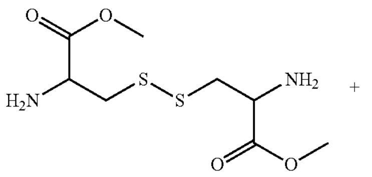

A
L-Cystine dimethyl ester

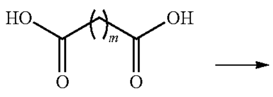

Fatty diacid

-continued

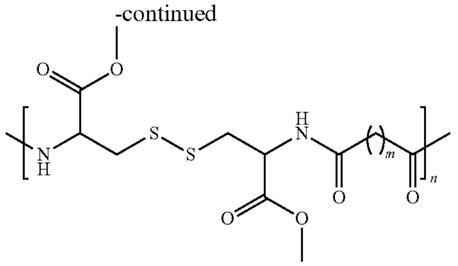

L-Cystine-based poly(disulfide amide)
(PDSA)

Redox-Responsive Behavior of the PDSA Polymers

GPC analysis was used to study the redox-responsive behavior of the PDSA polymers. The polymer (1 mg) was dissolved in 2 mL of DMF/H2O (9:1, V/V) and then GSH (6.2 mg, 0.02 mmol) was added to obtain a solution with GSH concentration of 10 mM. At predetermined intervals, 100 μL of the solution was taken for GPC analysis.

Preparation and Characterization of Nanoparticles (NPs)

The PDSA polymers were dissolved in DMF or DMSO to form a homogenous solution with a concentration of 20 mg/mL. Subsequently, 200 μL of this solution was taken and mixed with 140 μL of DSPE-PEG3000 (20 mg/mL in DMF), 50 μL of GO-C14 (5 mg/mL in DMF) and 1 nmol siRNA (0.1 nmol/μL aqueous solution). Under vigorously stirring (1000 rpm), the mixture was added dropwise to 5 mL of deionized water. The NP dispersion formed was transferred to an ultrafiltration device (EMD Millipore, MWCO 100 K) and centrifuged to remove the organic solvent and free compounds. After washing with PBS (pH 7.4) solution (3×5 mL), the siRNA loaded NPs were dispersed in 1 mL of phosphate buffered saline (PBS, pH 7.4) solution. Size and zeta potential were determined by DLS. The morphology of NPs was visualized on TEM. To determine the siRNA encapsulation efficiency, DY547-labelled GL3 siRNA (DY547-siRNA) loaded NPs were prepared according to the method described above. A small volume (50 μL) of the NP solution was withdrawn and mixed with 20-fold DMSO. The fluorescence intensity of DY547-siRNA was measured using a Synergy HT multi-mode microplate reader (BioTek Instruments) and compared to the free DY-547 labelled GL3 siRNA solution (1 nmol/mL PBS solution).

Redox-Responsive Behavior of the NPs

The siRNA loaded NPs were prepared as described above and dispersed in PBS containing 10 mM GSH. At predetermined time point, the particle size was examined by DLS and the particle morphology was observed on TEM. To evaluate the intracellular redox-responsive behavior, the NPs with Nile red and coumarin 6 encapsulated in their hydrophobic cores were prepared and then incubated with HeLa cells for different time. The fluorescence of Nile red and coumarin 6 was observed a FV1000 confocal laser scanning microscope (CLSM, Olympus). If the NPs respond to redox stimulus, the Nile red and coumarin 6 will release and only green fluorescence of coumarin 6 can be observed under CLSM. If the NPs are intact, the fluorescence of coumarin 6 will be quenched by Nile red and only red fluorescence can be observed under CLSM.

Evaluation of Endosomal Escape

Luc-HeLa cells (20,000 cells) were seeded in discs and incubated in 1 mL of RPMI 1640 medium containing 10% FBS for 24 h. Subsequently, the DY547-siRNA-loaded NPs were added, and the cells were allowed to incubate for 1 or 2 h. After removing the medium and subsequently washing with PBS (pH 7.4) solution thrice, the endosomes and nuclei were stained with lysotracker green and Hoechst 33342, respectively. The cells were then viewed under CLSM.

In Vitro siRNA Release

DY547-siRNA-loaded NPs were prepared as described above. Subsequently, the NPs were dispersed in 1 mL of PBS (pH 7.4) and then transferred to a Float-a-lyzer G2 dialysis device (MWCO 100 kDa, Spectrum) that was immersed in PBS (pH 7.4) at 37° C. At a predetermined interval, 5 μL of the NP solution was withdrawn and mixed with 20-fold DMSO. The fluorescence intensity of DY547-siRNA was determined by Synergy HT multi-mode microplate reader.

Luciferase Silencing

Luc-HeLa cells were seeded in 96-well plates (5,000 cells per well) and incubated in 0.1 mL of RPMI 1640 medium with 10% FBS for 24 h. Thereafter, the GL3 siRNA-loaded NPs were added. After incubating for 24 h, the cells were washed with fresh medium and allowed to incubate for another 48 h. The expression of firefly luciferase in HeLa cells was determined using Steady-Glo luciferase assay kits. Cytotoxicity was measured using the alamarBlue assay according to the manufacturer's protocol. The luminescence or fluorescence intensity was measured using a microplate reader, and the average value of five independent experiments was collected. As a control, the silencing effect of Lipo2K/GL3 siRNA complexes was also evaluated according to the procedure described above and compared to that of GL3 siRNA-loaded NPs.

In Vitro KIF11 Silencing

Prostate cancer cells (PC3, LNCaP, DU145 and 22Rv1) were seeded in 6-well plates (50,000 cells per well) and incubated in 1 mL of RPMI 1640 medium containing 10% FBS for 24 h. Subsequently, the cells were transfected with the KIF11 siRNA-loaded NPs for 24 h. After washing the cells with PBS thrice, the cells were further incubated in fresh medium for another 48 h. Thereafter, the cells were digested by trypsin and the proteins were extracted using modified radioimmunoprecipitation assay lysis buffer (50 mM Tris-HCl pH 7.4, 150 mM NaCl, 1% NP-40 substitute, 0.25% sodium deoxycholate, 1 mM sodium fluoride, 1 mM Na3VO4, 1 mM EDTA), supplemented with protease inhibitor cocktail and 1 mM phenylmethanesulfonyl fluoride (PMSF). The expression of KIF11 was examined using the western blot analysis.

In Vitro Cell Proliferation

PC3 cells were seeded in 6-well plates (20,000 cells per well) and incubated in 1 mL of RPMI 1640 medium containing 10% FBS for 24 h. Thereafter, the cells were transfected with the KIF11 siRNA-loaded NPs for 24 h and then washed with fresh medium for further incubation. At predetermined intervals, the cytotoxicity was measured using the alamarBlue assay according to the manufacturer's protocol. After each measurement, the alamarBlue agent was removed and the cells were incubated in fresh medium for further proliferation.

PC3 Xenograft Tumor Model

The tumor model was constructed by subcutaneous injection with 200 μL of LNCaP cell suspension (a mixture of RPMI 1640 medium and Matrigel in 1:1 volume ratio) with a density of $2\times10^6$ cells/mL into the back region of healthy male BALB/c nude mice. When the volume of the PC3 tumor xenograft reached ~50 $mm^3$, the mice were used for the following in vivo experiments.

Pharmacokinetics Study

Healthy male BALB/c mice were randomly divided into two groups (n=3) and given an intravenous injection of either (i) free DY647-labelled GL3 siRNA (DY647-siRNA) and (ii) DY647-siRNA-loaded NPs at a 650 μg/kg siRNA dose. At predetermined time intervals, orbital vein blood (20 μL) was withdrawn using a tube containing heparin, and the wound was pressed for several seconds to stop the bleeding. The fluorescence intensity of DY-647 labelled siRNA in the blood was determined using a microplate reader. The blood circulation half-life (t½) was calculated by first-order decay fit.

Biodistribution

PC3 tumor-bearing male BALB/c nude mice were randomly divided into two groups (n=3) and given an intravenous injection of either (i) free DY677-labelled GL3 siRNA (DY677-siRNA) or (ii) DY677-siRNA-loaded NPs at a 650 μg/kg siRNA dose. Twenty-four hours after the injection, the mice were imaged using the Maestro 2 In-Vivo Imaging System (Cri Inc). Main organs and tumors were then harvested and imaged. To quantify the accumulation of NPs in tumors and organs, the fluorescence intensity of each tissue was quantified by Image-J.

In Vivo KIF11 Silencing

PC3 tumor-bearing male BALB/c nude mice were randomly divided into two groups (n=3) and intravenously injected with (i) KIF11 siRNA-loaded NPs or (ii) GL3 siRNA-loaded NPs at a 650 μg/kg siRNA dose for three consecutive days. Twenty-four hours post the final injection, mice were sacrificed and tumors were harvested. The proteins in the tumor were extracted using modified radioimmunoprecipitation assay lysis buffer (50 mM Tris-HCl pH 7.4, 150 mM NaCl, 1% NP-40 substitute, 0.25% sodium deoxycholate, 1 mM sodium fluoride, 1 mM $Na_3VO_4$, 1 mM EDTA), supplemented with protease inhibitor cocktail and 1 mM phenylmethanesulfonyl fluoride (PMSF). The expression of KIF11 was examined using the aforementioned western blot analysis.

Inhibition of Tumor Growth

PC3 tumor-bearing male BALB/c nude mice were randomly divided into four groups (n=5) and intravenously injected with (i) PBS, (ii) Naked KIF11 siRNA, (iii) Blank NPs, and (iv) KIF11 siRNA-loaded NPs at a 650 μg/kg siRNA dose. All the mice were administrated four injections and the tumor growth was monitored every two days by measuring perpendicular diameters using a caliper and tumor volume was calculated as follows:

$$V=W^2\times L/2$$

where W and L are the shortest and longest diameters, respectively.

Histology

Healthy male BALB/c mice were randomly divided into three groups (n=3) and administered daily intravenous injections of either (i) PBS or (ii) KIF11 siRNA-loaded NPs at a 650 μg/kg siRNA dose. After four consecutive injections (once every two days), the main organs were collected 2 days post the final injection, fixed with 4% paraformaldehyde, and embedded in paraffin. Tissue sections were stained with hematoxylin-eosin (H&E) and viewed under an optical microscope.

Results

Besides amphiphilic copolymers, hydrophobic polymers can be also used to develop stimuli-responsive NPs for various biomedical applications. For these hydrophobic polymers, their NPs are prepared by using the mixture of the hydrophobic polymer and amphiphilic compound. The amphiphilic compound can be, but is not limited to, one or a plurality of the following: naturally derived lipids, lipid-like materials, surfactants, synthesized amphiphilic compounds, or combinations thereof.

Redox-responsive hydrophilic polymer was synthesized which could co-assemble with lipid-PEG to form spherical NPs for gene delivery and cancer therapy (FIG. 30). The intracellular levels of glutathione (GSH) are 100-1000 fold higher in cancer cells than in normal tissue. Redox-sensitive approach is particularly promising to enhance the exposure of cancer cells to therapeutic molecules. In this example, L-cystine dimethyl ester and fatty diacid were used to synthesize a library of L-cystine-based poly(disulfide amide) polymers (PDSA).

Feed compositions and molecular weight of the PDSA polymers are summarized in Table 7. Taking PDSA8-1, for example, with the presence of many disulfide bonds, there is a significant decrease in the molecule weight of PDSA8-1 incubated in 10 mM glutathione (GSH) solution. When mixing this redox-responsive polymer with DSPE-PEG3000, siRNA and cationic lipid (Xiaoyang Xu et al. *Proc Natl Acad Sci USA,* 110, 18638-18643(2013)) in water miscible solvent such as DMF, DMSO, THF, etc., spherical NPs with an average size of ~100 nm (as seen in TEM image of the NPs of the PDSA8-1) can be formed via nanoprecipitation method, in which hydrophilic PEG chains are on the outer shell and siRNA is encapsulated in the hydrophobic core. The physiochemical properties of other PDSA polymers are summarized in Table 8. With the redox-responsive characteristic to induce the breakage of the NPs of PDSA8-1 (FIG. 31A and observed by TEM imaging), the siRNA loaded NPs of PDSA8-1 show efficient endosomal escape ability as seen in fluorescent images of HeLa cells incubated with the siRNA loaded NPs of tPDSA8-1 for 1 hour and 4 hour time points; and high efficacy in down-regulation of luciferase expression in HeLa cells (>90% knockdown at 1 nM siRNA dose, FIG. 31B). These redox-responsive NPs can be used as a robust nanoplatform to deliver therapeutic siRNA for prostate cancer therapy. After treatment with the NPs loading kinesin family member 11 (KIF11) siRNA, there is a significant decrease in the expression of KIF11 in four prostate cancer cell lines (PC3, LNCaP, 22Rv1 and DU145) at a very low siRNA dose by Western blot analysis of KIF11 expression in prostate cancer cells treated with KIF11 siRNA loaded NPs of PDSA8-1. Especially for PC3 cells, there is nearly no KIF11 expression at an extremely low siRNA dose (5 nM) as seen by immunofluorescence analysis of PC3 cells treated by KIF11 siRNA loaded NPs of PDSA8-1 at a 0 and 5 nM siRNA dose. With this down-regulated KIF11 expression, the proliferation rate of PC3 cells is significantly inhibited and there is around 80% decrease in the cell number decreases at a siRNA dose of 10 nM (FIG. 32). In vivo experiment results demonstrated that these NPs have a long blood circulation (FIG. 33) and show high accumulation in PC3 xenograft tumor of mice as seen in overlaid fluorescent image of the PC3 xenograft tumor-bearing nude mice 24 h post systemic injection of naked DY677-siRNA, and DY677-siRNA loaded NPs of PDSA8-1. This lead to around 90% knockdown of KIF11 expression in tumor tissue assessed by Western blot analysis of KIF11 expression in the PC3 tumor tissue after systemic treatment by KIF11 siRNA loaded NPs of PDSA8-1 (FIG. 34), and significant inhibition of tumor growth within 52 days (FIG. 35).

TABLE 7

Feed compositions and molecular weight of the PDSA polymers.

| | Poly (disulfide amide) | $M_n$ [a] | $M_w$ [a] | Polydispesity [a] |
|---|---|---|---|---|
| m = 4 | PDSA4 | 2900 | 4300 | 1.48 |
| m = 6 | PDSA6 | 3900 | 5700 | 1.46 |
| m = 8 | PDSA8-1 | 5700 | 7300 | 1.43 |
| m = 10 | PDSA10 | 9100 | 13200 | 1.45 |
| m = 8 | PDSA8-2 | 4700 | 7800 | 1.66 |
| m = 8 | PDSA8-3 | 9300 | 15200 | 1.63 |
| m = 8 | PDSA8-4 | 11700 | 16600 | 1.42 |

[a] Determined by GPC using DMF as the eluent.

TABLE 8

Size, siRNA encapsulation efficiency (EE %) and zeta potential of the NPs of PDSA polymers.

| | PDSA4 | PDSA6 | PDSA8-1 | PDSA10 | PDSA8-2 | P DSAB-3 | PDSA8-4 |
|---|---|---|---|---|---|---|---|
| Size (nm) [a] | 155.7 | 134.5 | 102.9 | 87.6 | 118.9 | 99.4 | 93.4 |
| EE % [b] | 29.7 | 35.1 | 55.9 | 82.9 | 46.3 | 79.4 | 88.2 |
| ξ (mV) | −6.79 | −8.08 | −11.21 | −15.05 | −9.79 | −12.05 | −20.01 |

[a] N:P ratio is 20:1;
[b] siRNA encapsulation efficiency.

Example 7: Ultra pH-Responsive Nanoplatform for Anticancer Drug Delivery and Cancer Therapy

Methods and Materials

Synthesis of poly (2-(diisopropylamino) ethylmethacrylate (PDPA) DPA was synthesized by radical polymerization using 2-aminoethanethiol hydrochloride (AET·HCl) as a chain transfer agent. In brief, DPA-MA (4.27 g, 20 mmol), AET·HCl (0.88 mmol, 0.1 g), and AIBN (18 mg, 0.11 mmol) were dissolved in 15 mL of DMF. The solution was degassed by bubbling with nitrogen for 30 min. The mixture reacted at 70° C. for 6 h under nitrogen. Then, the product was precipitated by the addition of chilled methanol. The final PDPA was collected after drying in vacuum for 24 h.

Preparation and Characterization of Nanoparticles (NPs)

The PDPA polymer was dissolved in THF to form a homogenous solution with a concentration of 5 mg/mL. Subsequently, 250 μL of this solution was taken and mixed with 125 μL of DSPE-PEG3000 solution (5 mg/mL in DMF). Under vigorously stirring (1000 rpm), the mixture was added dropwise to 5 mL of deionized water. The NP dispersion formed was transferred to an ultrafiltration device (EMD Millipore, MWCO 100 K) and centrifuged to remove the organic solvent and free compounds. After washing with PBS (pH 7.4) solution (3×5 mL), the final NPs were dispersed in 1 mL of phosphate buffered saline (PBS, pH 7.4) solution. Size and zeta potential were determined by DLS. The morphology of NPs was visualized on TEM.

Ultra pH-Responsive Behavior of the NPs

The pH-responsive behavior of the NPs was evaluated by examining the particle size change at a pH below pKa. In brief, the NPs of PDPA were prepared as described above and then dispersed in deionized water. After adding concentrated HCl solution to adjust the solution pH to a value of 5.0, the particle size was examined by DLS.

Preparation of PTX Loaded Nanoparticles (NPs)

To prepare the paclitaxel (PTX) loaded NPs, a certain volume of polymer solution (5 mg/mL in THF) was taken and mixed with 125 μL of DSPE-PEG3000 solution (5 mg/mL in DMF) and PTX (20 μL, 20 mg/mL THF solution). Under vigorously stirring (1000 rpm), the mixture was added dropwise to 5 mL of deionized water. The NPs were collected and purified according to the same method describe above. To determine the PTX encapsulation efficiency, a small volume (50 μL) of the NP solution was withdrawn and mixed with 20-fold DMSO. The UV absorption was examined on a UV-Vis spectrometer and compared to the free PTX solution (5 μL stock solution mixed with 20-fold DMSO).

In Vitro Drug Release

The PTX loaded NPs were prepared as described above. Subsequently, the NPs were dispersed in 1 mL of PBS (pH 7.4) and then transferred to a Float-a-lyzer G2 dialysis device (MWCO 100 kDa, Spectrum) that was immersed in PBS (pH 7.4) at 37° C. At a predetermined interval, 5 μL of the NP solution was withdrawn and mixed with 20-fold DMSO. The UV absorption was examined on a UV-Vis spectrometer and compared to the standard PTX work curve. The average value of three independent experiments was collected and the cumulative PTX release was calculated as follows:

$$\text{Cumulative PTX release } (\%) = (Mt/M\infty)\times 100$$

where Mt is the amount of PTX released from the micelles and Mo is the amount of PTX loaded in the micelles.

In Vitro Cytotoxicity

Prostate cancer cells (PC3, DU145 and LNCaP) were seeded in a 96-well plate with a density of 5000 cells/well. After the incubation in 100 μL of RPMI-1640 containing 10% FBS for 24 h, a fixed amount of PTX loaded NPs dispersed in 100 μL of RPMI-1640 was added and the cells were allowed to incubate for another 48 h. After replacing the medium with 100 μL of fresh RPMI-1640, 10 μL of alamarBlue agent was added to each well and the cells were further incubated for 1 h. The cytotoxicity was measured using the alamarBlue assay according to the manufacturer's protocol. The average value of six independent experiments was collected and the cell viability was calculated as follows:

$$\text{Viability } (\%) = (\text{ODtreated}/\text{ODcontrol})\times 100$$

where ODcontrol is obtained in the absence of the PTX loaded NPs and ODtreated is obtained in the presence of the PTX loaded NPs Results Other than the previously discussed redox-responsive polymer, other hydrophobic polymers can be also used to mix with one or more amphiphilic polymers to prepare stimuli-responsive NPs for delivery of therapeutic and diagnostic agents including genes, chemotherapeutic drugs, or other small molecules. These hydrophobic polymers can be, but not limited to pH-, light-, and temperature-responsive polymers. Ultra pH-responsive polymer, poly(2-(diisopropylamino) ethylmethacrylate) (PDPA) was synthesized.

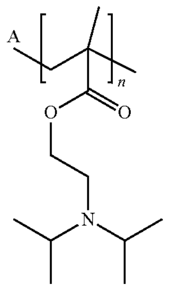

PDPA

This polymer is hydrophobic at a pH above pKa but becomes hydrophilic at a pH below pKa. Mixing this polymer with DSPE-PEG3000 and anticancer drug PTX in water miscible solvent, spherical NPs with an average size of 90 nm can be formed with PTX encapsulated into their hydrophobic core as seen by TEM imaging of the NPs of PDPA in PBS buffer at a pH of 7.4. Due to the ultra pH-responsive characteristic, these NPs show a super-fast PTX release at a pH below pKa seen by TEM imaging of the NPs of PDPA in PBS buffer at a pH of 5.0 (FIG. 22).

Example 8: Tumor Microenvironment (TME) pH-Responsive Multistaged Nanoparticle Platform for siRNA Delivery and Cancer Therapy Methods and Materials Materials 2-(Hexamethyleneimino) ethanol, methacryloyl chloride, and hydroquinone were purchased from Alfa Aesar Company and used directly. α-Bromoisobutyryl bromide, N,N'-dimethylformamide (DMF), triethylamine (TEA), N,N,N',N',N'-pentamethyldiethylenetriamine (PMDETA), copper (I) bromide (CuBr), isopropyl alcohol, dichloromethane (DCM), tetrahydrofuran (THF), and diethyl ether were provided by Sigma-Aldrich and used as received. Methoxyl-polyethylene glycol (Meo-$PEG_{113}$-OH) was purchased from JenKem Technology. Tumor-targeting and cell-penetrating peptide-amphiphiles (TCPA1: $C_{17}H_{35}$CONH-$GR_8$GRGDS-OH; TCPA2: $C_{17}H_{35}$CONH—($C_{17}H_{35}$CONH)-$KR_8$GRGDS-OH) were obtained from GL Biochem Ltd. 2-Aminoethyl methacrylate (AMA) were purchased from Polyscience Company. Cyanine5.5 NHS ester was purchased from Lumiprobe. Lipofectamine 2000 (Lipo2K) was purchased from Invitrogen. Steady-Glo luciferase assay system was provided by Promega. Fluorescent dye DY677-labelled Luc and BRD4 siRNAs were acquired from GE Dharmacon. The siRNA sequences are as follows: Luc siRNA, 5'-CUU ACG CUG AGU ACU UCG AdTdT-3' (sense) (SEQ ID NO:1) and 5'-UCG AAG UAC UCA GCG UAA GdTdT-3' (antisense) (SEQ ID NO:2); BRD4 siRNA, 5'-AAA CAC AAC UCA AGC AUC GUU-3' (sense) (SEQ ID NO:9) and 5'-CGA UGC UUG AGU UGU GUU UUU-3' (antisense) (SEQ ID NO:10). DY677 was labelled at the 5'-end of both the sense and antisense strands of Luc siRNA. Fluorescein and its quencher (Dabcyl)-labelled Luc siRNA was also provided by GE Dharmacon. Fluorescein was labelled at the 5'-end of the sense strand and Dabcyl was labelled at 3'-end of the antisense strand. HeLa cells stably expressing firefly luciferase (Luc-HeLa) were obtained from Alnylam Pharmaceuticals, Inc. The cells were incubated in RPMI 1640 medium (Invitrogen) with 10% fetal bovine serum (FBS, Sigma-Aldrich). All other reagents and solvents are of analytical grade and used without further purification.

Synthesis of 2-(hexamethyleneimino) ethyl methacrylate (HMEMA)

2-(Hexamethyleneimino) ethanol (0.1 mol, 14.3 g), TEA (0.12 mol, 12.1 g), and inhibitor hydroquinone (0.001 mol, 0.11 g) were dissolved in 100 mL of THF and then methacryloyl chloride (0.1 mol, 10.5 g) was added dropwise. After refluxing for 2 h, the precipitation was removed and the THF solvent was removed by rotary evaporator. The resulting residue was distilled under vacuum as a colorless liquid. The synthesis of HMEMA is shown below.

Synthesis Scheme of HMEMA

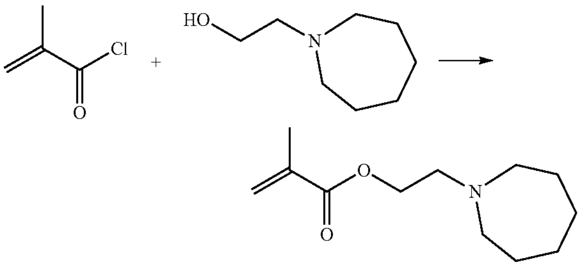

HMEMA

Synthesis of Meo-PEG-Br

Meo-PEG-Br was synthesized according to the same method described in Example 1.

Synthesis of methoxyl-polyethylene glycol-b-poly (2-(hexamethyleneimino) ethyl methacrylate) (Meo-PEG-b-PHMEMA)

Meo-PEG-b-PHMEMA block copolymer was synthesized by atom transfer radical polymerization (ATRP). HMEMA (12 mmol), Meo-PEG-Br (0.15 mmol), and PMDETA (0.15 mmol) were added to a polymerization tube. DMF (3 mL) and 2-propanol (3 mL) were then added to dissolve the monomer and initiator. After three cycles of freeze-pump-thaw to remove oxygen, CuBr (0.15 mmol) was added under nitrogen atmosphere and the polymerization tube was sealed under vacuum. After polymerization at 40° C. for 24 h, tetrahydrofuran (THF) was added to dilute the product, which was then passed through a neutral $Al_2O_3$ column to remove the catalyst. The resulting THF solution was concentrated and the residue was dialyzed against THF, followed by deionized water. The expected polymer was collected as a white powder after freeze-drying under vacuum. The synthesis of Meo-PEG-b-PHMEMA is shown below. The molecular weight was determined by gel permeation chromatography (GPC) using THF as eluent. $M_{n,GPC}$=2.34×10' (PDI=1.25); $M_{n,NMR}$=2.15×$10^4$.

Synthesis Scheme of Meo-PEG-b-PHMEMA

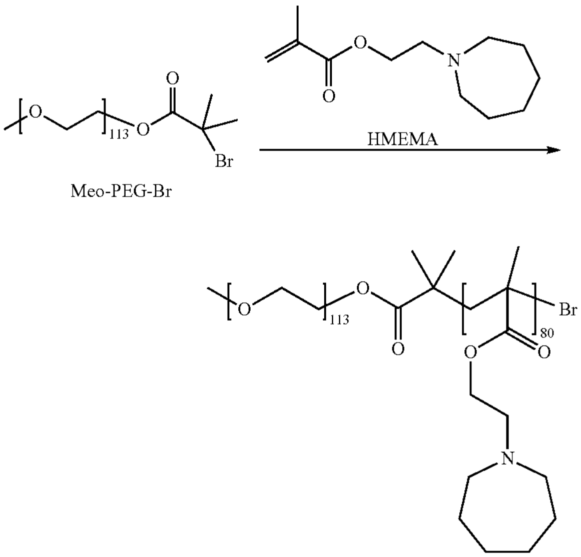

Meo-PEG-b-PHMEMA

Synthesis of methoxyl-polyethylene glycol-b-poly (2-(hexamethyleneimino) ethyl methacrylate-co-2-aminoethyl methacrylate) (Meo-PEG-b-P(HMEMA-co-AMA))

Meo-PEG-b-P(HMEMA-co-AMA) copolymer was synthesized by ATRP. HMEMA (6 mmol), Meo-PEG-Br (0.075 mmol), and PMDETA (0.075 mmol) were added to a polymerization tube. DMF (1.5 mL) and 2-propanol (1.5 mL) were then added to dissolve the monomer and initiator. After three cycles of freeze-pump-thaw to remove oxygen, CuBr (0.075 mmol) was added under nitrogen atmosphere and the polymerization tube was sealed under vacuum. After polymerization at 40° C. for 24 h, tetrahydrofuran (THF) was added to dilute the product, which was then passed through a neutral $Al_2O_3$ column to remove the catalyst. The resulting THF solution was concentrated and the residue was dialyzed against THF, followed by deionized water. The expected polymer was collected as a white powder after freeze-drying under vacuum. The synthesis of Meo-PEG-b-P(HMEMA-co-AMA) is shown below. The molecular weight was determined by gel permeation chromatography (GPC) using THF as eluent. $M_{n,GPC}$=2.42×$10^4$ (PDI=1.33); $M_{n,NMR}$=2.23×$10^4$.

Synthesis of Meo-PEG-b-P(HMEMA-co-AMA-Cy5.5)

Meo-PEG-b-P(HMEMA-co-AMA) (0.5 g) and Cy5.5 NHS ester (1.5-fold molar excess relative to the AMA repeating unit) were well dissolved in 15 mL of DMF. After constantly stirring in dark for 48 h, the solution was dialyzed against DMF for 48 h followed deionized water for 72 h. The product was collected after freeze-drying. The synthesis of Meo-PEG-b-P(HMEMA-co-AMA-Cy5.5) is shown below.

Synthesis Scheme of Meo-PEG-b-P(HMEMA-co-AMA) and Meo-PEG-b-P(HMEMA-co-AMA-Cy5.5)

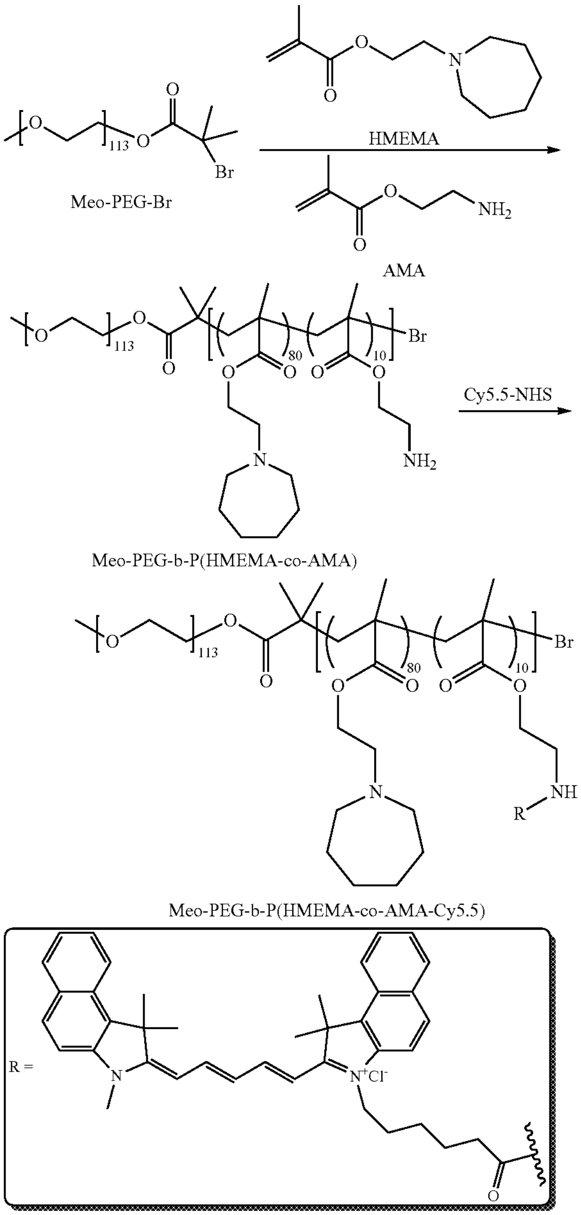

Meo-PEG-Br

Meo-PEG-b-P(HMEMA-co-AMA)

Meo-PEG-b-P(HMEMA-co-AMA-Cy5.5)

Gel Permeation Chromatography (GPC)

Number- and weight-average molecular weights ($M_n$ and $M_w$, respectively) of the polymers were determined by a gel permeation chromatographic system according to the same method described in Example 1.

$^1$H Nuclear Magnetic Resonance ($^1$HNMR)

The $^1$HNMR spectra of the polymers were recorded according to the same method described in Example 1.

Acid-Base Titration

Meo-PEG-b-PHMEMA was dispersed in deionized water, and a concentrated HCl aqueous solution was added until the copolymer was completely dissolved (1 mg/mL). Subsequently, 1 M NaOH aqueous solution was added in 1-5 μL increments. After each addition, the solution was constantly stirred for 3 min, and the solution pH was measured using a pH meter. The pKa of the copolymer was determined as the pH at which 50% of the copolymer turns ionized.

Evaluation of pH Sensitivity

A DMF solution of Meo-PEG-b-PHMEMA (5 mg/mL) and Meo-PEG-b-P(HMEMA-co-AMA-Cy5.5) (5 mg/mL) was mixed in a volume ratio of 1:1. Under vigorously stirring (1000 rpm 200 μL of the mixture was added dropwise to 5 mL of deionized water. After collection and purification using ultrafiltration device (EMD Millipore, MWCO 100 kDa), the NPs formed were dispersed in 1 mL of phosphate buffered saline (PBS, pH 7.4). Subsequently, 1 M NaOH or HCl aqueous solution was added in 1-5 μL increments, and fluorescence intensity with an excitation of 675 nm was measured on a Synergy HT multi-mode microplate reader (BioTek Instruments). The normalized fluorescence intensity (NFI) vs. pH profile was used to quantitatively assess the pH responsiveness. NFI is calculated as follows:

$$NFI=(F-F_{min})/(F_{max}-F_{min})$$

where F is the fluorescence intensity of the NPs at any given pH value and Fmax and Fmin are the maximal and minimal fluorescence intensity of the NPs, respectively.

Preparation of the siRNA Loaded Nanoparticles (NPs)

Meo-PEG-b-PHMEMA was dissolved in DMF to form a homogenous solution with a concentration of 10 mg/mL. Subsequently, a mixture of 1 nmol siRNA (0.1 nmol/μL aqueous solution) and TCPA (5 mg/mL in DMF) in an N/P molar ratio of 1:20 was prepared and mixed with 200 μL of Meo-PEG-b-PHMEMA solution. Under vigorously stirring (1000 rpm), the mixture was added dropwise to 5 mL of deionized water. The NP dispersion formed was transferred to an ultrafiltration device (EMD Millipore, MWCO 100 K) and centrifuged to remove the organic solvent and free compounds. After washing with PBS buffer (pH 7.4) (3×5 mL), the siRNA loaded NPs were dispersed in 1 mL of PBS buffer (pH 7.4).

Characterizations of NPs

Size and zeta potential were determined by dynamic light scattering (DLS, Brookhaven Instruments Corporation). The morphology of NPs was visualized on a Tecnai G2 Spirit BioTWIN transmission electron microscope (TEM). Before observation, the sample was stained with 1% uranyl acetate and dried under air. To determine siRNA encapsulation efficiency (EE %), DY677-labelled Luc siRNA (DY677-siRNA) loaded NPs were prepared according to the method aforementioned. A small volume (5 μL) of the NP solution was withdrawn and mixed with 20-fold DMSO. The standard was prepared by mixing 5 μL of naked DY677-siRNA solution (1 nmol/mL in pH 7.4 PBS buffer) with 20-fold DMSO. The fluorescence intensity of DY677-siRNA was measured using a microplate reader and the siRNA EE % is calculated as: EE %=$(FI_{NPs}/FI_{standard})\times100$.

Digestion Assay

NPs loaded with fluorescein- and Dabcyl-labelled Luc siRNA were prepared according to the method aforementioned, and then dispersed in 1 mL of PBS buffer. Subsequently, 20 U RNase was added and the sample was incubated in 37° C. At predetermined time intervals, the fluorescent emission spectra were examined using a microplate reader with excitation at 480 nm and emission data range between 490 and 650 nm.

In Vitro siRNA Release

DY677-labelled Luc siRNA loaded NPs were prepared as described above. Subsequently, the NPs were dispersed in 1 mL of PBS (pH 7.4) and then transferred to a Float-a-lyzer G2 dialysis device (MWCO 100 kDa, Spectrum) that was immersed in PBS buffer (pH 7.4 or 6.8) at 37° C. At a predetermined interval, 5 μL of the NP solution was withdrawn and mixed with 20-fold DMSO. The fluorescence intensity of DY677-labelled siRNA was determined using a microplate reader.

Flow Cytometry

Luc-HeLa (50,000 cells) were seeded in 6-well plate and incubated in 2 mL of RPMI1640 medium (pH 7.4) containing 10% FBS for 24 h. After replacing the medium with 2 mL of fresh medium at pH 7.4 or 6.8, DY677-labelled Luc siRNA loaded NPs were added, and the cells were allowed to incubate for 2 h. After removing the medium and subsequently washing with PBS buffer (pH 7.4) thrice, the cells were digested by trypsin and collected for flow cytometry quantitative analysis (DXP11 Analyzer).

Confocal Laser Scanning Microscope (CLSM)

Luc-HeLa (50,000 cells) were seeded in round discs and incubated in 2 mL of RPMI1640 medium (pH7.4) containing 10% FBS for 24 h. After replacing the medium with 2 mL of fresh medium at pH 7.4 or 6.8, DY677-labelled Luc siRNA loaded NPs were added, and the cells were allowed to incubate for 2 h. After removing the medium and subsequently washing with PBS buffer (pH 7.4) thrice, lysotracker green was added to stain the endosomes and the nuclei were stained by Hoechst 33342. The uptake of siRNA loaded NPs were viewed under a FV1000 CLSM (Olympus).

Luc Silencing

Luc-HeLa cells were seeded in 96-well plates (5,000 cells per well) and incubated in 0.1 mL of RPMI1640 medium (pH 7.4) with 10% FBS for 24 h. Thereafter, the medium was replaced by fresh medium at Luc siRNA-loaded NPs were added. After 24 h incubation, the cells were washed with PBS buffer (pH 7.4) and allowed to incubate in fresh medium (pH 7.4) for another 48 h. The Luc expression in HeLa cells was determined using Steady-Glo luciferase assay kits. Cytotoxicity was measured using AlamarBlue assay according to the manufacturer's protocol. The luminescence or fluorescence intensity was measured using a microplate reader, and the average value of five independent experiments was collected.

In Vitro BRD4 Silencing

LNCaP cells were seeded in 6-well plates (50,000 cells per well) and incubated in 2 mL of RPMI1640 medium (pH 7.4) containing 10% FBS for 24 h. Subsequently, the medium was replaced by fresh medium at pH 7.4 or 6.8, and then BRD4 siRNA loaded NPs were added. After incubation for 24 h, the cells were washed with PBS buffer (pH 7.4) and further incubated in fresh medium (pH 7.4) for another 48 h. Thereafter, the cells were digested by trypsin and the proteins were extracted using modified radioimmunoprecipitation assay lysis buffer (50 mM Tris-HCl pH 7.4, 150 mM NaCl, 1% NP-40 substitute, 0.25% sodium deoxycholate, 1 mM sodium fluoride, 1 mM Na3VO4, 1 mM EDTA), supplemented with protease inhibitor cocktail and 1 mM phenylmethanesulfonyl fluoride (PMSF). The BRD4 expression was examined using the western blot analysis.

Western Blot Analysis

Western blot analysis was carried according to the same method described in Example 1. BRD4 rabbit antibody (Abcam) and beta-actin rabbit antibody (Cell Signaling) were used. The BRD4 expression was detected with horseradish peroxidase (HRP)-conjugated secondary antibody (anti-rabbit IgG HRP-linked antibody, Cell Signaling) and an enhanced chemiluminescence (ECL) detection system (Pierce).

Apoptosis Analysis

LNCaP cells were seeded in 6-well plates (50,000 cells per well) and incubated in 2 mL of RPMI1640 medium (pH 7.4) containing 10% FBS for 24 h. Subsequently, the medium was replaced by fresh medium at pH 7.4 or 6.8, and then BRD4 siRNA loaded NPs were added. After incubation for 24 h, the cells were washed with PBS buffer (pH 7.4) and further incubated in fresh medium (pH 7.4) for another 48 h. Thereafter, the cells were digested by trypsin and the cells were collected for 7-amino-actinomycin (7-AAD) and PE Annexin V staining using PE Annexin V Apoptosis Detection Kit I (BD Pharmingen™). The apoptosis analysis was performed using a DXP11 Flow Cytometry Analyzer.

Immunofluorescence Staining

LNCaP cells (50,000 cells) were seeded in round disc and incubated in 2 mL of RPMI1640 medium (pH 7.4) containing 10% FBS for 24 h. After replacing the medium with fresh medium (pH 7.4 or 6.8), BRD4 siRNA loaded NPs were added and the cells were allowed to incubated for 24 h. Subsequently, the cells were washed with PBS buffer (pH 7.4) and fresh medium (pH 7.4) was added. After 48 h incubation, the cells were fixed with 4% paraformaldehyde. The cells were then permeabilized by incubation in 0.2% Triton X-100 in PBS buffer (pH 7.4) for 5 minutes, followed by washing with pH 7.4 PBS buffer (3×5 min). Thereafter, the cells were blocked with blocking buffer (2% normal goat serum, 2% BSA, and 0.2% gelatin in pH 7.4 PBS buffer) at room temperature for 1 h. After washing the cells with pH 7.4 PBS buffer (3×5 min), BRD4 rabbit antibody (Abcam) diluted in 1% BSA solution was added and the cells were incubated for 1 h. Subsequently, the cells were with pH 7.4 PBS buffer (3×5 min), and then further incubated with Alex Fluro 647-linked secondary antibody and Alex Fluro 488-conjugated phalloidin for another 1 h. After washing with pH 7.4 PBS buffer (3×5 min), the cells were viewed under a FV1000 CLSM.

In Vitro Cell Proliferation

LNCaP cells were seeded in 6-well plates (20,000 cells per well) and incubated in 2 mL of RPMI1640 medium (pH 7.4) containing 10% FBS for 24 h. Thereafter, the cells were treated with the BRD4 siRNA loaded NPs at pH 7.4 or 6.8 for 24 h and then washed with PBS buffer (pH 7.4) for further incubation. At predetermined intervals, the cytotoxicity was measured by AlamarBlue assay according to the manufacturer's protocol. After each measurement, the AlamarBlue agent was removed and 2 mL of fresh medium (pH 7.4) was added for further incubation.

Pharmacokinetics Study

Healthy male BALB/c mice were randomly divided into two groups (n=3) and given an intravenous injection of either (i) DY677-labelled naked Luc siRNA or (ii) DY677-labelled Luc siRNA loaded NPs at a 1 nmol siRNA dose per mouse. At predetermined time intervals, orbital vein blood (20 μL) was withdrawn using a tube containing heparin, and the wound was pressed for several seconds to stop the bleeding. The fluorescence intensity of DY677-labelled siRNA in the blood was determined by microplate reader. The blood circulation half-life ($t_{1/2}$) was calculated according to previous report (Winter H et al., *Antimicrob. Agents Chemother.* 57, 5516-5520 (2013)).

LNCaP Xenograft Tumor Model

LNCaP xenograft tumor model was constructed by subcutaneous injection with 200 μL of LNCaP cell suspension (a mixture of RPMI 1640 medium and Matrigel in 1:1 volume ratio) with a density $1\times10^7$ cells/mL into the back region of healthy male Athymic nude mice. When the volume of the LNCaP tumor xenograft reached ~70 $mm^3$, the mice were used for the following in vivo experiments.

Biodistribution

LNCaP tumor-bearing male Athymic nude mice were randomly divided into three groups (n=3) and given an intravenous injection of either (i) DY677-labelled naked Luc siRNA or (ii) DY677-labelled Luc siRNA loaded NPs at a 1 nmol siRNA dose per mouse. Twenty-four hours after the injection, the mice were imaged using the Maestro 2 In-Vivo Imaging System (Cri Inc). Organs and tumors were then harvested and imaged. To quantify the accumulation of NPs in tumors and organs, the fluorescence intensity of each tissue was quantified by Image-J.

In Vivo BRD4 Silencing

LNCaP tumor-bearing male Athymic nude mice were randomly divided into two groups (n=2) and intravenously injected with (i) Luc siRNA loaded NPs or (ii) BRD4 siRNA loaded NPs for three consecutive days. Twenty-four hours after the final injection, mice were sacrificed and tumors were harvested for western blot analysis, and immunohistochemistry and TUNEL staining. For the western blot analysis, the proteins in the tumor were extracted using modified radioimmunoprecipitation assay lysis buffer (50 mM Tris-HCl pH 7.4, 150 mM NaCl, 1% NP-40 substitute, 0.25% sodium deoxycholate, 1 mM sodium fluoride, 1 mM $Na_3VO_4$, 1 mM EDTA), supplemented with protease inhibitor cocktail and 1 mM phenylmethanesulfonyl fluoride (PMSF). Western blot was performed according to the method described above.

Immunohistochemistry (IHC) Staining

IHC staining was performed on formalin-fixed paraffin-embedded tumor sections. Briefly, tumor slides were first heated to 60° C. for 1 h, desparaffinized with xylene (3×5 min), and washed with different concentrations of alcohol. After retrieval of antigen using DAKO target retrieval solution at 95-99° C. for 40 min, followed by washing, the slides were blocked with peroxidase blocking buffer (DAKO Company) for 5 min. After washing buffer (DAKO Company), the slides were incubated with BRD4 rabbit antibody (Abcam) diluted in DAKO antibody solution for 1 h. The slides were then washed and incubated with peroxidase-labeled polymer for 30 min. After washing and staining with DAB+ substrate-chromogen solution and hematoxylin, the slides we remounted and viewed under a MVX10 MacroView Dissecting scope equipped with OlympusDP80 camera.

Immune Response

Healthy male BALB/c mice were randomly divided into three groups (n=3) and given an intravenous injection of either (i) PBS, (ii) naked BRD4 siRNA or (iii) BRD4 siRNA loaded NPs at a 1 nmol siRNA dose per mouse. Twenty-four hours after injection, blood was collected and serum isolated for measurements of representative cytokines (TNF-α, IL-6, IL-12, and IFN-γ) by enzyme-linked immunosorbent assay or ELISA (PBL Biomedical Laboratories and BD Biosciences) according to the manufacturer's instructions.

Histology

Healthy male BALB/c mice were randomly divided into three groups (n=3) and administered daily intravenous injections of either (i) PBS, (ii) naked BRD4 siRNA or (iii) BRD4 siRNA loaded NPs at a 1 nmol siRNA dose per mouse. After three consecutive injections, the main organs were collected 24 h post the final injection, fixed with 4% paraformaldehyde, and embedded in paraffin. Tissue sections were stained with hematoxylin-eosin (H&E) and then viewed under an optical microscope.

Inhibition of Tumor Growth

LNCaP tumor-bearing male Athymic nude mice were randomly divided into four groups (n=4) and intravenously injected with (i) PBS, (ii) naked BRD4 siRNA, (iii) Luc siRNA loaded NPs, or (iv) BRD4 siRNA loaded NPs at a 1 nmol siRNA dose per mouse once every three days. All the mice were administrated by administered four consecutive injections and the tumor growth was monitored every two days by measuring perpendicular diameters using a caliper and tumor volume was calculated as follows:

$$V=W^2\times L/2$$

where W and L are the shortest and longest diameters, respectively.

Statistical Analysis

Statistical significance was determined by a two-tailed Student's t test assuming equal variance. A p value<0.05 is considered statistically significant.

Results

Most of current delivery systems can overcome one or a few barriers, but unfortunately encounter various dilemmas (e.g., long circulation vs. weak uptake and active targeting vs. unfavorable circulation) to induce suboptimal therapeutic effect. RNAi technology has demonstrated the potential to make a huge impact on cancer treatment by silencing the expression of target gene(s), especially those that encode "undruggable" proteins (Kay, MA, *Nat Rev Genet* 2011, 12, (5), 316-328; Yin H et al., *Nat Rev Genet* 2014, 15, (8), 541-555; Grimm, D. *Advanced Drug Delivery Reviews* 2009, 61, (9), 672-703; Zhu X et al., *Proceedings of the National Academy of Sciences* 2015, 112, (25), 7779-7784; Xu X et al., *Angewandte Chemie* International Edition 2016, 55, (25), 7091-7094). 24-29 Nevertheless, systemic delivery of RNAi agents (e.g., siRNA) to solid tumor followed by sufficient cytosolic siRNA release has remained a barrier to the clinical translation of RNAi therapy (Pack D W et al., *Nat Rev Drug Discov* 2005, 4, (7), 581-593; Whitehead K A et al., *Nat Rev Drug Discov* 2009, 8, (2), 129-138; Tseng Y C et al., *Advanced Drug Delivery Reviews* 2009, 61, (9), 721-731; Pan D W et al., *Bioconjugate Chemistry* 2015, 26, (8), 1791-1803). Currently, the de-PEGylation technique is a commonly used strategy to promote siRNA delivery efficacy, in which PEG chains can be cleaved by the acidic pH34 or over-expressed metalloprotease (MMP) in tumor tissues to simultaneously achieve high tumor accumulation and enhanced cellular uptake (Hatakeyama H et al., Biomaterials 2011, 32, (18), 4306-4316; Wang H X et al., *Biomaterials* 2014, 35, (26), 7622-7634). However, the complicated TME stimuli-responsive chemistry involved in this strategy may introduce additional complexities in the synthesis and scale-up of therapeutic formulations.

Here, a tumor microenvironment (TME) pH-responsive multistaged NP platform for systemic siRNA delivery and effective cancer therapy has been developed. This NP platform is composed of a polyethylene glycol (PEG) outer shell and a super-fast TME pH-responsive core that can entrap the complex formed between siRNA and a tumor cell-targeting and -penetrating peptide-amphiphile (TCPA). After encapsulating siRNA, the resulting NP platform shows the following features for multistaged siRNA delivery (FIG. 37): i) polyethylene glycol (PEG) outer shell prolongs blood circulation and thus enhances tumor accumulation; ii) super-fast TME pH response of the hydrophobic poly(2-(hexamethyleneimino) ethyl methacrylate) (PHMEMA) induces the rapid exposure of siRNA/TCPA complexes at tumor site; iii) tumor cell-targeting ability of TCPA improves the uptake of the exposed siRNA/TCPA complexes by tumor cells; iv) cell-penetrating ability of TCPA enhances the cytosolic siRNA delivery to achieve efficient gene silencing; and v) ease of polymer synthesis and commercial available TCPA facilitate the scale-up of this multistaged NP platform using standard unit operations.

First, classic acid-base titration was used to examine the pKa of the TME pH-responsive polymer, methoxyl-poly-ethylene glycol-b-poly(2-(hexamethyleneimino) ethyl meth-acrylate) (Meo-PEG-b-PHMEMA), and the pKa value is determined as ~6.9, which is close to the pH of tumor extracellular fluid (6.5-6.8) (Wang Y et al., *Nat Mater* 2014, 13, (2), 204-212). This result suggests that a TME pH-responsive cargo release can be achieved when using a carrier formulated with the Meo-PEG-b-PHMEMA poly-mer. To further support this, a near-infrared dye, Cy5.5, was incorporated into the hydrophobic PHMEMA moiety (Meo-PEG-b-P(HMEMA-AMA-Cy5.5)). When mixing this Cy5.5-labelled polymer with Meo-PEG-b-PHMEMA (1:1 in molar ratio), they can self-assemble into well-dispersed NPs visualized by transmission electron microscopy (TEM), with an average size of ~40 nm determined by dynamic light scattering (DLS). Due to the quenching of the aggregated fluorophores inside the hydrophobic cores of these NPs, there is no fluorescence signal at a pH above pKa of Meo-PEG-b-PHMEMA (FIG. 38A). In contrast, at a pH below pKa, the protonated PHMEMA moiety leads to the disassembly of the NPs, visualized by TEM, and a dramatic increase in the fluorescence signal (FIG. 38A). Measurement of the fluorescence intensity upon pH change shows that the pH difference from 10 to 90% fluorescence activation ($\Delta$pH10-90%) is 0.24 (FIG. 38B), which is close to the previous report and much smaller than that of small mol-ecule dyes (about 2 pH units), demonstrating the super-fast TME pH response of the Meo-PEG-b-PHMEMA polymer (Zhou K et al., *Angewandte Chemie* International Edition 2011, 50, (27), 6109-6114; Urano Y et al., *Nat Med* 2009, 15, (1), 104-109).

The siRNA loading ability and TME pH-responsive behavior of the siRNA loaded NPs was investigated. Nano-precipitation method was employed to prepare the NPs by using a mixture of siRNA aqueous solution and dimethyl-formamide (DMF) solution of Meo-PEG-b-PHMEMA and TCPA. Two TCPAs (TCPA1: C17H35CONH-GR8GRGDS-OH; TCPA2: C17H35CONH—(C17H35CONH)-KR8GRGDS-OH, chemical structures shown below) were used to adjust the siRNA loading ability and physiochemical properties of the NPs (denoted TCPA1-NPs and TCPA2-NPs). Under the same conditions, the siRNA encapsulation efficiency (EE %, Table 9) of the TCPA1-NPs (~39%) is lower than that of TCPA2-NPs (~52%). In contrast, the size of the TCPA1-NPs (~90.1 nm, with PDI 0.279) is larger than that of the TCPA2-NPs (~72.8 nm, with PDI 0.194), deter-mined by DLS. The possible reason is that the two hydro-phobic tails of TCPA2 facilitate the formation of more compact TCPA2/siRNA complexes to improve the siRNA loading ability and decrease the size of the NPs (Lim Y B et al., *Angewandte Chemie* International Edition 2007, 46, (47), 9011-9014). In addition, the TCPA2-NPs show a strong ability to protect the siRNA stability. When encapsulating fluorescein and its quencher (Dabcyl)-labelled siRNA into the NPs, there is nearly no fluorescence change after 6 h incubation with RNase (FIG. 39). However, naked siRNA can be rapidly degraded by RNase at 5 min, 10 min, and 15 min, which induces the dissociation between fluorescein and Dabcyl, and thereby significant increase of the fluorescence intensity.

TABLE 9

Size, zeta potential, and siRNA encapsulation efficiency (EE %) of the siRNA loaded NPs made with of Meo-PEG-b-PHMEMA and TCPA1 or TCPA2.

| | siRNA | | Zeta potential (mv) | |
|---|---|---|---|---|
| Nps | EE (%) | Size (nm) | pH 7.4 | pH 6.8 |
| TCPA1-NPs | 39 | 90.1 | 9.27 | 29.2 |
| TCPA2-NPs | 52 | 72.8 | 5.69 | 27.6 |

The TCPA2-NPs were chosen to evaluate their TME pH-responsive behavior. The DY-677 siRNA loaded TCPA2-NPs showed a spherical morphology at pH 7.4 under TEM. After adjusting the solution pH to 6.8, there is a significant decrease in the NP number within 1 min (FIG. 40A), indicating the super-fast TME pH response of the siRNA loaded NPs. Transmission electron microscopy (TEM) measurements show that there are some large amor-phous aggregates and small size particles in the solution, which possibly correspond to the ionized polymer and exposed TCPA2/siRNA complexes. This result is further confirmed by DLS analysis, in which particles ranging from several nanometers to thousand nanometers can be detected (FIG. 40B). With this rapid disassembly upon pH change, the TCPA2-NPs offer a fast release of DY677-labelled siRNA (DY677-siRNA) (FIG. 40C). More than 80% of loaded siRNA has been released within 4 hours at pH 6.8. Within the same time frame, less than 20% of the loaded siRNA is released at pH 7.4.

Molecular Structures of TCPA1 and TCPA2

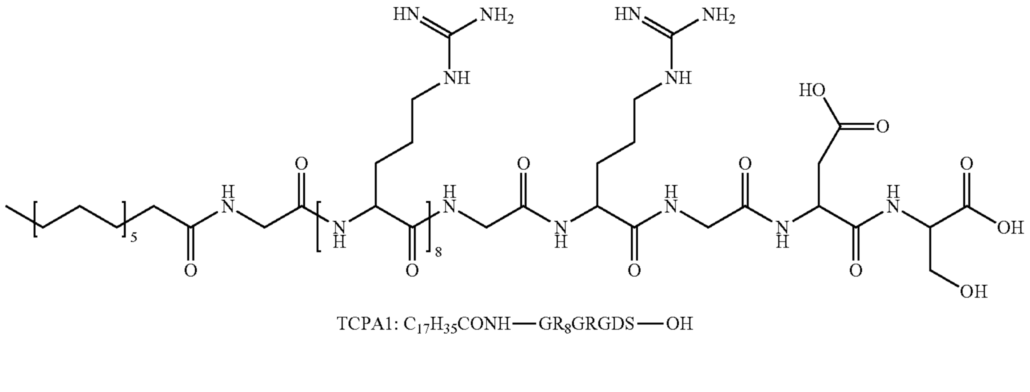

TCPA1: $C_{17}H_{35}CONH$—$GR_8GRGDS$—OH

-continued

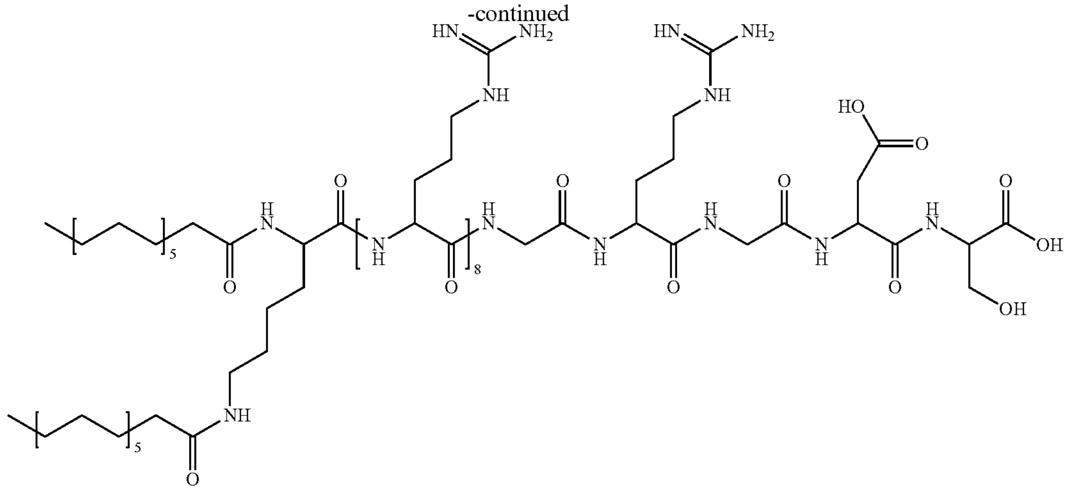

TCPA2: $C_{17}H_{35}CONH$—$(C_{17}H_{35}CONH)KR_8GRGDS$—OH

Figure 41A:
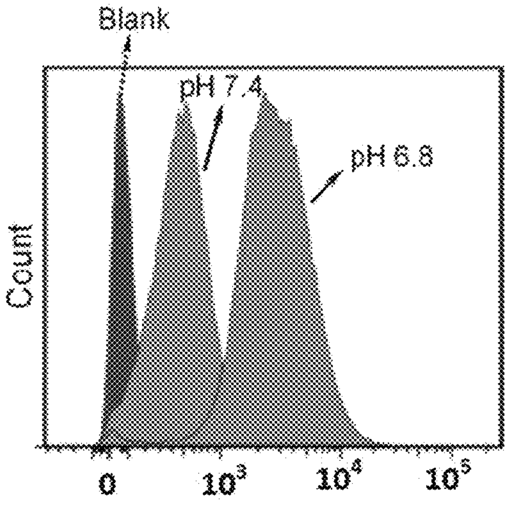
Figure 41B:
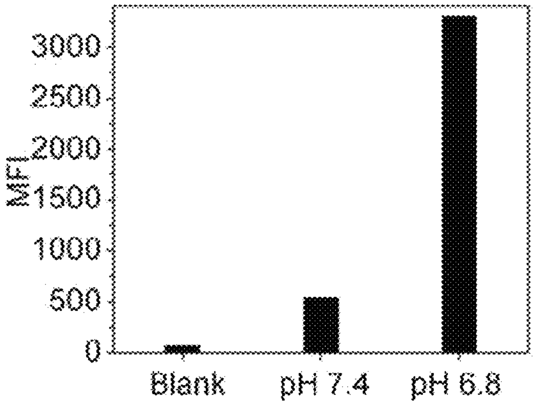

Next, the ability of this TME pH-triggered NP disassembly to improve cellular uptake of loaded siRNA and to enhance gene silencing was investigated. Luciferase-expressing HeLa (Luc-HeLa) cells were incubated with the DY677-siRNA loaded TCPA2-NPs at pH 6.8 or 7.4 for 2 h, and the cellular uptake was observed by confocal laser scanning microscopy (CLSM). Endosomes were stained by lysotracker green; nuclei were stained by Hoechst 33342. Compared to the cells incubated at pH 7.4, the brighter red fluorescence indicates a higher siRNA uptake at pH 6.8. More importantly, unlike the cells incubated at pH 7.4 with the internalized siRNA co-localizing with lysosomes and endosomes, lots of the internalized siRNA molecules at pH 6.8 are distributed in the cytoplasm where siRNA functions. Flow cytometry was used to quantitatively examine the uptake at different pHs. As shown in FIGS. 41A-41B, the siRNA uptake at pH 6.8 is more than 5-fold stronger than that of the cells incubated at pH 7.4. All these results strongly demonstrate that the TME pH-triggered disassembly of the TCPA2-NPs induces the rapid exposure of the TCPA2/siRNA complexes, which subsequently use their tumor cell-targeting and -penetrating functions to dramatically increase the cytosolic siRNA delivery (Sun C Y et al., Journal of the American Chemical Society 2015, 137, (48), 15217-15224; Xu X D et al., *Polymer Chemistry* 2012, 3, (9), 2479-2486; Ren Y et al., *Science translational medicine* 2012, 4, (147), 147ra112; Xu X et al., *ACS Nano* 2017).

Figure 41C:
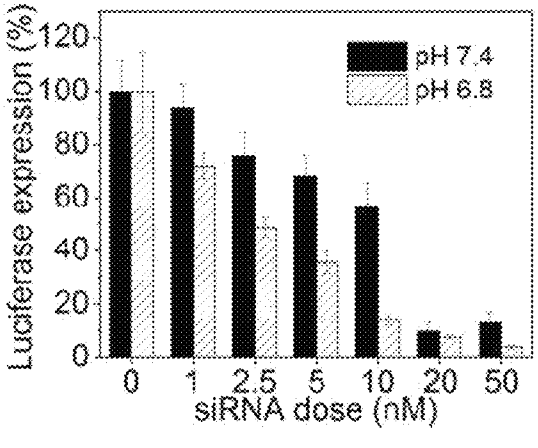
Figure 41D:
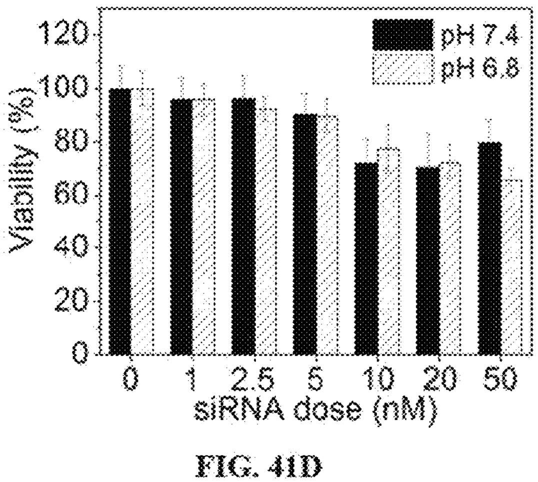

Next, Luc siRNA was encapsulated into the TCPA2-NPs and their gene silencing efficacy was evaluated using Luc-HeLa cells. As shown in FIG. 41C, the siRNA loaded NPs show a reduction in Luc expression at both pH 7.4 and 6.8. In comparison, due to rapid disassembly of the NPs at pH 6.8 to increase the cytosolic siRNA delivery (FIGS. 41A-41C), they offer much better gene silencing efficacy and can silence ~90% Luc expression without obvious cytotoxicity at a 10 nM siRNA dose (FIG. 41D). The ability of the TCPA2-NPs to silence the expression of BRD4 was examined. BRD4 is a conserved member of the BET family of chromatin readers that exhibits anti-proliferation effect in metastatic castration-resistant prostate cancer (mCRPC). LNCaP cells, an Androgen Receptor (AR) positive PCa cell line with high level of BRD4 expression compared to other PCa cells including PC3, 22RV1, and DU145. Thus, LNCaP cells were used as a model cell line. As shown in FIG. 42A, the BRD4 siRNA loaded NPs showed a higher efficacy in BRD4 silencing at pH 6.8, determined by Western blot. Around 60% BRD4 can be knocked down at a 10 nM siRNA dose and this BRD4 silencing reaches ~90% at a 20 nM siRNA dose. In comparison, for the cells treated with the BRD4 siRNA loaded NPs at pH 7.4, there is still a high level of BRD4 expression (>60%) at a 20 nM siRNA dose. Similar results can be also found in the immunofluorescence staining analysis. At a 20 nM siRNA dose, bright red fluorescence corresponding to the residual BRD4 was observed in the cells treated with the siRNA loaded NPs at pH 7.4. However, very weak red fluorescence is observable in the cells treated with the siRNA loaded NPs at pH 6.8. With this efficient BRD4 silencing at pH 6.8, the percentage of apoptotic (Annexin-V positive) or necrotic (Annexin V-negative and 7-ADD-positive) cells increases markedly to 39.5% or 36.3% (FIG. 42B), which is around 2.5-flood higher than that of the cells treated with the siRNA loaded NPs at pH 7.4. In addition, the BRD4 silencing also induces significant inhibition of cell proliferation. Only 20% of the LNCaP cells are alive after 6 days incubation (FIG. 42C). However, there is about 8-fold increase in the number of cells treated with the siRNA loaded NPs at pH 7.4.

The pharmacokinetics and biodistribution of the TCPA2-NPs was subsequent assessed. Pharmacokinetics was examined by intravenous injection of DY677-siRNA loaded NPs to health mice (1 nmol siRNA dose per mouse, n=3). As shown in FIG. 43A, with the protection of PEG outer layer, (Knop K et al., *Angewandte Chemie* International Edition 2010, 49, (36), 6288-6308) the TCPA2-NPs show long blood circulation with a half-life ($t_{1/2}$) of around 4.38 h. In contrast, the naked siRNA is rapidly cleared from the blood and its blood half-life ($t_{1/2}$) is less than 10 min. The biodistribution was evaluated by intravenously injecting DY677-siRNA loaded NPs into LNCaP xenograft tumor-bearing mice. Due to the long blood circulation characteristic of the TCPA2-NPs, they show a much higher tumor accumulation than naked siRNA when visualized using the fluorescent image of the LNCaP xenograft tumor-bearing nude mice 24 hours post injection of naked DY677-siRNA and siRNA loaded TCPA2-NPs. The tumors and main organs were harvested 24 h post injection and the biodistribution is shown in FIG. 43B. Naked siRNA has a high accumulation in kidney but very low accumulation in tumor.

However, the TCPA-NPs show an approximately 10-fold higher tumor accumulation than the naked siRNA.

The results of above in vitro and in vivo experiments demonstrate that the TCPA2-NPs have a high tumor accumulation via long blood circulation, and can respond to TME pH to target and penetrate tumor cells to induce efficient gene silencing, which is a typical multi-staged delivery characteristic (Wang S. et al., *ACS Nano* 2016, 10, (3), 2991-2994; Wang S. et al., Advanced materials 2016, 28, (34), 7340-64; Chen B et al., *Theranostics* 2017, 7, (3), 538-558).

As a proof of concept, bromodomain 4 (BRD4) was chosen as a therapeutic target and systematically evaluated the BRD4 siRNA delivery and its anticancer efficacy. BRD4 is a conserved member of the bromodomain and extraterminal (BET) family of chromatin readers, which plays a critical role in transcription by RNA polymerase II (RNA Pol II) by facilitating recruitment of the positive transcription elongation factor b (P-TEFb) (Jang, M K et al., *Molecular Cell* 2005, 19, (4), 523-534; Yang, Z et al., *Molecular Cell* 2005, 19, (4), 535-545). For mCRPC, BRD4 physically interacts with the N-terminal domain of androgen receptor (AR), a key factor that predominantly drives primary prostate cancer (PCa) to mCRPC after androgen-deprivation therapy (Taylor B S et al., Cancer Cell 2010, 18, (1), 11-22; Chen C D et al., *Nat Med,* 2004, 10, (1), 33-39; Visakorpi T et al., *Nat Genet,* 1995, 9, (4), 401-406). Recent studies demonstrated that BRD4 inhibition can disrupt AR recruitment to target gene loci and exhibits much more effective mCRPC treatment than direct AR antagonism (i.e., enzalutamide) (Asangani, I A. et al., *Nature* 2014, 510, (7504), 278-282).

Motivated by the important role of BRD4 to regulate AR signaling pathway and PCa progression, BRD4 siRNA was encapsulated in the multi-staged NP platform. It was evaluated whether this multi-staged siRNA delivery platform can silence the BRD4 expression in vivo and show anticancer effect. To assess the in vivo BRD4 silencing, the BRD4 siRNA loaded NPs were intravenously injected into the LNCaP xenograft tumor-bearing mice (1 nmol siRNA dose per mouse, n=3) for three consecutive days. Western blot analysis of the tumor tissue showed that the administration of BRD4 siRNA loaded NPs leads to around 85% knockdown in BRD4 expression compared to the control NPs loaded with Luc siRNA. A similar tendency was also observed in the immunohistochemistry (IHC) staining analysis. With this suppressed BRD4 expression, there is a significant increase in tumor cell apoptosis confirmed by TUNEL staining. Additionally, the administration of the TCPA2-NPs shows negligible in vivo side effects. After three consecutive injections of the NPs to healthy mice (once every two days at a 1 nmol siRNA dose per mouse, n=3), there were no noticeable histological changes in the tissues from heart, liver, spleen, lung or kidney. Blood serum analysis shows that TNF-α, IFN-γ, IL-6, and IL-12 levels are in the normal range 24 hour post injection. To confirm whether the NP-mediated BRD4 silencing has an anti-cancer effect, the BRD4 siRNA loaded NPs were intravenously injected into the LNCaP xenograft tumor-bearing mice once every three days at a 1 nmol siRNA dose per mouse (n=5). After four consecutive injections, the tumor growth is significantly inhibited compared to the mice treated with PBS, naked BRD4 siRNA or Luc siRNA loaded NPs (FIGS. 44A-45B). There is less than 1.5-fold increase (from ~63 to ~81 mm3) in tumor size of the mice treated with the BRD4 siRNA loaded NPs at day 16 (FIG. 44A). However, for the mice treated with other formulations, their tumor size (FIG. 44A) and weight (FIG. 44B) are more than 4-fold larger than that of mice treated with the BRD4 siRNA loaded NPs. In addition, similar as the histological analysis results, the BRD4 siRNA loaded NPs shows no obvious influence on mouse body weight, implying good biocompatibility of this NP platform. The results show that the systemic delivery of BRD4 siRNA can efficiently silence BRD4 expression in the tumor tissue and significantly inhibit PCa tumor growth with negligible toxicities.

Thus, a TME pH-responsive multi-staged NP platform for systemic siRNA delivery and effective cancer therapy has successfully developed. In vitro and in vivo results show that this multi-staged NP platform can first highly accumulate at tumor site via long blood circulation and then respond to TME pH to fast expose siRNA/TCPA complex, which subsequently target and penetrate to induce strong cytosolic siRNA delivery and efficient in vivo gene silencing.

We claim:

1. A stimulus responsive polymer comprising:

(a) a hydrophilic portion; and (b) a hydrophobic portion modified with a charged group, wherein the hydrophilic portion and the hydrophobic portion are connected by a covalent linker; and wherein the stimulus responsive polymer comprises Formula I: $(X)_m—(Y)_n$, wherein m and n are independently integers between one and 1000, X is a hydrophobic polymer in the hydrophobic portion and comprises a glycidyl methacrylate and Y is a hydrophilic polymer in the hydrophilic portion and comprises polyethylene glycol, and wherein the polymer comprises methoxyl-polyethylene glycol-b-poly (2-(diisopropylamino) ethylmethacrylate-co-glycidyl methacrylate-tetraethylenepentamine-C14) (Meo-PEG-b-P (DPA-CO-GMA-TEPA-C14)).

2. The stimulus responsive polymer of claim 1, wherein the charged group comprises a positive charge.

3. The stimulus responsive polymer of claim 1, wherein the stimulus comprises a pH buffer.

4. The stimulus responsive polymer of claim 3, wherein the buffer comprises a pH of about 4 to about 7.5.

5. The stimulus responsive polymer of claim 4, wherein the buffer comprises a pH of about 5 to about 7.

6. The stimulus responsive polymer of claim 1, wherein the hydrophobic portion further binds a nucleic acid.

7. The stimulus responsive polymer of claim 1, wherein the stimulus responsive polymer has a pKa between 6.0 and 6.5.

8. The stimulus responsive polymer of claim 1, wherein the stimulus responsive polymer is complexed with a nucleic acid.

9. The stimulus responsive polymer of claim 8, wherein the nucleic acid is an antisense oligonucleotide, an siRNA, a shRNA, an miRNA, a piRNA, an external guide sequence (EGS), a ribozyme, or an aptamer.

* * * * *

SEQUENCE LISTING

```
<160> NUMBER OF SEQ ID NOS: 15

<210> SEQ ID NO 1
<211> LENGTH: 19
<212> TYPE: RNA
<213> ORGANISM: Artificial Sequence
<220> FEATURE:
<223> OTHER INFORMATION: synthetic polynucleotide:siRNA
<220> FEATURE:
<221> NAME/KEY: misc_feature
<222> LOCATION: (19)..(19)
<223> OTHER INFORMATION: dTdT - Double nucleotide overhang TT

<400> SEQUENCE: 1

cuuacgcuga guacuucga                                         19


<210> SEQ ID NO 2
<211> LENGTH: 19
<212> TYPE: RNA
<213> ORGANISM: Artificial Sequence
<220> FEATURE:
<223> OTHER INFORMATION: synthetic polynucleotide: siRNA
<220> FEATURE:
```

```
<221> NAME/KEY: misc_feature
<222> LOCATION: (19)..(19)
<223> OTHER INFORMATION: dTdT - Double nucleotide overhang TT

<400> SEQUENCE: 2

ucgaaguacu cagcguaag                                                    19


<210> SEQ ID NO 3
<211> LENGTH: 19
<212> TYPE: RNA
<213> ORGANISM: Artificial Sequence
<220> FEATURE:
<223> OTHER INFORMATION: synthetic polynucleotide: siRNA
<220> FEATURE:
<221> NAME/KEY: misc_feature
<222> LOCATION: (19)..(19)
<223> OTHER INFORMATION: dTdT - Double nucleotide overhang TT

<400> SEQUENCE: 3

ggaccaccgc aucucuaca                                                    19


<210> SEQ ID NO 4
<211> LENGTH: 19
<212> TYPE: RNA
<213> ORGANISM: Artificial Sequence
<220> FEATURE:
<223> OTHER INFORMATION: synthetic polynucleotide: siRNA
<220> FEATURE:
<221> NAME/KEY: misc_feature
<222> LOCATION: (19)..(19)
<223> OTHER INFORMATION: dTdT - Double nucleotide overhang TT

<400> SEQUENCE: 4

uguagagaug cgguggcuc                                                    19


<210> SEQ ID NO 5
<211> LENGTH: 21
<212> TYPE: RNA
<213> ORGANISM: Artificial Sequence
<220> FEATURE:
<223> OTHER INFORMATION: synthetic polynucleotide: siRNA

<400> SEQUENCE: 5

gcgacgaccu uacagagcgu u                                                 21


<210> SEQ ID NO 6
<211> LENGTH: 21
<212> TYPE: RNA
<213> ORGANISM: Artificial Sequence
<220> FEATURE:
<223> OTHER INFORMATION: synthetic polynucleotide: siRNA

<400> SEQUENCE: 6

cgcucuguaa ggucgucgcu u                                                 21


<210> SEQ ID NO 7
<211> LENGTH: 21
<212> TYPE: RNA
<213> ORGANISM: Artificial Sequence
<220> FEATURE:
<223> OTHER INFORMATION: synthetic polynucleotide: siRNA

<400> SEQUENCE: 7

gaauaggguu acagaguugu u                                                 21


<210> SEQ ID NO 8
<211> LENGTH: 21
```

<212> TYPE: RNA
<213> ORGANISM: Artificial Sequence
<220> FEATURE:
<223> OTHER INFORMATION: synthetic polynucleotide: siRNA

<400> SEQUENCE: 8
caacucugua acccuauucu u 21

<210> SEQ ID NO 9
<211> LENGTH: 21
<212> TYPE: RNA
<213> ORGANISM: Artificial Sequence
<220> FEATURE:
<223> OTHER INFORMATION: synthetic polynucleotide: siRNA

<400> SEQUENCE: 9
aaacacaacu caagcaucgu u 21

<210> SEQ ID NO 10
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 10
cgaugcuuga guuguguuuu u 21

<210> SEQ ID NO 11
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 11

Cys Arg Gly Asp Arg Gly Pro Asp Cys
1 5

<210> SEQ ID NO 12
<211> LENGTH: 6
<212> TYPE: RNA
<213> ORGANISM: Artificial Sequence
<220> FEATURE:
<223> OTHER INFORMATION: synthetic polynucleotide - cleavage site

<400> SEQUENCE: 12 aauaaa 6

<210> SEQ ID NO 13
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 13

Cys Arg Glu Lys Ala
1 5

<210> SEQ ID NO 14
<211> LENGTH: 9
<212> TYPE: PRT
<213> ORGANISM: Artificial Sequence
<220> FEATURE:
<223> OTHER INFORMATION: synthetic polypeptide -continued

```
<400> SEQUENCE: 14

Cys Arg Lys Arg Leu Asp Arg Asn Cys
1               5


<210> SEQ ID NO 15
<211> LENGTH: 8
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (8)..(8)
<223> OTHER INFORMATION: -NH2 modification at C-terminus

<400> SEQUENCE: 15

Arg Arg Arg Arg Arg Arg Arg Arg
1               5
```